(12) United States Patent
Chan et al.

(10) Patent No.: US 11,274,157 B2
(45) Date of Patent: Mar. 15, 2022

(54) CONSTRUCTS TARGETING HISTONE H3 PEPTIDE/MHC COMPLEXES AND USES THEREOF

(71) Applicant: EUREKA THERAPEUTICS, INC., Emeryville, CA (US)

(72) Inventors: Vivien Wai-Fan Chan, Emeryville, CA (US); Hong Liu, El Sobrante, CA (US); Yoko Nakano, El Cerrito, CA (US); Yiyang Xu, Pleasanton, CA (US)

(73) Assignee: EUREKA THERAPEUTICS, INC., Emeryville, CA (US)

( * ) Notice: Subject to any disclaimer, the term of this patent is extended or adjusted under 35 U.S.C. 154(b) by 257 days.

(21) Appl. No.: 16/477,509

(22) PCT Filed: Jan. 11, 2018

(86) PCT No.: PCT/US2018/013362
§ 371 (c)(1),
(2) Date: Jul. 11, 2019

(87) PCT Pub. No.: WO2018/132597
PCT Pub. Date: Jul. 19, 2018

(65) Prior Publication Data
US 2019/0338035 A1  Nov. 7, 2019

Related U.S. Application Data

(60) Provisional application No. 62/572,300, filed on Oct. 13, 2017, provisional application No. 62/445,665, filed on Jan. 12, 2017.

(51) Int. Cl.
| | | |
|---|---|---|
| C07K 16/28 | (2006.01) |
| C07K 14/725 | (2006.01) |
| C07K 14/705 | (2006.01) |
| C07K 16/46 | (2006.01) |
| A61K 47/68 | (2017.01) |
| A61K 35/17 | (2015.01) |
| G01N 33/569 | (2006.01) |
| G01N 33/574 | (2006.01) |
| A61K 39/00 | (2006.01) |

(52) U.S. Cl.
CPC .......... *C07K 16/2833* (2013.01); *A61K 35/17* (2013.01); *A61K 47/6803* (2017.08); *A61K 47/6849* (2017.08); *C07K 14/7051* (2013.01); *C07K 14/70521* (2013.01); *C07K 14/70578* (2013.01); *C07K 16/2809* (2013.01); *C07K 16/468* (2013.01); *G01N 33/56977* (2013.01); *G01N 33/57407* (2013.01); *A61K 2039/505* (2013.01); *C07K 2317/31* (2013.01); *C07K 2317/33* (2013.01); *C07K 2317/622* (2013.01); *C07K 2317/92* (2013.01); *C07K 2319/02* (2013.01); *C07K 2319/03* (2013.01); *G01N 2410/00* (2013.01); *G01N 2496/05* (2013.01)

(58) Field of Classification Search
CPC ........ C07K 16/00–468; C07K 16/2833; C07K 14/7051; C07K 14/70521; C07K 14/70578; C07K 2317/31–92; A61K 35/17
See application file for complete search history.

(56) References Cited

U.S. PATENT DOCUMENTS

| | | |
|---|---|---|
| 3,773,919 A | 11/1973 | Boswell |
| 4,676,980 A | 6/1987 | Segal |
| 4,816,567 A | 3/1989 | Cabilly |
| 4,975,278 A | 12/1990 | Senter |
| 4,994,560 A | 2/1991 | Kruper, Jr. |
| 5,199,942 A | 4/1993 | Gillis |
| 5,208,020 A | 5/1993 | Chari |
| 5,229,275 A | 7/1993 | Goroff |
| 5,274,119 A | 12/1993 | Frazier |
| 5,342,604 A | 8/1994 | Wilson |
| 5,350,674 A | 9/1994 | Boenisch |
| 5,399,346 A | 3/1995 | Anderson |
| 5,428,139 A | 6/1995 | Kiefer |
| 5,435,990 A | 7/1995 | Cheng |
| 5,489,425 A | 2/1996 | Kruper, Jr. |
| 5,500,362 A | 3/1996 | Robinson |
| 5,505,931 A | 4/1996 | Pribish |
| 5,545,806 A | 8/1996 | Lonberg |
| 5,545,807 A | 8/1996 | Surani et al. |
| 5,567,610 A | 10/1996 | Borrebaeck |
| 5,569,825 A | 10/1996 | Lonberg |
| 5,580,859 A | 12/1996 | Felgner |
| 5,585,362 A | 12/1996 | Wilson |

(Continued)

FOREIGN PATENT DOCUMENTS

| | | |
|---|---|---|
| EP | 1176195 A1 | 1/2002 |
| EP | 1229125 A1 | 8/2002 |

(Continued)

OTHER PUBLICATIONS

Z. Eshhar, "The T-Body Approach: Redirecting T Cells with Antibody Specificity", pp. 329-342 in Therapeutic Antibodies: Handbook of Experimental Pharmacology 181, Eds. Y Chernajovsky & A Nissim, Springer-Verlag Berlin Heidelberg (Year: 2008).*

(Continued)

*Primary Examiner* — Jessica H Roark
(74) *Attorney, Agent, or Firm* — Morrison & Foerster LLP

(57) ABSTRACT

The present application provides constructs comprising an antibody moiety that specifically binds to a complex comprising a histone H3 peptide and an MHC class I protein. Also provided are methods of making and using these constructs.

28 Claims, 5 Drawing Sheets

Specification includes a Sequence Listing.

(56) References Cited

U.S. PATENT DOCUMENTS

| | | |
|---|---|---|
| 5,589,466 A | 12/1996 | Felgner |
| 5,591,669 A | 1/1997 | Krimpenfort |
| 5,624,821 A | 4/1997 | Winter |
| 5,625,126 A | 4/1997 | Lonberg |
| 5,633,425 A | 5/1997 | Lonberg |
| 5,648,260 A | 7/1997 | Winter |
| 5,652,361 A | 7/1997 | Simon |
| 5,661,016 A | 8/1997 | Lonberg |
| 5,696,239 A | 12/1997 | Wilson |
| 5,714,631 A | 2/1998 | Wilson |
| 5,731,168 A | 3/1998 | Carter |
| 5,750,373 A | 5/1998 | Garrard |
| 5,756,065 A | 5/1998 | Wilson |
| 5,808,003 A | 9/1998 | Subramanian |
| 5,821,337 A | 10/1998 | Carter |
| 5,858,358 A | 1/1999 | June |
| 5,883,223 A | 3/1999 | Gray |
| 6,194,551 B1 | 2/2001 | Idusogie |
| 6,326,193 B1 | 12/2001 | Liu |
| 6,352,694 B1 | 3/2002 | June |
| 6,534,055 B1 | 3/2003 | June |
| 6,602,684 B1 | 8/2003 | Umana et al. |
| 6,692,964 B1 | 2/2004 | June |
| 6,737,056 B1 | 5/2004 | Presta |
| 6,797,514 B2 | 9/2004 | Berenson |
| 6,867,041 B2 | 3/2005 | Berenson |
| 6,887,466 B2 | 5/2005 | June |
| 6,905,680 B2 | 6/2005 | June |
| 6,905,681 B1 | 6/2005 | June |
| 6,905,874 B2 | 6/2005 | Berenson |
| 7,067,318 B2 | 6/2006 | June |
| 7,144,575 B2 | 12/2006 | June |
| 7,172,869 B2 | 2/2007 | June |
| 7,175,843 B2 | 2/2007 | June |
| 7,232,566 B2 | 6/2007 | June |
| 7,332,581 B2 | 2/2008 | Presta |
| 7,371,826 B2 | 5/2008 | Presta |
| 7,446,190 B2 | 11/2008 | Sadelain |
| 7,521,541 B2 | 4/2009 | Eigenbrot |
| 7,741,465 B1 | 6/2010 | Eshhar |
| 8,278,421 B2 * | 10/2012 | Masat ............... A61P 35/00 530/387.1 |
| 2002/0164328 A1 | 11/2002 | Shinkawa |
| 2003/0115614 A1 | 6/2003 | Kanda |
| 2003/0157108 A1 | 8/2003 | Presta |
| 2004/0093621 A1 | 5/2004 | Shitara |
| 2004/0109865 A1 | 6/2004 | Niwa |
| 2004/0110282 A1 | 6/2004 | Kanda |
| 2004/0110704 A1 | 6/2004 | Yamane |
| 2004/0132140 A1 | 7/2004 | Satoh |
| 2005/0079574 A1 | 4/2005 | Bond |
| 2005/0119455 A1 | 6/2005 | Fuh |
| 2005/0123546 A1 | 6/2005 | Umana |
| 2005/0266000 A1 | 12/2005 | Bond |
| 2007/0117126 A1 | 5/2007 | Sidhu |
| 2007/0160598 A1 | 7/2007 | Dennis |
| 2007/0237764 A1 | 10/2007 | Birtalan |
| 2007/0292936 A1 | 12/2007 | Barthelemy |
| 2009/0002360 A1 | 1/2009 | Chen |
| 2016/0130333 A1 | 5/2016 | Chang |
| 2018/0148503 A1 * | 5/2018 | Scheinberg ........ C07K 16/2833 |

FOREIGN PATENT DOCUMENTS

| | | |
|---|---|---|
| EP | 1331266 A1 | 7/2003 |
| EP | 1391213 A1 | 2/2004 |
| EP | 1498491 A1 | 1/2005 |
| EP | 1502603 A1 | 2/2005 |
| EP | 1688439 A1 | 8/2006 |
| EP | 1705251 A1 | 9/2006 |
| JP | 2009278927 A | 12/2009 |
| WO | 1991000360 A1 | 1/1991 |
| WO | 1993008829 A1 | 5/1993 |
| WO | 1993011161 A1 | 6/1993 |
| WO | 1993021232 A1 | 10/1993 |
| WO | 1994011026 A2 | 5/1994 |
| WO | 1994029351 | 12/1994 |
| WO | 1997004801 A1 | 2/1997 |
| WO | 1997017852 A1 | 5/1997 |
| WO | 1997030087 A1 | 8/1997 |
| WO | 1998056418 A1 | 12/1998 |
| WO | 1998058964 A1 | 12/1998 |
| WO | 1999022764 A1 | 5/1999 |
| WO | 1999051642 A1 | 10/1999 |
| WO | 2000042072 A2 | 7/2000 |
| WO | 2001029058 A1 | 4/2001 |
| WO | 2001072768 A2 | 10/2001 |
| WO | 2001096584 A2 | 12/2001 |
| WO | 2003011878 A2 | 2/2003 |
| WO | 2003048731 A2 | 6/2003 |
| WO | 2004056312 A2 | 7/2004 |
| WO | 2005100402 A1 | 10/2005 |
| WO | 2006029879 A2 | 3/2006 |
| WO | 2005053742 A1 | 6/2007 |
| WO | 2008077546 A1 | 7/2008 |
| WO | 2009067800 A1 | 6/2009 |
| WO | 2009089004 A1 | 7/2009 |
| WO | 2011056983 A1 | 5/2011 |
| WO | 2011133886 A2 | 10/2011 |
| WO | 2012109659 A1 | 8/2012 |
| WO | 2014210545 A2 | 1/2015 |
| WO | WO-2016179326 A1 * | 11/2016 ............ A61P 35/00 |
| WO | 2018132597 A1 | 7/2018 |

OTHER PUBLICATIONS

International Preliminary Report on Patentability dated Jul. 25, 2019 for PCT Application No. PCT/US2018/013362 filed on Jan. 11, 2018, eight pages.

International Search Report and Written Opinion of the International Searching Authority dated May 10, 2018 for PCT Application No. PCT/US2018/013362 filed on Jan. 11, 2018, seventeen pages.

Invitation to Pay Additional fees and, where Applicable, Protest Fee dated Mar. 20, 2018, for PCT Application No. PCT/US2018/013362 filed on Jan. 11, 2018, two pages.

Rudikoff, S. et al. (Mar. 1982). "Single Amino Acid Substitution Altering Antigen-Binding Specificity," Proc. Natl. Acad. Sci. USA 79:1979-1983.

Ahmed, A. U. et al. (Sep. 2011). "Neural Stem Cell-based Cell Carriers Enhance Therapeutic Efficacy of an Oncolytic Adenovirus in an Orthotopic Mouse Model of Human Glioblastoma," Molecular Therapy 19(9):1714-1726.

Ali, A. et al. (Aug. 1, 2016, e-pub. Jul. 11, 2016). "HIV-1-Specific Chimeric Antigen Receptors Based on Broadly Neutralizing Antibodies," Journal of Virology 90(15):6999-7006.

Altman, J. D. et al. (Feb. 2003). "MHC-Peptide Tetramers to Visualize Antigen-Specific T Cells," Current Protocols in Immunology 53(1):17-3.

Andreatta, M. (Feb. 15, 2016, e-pub. Oct. 29, 2015). "Gapped Sequence Alignment Using Artificial Neural Networks: Application to the MHC Class I System," Nielsen M. Bioinformatics 32(4):511-517.

Ansari, M. et al. (Jul.-Sep. 2012). "Pediatric Glioblastoma Multiforme: A Single-Institution Experience," Indian J Med Paediatr Oncol. 33(3):155-160.

Baldwin, R.W. et al. (1986). "Monoclonal Antibodies in Cancer Treatment," Lancet 60:603-606.

Berg, I.J.M. et al. (Dec. 1998) "Selective Expansion of a Peripheral Blood CD8+ Memory T Cell Subset Expressing Both Granzyme B and L-Selectin During Primary Viral Infection in Renal Allograft Recipients," Transplant Proc. 30(8):39753977.

Boerner, P. et al. (Jul. 1, 1991). "Production of a Antigen-Specific Human Monoclonal Antibodies from In Vitro-Primed Human Splenocytes," J. Immunol. 147(1):86-95.

Brentjens et al. "Safety and persistence of adoptively transferred autologous CD19-targeted T cells in patients with relapsed or chemotherapy refractory B-cell leukemias," Blood (2011) 118(18):4817-4828.

(56) References Cited

OTHER PUBLICATIONS

Brischwein, K. et al. (Mar. 1, 2006). "MT110: A Novel Bispecific Single-Chain Antibody Construct With High Efficacy in Eradicating Established Tumors," Molecular Immunology 43(8):1129-1143.
Brodeur, B.R. et al. (1987). "Mouse-Human Myeloma Partners for the Production Monoclonal Antibody Production of Heterohybridomas," Chapter 4 in Techniques and Applications, Marcel Dekker, Inc., New York, pp. 51-63.
Brüggemann, M. et al. (1993). "Designer Mice: The Production of Human Antibody Repertoires in Transgenic Animals," Year in Immuno. 7:33-40.
Brüggemann, M. et al. (Nov. 1, 1987). "Comparison of the Effector Functions of Human Immunoglobulins Using a Matched Set of Chimeric Antibodies," J. Exp. Med. 166:1351-1361.
Burton, D.R. (1985). "Immunoglobulin G: Functional Sites," Molec. Immunol. 22(3):161-206.
Capel, P.J. et al. (Feb. 1994). "Heterogeneity of Human IgG Fc Receptors," Immunomethods 4(1):25-34.
Chames, P. et al. (Jul. 5, 2000). "Direct Selection of a Human Antibody Fragment Directed Against the Tumor T-Cell Epitope HLA-A1-MAGE-A1 From a Nonimmunized Phage-Fab Library," Proceedings of the National Academy of Sciences 97(14):7969-7974.
Chari, R.V.J. et al. (Jan. 1, 1992). "Immunoconjugates Containing Noveal maytansinoids: Promising Anticancer Drugs," Cancer Res. 52:127-131.
Chothia, C. et al. (Aug. 20, 1987). "Canonical Structures for the Hypervariable Regions of Immunoglobulins," J. Mol. Biol. 196(4):901-917.
Chowdhury, P.S. (2008). "Engineering Hot Spots for Affinity Enhancement of Antibodies," Methods Mol. Biol. 207:179-196.
Clackson, T. et al. (Aug. 15, 1991). "Making Antibody Fragments Using Phage Display Libraries," Nature 352:624-628.
Clynes, R. et al. (Jan. 1998). "Fc Receptors are Required in Passive and Active Immunity to Melanoma," Proc. Natl. Acad. Sci. U.S.A. 95:652-656.
Colcher, D. et al. (Jan. 1986). "Use of Monoclonal Antibodies as Radiopharmaceuticals for the Localization of Human Carcinoma Xenografts in Athymic Mice," Methods Enzymol. 121 802-816.
Cole, S.P.C. et al. (1985). "The EBV-Hybridoma Technique and its Applicaton to Human Lung Cancer," in Monoclonal Antibodies and Cancer Therapy, Alan R. Liss, p. 77-96.
Cragg, M.S. et al. (Apr. 1, 2004). "Antibody Specificity Controls In Vivo Effector Mechanisms of Anti-CD20 Reagents," Blood 103(7):2738-2743.
Cragg, M.S. et al. (Feb. 1, 2003). "Complement-Mediated Lysis by Anti-CD20 Mab Correlates With Segregation Into Lipid Rafts," Blood 101(3):1045-1052.
Cunningham, B.C. et al. (Jun. 2, 1989). "High-Resolution Epitope Mapping of hGH-Receptor Interactions by Alanine-Scanning Mutagenesis," Science 244:1081-1085.
Dao, T. et al. (Mar. 13, 2013). "Targeting the Intracellular WT1 Oncogene Product With a Therapeutic Human Antibody," Sci. Transl. Med. 5(176):176ra33, 22 pages.
David, G.S. et al. (1974). "Protein Iodination With Solid State Lactoperoxidase," Biochemistry 13(5):1014-1021.
Davis, M.M. et al. (Apr. 1998). "Ligand Recognition by αβ T Cell Receptors," Annu Rev Immunol 16:(15):523-544.
Davis, M.M. et al. (Aug. 4, 1988). "T-Cell Antigen Receptor Genes and T-Cell Recognition," Nature 334:395-402.
Daëron, M. (1997). "Fc Receptor Biology," Ann. Rev. Immunol. 15:203-234.
De Haas, M. et al. (1995). "Fcγ Receptor of Phagocytes," J. Lab. Clin. Med. 126(4):330-341.
Duncan, A.R. et al. (Apr. 21, 1988). "The Binding Site for C1q on IgG," Nature 322:738-740.
Edgar, R.C. (2004, e-pub. Mar. 19, 2004). "MUSCLE: Multiple Sequence Alignment With High Accuracy and High Throughput," Nucleic Acids Research 32(5):1792-1797.
Edgar, R.C. (Aug. 19, 2004). "MUSCLE: A Multiple Sequence Alignment Method With Reduced Time and Space Complexity," BMC Bioinformatics 5(113):1-19.
Fellouse, F.A. et al. (Aug. 24, 2004). "Synthetic Antibodies from a Four-Amino-Acid Code: A Dominant Role for Tyrosine in Antigen Recognition," Proc. Natl. Acad. Sci. USA 101(34):12467-12472.
Ferrara, C. et al. (2006, e-pub. Jan. 24, 2006). "Modulation of Therapeutic Antibody Effector Functions by Glycosylation Engineering: Influence of Golgi Enzyme Localization Domain and Co-Expression of Heterologous β1, 4-N-Acetylglucosaminyltransferase III and Golgi α-Mannosidase," Biotechnology and Bioengineering 93(5):851-861.
Filbin, M.G. et al. (May 23, 2016). "Gliomas Genomics and Epigenomics: Arriving at the Start and Knowing It for the First Time," Annual Review of Pathology: Mechanisms of Disease 11:497-521.
Fishwild, D.M. et al. (Jul. 1996). "High-Avidity Human IgGK Monoclonal Antibodies from a Novel Strain of Minilocus Transgenic Mice," Nature Biotechnol. 14:845-851.
Fraker, P.J. et al. (Feb. 28, 1978). "Protein and cell membrane iodinations with a sparingly soluble chloroamide, 1,3,4,6-tetrachloro-3a,6a-diphrenylglycoluril," Biochem Biophys Res Commun. 80(4):849-857.
Funato, K. et al. (Dec. 19, 2014). "Use of Human Embryonic Stem Cells to Model Pediatric Gliomas With H3. 3K27M Histone Mutation," Science 346(6216):1529-1533.
Garland, R.J. et al. (Jul. 1999) "The Use of Teflon Cell Culture Bags to Expand Functionally Active CD8+ Cytotoxic T Lymphocytes," J. Immunol Meth. 227(1-2):53-63.
Gazzano-Santoro, H. et al. (Mar. 28, 1997). "A Non-Radioactive Complement-Dependent Cytotoxicity Assay for Anti-CD20 Monoclonal Antibody," J. Immunol. Methods 202:163-171.
Ghetie, V. et al. (2000). "Multiple Roles for the Major Histocompatibility Complex Class I-Related Receptor FCRN," Annu. Rev. Immunol. 18:739-766.
Griffiths, A.D. et al. (1993), "Human Anti-Self Antibodies with High Specificity from Phage Display Libraries," EMBO J. 12(2):725-734.
Grillo-López, A.J. (Jun. 1, 2002). "Anticd20 Mabs: Modifying Therapeutic Strategies and Outcomes in the Treatment of Lymphoma Patients," Expert Review of Anticancer Therapy 2(3):323-329.
Gu, J. et al. (Jan. 1, 2012). "Generation of Dual-Variable-Domain Immunoglobulin Molecules for Dual-Specific Targeting," Methods in Enzymology 502:25-41.
Guyer, R.L. et al. (Aug. 1976). "Immunoglobulin Binding by Mouse Intestinal Epithelial Cell Receptors," J. Immunol. 117(2):587-593.
Haanen, J.B. et al. (1999), "Selective Expansion of Cross-Reactive CD8+ Memory T Cells by Viral Variants." The Journal of Experimental Medicine 190(9):1319-1328.
Hashizume, R. et al. (Dec. 2012). "Characterization of a Diffuse Intrinsic Pontine Glioma Cell Line Implications for Future Investigations and Treatment," Journal of Neuro-Oncology 110(3):305-313.
Held, G. et al. (Oct. 2004). "Dissecting Cytotoxic T Cell Responses Towards the NY-ESO-1 Protein by Peptide/MHC-Specific Antibody Fragments," European Journal of Immunology 34(10):2919-2929.
Hellstrom, I. et al. (Mar. 1985). "Strong Antitumor Activities of IgG3 Antibodies to a Human Melanoma-associated Ganglioside," Proc. Natl. Acad. Sci. USA. 82:1499-1502.
Hellstrom, I. et al. (Sep. 1986). "Antitumor Effects of L6, an IgG2a Antibody That Reacts With Most Human Carcinomas," Proc. Natl. Acad. Sci. USA 83:7059-7063.
Hinman, L.M. et al. (Jul. 15, 1993). "Preparation and Characterization of Monoclonal Antibody Conjugates of the Calicheamicins: A Novel and Potent Family of Antitumor Antibiotics," Cancer Res. 53:3336-3342.
Hoet, R.M. et al. (2005), "Generation of high-affinity human antibodies by combining donor-derived and synthetic complementarity-determining-region diversity," Nat Biotechnol, 23(3):344-348.
Holliger, P. et al. (Jul. 1993). "'Diabodies': Small Bivalent and Bispecific Antibody Fragments," Proceedings of the National Academy of Sciences USA 90:6444-6448.

(56) References Cited

OTHER PUBLICATIONS

Hoogenboom, H.R. et al. (2001). "Overview of Antibody Phage-Display Technology and Its Applications," Chapter 1 in Methods in Molecular Biology, O'Brien et al. ed., Humana Press, Totowa, NJ, 178:1-37.

Hoogenboom, H.R. et al. (Sep. 20, 1992). "By-Passing Immunisation Human Antibodies From Synthetic Repertoires of Germline VH Gene Segments Rearranged In Vitro," J. Mol. Biol. 227(2):381-388.

Hunter, W.M. et al. (May 5, 1962). "Preparation Iodine-131 Labelled Human Growth Hormone of High Specific Activiey," Nature 144:495-496.

Idusogie, E.E. et al. (2000). "Mapping of the C1q Binding Site on Rituxan, a Chimeric Antibody With a Human IgGl Fc,"J. Immunol. 164:4178-4184.

Jakobovits, A. et al. (Mar. 18, 1993). "Germ-Line Transmission and Expression of a Human-Derived Yeast Artificial Chromosome," Nature 362:255-258.

Jakobovits, A. et al. (Mar. 1993). "Analysis of Homozygous Mutant Chimeric Mice: Deletion of the Immunoglobulin Heavy-Chain Joining Region Blocks B-Cell Development and Antibody Production," Proc. Natl. Acad. Sci. USA 90 (6):2551-2555.

Jones, P. et al. (May 29, 1986). "Replacing the Complementarity-Determining Regions in a Human Antibody With Those From a Mouse," Nature 321:522-525.

Kabat, E.A. et al. (Oct. 10, 1977). "Unusual Distributions of Amino Acids in Complementarity-Determining (Hypervariable) Segments of Heavy and Light Chains of Immunoglobulins and Their Possible Roles in Specificity of Antibody-Combining Sites," J. Biol. Chem. 252(19):6609-6616.

Kam, N.W.S. et al. (Aug. 16, 2005). "Carbon Nanotubes as Multifunctional Biological Transporters and Near-Infrared Agents for Selective Cancer Cell Destruction," PNAS 102(33):11600-11605, 6 pages.

Kanda, Y. et al. (Jul. 5, 2006, e-pub. Apr. 11, 2006). "Comparison of Cell Line for Stable Production of Fucose-Negative Antibodies with Enhanced ADCC," Biotechnol. Bioeng. 94(4):680-688.

Kim, J-K. et al. (1994). "Localization of the Site of the Murine IgGl Molecule That is Involved in Binding to the Murine Intestinal Fc Receptor," Eur. J. Immunol. 24:2429-2434.

Klechevsky, E. et al. (Aug. 1, 2008). "Antitumor Activity of Immunotoxins With T-Cell Receptor-Like Specificity Against Human Melanoma Xenografts," Cancer Research 68(15):6360-6367.

Kochenderfer, J.N. et al. (Nov. 18, 2010), "Eradication of B-Lineage Cells and Regression of Lymphoma in a Patient Treated With Autologous T Cells Genetically Engineered to Recognize CD19," Blood, The Journal of the American Society of Hematology 116(20):4099-4102.

Kohler, G. et al. (Aug. 7, 1975) "Continuous Cultures of Fused Cells Secreting Antibody of Predefined Specificity," Nature 256:495-497.

Kostelny, S.A. et al. (Mar. 1, 1992), "Formation of a Bispecific Antibody by the Use of Leucine Zippers," J. Immunol. 148(5):1547-1553.

Kozbor, D. (Dec. 1984). "A Human Hybrid Myeloma for Production of Human Monoclonal Antibodies," J. Immunol. 133(6):3001-3005.

König, R. (Feb. 1, 2002). "Interactions Between MHC Molecules and Co-Receptors of the TCR," Current Opinion in Immunology 14(1)75-83.

Labrijn, A.F. et al. (Mar. 26, 2013). "Efficient Generation of stable Bispecific IgG1 by Controlled Fab-arm Exchange," Proc. Natl. Acad. Sci. USA 110(13):5145-5150.

Lee, C.V. et al. (2004). "Bivalent Antibody Phage Display Mimics Natural Immunoglobulin," .J. Immunol. Methods 284(1-2):119-132.

Lee, C.V. et al. (2004). "High-Affinity Human Antibodies From Phage-Displayed Synthetic Fab Libraries With a Single Framework Scaffold," J. Mol. Biol. 340:1073-1093.

Lev, A. et al., (Jun. 1, 2002). "Isolation and Characterization of Human Recombinant Antibodies Endowed With the Antigen-Specific, Major Histocompatibility Complex-Restricted Specificity of T Cells Directed Toward the Widely Expressed Tumor T-Cell Epitopes of the Telomerase Catalytic Subunit," Cancer Research 62(11):3184-3194.

Lewis, P.W. et al. (May 17, 2013). "Inhibition of PRC2 Activity by a Gain-of-Function H3 Mutation Found in Pediatric Glioblastoma," Science 340(6134):857-861.

Lindhofer, H. et al., "Preferential species-restricted heavy/light chain pairing in rat/mouse quadromas. Implications for a single-step purification of bispecific antibodies," J Immunol (1995) 55(1):219-225.

Liu, C. et al. (Aug. 1996). "Eradication of Large Colon Tumor Xenografts by Targeted Delivery of Maytansinoids," Proc. Natl. Acad. Sci. USA 93:8618-8623.

Liu, X. et al. (2014). "Histone H3 Mutations in Pediatric Brain Tumors," Cold Spring Harbor Perspectives in Biology 6(4):a018689, 6 pages.

Lode, H.N. et al. (Jul. 15, 1998). "Targeted Therapy with a Novel Enediyene Antibiotic Calicheamicin 011 Effectively Suppresses Growth and Dissemination of Liver Metastases in a Syngeneic Model of Murine Neuroblastoma," Cancer Res. 58:2925-2928.

Lonberg, N. et al. (1995, e-pub, Jul. 10, 2009), "Human Antibodies From Transgenic Mice," Int. Rev. Immunol. 13(1):65-93.

Lonberg, N. et al. (Apr. 28, 1994). "Antigen-Specific Human Antibodies From Mice Comprising Four Distinct Genetic Modifications," Nature 368(6474):856-859.

Louis, C.U. et al. (Dec. 1, 2011). "Antitumor Activity and Long-Term Fate of Chimeric Antigen Receptor-Positive T Cells in Patients With Neuroblastoma," Blood, The Journal of the American Society of Hematology 118(23):6050-6056.

MacCallum, R.M. et al. (1996). "Antibody-Antigen Interactions: Contact Analysis and Binding Site Topography," J. Mol. Biol. 262:732-745.

Mack, M. et al. (Jul. 1995). "A Small Bispecific Antibody Construct Expressed as a Functional Single-Chain Molecule With High Tumor Cell Cytotoxicity," Proc. Natl. Acad. Sci. USA 92:7021-7025.

Mackall, C.L. et al. (Dec. 2014). "Immune-Based Therapies for Childhood Cancer," Nature Reviews Clinical Oncology 11(12):693-703.

Mandler, R. et al. (2000). "Synthesis and Evaluation of Antiproliferative Activity of a Geldanamycin-Herceptin TM Immunoconjugate," Bioorganic & Med. Chem. Letters 10:1025-1028.

Mandler, R. et al. (2002, e-pub. Jun. 19, 2002). "Modifications in Synthesis Strategy Improve the Yield and Efficacy of Geldanamycin-Herceptin Immunoconjugates," Bioconjugate Chem. 13:786-791.

Mandler, R. et al. (Oct. 2000). "Immunoconjugates of Geldanan1ycin and Anti-HER2 Monoclonal Antibodies: Antiproliferative Activity on Human Breast Carcinoma Cell Lines," J. Nat. Cancer Inst. 92(19):1573-1581.

Marks, J.D. et al. (1991). "By-Passing Immunization Human Antibodies from V-gene Libraries Displayed on Phage," J. Mol. Biol. 222:581-597.

Marks, J.D. et al. (2004) "Selection of Human Antibodies from Phage Display Libraries," Chapter 8 in Methods in Molecular Biology, LO, B.K.C. (ed.), Humana Press Inc., Totowa, NJ, 248:161-176, 29 pages.

Marks, J.D. et al. (Jul. 1992), "By-Passing Immunization: Building High Affinity Human Antibodies by Chain Shuffling," Bio/Technology 10:779-783.

Martens, T. et al. (Sep. 1, 2008). "Inhibition of Glioblastoma Growth in a Highly Invasive Nude Mouse Model Can Be Achieved by Targeting Epidermal Growth Factor Receptor But Not Vascular Endothelial Growth Factor Receptor-2," Clinical Cancer Research 14(17):5447-5458.

Martin, S.F. et al. (Mar. 19, 1998). "Application of Alme3-Mediated Amidation Reactions to Solution Phase Peptide Synthesis," Tetrahedron Letters 39(12):1517-1520.

Maude, S.L. et al. (Oct. 16, 2014). "Chimeric Antigen Receptor T Cells for Sustained Remissions in Leukemia," N Engl J Med. 371(16):1507-1517.

McCafferty, J. et al. (Dec. 6, 1990). "Phage Antibodies: Filamentous Phage Displaying Antibody Variable Domains," Nature 348:552-554.

(56) References Cited

OTHER PUBLICATIONS

Milenic, D.E. (Sep. 1, 2002). "Monoclonal Antibody-Based Therapy Strategies: Providing Options for the Cancer Patient," Current Pharmaceutical Design 8(19):1749-1764.
Milstein, C. et al., (Oct. 6, 1983). "Hybrid Hybridomas and Their Use in Immunohistochemistry," Nature 305:537-539.
Morris, E. et al. (Mar. 1, 2006). "Generation of Tumor-Specific T-Cell Therapies," Blood Reviews 20(2):61-69.
Morrison, S.C. et al. (Nov. 1984). "Chimeric Human Antibody Molecules: Mouse Antigen-Binding Domains With Human Constant Region Domains," Proc. Natl. Acad. Sci. USA 81:6851-6855.
Morrison, S.L. (Apr. 28, 1994). "Success in Specification," Nature 368:812-813.
Munson, P.J. et al. (1980). "Ligand: A Versatile Computerize Approach for Characterization of Ligand-Binding Systems," Anal. Biochem. 107:220-239.
Neuberger, M. (Jul. 1996). "Generating High-Avidity Human Mabs in Mice," Nature Biotechnology 14:826.
Neuberger, M.S. et al. (Dec. 13, 1984). "Recombinant antibodies processing novel effector functions," Nature 312:604-608.
Niculesu-Duvaz, I. et al. (1997). "Antibody-Directed Enzyme Prodrug Therapy (ADEPT): A Review," Adv. Drug Del. Rev. 26:151-172.
Noy, R. et al. (Jun. 1, 2005). "T-Cell Receptor-Like Antibodies: Novel Reagents for Clinical Cancer Immunology and Immunotherapy," Expert Review of Anticancer Therapy 5(3):523-536.
Nygren, H. (May 1982). "Conjugation of Horseradish Peroxidase to Fab Fragments With Different Homobifunctional and Heterobifunctional Cross-Linking Reagents. A Comparative Study," J. Histochem. and Cytochem. 30(5):407-412.
Okazaki, A. et al. (Mar. 5, 2004). "Fucose Depletion From Human IgG1 Oligosaccharide Enhances Binding Enthalpy and Association Rate Between IgG1 and FcγRIIIa," J. Mol. Biol. 336(5):1239-1249.
Pain, D. et al. (1981), "Preparation of Protein A-Peroxidase Monoconjugate Using a Heterobifunctional Reagent, and Its Use in Enzyme Immunoassays," J. Immunol. Methods 40:219-230.
Parker, K.C. et al. (Jan. 1994). "Scheme for Ranking Potential HLA-A2 Binding Peptides Based on Independent Binding of Individual Peptide Side-Chains," The Journal of Immunology 152(1):163-175.
Paul, S. et al. (Aug. 2016). "Tepitool: A Pipeline for Computational Prediction of T Ceil Epitope Candidates," Current Protocols in Immunology 114(1):18-19.
Petkova, S.B. et al. (2006, e-pub. Oct. 31, 2006). "Enhanced Half-Life of Genetically Engineered Human IgG1 Antibodies in a Humanized FcRn Mouse Model: Potential Application in Humorally Mediated Autoimmune Disease," Int'l. Immunol. 18(12):1759-1769.
Plückthun, A. (1994). "Antibodies from *Escherichia coil*," in Chapter 11 The Pharmacology of Monoclonal Antibodies, vol. 113, Rosenburg and Moore eds., Springer-Verlag, New York, pp. 269-315, 48 pages.
Presta, L.G. (1992). "Antibody Engineering," Current Opinion in Structural Biology 2:593-596.
Pullarkat, V. et al. (Apr. 1, 1999). "A Phase I Study of a HER2/Neu Bispecific Antibody With Granulocyte-Colony-Stimulating Factor in Patients With Metastatic Breast Cancer That Overexpresses HER2/Neu," Cancer Immunology, Immunotherapy 48(1):9-21.
Rammensee, H. et al. (Nov. 1999). "SYFPEITHI: Database for MHC Ligands and Peptide Motifs," Immunogenetics. 50(3-4):213-219.
Ravetch, J.V. et al. (1991). "Fc Receptors," Annu. Rev. Immunol. 9:457-492.
Reche, P.A. et al. (2007). "Prediction of Peptide-MHC Binding Using Profiles," Immunoinformatics, Humana Press, pp. 185-200.
Reddy, M.M. et al. (2012). "Targeting JAK2 in the Therapy of Myeloproliferative Neoplasms," Expert Opinion on Therapeutic Targets 16(3):313-324.
Ridgway et al., "'Knobs-into-holes' engineering of antibody CH3 domains for heavy chain heterodimerization," Protein Eng. (1996) 9(7):617-621.
Riechmann, L. et al. (Mar. 24, 1988). "Reshaping Human Antibodies for Therapy," Nature 332:323-329.
Ripka, J. et al. (Sep. 1986). "Two Chinese Hamster Ovary Glycosylation Mutants Affected in the Conversion of GDP-Mannose to GDP-Fucose," Arch Biochem Biophys. 249(2):533-545.
Rosenberg, S.A. et al. (Dec. 22, 1988). "Use of Tumor-Infiltrating Lymphocytes and Interleukin-2 in the Immunotherapy of Patients With Metastatic Melanoma. A Preliminary Report," N Engl J Med. 319(25):1676-1680.
Rossi, E.A. et al. (May 2, 2006). "Stably Tethered Multifunctional Structures of Defined Composition Made by the Dock and Lock Method for Use in Cancer Targeting," Proceedings of the National Academy of Sciences 103 (18):6841-6846.
Rowland, G.F. et al. (1986). "Drug Localisation and Growth Inhibition Studies of Vindesine-Monoclonal Anti-CEA Conjugates in a Human Tumour Xenograft," Cancer Immunol. Immunother. 21:183-187.
Roychowdhury, S. et al. (Nov. 2011). "Managing Resistance in Chronic Myeloid Leukemia," Blood Rev. 25(6):279-290.
Schuler, M.M. et al. (2007). "SYFPEITHI: Database for Searching and T-Cell Epitope Prediction," Immunoinformatics Methods in Molecular Biology 409(1):75-93.
Schwartzentruber, J. et al., (Jan. 29, 2012). "Driver Mutations in Histone H3.3 and Chromatin Remodelling Genes in Paediatric Glioblastoma," Nature 482:226-231.
Sergeeva, A. et al. (Apr. 21, 2011, e-pub. Feb. 4, 2011). "An Anti-PR1/HLA-A2 T-Cell Receptor-Like Antibody Mediates Complement-Dependent Cytotoxicity Against Acute Myeloid Leukemia Progenitor Cells," Blood 117 (16):4262-4272.
Shields, R.L. et al. (Mar. 2, 2001). "High Resolution Mapping of the Binding Site on Human IgG1 for FcγRI, FcγRII, FcγRIII, and FcRn and Design of IgG1 Variants With improved Binding to the FcγR," J. Biol.Chem. 276(9):6591-6604.
Sidhu, S.S. et al. (2004). "Phage-Displayed Antibody Libraries of Synthetic Heavy Chain Complementarity Determining Regions," J. Mol. Biol. 338(2):299-310.
Singh, H. et al. (Dec. 1, 2001). "Propred: Prediction of HLA-DR Binding Sites," Bioinformatics. 17(12):1236-1237.
Suresh, M.R. et al. (1986). "Bispecific Monoclonal Antibodies From Hybrid Hybridomas," Methods in Enzymology 121:210-228, 19 pages.
Syrigos, K. et al. (1999). "Antibody Directed Enzyme Prodrug Therapy (ADEPT): A Review of the Experimental and Clinical Considerations," Anticancer Research 19:605-614.
Takeuchi, K. (2011). "Receptor Tyrosine Kinases and Targeted Cancer Therapeutics," Biol. Pharm. Bull, 34(12):1774-1780.
Thorpe, (1985). "Antibody Carriers of Cytotoxic Agents in Cancer Therapy: A Review," in Monoclonal Antibodies '84: Biological and Clinical Applications, Pinchera et al. (eds.), pp. 475-506.
Tomimatsu, K. et al. (2009, e-pub. Jul. 7, 2009). "Production of Human Monoclonal Antibodies against FcεRIa by a Method Combining in Vitro Immunization with Phage Display," Biosci. Biotechnol. Biochem. 73(7):1465-1469.
Traunecker, A. et al. (1991). "Bispecific Single Chain Molecules (Janusins) Target Cytotoxic Lymphocytes on HIV Infected Cells," EMBO J. 10(12):3655-3659.
Tutt, A. et al. (Jul. 1, 1991) "Trispecific F(ab')3 Derivatives that use Cooperative Signaling Via the TCR/CD3 Complex and CD2 to Activate and Redirect Resting Cytotoxic T Cells," J. Immunol. 147(1):60-69.
Ul-Tel, K. et al. (2000). "Sensitive Assay of RNA Interference in *Drosophila* and Chinese Hamster Cultured Cells Using Firefly Luciferase Gene as Target," FEBS Letters 479:79-82.
Varela-Rohena et al., "Control of HIV-1 immune escape by CD8 T cellsexpressing enhanced T-cell receptor," Nat Med. (2008) 14: 1390-1395.
Veomett, N. et al. (Aug. 1, 2004). "Therapeutic Efficacy of an Fc-Enhanced TCR-Like Antibody to the Intracellular WT1 Oncoprotein," Clinical Cancer Research 20(15):4036-4046.
Verhoeyen, M. et al. (Mar. 25, 1988). "Reshaping Human Antibodies: Grafting an Antilysozyme Activity," Science 239(4857):1534-1536.

(56) References Cited

OTHER PUBLICATIONS

Veri, M.-C. et al. (Jul. 2010). "Therapeutic Control of B Cell Activation via Recruitment of Fcγ Receptor IIb (CD32B) Inhibitory Function With a Novel Bispecific Antibody Scaffold," Arthritis & Rheumatism, 62(7):1933-1943.

Vitetta, E.S. et al. (Nov. 20, 1987). "Redesigning Nature's Poisons to Create Anti-Tumor Reagents," Science 238:1098-1104.

Warren, K. E. (2012, e-pub. Dec. 28, 2012). "Diffuse Intrinsic Pontine Glioma: Poised for Progress," Front Oncol. 2(205)1-9.

Winter, G. el al. (1994). "Making Antibodies by Phage Display Technology," Ann. Rev. Immunol. 12:433-455.

Wright, A. et al. (Jan. 1997). "Effect of Glycosylation on Antibody Function: Implications for Genetics Engineering," Trends Biotechnol. 15:26-32.

Wu, G. et al. (Mar. 2012, Jan. 29, 2012). "Somatic Histone H3 Alterations in Paediatric Diffuse Intrinsic Pontine Gliomas and Non-Brainstem Glioblastomas," Nat Genet (2012) 44(3):251-253.

Yamane-Ohnuki, N. et al. (Sep. 5, 2004, e-pub Aug. 6, 2004). "Establishment of FUT8 Knockout Chinese Hamster Ovary Cells: An Ideal Host Cell Line for Producing Completely Defucosylated Antibodies With Enhanced Antibody-Dependent Cellular Cytotoxicity," Biotechnology and Bioengineering 87(5):614-622.

\* cited by examiner

SEQUENCE LISTING

<160> NUMBER OF SEQ ID NOS: 167

<210> SEQ ID NO 1
<211> LENGTH: 135
<212> TYPE: PRT
<213> ORGANISM: Artificial Sequence
<220> FEATURE:
<223> OTHER INFORMATION: Histone H3.3

<400> SEQUENCE: 1

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ser Thr
                20                  25                  30

Gly Gly Val Lys Lys Pro His Arg Tyr Arg Pro Gly Thr Val Ala Leu
            35                  40                  45

Arg Glu Ile Arg Arg Tyr Gln Lys Ser Thr Glu Leu Leu Ile Arg Lys
        50                  55                  60

Leu Pro Phe Gln Arg Leu Val Arg Glu Ile Ala Gln Asp Phe Lys Thr
65                  70                  75                  80

Asp Leu Arg Phe Gln Ser Ala Ala Ile Gly Ala Leu Gln Glu Ala Ser
                85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
            115                 120                 125

Arg Ile Arg Gly Glu Arg Ala
        130             135

<210> SEQ ID NO 2
<211> LENGTH: 135
<212> TYPE: PRT
<213> ORGANISM: Artificial Sequence
<220> FEATURE:
<223> OTHER INFORMATION: Histone H3.1

<400> SEQUENCE: 2

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Lys Ser Ala Pro Ala Thr
            20                  25                  30

Gly Gly Val Lys Lys Pro His Arg Tyr Arg Pro Gly Thr Val Ala Leu
            35                  40                  45

Arg Glu Ile Arg Arg Tyr Gln Lys Ser Thr Glu Leu Leu Ile Arg Lys
    50                  55                  60

Leu Pro Phe Gln Arg Leu Val Arg Glu Ile Ala Gln Asp Phe Lys Thr
65                  70                  75                  80

Asp Leu Arg Phe Gln Ser Ser Ala Val Met Ala Leu Gln Glu Ala Cys
            85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
            115                 120                 125

Arg Ile Arg Gly Glu Arg Ala
        130             135

<210> SEQ ID NO 3
<211> LENGTH: 135
<212> TYPE: PRT
<213> ORGANISM: Artificial Sequence
<220> FEATURE:
<223> OTHER INFORMATION: Histone K27M-H3.3

<400> SEQUENCE: 3

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Met Ser Ala Pro Ser Thr
            20                  25                  30

Gly Gly Val Lys Lys Pro His Arg Tyr Arg Pro Gly Thr Val Ala Leu
            35                  40                  45

Arg Glu Ile Arg Arg Tyr Gln Lys Ser Thr Glu Leu Leu Ile Arg Lys
    50                  55                  60

Leu Pro Phe Gln Arg Leu Val Arg Glu Ile Ala Gln Asp Phe Lys Thr
65                  70                  75                  80

Asp Leu Arg Phe Gln Ser Ala Ala Ile Gly Ala Leu Gln Glu Ala Ser
            85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
            115                 120                 125

```
Arg Ile Arg Gly Glu Arg Ala
    130                 135

<210> SEQ ID NO 4
<211> LENGTH: 135
<212> TYPE: PRT
<213> ORGANISM: Artificial Sequence
<220> FEATURE:
<223> OTHER INFORMATION: Histone K27M-H3.1

<400> SEQUENCE: 4

Ala Arg Thr Lys Gln Thr Ala Arg Lys Ser Thr Gly Gly Lys Ala Pro
1               5                   10                  15

Arg Lys Gln Leu Ala Thr Lys Ala Ala Arg Met Ser Ala Pro Ala Thr
            20                  25                  30

Gly Gly Val Lys Lys Pro His Arg Tyr Arg Pro Gly Thr Val Ala Leu
        35                  40                  45

Arg Glu Ile Arg Arg Tyr Gln Lys Ser Thr Glu Leu Leu Ile Arg Lys
    50                  55                  60

Leu Pro Phe Gln Arg Leu Val Arg Glu Ile Ala Gln Asp Phe Lys Thr
65                  70                  75                  80

Asp Leu Arg Phe Gln Ser Ser Ala Val Met Ala Leu Gln Glu Ala Cys
                85                  90                  95

Glu Ala Tyr Leu Val Gly Leu Phe Glu Asp Thr Asn Leu Cys Ala Ile
            100                 105                 110

His Ala Lys Arg Val Thr Ile Met Pro Lys Asp Ile Gln Leu Ala Arg
        115                 120                 125

Arg Ile Arg Gly Glu Arg Ala
    130                 135

<210> SEQ ID NO 5
<211> LENGTH: 10
<212> TYPE: PRT
<213> ORGANISM: Artificial Sequence
<220> FEATURE:
<223> OTHER INFORMATION: Histone H3.3 26-35

<400> SEQUENCE: 5

Arg Lys Ser Ala Pro Ser Thr Gly Gly Val
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Histone H3.1 26-35

<400> SEQUENCE: 6

Arg Lys Ser Ala Pro Ala Thr Gly Gly Val
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Histone H3.3 26-35 K27M

<400> SEQUENCE: 7

Arg Met Ser Ala Pro Ser Thr Gly Gly Val
1               5                   10
```

```
<210> SEQ ID NO 8
<211> LENGTH: 10
<212> TYPE: PRT
<213> ORGANISM: Artificial Sequence
<220> FEATURE:
<223> OTHER INFORMATION: Histone H3.1 26-35 K27M

<400> SEQUENCE: 8

Arg Met Ser Ala Pro Ala Thr Gly Gly Val
1               5                   10

<210> SEQ ID NO 9
<211> LENGTH: 10
<212> TYPE: PRT
<213> ORGANISM: Artificial Sequence
<220> FEATURE:
<223> OTHER INFORMATION: K27M-H3.3 A1

<400> SEQUENCE: 9

Ala Met Ser Ala Pro Ser Thr Gly Gly Val
1               5                   10

<210> SEQ ID NO 10
<211> LENGTH: 10
<212> TYPE: PRT
<213> ORGANISM: Artificial Sequence
<220> FEATURE:
<223> OTHER INFORMATION: K27M-H3.3 A2

<400> SEQUENCE: 10

Arg Ala Ser Ala Pro Ser Thr Gly Gly Val
1               5                   10

<210> SEQ ID NO 11
<211> LENGTH: 10
<212> TYPE: PRT
<213> ORGANISM: Artificial Sequence
<220> FEATURE:
<223> OTHER INFORMATION: K27M-H3.3 A3

<400> SEQUENCE: 11

Arg Met Ala Ala Pro Ser Thr Gly Gly Val
1               5                   10

<210> SEQ ID NO 12
<211> LENGTH: 10
<212> TYPE: PRT
<213> ORGANISM: Artificial Sequence
<220> FEATURE:
<223> OTHER INFORMATION: K27M-H3.3 A5

<400> SEQUENCE: 12

Arg Met Ser Ala Ala Ser Thr Gly Gly Val
1               5                   10

<210> SEQ ID NO 13
<211> LENGTH: 10
<212> TYPE: PRT
<213> ORGANISM: Artificial Sequence
<220> FEATURE:
<223> OTHER INFORMATION: K27M-H3.3 A7

<400> SEQUENCE: 13

Arg Met Ser Ala Pro Ser Ala Gly Gly Val
1               5                   10
```

<210> SEQ ID NO 14
<211> LENGTH: 10
<212> TYPE: PRT
<213> ORGANISM: Artificial Sequence
<220> FEATURE:
<223> OTHER INFORMATION: K27M-H3.3 A8

<400> SEQUENCE: 14

Arg Met Ser Ala Pro Ser Thr Ala Gly Val
1               5                   10

<210> SEQ ID NO 15
<211> LENGTH: 10
<212> TYPE: PRT
<213> ORGANISM: Artificial Sequence
<220> FEATURE:
<223> OTHER INFORMATION: K27M-H3.3 A9

<400> SEQUENCE: 15

Arg Met Ser Ala Pro Ser Thr Gly Ala Val
1               5                   10

<210> SEQ ID NO 16
<211> LENGTH: 10
<212> TYPE: PRT
<213> ORGANISM: Artificial Sequence
<220> FEATURE:
<223> OTHER INFORMATION: K27M-H3.3 A10

<400> SEQUENCE: 16

Arg Met Ser Ala Pro Ser Thr Gly Gly Ala
1               5                   10

<210> SEQ ID NO 17
<211> LENGTH: 10
<212> TYPE: PRT
<213> ORGANISM: Artificial Sequence
<220> FEATURE:
<223> OTHER INFORMATION: K27M-H3.1 A1

<400> SEQUENCE: 17

Ala Met Ser Ala Pro Ala Thr Gly Gly Val
1               5                   10

<210> SEQ ID NO 18
<211> LENGTH: 10
<212> TYPE: PRT
<213> ORGANISM: Artificial Sequence
<220> FEATURE:
<223> OTHER INFORMATION: K27M-H3.1 A2

<400> SEQUENCE: 18

Arg Ala Ser Ala Pro Ala Thr Gly Gly Val
1               5                   10

<210> SEQ ID NO 19
<211> LENGTH: 10
<212> TYPE: PRT
<213> ORGANISM: Artificial Sequence
<220> FEATURE:
<223> OTHER INFORMATION: K27M-H3.1 A3

<400> SEQUENCE: 19

Arg Met Ala Ala Pro Ala Thr Gly Gly Val
1               5                   10

```
<210> SEQ ID NO 20
<211> LENGTH: 10
<212> TYPE: PRT
<213> ORGANISM: Artificial Sequence
<220> FEATURE:
<223> OTHER INFORMATION: K27M-H3.1 A5

<400> SEQUENCE: 20

Arg Met Ser Ala Ala Ala Thr Gly Gly Val
1               5                   10

<210> SEQ ID NO 21
<211> LENGTH: 10
<212> TYPE: PRT
<213> ORGANISM: Artificial Sequence
<220> FEATURE:
<223> OTHER INFORMATION: K27M-H3.1 A7

<400> SEQUENCE: 21

Arg Met Ser Ala Pro Ala Ala Gly Gly Val
1               5                   10

<210> SEQ ID NO 22
<211> LENGTH: 10
<212> TYPE: PRT
<213> ORGANISM: Artificial Sequence
<220> FEATURE:
<223> OTHER INFORMATION: K27M-H3.1 A8

<400> SEQUENCE: 22

Arg Met Ser Ala Pro Ala Thr Ala Gly Val
1               5                   10

<210> SEQ ID NO 23
<211> LENGTH: 10
<212> TYPE: PRT
<213> ORGANISM: Artificial Sequence
<220> FEATURE:
<223> OTHER INFORMATION: K27M-H3.1 A9

<400> SEQUENCE: 23

Arg Met Ser Ala Pro Ala Thr Gly Ala Val
1               5                   10

<210> SEQ ID NO 24
<211> LENGTH: 10
<212> TYPE: PRT
<213> ORGANISM: Artificial Sequence
<220> FEATURE:
<223> OTHER INFORMATION: K27M-H3.1 A10

<400> SEQUENCE: 24

Arg Met Ser Ala Pro Ala Thr Gly Gly Ala
1               5                   10

<210> SEQ ID NO 25
<211> LENGTH: 9
<212> TYPE: PRT
<213> ORGANISM: Artificial Sequence
<220> FEATURE:
<223> OTHER INFORMATION: C3 control peptide (A2E-7)

<400> SEQUENCE: 25

Tyr Leu Leu Pro Ala Ile Val His Ile
1               5

<210> SEQ ID NO 26
```

```
<211> LENGTH: 9
<212> TYPE: PRT
<213> ORGANISM: Artificial Sequence
<220> FEATURE:
<223> OTHER INFORMATION: A2E-1

<400> SEQUENCE: 26

Leu Leu Asp Val Pro Thr Ala Ala Val
1               5

<210> SEQ ID NO 27
<211> LENGTH: 9
<212> TYPE: PRT
<213> ORGANISM: Artificial Sequence
<220> FEATURE:
<223> OTHER INFORMATION: A2E-2

<400> SEQUENCE: 27

Thr Leu Trp Val Asp Pro Tyr Glu Val
1               5

<210> SEQ ID NO 28
<211> LENGTH: 9
<212> TYPE: PRT
<213> ORGANISM: Artificial Sequence
<220> FEATURE:
<223> OTHER INFORMATION: A2E-3

<400> SEQUENCE: 28

Phe Leu Leu Asp His Leu Lys Arg Val
1               5

<210> SEQ ID NO 29
<211> LENGTH: 10
<212> TYPE: PRT
<213> ORGANISM: Artificial Sequence
<220> FEATURE:
<223> OTHER INFORMATION: A2E-4

<400> SEQUENCE: 29

Leu Leu Leu Asp Val Pro Thr Ala Ala Val
1               5                   10

<210> SEQ ID NO 30
<211> LENGTH: 13
<212> TYPE: PRT
<213> ORGANISM: Artificial Sequence
<220> FEATURE:
<223> OTHER INFORMATION: A2E-5

<400> SEQUENCE: 30

Val Leu Phe Arg Gly Gly Pro Arg Gly Leu Leu Ala Val
1               5                   10

<210> SEQ ID NO 31
<211> LENGTH: 9
<212> TYPE: PRT
<213> ORGANISM: Artificial Sequence
<220> FEATURE:
<223> OTHER INFORMATION: A2E-6

<400> SEQUENCE: 31

Ser Leu Leu Pro Ala Ile Val Glu Leu
1               5

<210> SEQ ID NO 32
<211> LENGTH: 9
```

```
<212> TYPE: PRT
<213> ORGANISM: Artificial Sequence
<220> FEATURE:
<223> OTHER INFORMATION: A2E-8

<400> SEQUENCE: 32

Phe Leu Leu Pro Thr Gly Ala Glu Ala
1               5

<210> SEQ ID NO 33
<211> LENGTH: 10
<212> TYPE: PRT
<213> ORGANISM: Artificial Sequence
<220> FEATURE:
<223> OTHER INFORMATION: A2E-9

<400> SEQUENCE: 33

Leu Leu Asp Pro Lys Leu Cys Tyr Leu Leu
1               5                   10

<210> SEQ ID NO 34
<211> LENGTH: 10
<212> TYPE: PRT
<213> ORGANISM: Artificial Sequence
<220> FEATURE:
<223> OTHER INFORMATION: A2E-11

<400> SEQUENCE: 34

Met Leu Leu Ser Val Pro Leu Leu Leu Gly
1               5                   10

<210> SEQ ID NO 35
<211> LENGTH: 9
<212> TYPE: PRT
<213> ORGANISM: Artificial Sequence
<220> FEATURE:
<223> OTHER INFORMATION: A2E-17

<400> SEQUENCE: 35

Met Val Asp Gly Thr Leu Leu Leu Leu
1               5

<210> SEQ ID NO 36
<211> LENGTH: 10
<212> TYPE: PRT
<213> ORGANISM: Artificial Sequence
<220> FEATURE:
<223> OTHER INFORMATION: DMTN  control

<400> SEQUENCE: 36

Ser Leu Pro His Phe His His Pro Glu Thr
1               5                   10

<210> SEQ ID NO 37
<211> LENGTH: 11
<212> TYPE: PRT
<213> ORGANISM: Artificial Sequence
<220> FEATURE:
<223> OTHER INFORMATION: PIM1  control

<400> SEQUENCE: 37

Leu Leu Tyr Asp Met Val Cys Gly Asp Ile Pro
1               5                   10

<210> SEQ ID NO 38
<211> LENGTH: 11
<212> TYPE: PRT
```

<213> ORGANISM: Artificial Sequence
<220> FEATURE:
<223> OTHER INFORMATION: IFI30 control

<400> SEQUENCE: 38

Leu Leu Leu Asp Val Pro Thr Ala Ala Val Gln
1               5                   10

<210> SEQ ID NO 39
<211> LENGTH: 12
<212> TYPE: PRT
<213> ORGANISM: Artificial Sequence
<220> FEATURE:
<223> OTHER INFORMATION: IFI30 control

<400> SEQUENCE: 39

Leu Leu Leu Asp Val Pro Thr Ala Ala Val Gln Ala
1               5                   10

<210> SEQ ID NO 40
<211> LENGTH: 14
<212> TYPE: PRT
<213> ORGANISM: Artificial Sequence
<220> FEATURE:
<223> OTHER INFORMATION: SSR1 control

<400> SEQUENCE: 40

Val Leu Phe Arg Gly Gly Pro Arg Gly Leu Leu Ala Val Ala
1               5                   10

<210> SEQ ID NO 41
<211> LENGTH: 10
<212> TYPE: PRT
<213> ORGANISM: Artificial Sequence
<220> FEATURE:
<223> OTHER INFORMATION: RPS6KB1 control

<400> SEQUENCE: 41

Tyr Met Ala Pro Glu Ile Leu Met Arg Ser
1               5                   10

<210> SEQ ID NO 42
<211> LENGTH: 10
<212> TYPE: PRT
<213> ORGANISM: Artificial Sequence
<220> FEATURE:
<223> OTHER INFORMATION: CSF2RA control

<400> SEQUENCE: 42

Phe Ile Tyr Asn Ala Asp Leu Met Asn Cys
1               5                   10

<210> SEQ ID NO 43
<211> LENGTH: 11
<212> TYPE: PRT
<213> ORGANISM: Artificial Sequence
<220> FEATURE:
<223> OTHER INFORMATION: IL7 control

<400> SEQUENCE: 43

Lys Gln Tyr Glu Ser Val Leu Met Val Ser Ile
1               5                   10

<210> SEQ ID NO 44
<211> LENGTH: 10
<212> TYPE: PRT
<213> ORGANISM: Artificial Sequence

```
<220> FEATURE:
<223> OTHER INFORMATION: Beta globin control

<400> SEQUENCE: 44

Lys Val Asn Val Asp Glu Val Gly Gly Glu
1               5                   10

<210> SEQ ID NO 45
<211> LENGTH: 247
<212> TYPE: PRT
<213> ORGANISM: Artificial Sequence
<220> FEATURE:
<223> OTHER INFORMATION: anti-HMC scFv 5

<400> SEQUENCE: 45

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asn Gly Asn Thr Tyr Leu Asn Trp Phe His Gln Arg Pro Gly Gln Ser
        35                  40                  45

Pro Arg Arg Leu Ile Tyr Glu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gly Gly Thr Lys Leu Glu Ile Lys
            100                 105                 110

Arg Ser Arg Gly Gly Gly Gly Ser Gly Gly Gly Gly Ser Gly Gly Gly
        115                 120                 125

Gly Ser Leu Glu Met Ala Glu Val Gln Leu Val Gln Ser Gly Ala Glu
    130                 135                 140

Val Lys Lys Pro Gly Glu Ser Leu Lys Ile Ser Cys Lys Gly Ser Gly
145                 150                 155                 160

Tyr Ser Phe Thr Ser Tyr Trp Ile Gly Trp Val Arg Gln Met Pro Gly
                165                 170                 175

Lys Gly Leu Glu Trp Met Gly Ile Ile Tyr Pro Gly Asp Ser Asp Thr
            180                 185                 190

Arg Tyr Ser Pro Ser Phe Gln Gly Gln Val Thr Ile Ser Ala Asp Lys
        195                 200                 205

Ser Ile Ser Thr Ala Tyr Leu Gln Trp Ser Ser Leu Lys Ala Ser Asp
    210                 215                 220

Thr Ala Met Tyr Tyr Cys Ala Arg Gly Tyr Asp Gly Trp Gly Gln Gly
225                 230                 235                 240

Thr Leu Val Thr Val Ser Ser
                245

<210> SEQ ID NO 46
<211> LENGTH: 21
<212> TYPE: PRT
<213> ORGANISM: Artificial Sequence
<220> FEATURE:
<223> OTHER INFORMATION: scFv linker

<400> SEQUENCE: 46

Ser Arg Gly Gly Gly Gly Ser Gly Gly Gly Gly Ser Gly Gly Gly Gly
1               5                   10                  15
```

Ser Leu Glu Met Ala
            20

<210> SEQ ID NO 47
<211> LENGTH: 243
<212> TYPE: PRT
<213> ORGANISM: Artificial Sequence
<220> FEATURE:
<223> OTHER INFORMATION: anti-CD3 scFv

<400> SEQUENCE: 47

Asp Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser Gly Glu Gly Thr Ser Thr Gly Ser Gly
        115                 120                 125

Gly Ser Gly Gly Ser Gly Ala Asp Asp Ile Val Leu Thr Gln Ser
    130                 135                 140

Pro Ala Thr Leu Ser Leu Ser Pro Gly Glu Arg Ala Thr Leu Ser Cys
145                 150                 155                 160

Arg Ala Ser Gln Ser Val Ser Tyr Met Asn Trp Tyr Gln Gln Lys Pro
                165                 170                 175

Gly Lys Ala Pro Lys Arg Trp Ile Tyr Asp Thr Ser Lys Val Ala Ser
            180                 185                 190

Gly Val Pro Ala Arg Phe Ser Gly Ser Gly Ser Gly Thr Asp Tyr Ser
        195                 200                 205

Leu Thr Ile Asn Ser Leu Glu Ala Glu Asp Ala Ala Thr Tyr Tyr Cys
    210                 215                 220

Gln Gln Trp Ser Ser Asn Pro Leu Thr Phe Gly Gly Gly Thr Lys Val
225                 230                 235                 240

Glu Ile Lys

<210> SEQ ID NO 48
<211> LENGTH: 7
<212> TYPE: PRT
<213> ORGANISM: Artificial Sequence
<220> FEATURE:
<223> OTHER INFORMATION: BiTE linker

<400> SEQUENCE: 48

Thr Ser Gly Gly Gly Gly Ser
1               5

<210> SEQ ID NO 49
<211> LENGTH: 222
<212> TYPE: PRT
<213> ORGANISM: Artificial Sequence
<220> FEATURE:

<223> OTHER INFORMATION: CD28/CD3zeta

<400> SEQUENCE: 49

| | | | | | | | | | | | | | | | |
|---|---|---|---|---|---|---|---|---|---|---|---|---|---|---|---|
| Ala | Ala | Ala | Ile | Glu | Val | Met | Tyr | Pro | Pro | Tyr | Leu | Asp | Asn | Glu |
| 1 | | | | 5 | | | | | 10 | | | | | 15 |
| Lys | Ser | Asn | Gly | Thr | Ile | Ile | His | Val | Lys | Gly | Lys | His | Leu | Cys | Pro |
| | | | 20 | | | | | 25 | | | | | 30 | | |
| Ser | Pro | Leu | Phe | Pro | Gly | Pro | Ser | Lys | Pro | Phe | Trp | Val | Leu | Val | Val |
| | | | 35 | | | | 40 | | | | | 45 | | | |
| Val | Gly | Gly | Val | Leu | Ala | Cys | Tyr | Ser | Leu | Leu | Val | Thr | Val | Ala | Phe |
| | 50 | | | | | 55 | | | | | 60 | | | | |
| Ile | Ile | Phe | Trp | Val | Arg | Ser | Lys | Arg | Ser | Arg | Leu | Leu | His | Ser | Asp |
| 65 | | | | | 70 | | | | | 75 | | | | | 80 |
| Tyr | Met | Asn | Met | Thr | Pro | Arg | Arg | Pro | Gly | Pro | Thr | Arg | Lys | His | Tyr |
| | | | | 85 | | | | | 90 | | | | | 95 | |
| Gln | Pro | Tyr | Ala | Pro | Pro | Arg | Asp | Phe | Ala | Ala | Tyr | Arg | Ser | Arg | Val |
| | | | 100 | | | | | 105 | | | | | 110 | | |
| Lys | Phe | Ser | Arg | Ser | Ala | Asp | Ala | Pro | Ala | Tyr | Gln | Gln | Gly | Gln | Asn |
| | | | 115 | | | | | 120 | | | | | 125 | | |
| Gln | Leu | Tyr | Asn | Glu | Leu | Asn | Leu | Gly | Arg | Arg | Glu | Glu | Tyr | Asp | Val |
| | | | 130 | | | | | 135 | | | | | 140 | | |
| Leu | Asp | Lys | Arg | Arg | Gly | Arg | Asp | Pro | Glu | Met | Gly | Gly | Lys | Pro | Arg |
| 145 | | | | | 150 | | | | | 155 | | | | | 160 |
| Arg | Lys | Asn | Pro | Gln | Glu | Gly | Leu | Tyr | Asn | Glu | Leu | Gln | Lys | Asp | Lys |
| | | | | 165 | | | | | 170 | | | | | 175 | |
| Met | Ala | Glu | Ala | Tyr | Ser | Glu | Ile | Gly | Met | Lys | Gly | Glu | Arg | Arg | Arg |
| | | | 180 | | | | | 185 | | | | | 190 | | |
| Gly | Lys | Gly | His | Asp | Gly | Leu | Tyr | Gln | Gly | Leu | Ser | Thr | Ala | Thr | Lys |
| | | 195 | | | | | 200 | | | | | 205 | | | |
| Asp | Thr | Tyr | Asp | Ala | Leu | His | Met | Gln | Ala | Leu | Pro | Pro | Arg |
| | 210 | | | | | 215 | | | | | 220 | | |

<210> SEQ ID NO 50
<211> LENGTH: 225
<212> TYPE: PRT
<213> ORGANISM: Artificial Sequence
<220> FEATURE:
<223> OTHER INFORMATION: 4-1BB/CD3zeta

<400> SEQUENCE: 50

| | | | | | | | | | | | | | | | |
|---|---|---|---|---|---|---|---|---|---|---|---|---|---|---|---|
| Thr | Gly | Thr | Thr | Thr | Pro | Ala | Pro | Arg | Pro | Pro | Thr | Pro | Ala | Pro | Thr |
| 1 | | | | 5 | | | | | 10 | | | | | 15 | |
| Ile | Ala | Ser | Gln | Pro | Leu | Ser | Leu | Arg | Pro | Glu | Ala | Cys | Arg | Pro | Ala |
| | | | 20 | | | | | 25 | | | | | 30 | | |
| Ala | Gly | Gly | Ala | Val | His | Thr | Arg | Gly | Leu | Asp | Phe | Ala | Cys | Asp | Ile |
| | | | 35 | | | | | 40 | | | | | 45 | | |
| Tyr | Ile | Trp | Ala | Pro | Leu | Ala | Gly | Thr | Cys | Gly | Val | Leu | Leu | Leu | Ser |
| | 50 | | | | | 55 | | | | | 60 | | | | |
| Leu | Val | Ile | Thr | Leu | Tyr | Cys | Lys | Arg | Gly | Arg | Lys | Lys | Leu | Leu | Tyr |
| 65 | | | | | 70 | | | | | 75 | | | | | 80 |
| Ile | Phe | Lys | Gln | Pro | Phe | Met | Arg | Pro | Val | Gln | Thr | Thr | Gln | Glu | Glu |
| | | | | 85 | | | | | 90 | | | | | 95 | |
| Asp | Gly | Cys | Ser | Cys | Arg | Phe | Pro | Glu | Glu | Glu | Glu | Gly | Gly | Cys | Glu |
| | | | 100 | | | | | 105 | | | | | 110 | | |
| Leu | Arg | Val | Lys | Phe | Ser | Arg | Ser | Ala | Asp | Ala | Pro | Ala | Tyr | Gln | Gln |
| | | | 115 | | | | | 120 | | | | | 125 | | |

Gly Gln Asn Gln Leu Tyr Asn Glu Leu Asn Leu Gly Arg Arg Glu Glu
            130                 135                 140

Tyr Asp Val Leu Asp Lys Arg Gly Arg Asp Pro Glu Met Gly Gly
145                 150                 155                 160

Lys Pro Arg Arg Lys Asn Pro Gln Glu Gly Leu Tyr Asn Glu Leu Gln
                165                 170                 175

Lys Asp Lys Met Ala Glu Ala Tyr Ser Glu Ile Gly Met Lys Gly Glu
            180                 185                 190

Arg Arg Arg Gly Lys Gly His Asp Gly Leu Tyr Gln Gly Leu Ser Thr
        195                 200                 205

Ala Thr Lys Asp Thr Tyr Asp Ala Leu His Met Gln Ala Leu Pro Pro
    210                 215                 220

Arg
225

<210> SEQ ID NO 51
<211> LENGTH: 142
<212> TYPE: PRT
<213> ORGANISM: Artificial Sequence
<220> FEATURE:
<223> OTHER INFORMATION: TCRalpha constant domain

<400> SEQUENCE: 51

Pro Asn Ile Gln Asn Pro Asp Pro Ala Val Tyr Gln Leu Arg Asp Ser
1               5                   10                  15

Lys Ser Ser Asp Lys Ser Val Cys Leu Phe Thr Asp Phe Asp Ser Gln
                20                  25                  30

Thr Asn Val Ser Gln Ser Lys Asp Ser Asp Val Tyr Ile Thr Asp Lys
            35                  40                  45

Thr Val Leu Asp Met Arg Ser Met Asp Phe Lys Ser Asn Ser Ala Val
        50                  55                  60

Ala Trp Ser Asn Lys Ser Asp Phe Ala Cys Ala Asn Ala Phe Asn Asn
65                  70                  75                  80

Ser Ile Ile Pro Glu Asp Thr Phe Phe Pro Ser Pro Glu Ser Ser Cys
                85                  90                  95

Asp Val Lys Leu Val Glu Lys Ser Phe Glu Thr Asp Thr Asn Leu Asn
                100                 105                 110

Phe Gln Asn Leu Ser Val Ile Gly Phe Arg Ile Leu Leu Leu Lys Val
            115                 120                 125

Ala Gly Phe Asn Leu Leu Met Thr Leu Arg Leu Trp Ser Ser
        130                 135                 140

<210> SEQ ID NO 52
<211> LENGTH: 177
<212> TYPE: PRT
<213> ORGANISM: Artificial Sequence
<220> FEATURE:
<223> OTHER INFORMATION: TCRbeta constant domain

<400> SEQUENCE: 52

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Phe Pro Asp His Val Glu Leu Ser Trp Trp Val Asn
            35                  40                  45

Gly Lys Glu Val His Ser Gly Val Ser Thr Asp Pro Gln Pro Leu Lys

```
               50                  55                  60
Glu Gln Pro Ala Leu Asn Asp Ser Arg Tyr Cys Leu Ser Arg Leu
 65                  70                  75                  80

Arg Val Ser Ala Thr Phe Trp Gln Asn Pro Arg Asn His Phe Arg Cys
                 85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
                115                 120                 125

Ala Asp Cys Gly Phe Thr Ser Val Ser Tyr Gln Gln Gly Val Leu Ser
                130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 53
<211> LENGTH: 153
<212> TYPE: PRT
<213> ORGANISM: Artificial Sequence
<220> FEATURE:
<223> OTHER INFORMATION: TCRdelta constant domain

<400> SEQUENCE: 53

Ser Gln Pro His Thr Lys Pro Ser Val Phe Val Met Lys Asn Gly Thr
 1               5                  10                  15

Asn Val Ala Cys Leu Val Lys Glu Phe Tyr Pro Lys Asp Ile Arg Ile
                20                  25                  30

Asn Leu Val Ser Ser Lys Lys Ile Thr Glu Phe Asp Pro Ala Ile Val
                35                  40                  45

Ile Ser Pro Ser Gly Lys Tyr Asn Ala Val Lys Leu Gly Lys Tyr Glu
 50                  55                  60

Asp Ser Asn Ser Val Thr Cys Ser Val Gln His Asp Asn Lys Thr Val
 65                  70                  75                  80

His Ser Thr Asp Phe Glu Val Lys Thr Asp Ser Thr Asp His Val Lys
                85                  90                  95

Pro Lys Glu Thr Glu Asn Thr Lys Gln Pro Ser Lys Ser Cys His Lys
                100                 105                 110

Pro Lys Ala Ile Val His Thr Glu Lys Val Asn Met Met Ser Leu Thr
                115                 120                 125

Val Leu Gly Leu Arg Met Leu Phe Ala Lys Thr Val Ala Val Asn Phe
                130                 135                 140

Leu Leu Thr Ala Lys Leu Phe Phe Leu
145                 150

<210> SEQ ID NO 54
<211> LENGTH: 173
<212> TYPE: PRT
<213> ORGANISM: Artificial Sequence
<220> FEATURE:
<223> OTHER INFORMATION: TCRgamma constant domain

<400> SEQUENCE: 54

Asp Lys Gln Leu Asp Ala Asp Val Ser Pro Lys Pro Thr Ile Phe Leu
 1               5                  10                  15

Pro Ser Ile Ala Glu Thr Lys Leu Gln Lys Ala Gly Thr Tyr Leu Cys
```

```
                    20                  25                  30
Leu Leu Glu Lys Phe Phe Pro Asp Val Ile Lys Ile His Trp Gln Glu
                35                  40                  45
Lys Lys Ser Asn Thr Ile Leu Gly Ser Gln Glu Gly Asn Thr Met Lys
 50                  55                  60
Thr Asn Asp Thr Tyr Met Lys Phe Ser Trp Leu Thr Val Pro Glu Lys
 65                  70                  75                  80
Ser Leu Asp Lys Glu His Arg Cys Ile Val Arg His Glu Asn Asn Lys
                85                  90                  95
Asn Gly Val Asp Gln Glu Ile Ile Phe Pro Pro Ile Lys Thr Asp Val
                100                 105                 110
Ile Thr Met Asp Pro Lys Asp Asn Cys Ser Lys Asp Ala Asn Asp Thr
                115                 120                 125
Leu Leu Leu Gln Leu Thr Asn Thr Ser Ala Tyr Tyr Met Tyr Leu Leu
                130                 135                 140
Leu Leu Leu Lys Ser Val Val Tyr Phe Ala Ile Ile Thr Cys Cys Leu
145                 150                 155                 160
Leu Arg Arg Thr Ala Phe Cys Cys Asn Gly Glu Lys Ser
                165                 170

<210> SEQ ID NO 55
<211> LENGTH: 20
<212> TYPE: PRT
<213> ORGANISM: Artificial Sequence
<220> FEATURE:
<223> OTHER INFORMATION: TCRalpha transmembrane domain

<400> SEQUENCE: 55

Ile Leu Leu Leu Lys Val Ala Gly Phe Asn Leu Leu Met Thr Leu Arg
1               5                   10                  15

Leu Trp Ser Ser
            20

<210> SEQ ID NO 56
<211> LENGTH: 23
<212> TYPE: PRT
<213> ORGANISM: Artificial Sequence
<220> FEATURE:
<223> OTHER INFORMATION: TCRbeta transmembrane domain

<400> SEQUENCE: 56

Thr Ile Leu Tyr Glu Ile Leu Leu Gly Lys Ala Thr Leu Tyr Ala Val
1               5                   10                  15

Leu Val Ser Ala Leu Val Leu
            20

<210> SEQ ID NO 57
<211> LENGTH: 20
<212> TYPE: PRT
<213> ORGANISM: Artificial Sequence
<220> FEATURE:
<223> OTHER INFORMATION: TCRdelta transmembrane domain

<400> SEQUENCE: 57

Met Leu Phe Ala Lys Thr Val Ala Val Asn Phe Leu Leu Thr Ala Lys
1               5                   10                  15

Leu Phe Phe Leu
            20

<210> SEQ ID NO 58
```

```
<211> LENGTH: 23
<212> TYPE: PRT
<213> ORGANISM: Artificial Sequence
<220> FEATURE:
<223> OTHER INFORMATION: TCRgamma transmembrane domain

<400> SEQUENCE: 58

Tyr Tyr Met Tyr Leu Leu Leu Leu Lys Ser Val Val Tyr Phe Ala
1               5                   10                  15

Ile Ile Thr Cys Cys Leu Leu
            20

<210> SEQ ID NO 59
<211> LENGTH: 30
<212> TYPE: PRT
<213> ORGANISM: Artificial Sequence
<220> FEATURE:
<223> OTHER INFORMATION: TCRalpha connecting peptide

<400> SEQUENCE: 59

Glu Ser Ser Cys Asp Val Lys Leu Val Glu Lys Ser Phe Glu Thr Asp
1               5                   10                  15

Thr Asn Leu Asn Phe Gln Asn Leu Ser Val Ile Gly Phe Arg
            20                  25                  30

<210> SEQ ID NO 60
<211> LENGTH: 17
<212> TYPE: PRT
<213> ORGANISM: Artificial Sequence
<220> FEATURE:
<223> OTHER INFORMATION: TCRbeta connecting peptide

<400> SEQUENCE: 60

Ala Asp Cys Gly Phe Thr Ser Val Ser Tyr Gln Gln Gly Val Leu Ser
1               5                   10                  15

Ala

<210> SEQ ID NO 61
<211> LENGTH: 41
<212> TYPE: PRT
<213> ORGANISM: Artificial Sequence
<220> FEATURE:
<223> OTHER INFORMATION: TCRdelta connecting peptide

<400> SEQUENCE: 61

Asp His Val Lys Pro Lys Glu Thr Glu Asn Thr Lys Gln Pro Ser Lys
1               5                   10                  15

Ser Cys His Lys Pro Lys Ala Ile Val His Thr Glu Lys Val Asn Met
            20                  25                  30

Met Ser Leu Thr Val Leu Gly Leu Arg
        35                  40

<210> SEQ ID NO 62
<211> LENGTH: 24
<212> TYPE: PRT
<213> ORGANISM: Artificial Sequence
<220> FEATURE:
<223> OTHER INFORMATION: TCRgamma connecting peptide

<400> SEQUENCE: 62

Met Asp Pro Lys Asp Asn Cys Ser Lys Asp Ala Asn Asp Thr Leu Leu
1               5                   10                  15

Leu Gln Leu Thr Asn Thr Ser Ala
            20
```

<210> SEQ ID NO 63
<211> LENGTH: 40
<212> TYPE: PRT
<213> ORGANISM: Artificial Sequence
<220> FEATURE:
<223> OTHER INFORMATION: TCRalpha connecting peptide MD

<400> SEQUENCE: 63

```
Ile Pro Glu Asp Thr Phe Phe Pro Ser Pro Glu Ser Ser Cys Asp Val
 1               5                  10                  15

Lys Leu Val Glu Lys Ser Phe Glu Thr Asp Thr Asn Leu Asn Phe Gln
             20                  25                  30

Asn Leu Ser Val Ile Gly Phe Arg
         35                  40
```

<210> SEQ ID NO 64
<211> LENGTH: 19
<212> TYPE: PRT
<213> ORGANISM: Artificial Sequence
<220> FEATURE:
<223> OTHER INFORMATION: TCRbeta connecting peptide MD

<400> SEQUENCE: 64

```
Gly Arg Ala Asp Cys Gly Phe Thr Ser Val Ser Tyr Gln Gln Gly Val
 1               5                  10                  15

Leu Ser Ala
```

<210> SEQ ID NO 65
<211> LENGTH: 48
<212> TYPE: PRT
<213> ORGANISM: Artificial Sequence
<220> FEATURE:
<223> OTHER INFORMATION: TCRdelta connecting peptide MD

<400> SEQUENCE: 65

```
Glu Val Lys Thr Asp Ser Thr Asp His Val Lys Pro Lys Glu Thr Glu
 1               5                  10                  15

Asn Thr Lys Gln Pro Ser Lys Ser Cys His Lys Pro Lys Ala Ile Val
             20                  25                  30

His Thr Glu Lys Val Asn Met Met Ser Leu Thr Val Leu Gly Leu Arg
         35                  40                  45
```

<210> SEQ ID NO 66
<211> LENGTH: 32
<212> TYPE: PRT
<213> ORGANISM: Artificial Sequence
<220> FEATURE:
<223> OTHER INFORMATION: TCRgamma connecting peptide MD

<400> SEQUENCE: 66

```
Pro Ile Lys Thr Asp Val Ile Thr Met Asp Pro Lys Asp Asn Cys Ser
 1               5                  10                  15

Lys Asp Ala Asn Asp Thr Leu Leu Leu Gln Leu Thr Asn Thr Ser Ala
             20                  25                  30
```

<210> SEQ ID NO 67
<211> LENGTH: 9
<212> TYPE: PRT
<213> ORGANISM: Artificial Sequence
<220> FEATURE:
<223> OTHER INFORMATION: TCRbeta intracellular domain

<400> SEQUENCE: 67

Met Ala Met Val Lys Arg Lys Asp Phe
1               5

<210> SEQ ID NO 68
<211> LENGTH: 12
<212> TYPE: PRT
<213> ORGANISM: Artificial Sequence
<220> FEATURE:
<223> OTHER INFORMATION: TCRgamma intracellular domain

<400> SEQUENCE: 68

Arg Arg Thr Ala Phe Cys Cys Asn Gly Glu Lys Ser
1               5                   10

<210> SEQ ID NO 69
<211> LENGTH: 68
<212> TYPE: PRT
<213> ORGANISM: Artificial Sequence
<220> FEATURE:
<223> OTHER INFORMATION: T cell receptor domain delta

<400> SEQUENCE: 69

Glu Val Lys Thr Asp Ser Thr Asp His Val Lys Pro Lys Glu Thr Glu
1               5                   10                  15

Asn Thr Lys Gln Pro Ser Lys Ser Cys His Lys Pro Lys Ala Ile Val
                20                  25                  30

His Thr Glu Lys Val Asn Met Met Ser Leu Thr Val Leu Gly Leu Arg
            35                  40                  45

Met Leu Phe Ala Lys Thr Val Ala Val Asn Phe Leu Leu Thr Ala Lys
        50                  55                  60

Leu Phe Phe Leu
65

<210> SEQ ID NO 70
<211> LENGTH: 67
<212> TYPE: PRT
<213> ORGANISM: Artificial Sequence
<220> FEATURE:
<223> OTHER INFORMATION: T cell receptor domain gamma

<400> SEQUENCE: 70

Pro Ile Lys Thr Asp Val Ile Thr Met Asp Pro Lys Asp Asn Cys Ser
1               5                   10                  15

Lys Asp Ala Asn Asp Thr Leu Leu Leu Gln Leu Thr Asn Thr Ser Ala
                20                  25                  30

Tyr Tyr Met Tyr Leu Leu Leu Leu Lys Ser Val Val Tyr Phe Ala
            35                  40                  45

Ile Ile Thr Cys Cys Leu Leu Arg Arg Thr Ala Phe Cys Cys Asn Gly
        50                  55                  60

Glu Lys Ser
65

<210> SEQ ID NO 71
<211> LENGTH: 60
<212> TYPE: PRT
<213> ORGANISM: Artificial Sequence
<220> FEATURE:
<223> OTHER INFORMATION: T cell receptor domain alpha

<400> SEQUENCE: 71

Ile Pro Glu Asp Thr Phe Phe Pro Ser Pro Glu Ser Ser Cys Asp Val
1               5                   10                  15

Lys Leu Val Glu Lys Ser Phe Glu Thr Asp Thr Asn Leu Asn Phe Gln
            20                  25                  30

Asn Leu Ser Val Ile Gly Phe Arg Ile Leu Leu Lys Val Ala Gly
            35                  40                  45

Phe Asn Leu Leu Met Thr Leu Arg Leu Trp Ser Ser
 50                  55                  60

<210> SEQ ID NO 72
<211> LENGTH: 51
<212> TYPE: PRT
<213> ORGANISM: Artificial Sequence
<220> FEATURE:
<223> OTHER INFORMATION: T cell receptor domain beta

<400> SEQUENCE: 72

Gly Arg Ala Asp Cys Gly Phe Thr Ser Val Ser Tyr Gln Gln Gly Val
 1               5                  10                  15

Leu Ser Ala Thr Ile Leu Tyr Glu Ile Leu Leu Gly Lys Ala Thr Leu
            20                  25                  30

Tyr Ala Val Leu Val Ser Ala Leu Val Leu Met Ala Met Val Lys Arg
            35                  40                  45

Lys Asp Phe
 50

<210> SEQ ID NO 73
<211> LENGTH: 20
<212> TYPE: PRT
<213> ORGANISM: Artificial Sequence
<220> FEATURE:
<223> OTHER INFORMATION: Signal peptide

<400> SEQUENCE: 73

Met Glu Thr Asp Thr Leu Leu Leu Trp Val Leu Leu Leu Trp Val Pro
 1               5                  10                  15

Gly Ser Thr Gly
            20

<210> SEQ ID NO 74
<211> LENGTH: 107
<212> TYPE: PRT
<213> ORGANISM: Artificial Sequence
<220> FEATURE:
<223> OTHER INFORMATION: fragment of CD28

<400> SEQUENCE: 74

Ile Glu Val Met Tyr Pro Pro Pro Tyr Leu Asp Asn Glu Lys Ser Asn
 1               5                  10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
            35                  40                  45

Val Leu Ala Cys Tyr Ser Leu Leu Val Thr Val Ala Phe Ile Ile Phe
 50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                    85                  90                  95

Ala Pro Pro Arg Asp Phe Ala Ala Tyr Arg Ser
                100                 105

<210> SEQ ID NO 75
<211> LENGTH: 113
<212> TYPE: PRT
<213> ORGANISM: Artificial Sequence
<220> FEATURE:
<223> OTHER INFORMATION: HCVR 5

<400> SEQUENCE: 75

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Asp Gly Trp Gly Gln Gly Thr Leu Val Thr Val Ser
            100                 105                 110

Ser
```

<210> SEQ ID NO 76
<211> LENGTH: 113
<212> TYPE: PRT
<213> ORGANISM: Artificial Sequence
<220> FEATURE:
<223> OTHER INFORMATION: HCVR 10

<400> SEQUENCE: 76

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Phe Asp Asn Trp Gly Gln Gly Thr Leu Val Thr Val Ser
            100                 105                 110

Ser
```

<210> SEQ ID NO 77
<211> LENGTH: 113
<212> TYPE: PRT
<213> ORGANISM: Artificial Sequence
<220> FEATURE:
<223> OTHER INFORMATION: HCVR 13

<400> SEQUENCE: 77

```
Glu Val Gln Leu Val Gln Ser Gly Ala Glu Val Lys Lys Pro Gly Glu
1               5                   10                  15
```

```
Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Asp Val Trp Gly Gln Gly Thr Leu Val Thr Val Ser
            100                 105                 110

Ser
```

<210> SEQ ID NO 78
<211> LENGTH: 113
<212> TYPE: PRT
<213> ORGANISM: Artificial Sequence
<220> FEATURE:
<223> OTHER INFORMATION: HCVR 16

<400> SEQUENCE: 78

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Ser Tyr
            20                  25                  30

Trp Ile Gly Trp Val Arg Gln Met Pro Gly Lys Gly Leu Glu Trp Met
        35                  40                  45

Gly Ile Ile Tyr Pro Gly Asp Ser Asp Thr Arg Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Gly Tyr Asp Ser Trp Gly Gln Gly Thr Leu Val Thr Val Ser
            100                 105                 110

Ser
```

<210> SEQ ID NO 79
<211> LENGTH: 120
<212> TYPE: PRT
<213> ORGANISM: Artificial Sequence
<220> FEATURE:
<223> OTHER INFORMATION: HCVR 31

<400> SEQUENCE: 79

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Leu Thr Phe Asp Arg Tyr
            20                  25                  30

Ala Met Ser Trp Val Arg Gln Ala Ala Gly Lys Gly Leu Glu Arg Phe
        35                  40                  45

Ser Ala Ile Thr Gly Asp Gly Tyr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Gly Ala Glu Asp Thr Ala Val Tyr Tyr Cys
```

```
                85                  90                  95
Ala Arg Leu Ser Gly Ile Gly Arg Ser Ser Tyr Asp Gly Trp Gly Gln
            100                 105                 110
Gly Thr Leu Val Thr Val Ser Ser
        115                 120

<210> SEQ ID NO 80
<211> LENGTH: 119
<212> TYPE: PRT
<213> ORGANISM: Artificial Sequence
<220> FEATURE:
<223> OTHER INFORMATION: HCVR 32

<400> SEQUENCE: 80

Gln Val Gln Leu Val Glu Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Thr Ile Thr Trp Val Arg Gln Ala Pro Gly Gln Gly Leu Glu Trp Met
        35                  40                  45

Gly Trp Ile Ser Pro Tyr Asn Gly Asn Thr Asn Tyr Ala Gln Asn Leu
    50                  55                  60

Gln Gly Arg Val Thr Met Thr Thr Asp Thr Ser Thr Thr Thr Ala Tyr
65                  70                  75                  80

Met Glu Leu Arg Ser Leu Thr Ser Asp Asp Thr Ala Val Tyr Tyr Cys
                85                  90                  95

Ala Arg Ser Trp Glu His Gly Phe Pro Tyr Asp Glu Trp Gly Gln Gly
            100                 105                 110

Thr Leu Val Thr Val Ser Ser
        115

<210> SEQ ID NO 81
<211> LENGTH: 118
<212> TYPE: PRT
<213> ORGANISM: Artificial Sequence
<220> FEATURE:
<223> OTHER INFORMATION: HCVR 33

<400> SEQUENCE: 81

Glu Val Gln Leu Val Gln Ser Gly Ala Glu Val Arg Lys Pro Gly Ser
1               5                   10                  15

Ser Val Lys Val Ser Cys Lys Ala Ser Ala Gly Thr Phe Asn Arg Tyr
            20                  25                  30

Ser Leu Ser Trp Val Arg Gln Ala Pro Gly Gln Gly Leu Glu Trp Val
        35                  40                  45

Gly Arg Ile Ile Pro Ile Ile Gly Val Ala Asp Tyr Ala Gln Lys Phe
    50                  55                  60

Gln Gly Arg Val Thr Ile Thr Ala Asp Lys Ser Ala Thr Thr Ala Tyr
65                  70                  75                  80

Met Glu Leu His Ser Leu Arg Ser Glu Asp Thr Ala Val Tyr Tyr Cys
                85                  90                  95

Ala Arg Gln Glu Tyr Ser Tyr Ala Met Asp Tyr Trp Gly Gln Gly Thr
            100                 105                 110

Leu Val Thr Val Ser Ser
        115

<210> SEQ ID NO 82
<211> LENGTH: 120
```

```
<212> TYPE: PRT
<213> ORGANISM: Artificial Sequence
<220> FEATURE:
<223> OTHER INFORMATION: HCVR 34

<400> SEQUENCE: 82
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Trp Thr Phe Glu Tyr Ser Ile Asp Ser Trp Gly Gln
            100                 105                 110

Gly Thr Leu Val Thr Val Ser Ser
        115                 120

```
<210> SEQ ID NO 83
<211> LENGTH: 119
<212> TYPE: PRT
<213> ORGANISM: Artificial Sequence
<220> FEATURE:
<223> OTHER INFORMATION: HCVR 35

<400> SEQUENCE: 83
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Tyr Glu Ser Gly Tyr Pro Phe Asp Trp Trp Gly Gln Gly
            100                 105                 110

Thr Leu Val Thr Val Ser Ser
        115

```
<210> SEQ ID NO 84
<211> LENGTH: 121
<212> TYPE: PRT
<213> ORGANISM: Artificial Sequence
<220> FEATURE:
<223> OTHER INFORMATION: HCVR 36

<400> SEQUENCE: 84
```

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr

```
            20                  25                  30
Tyr Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Trp Ser Pro Val Thr Tyr Tyr Asp Ile Trp Gly
            100                 105                 110

Gln Gly Thr Leu Val Thr Val Ser Ser
        115                 120

<210> SEQ ID NO 85
<211> LENGTH: 123
<212> TYPE: PRT
<213> ORGANISM: Artificial Sequence
<220> FEATURE:
<223> OTHER INFORMATION: HCVR 37

<400> SEQUENCE: 85

Gln Met Gln Leu Val Gln Ser Gly Ala Glu Val Lys Lys Pro Gly Ala
1               5                   10                  15

Ser Met Lys Val Ser Cys Lys Ala Ser Gly Tyr Thr Val Thr Ser Tyr
            20                  25                  30

Gly Leu Ser Trp Val Arg Gln Ala Pro Gly Gln Gly Leu Glu Trp Val
        35                  40                  45

Gly Trp Ile Ser Ala Tyr Asn Gly Asp Thr Ile Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Met Tyr Tyr Cys
                85                  90                  95

Ala Arg Ser Ser Leu Pro Phe Gly Val Val Pro Asn Ala Phe Asp Ile
            100                 105                 110

Trp Gly Gln Gly Thr Met Val Thr Val Ser Ser
        115                 120

<210> SEQ ID NO 86
<211> LENGTH: 120
<212> TYPE: PRT
<213> ORGANISM: Artificial Sequence
<220> FEATURE:
<223> OTHER INFORMATION: HCVR 38

<400> SEQUENCE: 86

Gln Met Gln Leu Val Gln Ser Gly Ala Glu Val Lys Thr Thr Gly Ala
1               5                   10                  15

Ser Val Arg Val Ser Cys Lys Ala Ser Gly Tyr Thr Phe Thr Asp Tyr
            20                  25                  30

Tyr Leu His Trp Val Arg Gln Ala Pro Gly Gln Gly Leu Glu Trp Met
        35                  40                  45

Gly Trp Ile Asn Pro His Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80
```

```
Met Glu Leu Ser Ser Leu Arg Ser Asp Asp Thr Ala Val Tyr Tyr Cys
                85                  90                  95

Ala Arg Glu Asp Tyr Ser Gly Ser Gly Ser Ser Asp Ala Trp Gly Gln
            100                 105                 110

Gly Thr Leu Val Thr Val Ser Ser
        115                 120
```

<210> SEQ ID NO 87
<211> LENGTH: 113
<212> TYPE: PRT
<213> ORGANISM: Artificial Sequence
<220> FEATURE:
<223> OTHER INFORMATION: LCVR 5

<400> SEQUENCE: 87

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asn Gly Asn Thr Tyr Leu Asn Trp Phe His Gln Arg Pro Gly Gln Ser
        35                  40                  45

Pro Arg Arg Leu Ile Tyr Glu Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro Pro Thr Phe Gly Gly Gly Thr Lys Leu Glu Ile Lys
            100                 105                 110

Arg
```

<210> SEQ ID NO 88
<211> LENGTH: 113
<212> TYPE: PRT
<213> ORGANISM: Artificial Sequence
<220> FEATURE:
<223> OTHER INFORMATION: LCVR 10

<400> SEQUENCE: 88

```
Glu Ile Val Leu Thr Gln Ser Pro Leu Ser Leu Pro Val Thr Leu Gly
1               5                   10                  15

Gln Pro Ala Ser Ile Ser Cys Arg Ser Ser Gln Ser Leu Val Tyr Ser
            20                  25                  30

Asn Gly Asn Thr Tyr Leu Ser Trp Phe His Gln Arg Pro Gly Gln Ser
        35                  40                  45

Pro Arg Arg Leu Ile Tyr Lys Val Ser Lys Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Phe Tyr Cys Met Gln Gly
                85                  90                  95

Thr Tyr Trp Pro Tyr Thr Phe Gly Gln Gly Thr Lys Leu Glu Ile Lys
            100                 105                 110

Arg
```

<210> SEQ ID NO 89
<211> LENGTH: 113
<212> TYPE: PRT

<213> ORGANISM: Artificial Sequence
<220> FEATURE:
<223> OTHER INFORMATION: LCVR 13

<400> SEQUENCE: 89

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Ile Tyr Ser
            20                  25                  30

Asn Gly Asn Thr Tyr Leu Thr Trp Phe His Gln Arg Pro Gly Gln Pro
        35                  40                  45

Pro Arg Arg Leu Ile His Lys Val Ser Asn Arg Asp Ser Gly Val Pro
    50                  55                  60

Asp Arg Phe Ser Gly Ser Gly Ser Gly Ser Asp Phe Thr Leu Lys Ile
65                  70                  75                  80

Ser Arg Val Glu Ala Glu Asp Val Gly Ile Tyr Tyr Cys Met Gln Gly
                85                  90                  95

Thr His Trp Pro Pro Thr Phe Gly Gly Gly Thr Lys Leu Glu Ile Lys
            100                 105                 110

Arg

<210> SEQ ID NO 90
<211> LENGTH: 113
<212> TYPE: PRT
<213> ORGANISM: Artificial Sequence
<220> FEATURE:
<223> OTHER INFORMATION: LCVR 16

<400> SEQUENCE: 90

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Ile Tyr Ser
            20                  25                  30

Asn Gly Asn Thr Tyr Leu Thr Trp Phe His Gln Arg Pro Gly Gln Pro
        35                  40                  45

Pro Arg Arg Leu Ile His Lys Val Ser Asn Arg Asp Ser Gly Val Pro
    50                  55                  60

Asp Arg Phe Ser Gly Ser Gly Ser Gly Ser Asp Phe Thr Leu Lys Ile
65                  70                  75                  80

Ser Arg Val Glu Ala Glu Asp Val Gly Ile Tyr Tyr Cys Met Gln Gly
                85                  90                  95

Thr His Trp Pro Pro Thr Phe Gly Gly Gly Thr Lys Leu Glu Ile Lys
            100                 105                 110

Arg

<210> SEQ ID NO 91
<211> LENGTH: 116
<212> TYPE: PRT
<213> ORGANISM: Artificial Sequence
<220> FEATURE:
<223> OTHER INFORMATION: LCVR 31

<400> SEQUENCE: 91

Gln Ala Val Leu Thr Gln Pro Ser Ser Leu Ser Ala Ser Pro Gly Ala
1               5                   10                  15

Ser Ala Ser Leu Thr Cys Thr Leu Arg Ser Gly Ile Asn Val Gly Thr
            20                  25                  30

Tyr Arg Ile Tyr Trp Tyr Gln Gln Lys Pro Gly Ser Pro Pro Gln Tyr

```
                35                  40                  45
Leu Leu Arg Tyr Lys Ser Asp Ser Asp Lys Gln Gln Gly Ser Gly Val
            50                  55                  60
Pro Ser Arg Phe Ser Gly Ser Lys Asp Ala Ser Ala Asn Ala Gly Ile
65                  70                  75                  80
Leu Leu Ile Ser Gly Leu Gln Ser Glu Asp Glu Ala Asp Tyr Tyr Cys
                85                  90                  95
Met Ile Trp His Ser Ser Ala Trp Val Phe Gly Gly Gly Thr Lys Leu
                100                 105                 110
Thr Val Leu Gly
        115

<210> SEQ ID NO 92
<211> LENGTH: 112
<212> TYPE: PRT
<213> ORGANISM: Artificial Sequence
<220> FEATURE:
<223> OTHER INFORMATION: LCVR 32

<400> SEQUENCE: 92

Gln Ser Val Leu Thr Gln Pro Pro Ser Val Ser Gly Ala Pro Gly Gln
1               5                   10                  15
Arg Val Thr Ile Ser Cys Thr Gly Ser Ser Ser Asn Leu Gly Ala Gly
            20                  25                  30
Tyr Asp Val His Trp Tyr Gln Gln Leu Pro Gly Thr Ala Pro Lys Val
        35                  40                  45
Leu Val Tyr Phe Asn Asn Asn Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Gln Ser Tyr Asp Ser Ser
                85                  90                  95
Leu Ser Ala Ser Val Phe Gly Thr Gly Thr Lys Val Thr Val Leu Gly
                100                 105                 110

<210> SEQ ID NO 93
<211> LENGTH: 111
<212> TYPE: PRT
<213> ORGANISM: Artificial Sequence
<220> FEATURE:
<223> OTHER INFORMATION: LCVR 33

<400> SEQUENCE: 93

Gln Ser Val Leu Thr Gln Pro Pro Ser Val Ser Gly Ala Pro Gly Gln
1               5                   10                  15
Arg Val Thr Ile Phe Cys Thr Gly Ser Ser Ser Asn Ile Gly Ala Gly
            20                  25                  30
Tyr Asp Val His Trp Tyr Gln Gln Leu Pro Gly Thr Ala Pro Lys Leu
        35                  40                  45
Leu Ile Tyr Gly Asn Asn Asn Arg Pro Ser Gly Val Pro Asp Arg Phe
    50                  55                  60
Ser Gly Ser Lys Ser Gly Thr Ser Ala Ser Leu Ala Ile Thr Gly Leu
65                  70                  75                  80
Gln Ala Glu Asp Glu Ala Asp Tyr Tyr Cys Gln Ser Tyr Asp Thr Ser
                85                  90                  95
Leu Thr Pro Val Phe Gly Gly Gly Thr Lys Leu Thr Val Leu Gly
                100                 105                 110
```

```
<210> SEQ ID NO 94
<211> LENGTH: 112
<212> TYPE: PRT
<213> ORGANISM: Artificial Sequence
<220> FEATURE:
<223> OTHER INFORMATION: LCVR 34

<400> SEQUENCE: 94

Gln Ser Val Leu Thr Gln Pro Pro Ser Val Ser Gly Ala Pro Gly Gln
1               5                   10                  15

Arg Val Thr Ile Ser Cys Thr Gly Ser Ser Leu Asn Leu Gly Ala Gly
            20                  25                  30

Tyr Asp Val His Trp Tyr Gln Gln Phe Pro Gly Thr Ala Pro Lys Leu
        35                  40                  45

Leu Ile Phe Ala Asn Thr Asn Arg Pro Ser Gly Val Pro Asp Arg Phe
    50                  55                  60

Ser Ala Ser Lys Ser Gly Thr Ser Ala Ser Leu Ala Ile Thr Gly Leu
65                  70                  75                  80

Gln Ala Glu Asp Glu Ala Asp Tyr Phe Cys Gln Ser Tyr Asp Asn Ser
                85                  90                  95

Leu Ser Gly Tyr Val Phe Gly Thr Gly Thr Lys Val Thr Val Leu Gly
            100                 105                 110

<210> SEQ ID NO 95
<211> LENGTH: 112
<212> TYPE: PRT
<213> ORGANISM: Artificial Sequence
<220> FEATURE:
<223> OTHER INFORMATION: LCVR 35

<400> SEQUENCE: 95

Ser Tyr Val Leu Thr Gln Pro Pro Ser Ala Ser Gly Thr Pro Gly Gln
1               5                   10                  15

Arg Val Thr Ile Ser Cys Ser Gly Ser Thr Phe Asn Ile Gly Ser Asn
            20                  25                  30

Thr Val Asn Trp Tyr Gln Gln Leu Pro Ala Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Ala Ala Ala Tyr Tyr Cys Ala Ala Trp Asp Asp Ser Leu
                85                  90                  95

Ser Gly His Val Val Phe Gly Gly Gly Thr Lys Leu Thr Val Leu Gly
            100                 105                 110

<210> SEQ ID NO 96
<211> LENGTH: 109
<212> TYPE: PRT
<213> ORGANISM: Artificial Sequence
<220> FEATURE:
<223> OTHER INFORMATION: LCVR 36

<400> SEQUENCE: 96

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Asn Trp Tyr Gln Gln Lys Pro Gly Gln Ala Pro Val Leu Val Ile Tyr
```

```
                35                  40                  45
Ala Lys Ser Asn Arg Pro Ser Gly Ile Ala Asp Arg Phe Ser Gly Ser
            50                  55                  60
Ser Ser Gly Asn Thr Ala Ser Leu Thr Ile Thr Gly Ala Gln Ala Glu
65                  70                  75                  80
Asp Glu Ala Asp Tyr Tyr Cys Asn Ser Arg Asp Ser Ser Gly Asn Arg
                85                  90                  95
Trp Val Phe Gly Gly Gly Thr Lys Val Thr Val Leu Gly
            100                 105
```

<210> SEQ ID NO 97
<211> LENGTH: 111
<212> TYPE: PRT
<213> ORGANISM: Artificial Sequence
<220> FEATURE:
<223> OTHER INFORMATION: LCVR 37

<400> SEQUENCE: 97

```
Ser Tyr Val Leu Thr Gln Pro Pro Ser Ala Ser Gly Thr Pro Gly Gln
1               5                   10                  15
Arg Val Thr Ile Ser Cys Ser Gly Ser Ser Asn Ile Gly Ser Asn
            20                  25                  30
Thr Val Asn Trp Tyr Gln Gln Leu Pro Gly Thr Ala Pro Lys Leu Leu
                35                  40                  45
Ile Tyr Ser Asn Asn Gln Arg Pro Ser Gly Val Pro Asp Arg Phe Ser
            50                  55                  60
Gly Ser Lys Ser Gly Thr Ser Ala Ser Leu Ala Ile Ser Gly Leu Gln
65                  70                  75                  80
Ser Glu Asp Glu Ala Asp Tyr Tyr Cys Ala Ala Trp Asp Asp Ser Leu
                85                  90                  95
Asn Gly Tyr Val Phe Gly Thr Gly Thr Lys Val Thr Val Leu Gly
            100                 105                 110
```

<210> SEQ ID NO 98
<211> LENGTH: 109
<212> TYPE: PRT
<213> ORGANISM: Artificial Sequence
<220> FEATURE:
<223> OTHER INFORMATION: LCVR 38

<400> SEQUENCE: 98

```
Ser Tyr Glu Leu Thr Gln Pro Pro Ser Val Ser Val Ala Pro Gly Lys
1               5                   10                  15
Thr Ala Arg Ile Thr Cys Gly Gly Asn Asn Ile Gly Ser Lys Ser Val
            20                  25                  30
Asn Trp Tyr Gln Gln Lys Pro Gly Gln Ala Pro Val Leu Val Ile Tyr
                35                  40                  45
Tyr Asp Asn Asp Arg Pro Ser Gly Ile Pro Glu Arg Phe Ser Gly Ser
            50                  55                  60
Asn Ser Gly Asn Thr Ala Thr Leu Thr Ile Ser Arg Val Glu Ala Gly
65                  70                  75                  80
Asp Glu Ala Asp Tyr Tyr Cys Gln Val Trp Asn Ser Ser Ser Asp His
                85                  90                  95
Tyr Val Phe Gly Thr Gly Thr Lys Val Thr Val Leu Gly
            100                 105
```

<210> SEQ ID NO 99
<211> LENGTH: 8

```
<212> TYPE: PRT
<213> ORGANISM: Artificial Sequence
<220> FEATURE:
<223> OTHER INFORMATION: HC-CDR1 1 5

<400> SEQUENCE: 99

Gly Tyr Ser Phe Thr Ser Tyr Trp
1               5

<210> SEQ ID NO 100
<211> LENGTH: 8
<212> TYPE: PRT
<213> ORGANISM: Artificial Sequence
<220> FEATURE:
<223> OTHER INFORMATION: HC-CDR1 1 31

<400> SEQUENCE: 100

Gly Leu Thr Phe Asp Arg Tyr Ala
1               5

<210> SEQ ID NO 101
<211> LENGTH: 8
<212> TYPE: PRT
<213> ORGANISM: Artificial Sequence
<220> FEATURE:
<223> OTHER INFORMATION: HC-CDR1 1 32

<400> SEQUENCE: 101

Gly Tyr Thr Phe Thr Ser Tyr Thr
1               5

<210> SEQ ID NO 102
<211> LENGTH: 8
<212> TYPE: PRT
<213> ORGANISM: Artificial Sequence
<220> FEATURE:
<223> OTHER INFORMATION: HC-CDR1 1 33

<400> SEQUENCE: 102

Ala Gly Thr Phe Asn Arg Tyr Ser
1               5

<210> SEQ ID NO 103
<211> LENGTH: 8
<212> TYPE: PRT
<213> ORGANISM: Artificial Sequence
<220> FEATURE:
<223> OTHER INFORMATION: HC-CDR1 1 34

<400> SEQUENCE: 103

Gly Gly Thr Phe Ser Ser Tyr Ala
1               5

<210> SEQ ID NO 104
<211> LENGTH: 8
<212> TYPE: PRT
<213> ORGANISM: Artificial Sequence
<220> FEATURE:
<223> OTHER INFORMATION: HC-CDR1 1 35

<400> SEQUENCE: 104

Gly Tyr Thr Phe Thr Ser Tyr Gly
1               5

<210> SEQ ID NO 105
<211> LENGTH: 8
<212> TYPE: PRT
```

```
<213> ORGANISM: Artificial Sequence
<220> FEATURE:
<223> OTHER INFORMATION: HC-CDR1 1 36

<400> SEQUENCE: 105

Gly Tyr Thr Phe Thr Gly Tyr Tyr
1               5

<210> SEQ ID NO 106
<211> LENGTH: 8
<212> TYPE: PRT
<213> ORGANISM: Artificial Sequence
<220> FEATURE:
<223> OTHER INFORMATION: HC-CDR1 1 37

<400> SEQUENCE: 106

Gly Tyr Thr Val Thr Ser Tyr Gly
1               5

<210> SEQ ID NO 107
<211> LENGTH: 8
<212> TYPE: PRT
<213> ORGANISM: Artificial Sequence
<220> FEATURE:
<223> OTHER INFORMATION: HC-CDR1 1 38

<400> SEQUENCE: 107

Gly Tyr Thr Phe Thr Asp Tyr Tyr
1               5

<210> SEQ ID NO 108
<211> LENGTH: 8
<212> TYPE: PRT
<213> ORGANISM: Artificial Sequence
<220> FEATURE:
<223> OTHER INFORMATION: HC-CDR2 1 5

<400> SEQUENCE: 108

Ile Tyr Pro Gly Asp Ser Asp Thr
1               5

<210> SEQ ID NO 109
<211> LENGTH: 8
<212> TYPE: PRT
<213> ORGANISM: Artificial Sequence
<220> FEATURE:
<223> OTHER INFORMATION: HC-CDR2 1 31

<400> SEQUENCE: 109

Ile Thr Gly Asp Gly Tyr Tyr Thr
1               5

<210> SEQ ID NO 110
<211> LENGTH: 8
<212> TYPE: PRT
<213> ORGANISM: Artificial Sequence
<220> FEATURE:
<223> OTHER INFORMATION: HC-CDR2 1 32

<400> SEQUENCE: 110

Ile Ser Pro Tyr Asn Gly Asn Thr
1               5

<210> SEQ ID NO 111
<211> LENGTH: 8
<212> TYPE: PRT
<213> ORGANISM: Artificial Sequence
```

```
<220> FEATURE:
<223> OTHER INFORMATION: HC-CDR2 1 33

<400> SEQUENCE: 111

Ile Ile Pro Ile Ile Gly Val Ala
1               5

<210> SEQ ID NO 112
<211> LENGTH: 8
<212> TYPE: PRT
<213> ORGANISM: Artificial Sequence
<220> FEATURE:
<223> OTHER INFORMATION: HC-CDR2 1 34

<400> SEQUENCE: 112

Ile Ile Pro Ile Phe Gly Thr Ala
1               5

<210> SEQ ID NO 113
<211> LENGTH: 8
<212> TYPE: PRT
<213> ORGANISM: Artificial Sequence
<220> FEATURE:
<223> OTHER INFORMATION: HC-CDR2 1 35

<400> SEQUENCE: 113

Ile Ser Ala Tyr Asn Gly Asn Thr
1               5

<210> SEQ ID NO 114
<211> LENGTH: 8
<212> TYPE: PRT
<213> ORGANISM: Artificial Sequence
<220> FEATURE:
<223> OTHER INFORMATION: HC-CDR2 1 36

<400> SEQUENCE: 114

Phe Asp Pro Glu Asp Gly Glu Thr
1               5

<210> SEQ ID NO 115
<211> LENGTH: 8
<212> TYPE: PRT
<213> ORGANISM: Artificial Sequence
<220> FEATURE:
<223> OTHER INFORMATION: HC-CDR2 1 37

<400> SEQUENCE: 115

Ile Ser Ala Tyr Asn Gly Asp Thr
1               5

<210> SEQ ID NO 116
<211> LENGTH: 8
<212> TYPE: PRT
<213> ORGANISM: Artificial Sequence
<220> FEATURE:
<223> OTHER INFORMATION: HC-CDR2 1 38

<400> SEQUENCE: 116

Ile Asn Pro His Ser Gly Gly Thr
1               5

<210> SEQ ID NO 117
<211> LENGTH: 6
<212> TYPE: PRT
<213> ORGANISM: Artificial Sequence
<220> FEATURE:
```

```
<223> OTHER INFORMATION: HC-CDR3 1 5

<400> SEQUENCE: 117

Ala Arg Gly Tyr Asp Gly
1               5

<210> SEQ ID NO 118
<211> LENGTH: 6
<212> TYPE: PRT
<213> ORGANISM: Artificial Sequence
<220> FEATURE:
<223> OTHER INFORMATION: HC-CDR3 1 10

<400> SEQUENCE: 118

Ala Arg Gly Phe Asp Asn
1               5

<210> SEQ ID NO 119
<211> LENGTH: 6
<212> TYPE: PRT
<213> ORGANISM: Artificial Sequence
<220> FEATURE:
<223> OTHER INFORMATION: HC-CDR3 1 13

<400> SEQUENCE: 119

Ala Arg Gly Tyr Asp Val
1               5

<210> SEQ ID NO 120
<211> LENGTH: 6
<212> TYPE: PRT
<213> ORGANISM: Artificial Sequence
<220> FEATURE:
<223> OTHER INFORMATION: HC-CDR3 1 16

<400> SEQUENCE: 120

Ala Arg Gly Tyr Asp Ser
1               5

<210> SEQ ID NO 121
<211> LENGTH: 13
<212> TYPE: PRT
<213> ORGANISM: Artificial Sequence
<220> FEATURE:
<223> OTHER INFORMATION: HC-CDR3 1 31

<400> SEQUENCE: 121

Ala Arg Leu Ser Gly Ile Gly Arg Ser Ser Tyr Asp Gly
1               5                   10

<210> SEQ ID NO 122
<211> LENGTH: 12
<212> TYPE: PRT
<213> ORGANISM: Artificial Sequence
<220> FEATURE:
<223> OTHER INFORMATION: HC-CDR3 1 32

<400> SEQUENCE: 122

Ala Arg Ser Trp Glu His Gly Phe Pro Tyr Asp Glu
1               5                   10

<210> SEQ ID NO 123
<211> LENGTH: 11
<212> TYPE: PRT
<213> ORGANISM: Artificial Sequence
<220> FEATURE:
<223> OTHER INFORMATION: HC-CDR3 1 33
```

```
<400> SEQUENCE: 123

Ala Arg Gln Glu Tyr Ser Tyr Ala Met Asp Tyr
1               5                   10

<210> SEQ ID NO 124
<211> LENGTH: 13
<212> TYPE: PRT
<213> ORGANISM: Artificial Sequence
<220> FEATURE:
<223> OTHER INFORMATION: HC-CDR3 1 34

<400> SEQUENCE: 124

Ala Arg Ser Tyr Trp Thr Phe Glu Tyr Ser Ile Asp Ser
1               5                   10

<210> SEQ ID NO 125
<211> LENGTH: 12
<212> TYPE: PRT
<213> ORGANISM: Artificial Sequence
<220> FEATURE:
<223> OTHER INFORMATION: HC-CDR3 1 35

<400> SEQUENCE: 125

Ala Arg Tyr Tyr Glu Ser Gly Tyr Pro Phe Asp Trp
1               5                   10

<210> SEQ ID NO 126
<211> LENGTH: 14
<212> TYPE: PRT
<213> ORGANISM: Artificial Sequence
<220> FEATURE:
<223> OTHER INFORMATION: HC-CDR3 1 36

<400> SEQUENCE: 126

Ala Arg Ser Ser Trp Trp Ser Pro Val Thr Tyr Tyr Asp Ile
1               5                   10

<210> SEQ ID NO 127
<211> LENGTH: 16
<212> TYPE: PRT
<213> ORGANISM: Artificial Sequence
<220> FEATURE:
<223> OTHER INFORMATION: HC-CDR3 1 37

<400> SEQUENCE: 127

Ala Arg Ser Ser Leu Pro Phe Gly Val Val Pro Asn Ala Phe Asp Ile
1               5                   10                  15

<210> SEQ ID NO 128
<211> LENGTH: 13
<212> TYPE: PRT
<213> ORGANISM: Artificial Sequence
<220> FEATURE:
<223> OTHER INFORMATION: HC-CDR3 1 38

<400> SEQUENCE: 128

Ala Arg Glu Asp Tyr Ser Gly Ser Gly Ser Ser Asp Ala
1               5                   10

<210> SEQ ID NO 129
<211> LENGTH: 11
<212> TYPE: PRT
<213> ORGANISM: Artificial Sequence
<220> FEATURE:
<223> OTHER INFORMATION: LC-CDR1 1 5
```

```
<400> SEQUENCE: 129

Gln Ser Leu Val Tyr Ser Asn Gly Asn Thr Tyr
1               5                   10

<210> SEQ ID NO 130
<211> LENGTH: 11
<212> TYPE: PRT
<213> ORGANISM: Artificial Sequence
<220> FEATURE:
<223> OTHER INFORMATION: LC-CDR1 1 13

<400> SEQUENCE: 130

Gln Ser Leu Ile Tyr Ser Asn Gly Asn Thr Tyr
1               5                   10

<210> SEQ ID NO 131
<211> LENGTH: 9
<212> TYPE: PRT
<213> ORGANISM: Artificial Sequence
<220> FEATURE:
<223> OTHER INFORMATION: LC-CDR1 1 31

<400> SEQUENCE: 131

Ser Gly Ile Asn Val Gly Thr Tyr Arg
1               5

<210> SEQ ID NO 132
<211> LENGTH: 9
<212> TYPE: PRT
<213> ORGANISM: Artificial Sequence
<220> FEATURE:
<223> OTHER INFORMATION: LC-CDR1 1 32

<400> SEQUENCE: 132

Ser Ser Asn Leu Gly Ala Gly Tyr Asp
1               5

<210> SEQ ID NO 133
<211> LENGTH: 9
<212> TYPE: PRT
<213> ORGANISM: Artificial Sequence
<220> FEATURE:
<223> OTHER INFORMATION: LC-CDR1 1 33

<400> SEQUENCE: 133

Ser Ser Asn Ile Gly Ala Gly Tyr Asp
1               5

<210> SEQ ID NO 134
<211> LENGTH: 9
<212> TYPE: PRT
<213> ORGANISM: Artificial Sequence
<220> FEATURE:
<223> OTHER INFORMATION: LC-CDR1 1 34

<400> SEQUENCE: 134

Ser Leu Asn Leu Gly Ala Gly Tyr Asp
1               5

<210> SEQ ID NO 135
<211> LENGTH: 8
<212> TYPE: PRT
<213> ORGANISM: Artificial Sequence
<220> FEATURE:
<223> OTHER INFORMATION: LC-CDR1 1 35

<400> SEQUENCE: 135
```

Thr Phe Asn Ile Gly Ser Asn Thr
1               5

<210> SEQ ID NO 136
<211> LENGTH: 6
<212> TYPE: PRT
<213> ORGANISM: Artificial Sequence
<220> FEATURE:
<223> OTHER INFORMATION: LC-CDR1 1 36

<400> SEQUENCE: 136

Ser Leu Arg Ser Tyr Tyr
1               5

<210> SEQ ID NO 137
<211> LENGTH: 8
<212> TYPE: PRT
<213> ORGANISM: Artificial Sequence
<220> FEATURE:
<223> OTHER INFORMATION: LC-CDR1 1 37

<400> SEQUENCE: 137

Ser Ser Asn Ile Gly Ser Asn Thr
1               5

<210> SEQ ID NO 138
<211> LENGTH: 6
<212> TYPE: PRT
<213> ORGANISM: Artificial Sequence
<220> FEATURE:
<223> OTHER INFORMATION: LC-CDR1 1 38

<400> SEQUENCE: 138

Asn Ile Gly Ser Lys Ser
1               5

<210> SEQ ID NO 139
<211> LENGTH: 3
<212> TYPE: PRT
<213> ORGANISM: Artificial Sequence
<220> FEATURE:
<223> OTHER INFORMATION: LC-CDR2 1 5

<400> SEQUENCE: 139

Glu Val Ser
1

<210> SEQ ID NO 140
<211> LENGTH: 3
<212> TYPE: PRT
<213> ORGANISM: Artificial Sequence
<220> FEATURE:
<223> OTHER INFORMATION: LC-CDR2 1 10

<400> SEQUENCE: 140

Lys Val Ser
1

<210> SEQ ID NO 141
<211> LENGTH: 7
<212> TYPE: PRT
<213> ORGANISM: Artificial Sequence
<220> FEATURE:
<223> OTHER INFORMATION: LC-CDR2 1 31

<400> SEQUENCE: 141

Tyr Lys Ser Asp Ser Asp Lys
1               5

<210> SEQ ID NO 142
<211> LENGTH: 3
<212> TYPE: PRT
<213> ORGANISM: Artificial Sequence
<220> FEATURE:
<223> OTHER INFORMATION: LC-CDR2 1 32

<400> SEQUENCE: 142

Phe Asn Asn
1

<210> SEQ ID NO 143
<211> LENGTH: 3
<212> TYPE: PRT
<213> ORGANISM: Artificial Sequence
<220> FEATURE:
<223> OTHER INFORMATION: LC-CDR2 1 33

<400> SEQUENCE: 143

Gly Asn Asn
1

<210> SEQ ID NO 144
<211> LENGTH: 3
<212> TYPE: PRT
<213> ORGANISM: Artificial Sequence
<220> FEATURE:
<223> OTHER INFORMATION: LC-CDR2 1 34

<400> SEQUENCE: 144

Ala Asn Thr
1

<210> SEQ ID NO 145
<211> LENGTH: 3
<212> TYPE: PRT
<213> ORGANISM: Artificial Sequence
<220> FEATURE:
<223> OTHER INFORMATION: LC-CDR2 1 35

<400> SEQUENCE: 145

Ser Asn Asn
1

<210> SEQ ID NO 146
<211> LENGTH: 3
<212> TYPE: PRT
<213> ORGANISM: Artificial Sequence
<220> FEATURE:
<223> OTHER INFORMATION: LC-CDR2 1 36

<400> SEQUENCE: 146

Ala Lys Ser
1

<210> SEQ ID NO 147
<211> LENGTH: 3
<212> TYPE: PRT
<213> ORGANISM: Artificial Sequence
<220> FEATURE:
<223> OTHER INFORMATION: LC-CDR2 1 38

<400> SEQUENCE: 147

Tyr Asp Asn

```
<210> SEQ ID NO 148
<211> LENGTH: 9
<212> TYPE: PRT
<213> ORGANISM: Artificial Sequence
<220> FEATURE:
<223> OTHER INFORMATION: LC-CDR3 1 5

<400> SEQUENCE: 148

Met Gln Gly Thr His Trp Pro Pro Thr
1               5

<210> SEQ ID NO 149
<211> LENGTH: 9
<212> TYPE: PRT
<213> ORGANISM: Artificial Sequence
<220> FEATURE:
<223> OTHER INFORMATION: LC-CDR3 1 10

<400> SEQUENCE: 149

Met Gln Gly Thr Tyr Trp Pro Tyr Thr
1               5

<210> SEQ ID NO 150
<211> LENGTH: 7
<212> TYPE: PRT
<213> ORGANISM: Artificial Sequence
<220> FEATURE:
<223> OTHER INFORMATION: LC-CDR3 1 31

<400> SEQUENCE: 150

Met Ile Trp His Ser Ser Ala
1               5

<210> SEQ ID NO 151
<211> LENGTH: 11
<212> TYPE: PRT
<213> ORGANISM: Artificial Sequence
<220> FEATURE:
<223> OTHER INFORMATION: LC-CDR3 1 32

<400> SEQUENCE: 151

Gln Ser Tyr Asp Ser Ser Leu Ser Ala Ser Val
1               5                   10

<210> SEQ ID NO 152
<211> LENGTH: 10
<212> TYPE: PRT
<213> ORGANISM: Artificial Sequence
<220> FEATURE:
<223> OTHER INFORMATION: LC-CDR3 1 33

<400> SEQUENCE: 152

Gln Ser Tyr Asp Thr Ser Leu Thr Pro Val
1               5                   10

<210> SEQ ID NO 153
<211> LENGTH: 11
<212> TYPE: PRT
<213> ORGANISM: Artificial Sequence
<220> FEATURE:
<223> OTHER INFORMATION: LC-CDR3 1 34

<400> SEQUENCE: 153

Gln Ser Tyr Asp Asn Ser Leu Ser Gly Tyr Val
1               5                   10
```

<210> SEQ ID NO 154
<211> LENGTH: 12
<212> TYPE: PRT
<213> ORGANISM: Artificial Sequence
<220> FEATURE:
<223> OTHER INFORMATION: LC-CDR3 1 35

<400> SEQUENCE: 154

Ala Ala Trp Asp Asp Ser Leu Ser Gly His Val Val
1               5                   10

<210> SEQ ID NO 155
<211> LENGTH: 9
<212> TYPE: PRT
<213> ORGANISM: Artificial Sequence
<220> FEATURE:
<223> OTHER INFORMATION: LC-CDR3 1 36

<400> SEQUENCE: 155

Asn Ser Arg Asp Ser Ser Gly Asn Arg
1               5

<210> SEQ ID NO 156
<211> LENGTH: 11
<212> TYPE: PRT
<213> ORGANISM: Artificial Sequence
<220> FEATURE:
<223> OTHER INFORMATION: LC-CDR3 1 37

<400> SEQUENCE: 156

Ala Ala Trp Asp Asp Ser Leu Asn Gly Tyr Val
1               5                   10

<210> SEQ ID NO 157
<211> LENGTH: 11
<212> TYPE: PRT
<213> ORGANISM: Artificial Sequence
<220> FEATURE:
<223> OTHER INFORMATION: LC-CDR3 1 38

<400> SEQUENCE: 157

Gln Val Trp Asn Ser Ser Ser Asp His Tyr Val
1               5                   10

<210> SEQ ID NO 158
<211> LENGTH: 7
<212> TYPE: PRT
<213> ORGANISM: Artificial Sequence
<220> FEATURE:
<223> OTHER INFORMATION: HC-CDR1 consensus
<220> FEATURE:
<221> NAME/KEY: VARIANT
<222> LOCATION: 1
<223> OTHER INFORMATION: Xaa = Ala or Gly
<220> FEATURE:
<221> NAME/KEY: VARIANT
<222> LOCATION: 2
<223> OTHER INFORMATION: Xaa = Gly or Tyr
<220> FEATURE:
<221> NAME/KEY: VARIANT
<222> LOCATION: 3
<223> OTHER INFORMATION: Xaa = Ser or Thr
<220> FEATURE:
<221> NAME/KEY: VARIANT
<222> LOCATION: 5
<223> OTHER INFORMATION: Xaa = Ser or Thr
<220> FEATURE:
<221> NAME/KEY: VARIANT
<222> LOCATION: 6

```
<223> OTHER INFORMATION: Xaa = Any Amino Acid

<400> SEQUENCE: 158

Xaa Xaa Xaa Phe Xaa Xaa Tyr
1               5

<210> SEQ ID NO 159
<211> LENGTH: 8
<212> TYPE: PRT
<213> ORGANISM: Artificial Sequence
<220> FEATURE:
<223> OTHER INFORMATION: HC-CDR2 consensus
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 3
<223> OTHER INFORMATION: Xaa = Ala or Pro
<220> FEATURE:
<221> NAME/KEY: VARIANT
<222> LOCATION: 4
<223> OTHER INFORMATION: Xaa = Any Amino Acid
<220> FEATURE:
<221> NAME/KEY: VARIANT
<222> LOCATION: 5
<223> OTHER INFORMATION: Xaa = Any Amino Acid
<220> FEATURE:
<221> NAME/KEY: VARIANT
<222> LOCATION: 7
<223> OTHER INFORMATION: Xaa = Any Amino Acid
<220> FEATURE:
<221> NAME/KEY: VARIANT
<222> LOCATION: 8
<223> OTHER INFORMATION: Xaa = Ala or Thr

<400> SEQUENCE: 159

Ile Xaa Xaa Xaa Xaa Gly Xaa Xaa
1               5

<210> SEQ ID NO 160
<211> LENGTH: 5
<212> TYPE: PRT
<213> ORGANISM: Artificial Sequence
<220> FEATURE:
<223> OTHER INFORMATION: HC-CDR3 consensus 1
<220> FEATURE:
<221> NAME/KEY: VARIANT
<222> LOCATION: 4
<223> OTHER INFORMATION: Xaa = Phe or Tyr

<400> SEQUENCE: 160

Ala Arg Gly Xaa Asp
1               5

<210> SEQ ID NO 161
<211> LENGTH: 11
<212> TYPE: PRT
<213> ORGANISM: Artificial Sequence
<220> FEATURE:
<223> OTHER INFORMATION: HC-CDR3 consensus 2
<220> FEATURE:
<221> NAME/KEY: VARIANT
<222> LOCATION: 3
<223> OTHER INFORMATION: Xaa = Any Amino Acid
<220> FEATURE:
<221> NAME/KEY: VARIANT
<222> LOCATION: 4
<223> OTHER INFORMATION: Xaa = Trp or Tyr
<220> FEATURE:
<221> NAME/KEY: VARIANT
<222> LOCATION: 6
```

-continued

```
<223> OTHER INFORMATION: Xaa = Any Amino Acid
<220> FEATURE:
<221> NAME/KEY: VARIANT
<222> LOCATION: 8
<223> OTHER INFORMATION: Xaa = Phe or Tyr
<220> FEATURE:
<221> NAME/KEY: VARIANT
<222> LOCATION: 10
<223> OTHER INFORMATION: Xaa = Phe or Tyr

<400> SEQUENCE: 161

Ala Arg Xaa Xaa Glu Xaa Gly Xaa Pro Xaa Asp
1               5                   10

<210> SEQ ID NO 162
<211> LENGTH: 6
<212> TYPE: PRT
<213> ORGANISM: Artificial Sequence
<220> FEATURE:
<223> OTHER INFORMATION: LC-CDR1 consensus
<220> FEATURE:
<221> NAME/KEY: VARIANT
<222> LOCATION: 1
<223> OTHER INFORMATION: Xaa = Ser or Thr
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 4
<223> OTHER INFORMATION: Xaa = Ile, Leu, or Asn
<220> FEATURE:
<221> NAME/KEY: VARIANT
<222> LOCATION: 6
<223> OTHER INFORMATION: Xaa = Ala, Ser, or Thr

<400> SEQUENCE: 162

Xaa Xaa Asn Xaa Gly Xaa
1               5

<210> SEQ ID NO 163
<211> LENGTH: 7
<212> TYPE: PRT
<213> ORGANISM: Artificial Sequence
<220> FEATURE:
<223> OTHER INFORMATION: LC-CDR3 consensus
<220> FEATURE:
<221> NAME/KEY: VARIANT
<222> LOCATION: 1
<223> OTHER INFORMATION: Xaa = Ala or Gln
<220> FEATURE:
<221> NAME/KEY: VARIANT
<222> LOCATION: 2
<223> OTHER INFORMATION: Xaa = Ala or Ser
<220> FEATURE:
<221> NAME/KEY: VARIANT
<222> LOCATION: 3
<223> OTHER INFORMATION: Xaa = Trp or Tyr
<220> FEATURE:
<221> NAME/KEY: VARIANT
<222> LOCATION: 5
<223> OTHER INFORMATION: Xaa = Any Amino Acid

<400> SEQUENCE: 163

Xaa Xaa Xaa Asp Xaa Ser Leu
1               5

<210> SEQ ID NO 164
<211> LENGTH: 502
<212> TYPE: PRT
<213> ORGANISM: Artificial Sequence
<220> FEATURE:
```

-continued

<223> OTHER INFORMATION: BsAb #32

<400> SEQUENCE: 164

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Leu Gly Ala Gly
            20                  25                  30

Tyr Asp Val His Trp Tyr Gln Gln Leu Pro Gly Thr Ala Pro Lys Val
        35                  40                  45

Leu Val Tyr Phe Asn Asn Asn Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Ala Ser Val Phe Gly Thr Gly Thr Lys Val Thr Val Leu Gly
            100                 105                 110

Ser Arg Gly Gly Gly Gly Ser Gly Gly Gly Ser Gly Gly Gly Gly
            115                 120                 125

Ser Leu Glu Met Ala Gln Val Gln Leu Val Gln Ser Gly Ala Glu Val
130                 135                 140

Lys Lys Pro Gly Ala Ser Val Lys Val Ser Cys Lys Ala Ser Gly Tyr
145                 150                 155                 160

Thr Phe Thr Ser Tyr Thr Ile Thr Trp Val Arg Gln Ala Pro Gly Gln
            165                 170                 175

Gly Leu Glu Trp Met Gly Trp Ile Ser Pro Tyr Asn Gly Asn Thr Asn
            180                 185                 190

Tyr Ala Gln Asn Leu Gln Gly Arg Val Thr Met Thr Thr Asp Thr Ser
        195                 200                 205

Thr Thr Thr Ala Tyr Met Glu Leu Arg Ser Leu Thr Ser Asp Asp Thr
    210                 215                 220

Ala Val Tyr Tyr Cys Ala Arg Ser Trp Glu His Gly Phe Pro Tyr Asp
225                 230                 235                 240

Glu Trp Gly Gln Gly Thr Leu Val Thr Val Ser Ser Thr Ser Gly Gly
                245                 250                 255

Gly Gly Ser Asp Val Gln Leu Val Gln Ser Gly Ala Glu Val Lys Lys
            260                 265                 270

Pro Gly Ala Ser Val Lys Val Ser Cys Lys Ala Ser Gly Tyr Thr Phe
        275                 280                 285

Thr Arg Tyr Thr Met His Trp Val Arg Gln Ala Pro Gly Gln Gly Leu
    290                 295                 300

Glu Trp Ile Gly Tyr Ile Asn Pro Ser Arg Gly Tyr Thr Asn Tyr Ala
305                 310                 315                 320

Asp Ser Val Lys Gly Arg Phe Thr Ile Thr Asp Lys Ser Thr Ser Thr
                325                 330                 335

Thr Ala Tyr Met Glu Leu Ser Ser Leu Arg Ser Glu Asp Thr Ala Thr
            340                 345                 350

Tyr Tyr Cys Ala Arg Tyr Tyr Asp Asp His Tyr Cys Leu Asp Tyr Trp
        355                 360                 365

Gly Gln Gly Thr Thr Val Thr Val Ser Ser Gly Glu Gly Thr Ser Thr
    370                 375                 380

Gly Ser Gly Gly Ser Gly Gly Ser Gly Gly Ala Asp Asp Ile Val Leu
385                 390                 395                 400

```
Thr Gln Ser Pro Ala Thr Leu Ser Leu Ser Pro Gly Glu Arg Ala Thr
                405                 410                 415
Leu Ser Cys Arg Ala Ser Gln Ser Val Ser Tyr Met Asn Trp Tyr Gln
            420                 425                 430
Gln Lys Pro Gly Lys Ala Pro Lys Arg Trp Ile Tyr Asp Thr Ser Lys
        435                 440                 445
Val Ala Ser Gly Val Pro Ala Arg Phe Ser Gly Ser Gly Ser Gly Thr
    450                 455                 460
Asp Tyr Ser Leu Thr Ile Asn Ser Leu Glu Ala Glu Asp Ala Ala Thr
465                 470                 475                 480
Tyr Tyr Cys Gln Gln Trp Ser Ser Asn Pro Leu Thr Phe Gly Gly Gly
                485                 490                 495
Thr Lys Val Glu Ile Lys
                500

<210> SEQ ID NO 165
<211> LENGTH: 503
<212> TYPE: PRT
<213> ORGANISM: Artificial Sequence
<220> FEATURE:
<223> OTHER INFORMATION: BsAb #34

<400> SEQUENCE: 165

Gln Ser Val Leu Thr Gln Pro Pro Ser Val Ser Gly Ala Pro Gly Gln
1               5                   10                  15
Arg Val Thr Ile Ser Cys Thr Gly Ser Ser Leu Asn Leu Gly Ala Gly
            20                  25                  30
Tyr Asp Val His Trp Tyr Gln Gln Phe Pro Gly Thr Ala Pro Lys Leu
        35                  40                  45
Leu Ile Phe Ala Asn Thr Asn Arg Pro Ser Gly Val Pro Asp Arg Phe
    50                  55                  60
Ser Ala Ser Lys Ser Gly Thr Ser Ala Ser Leu Ala Ile Thr Gly Leu
65                  70                  75                  80
Gln Ala Glu Asp Glu Ala Asp Tyr Phe Cys Gln Ser Tyr Asp Asn Ser
                85                  90                  95
Leu Ser Gly Tyr Val Phe Gly Thr Gly Thr Lys Val Thr Val Leu Gly
                100                 105                 110
Ser Arg Gly Gly Gly Gly Ser Gly Gly Gly Ser Gly Gly Gly Gly
            115                 120                 125
Ser Leu Glu Met Ala Gln Val Gln Leu Val Gln Ser Gly Ala Glu Val
        130                 135                 140
Lys Lys Pro Gly Ser Ser Val Lys Val Ser Cys Lys Ala Ser Gly Gly
145                 150                 155                 160
Thr Phe Ser Ser Tyr Ala Ile Ser Trp Val Arg Gln Ala Pro Gly Gln
                165                 170                 175
Gly Leu Glu Trp Met Gly Gly Ile Ile Pro Ile Phe Gly Thr Ala Asn
            180                 185                 190
Tyr Ala Gln Lys Phe Gln Gly Arg Val Thr Ile Thr Ala Asp Glu Ser
        195                 200                 205
Thr Ser Thr Ala Tyr Met Glu Leu Ser Ser Leu Arg Ser Glu Asp Thr
    210                 215                 220
Ala Val Tyr Tyr Cys Ala Arg Ser Tyr Trp Thr Phe Glu Tyr Ser Ile
225                 230                 235                 240
Asp Ser Trp Gly Gln Gly Thr Leu Val Thr Val Ser Ser Thr Ser Gly
                245                 250                 255
```

```
Gly Gly Gly Ser Asp Val Gln Leu Val Gln Ser Gly Ala Glu Val Lys
            260                 265                 270
Lys Pro Gly Ala Ser Val Lys Val Ser Cys Lys Ala Ser Gly Tyr Thr
        275                 280                 285
Phe Thr Arg Tyr Thr Met His Trp Val Arg Gln Ala Pro Gly Gln Gly
290                 295                 300
Leu Glu Trp Ile Gly Tyr Ile Asn Pro Ser Arg Gly Tyr Thr Asn Tyr
305                 310                 315                 320
Ala Asp Ser Val Lys Gly Arg Phe Thr Ile Thr Thr Asp Lys Ser Thr
                325                 330                 335
Ser Thr Ala Tyr Met Glu Leu Ser Ser Leu Arg Ser Glu Asp Thr Ala
            340                 345                 350
Thr Tyr Tyr Cys Ala Arg Tyr Tyr Asp Asp His Tyr Cys Leu Asp Tyr
        355                 360                 365
Trp Gly Gln Gly Thr Thr Val Thr Val Ser Ser Gly Glu Gly Thr Ser
370                 375                 380
Thr Gly Ser Gly Gly Ser Gly Gly Ser Gly Gly Ala Asp Asp Ile Val
385                 390                 395                 400
Leu Thr Gln Ser Pro Ala Thr Leu Ser Leu Ser Pro Gly Glu Arg Ala
                405                 410                 415
Thr Leu Ser Cys Arg Ala Ser Gln Ser Val Ser Tyr Met Asn Trp Tyr
            420                 425                 430
Gln Gln Lys Pro Gly Lys Ala Pro Lys Arg Trp Ile Tyr Asp Thr Ser
        435                 440                 445
Lys Val Ala Ser Gly Val Pro Ala Arg Phe Ser Gly Ser Gly Ser Gly
450                 455                 460
Thr Asp Tyr Ser Leu Thr Ile Asn Ser Leu Glu Ala Glu Asp Ala Ala
465                 470                 475                 480
Thr Tyr Tyr Cys Gln Gln Trp Ser Ser Asn Pro Leu Thr Phe Gly Gly
                485                 490                 495
Gly Thr Lys Val Glu Ile Lys
            500

<210> SEQ ID NO 166
<211> LENGTH: 502
<212> TYPE: PRT
<213> ORGANISM: Artificial Sequence
<220> FEATURE:
<223> OTHER INFORMATION: BsAb #35

<400> SEQUENCE: 166

Ser Tyr Val Leu Thr Gln Pro Pro Ser Ala Ser Gly Thr Pro Gly Gln
1               5                   10                  15
Arg Val Thr Ile Ser Cys Ser Gly Ser Thr Phe Asn Ile Gly Ser Asn
            20                  25                  30
Thr Val Asn Trp Tyr Gln Gln Leu Pro Ala Thr Ala Pro Lys Leu Leu
        35                  40                  45
Ile Tyr Ser Asn Asn Gln Arg Pro Ser Gly Val Pro Asp Arg Phe Ser
    50                  55                  60
Gly Ser Lys Ser Gly Thr Ser Ala Ser Leu Ala Ile Ser Gly Leu Gln
65                  70                  75                  80
Ser Glu Asp Ala Ala Ala Tyr Tyr Cys Ala Ala Trp Asp Asp Ser Leu
                85                  90                  95
Ser Gly His Val Val Phe Gly Gly Gly Thr Lys Leu Thr Val Leu Gly
            100                 105                 110
```

Ser Arg Gly Gly Gly Ser Gly Gly Gly Ser Gly Gly Gly
            115                 120                 125

Ser Leu Glu Met Ala Glu Val Gln Leu Val Gln Ser Gly Ala Glu Val
130                 135                 140

Lys Lys Pro Gly Ala Ser Val Lys Val Ser Cys Lys Ala Ser Gly Tyr
145                 150                 155                 160

Thr Phe Thr Ser Tyr Gly Ile Ser Trp Val Arg Gln Ala Pro Gly Gln
                165                 170                 175

Gly Leu Glu Trp Met Gly Trp Ile Ser Ala Tyr Asn Gly Asn Thr Asn
            180                 185                 190

Tyr Ala Gln Lys Leu Gln Gly Arg Val Thr Met Thr Thr Asp Thr Ser
        195                 200                 205

Thr Ser Thr Ala Tyr Met Glu Leu Arg Ser Leu Arg Ser Asp Asp Thr
    210                 215                 220

Ala Val Tyr Tyr Cys Ala Arg Tyr Tyr Glu Ser Gly Tyr Pro Phe Asp
225                 230                 235                 240

Trp Trp Gly Gln Gly Thr Leu Val Thr Val Ser Ser Thr Ser Gly Gly
                245                 250                 255

Gly Gly Ser Asp Val Gln Leu Val Gln Ser Gly Ala Glu Val Lys Lys
            260                 265                 270

Pro Gly Ala Ser Val Lys Val Ser Cys Lys Ala Ser Gly Tyr Thr Phe
        275                 280                 285

Thr Arg Tyr Thr Met His Trp Val Arg Gln Ala Pro Gly Gln Gly Leu
    290                 295                 300

Glu Trp Ile Gly Tyr Ile Asn Pro Ser Arg Gly Tyr Thr Asn Tyr Ala
305                 310                 315                 320

Asp Ser Val Lys Gly Arg Phe Thr Ile Thr Thr Asp Lys Ser Thr Ser
                325                 330                 335

Thr Ala Tyr Met Glu Leu Ser Ser Leu Arg Ser Glu Asp Thr Ala Thr
            340                 345                 350

Tyr Tyr Cys Ala Arg Tyr Tyr Asp Asp His Tyr Cys Leu Asp Tyr Trp
        355                 360                 365

Gly Gln Gly Thr Thr Val Thr Val Ser Ser Gly Glu Gly Thr Ser Thr
    370                 375                 380

Gly Ser Gly Gly Ser Gly Gly Ser Gly Gly Ala Asp Asp Ile Val Leu
385                 390                 395                 400

Thr Gln Ser Pro Ala Thr Leu Ser Leu Ser Pro Gly Glu Arg Ala Thr
                405                 410                 415

Leu Ser Cys Arg Ala Ser Gln Ser Val Ser Tyr Met Asn Trp Tyr Gln
            420                 425                 430

Gln Lys Pro Gly Lys Ala Pro Lys Arg Trp Ile Tyr Asp Thr Ser Lys
        435                 440                 445

Val Ala Ser Gly Val Pro Ala Arg Phe Ser Gly Ser Gly Ser Gly Thr
    450                 455                 460

Asp Tyr Ser Leu Thr Ile Asn Ser Leu Glu Ala Glu Asp Ala Ala Thr
465                 470                 475                 480

Tyr Tyr Cys Gln Gln Trp Ser Ser Asn Pro Leu Thr Phe Gly Gly Gly
                485                 490                 495

Thr Lys Val Glu Ile Lys
            500

<210> SEQ ID NO 167
<211> LENGTH: 9
<212> TYPE: PRT

```
<213> ORGANISM: Artificial Sequence
<220> FEATURE:
<223> OTHER INFORMATION: Control HIV peptide

<400> SEQUENCE: 167

Tyr Gln Tyr Met Asp Asp Leu Tyr Val
1               5
```

CONSTRUCTS TARGETING HISTONE H3 PEPTIDE/MHC COMPLEXES AND USES THEREOF

CROSS-REFERENCE TO RELATED APPLICATIONS

This application is a U.S. national phase application under 35 U.S.C § 371 of International Application No. PCT/US2018/013362 filed on Jan. 11, 2018, which claims priority to U.S. Provisional Application No. 62/445,665, filed on Jan. 12, 2017, and U.S. Provisional Application No. 62/572,300, filed on Oct. 13, 2017, all of which are hereby incorporated by reference in their entireties.

FIELD OF THE INVENTION

This invention pertains to constructs comprising an antibody moiety that specifically binds to a complex comprising a histone H3 peptide and an MHC class I protein, and methods of making and using these constructs.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 750042000900SEQLIST.TXT, date recorded: Jul. 11, 2019, size: 85 KB).

BACKGROUND OF THE INVENTION

Cell surface proteins constitute only a small fraction of the cellular proteins and these proteins are often not tumor-specific. Because of the inability to easily penetrate cells, marketed therapeutic monoclonal antibodies (mAbs) recognize these cell surface proteins, most of which are lineage or differentiation antigens (Milenic, E. D., *Curr. Pharm. Des.* 8:1794-1764, 2002; Grillo-Lopez, A. J., *Expert Rev. Anticancer Ther.* 2(3):323-329, 2002; Jones, K. L. & Buzdat, A. U., *Lancet Oncol.* 10(12):1179-1187, 2009). In contrast, mutated or oncogenic tumor-associated proteins are typically nuclear, cytoplasmic or secreted, which are currently best addressed either by small molecule drugs, or in the case of secreted proteins, hardly addressed as anti-cancer drug targets (Reddy et al., *Expert Opin. Ther. Targets* 3:313-324, 2012; Takeuchi, K. & Ito, F., *Biol. Pharm. Bull.* 34(12): 1774-1780; Roychowdhury, S. & Talpaz, M., *Blood Rev.* 6:279-290, 2011). However, most intracellular proteins can be proteosomally degraded, processed and presented by MHC molecules on the cell surface as T cell peptide epitopes in the context of MHC molecules that are recognized by T cell receptors (TCRs) (Morris et al., *Blood Rev.* 20:61-69, 2006; Konnig, R., *Curr. Opin. Immunol.* 14(1): 75-83, 2002). Therefore, generating therapeutic mAbs that recognize the secreted or intracellular tumor antigen-derived peptide/MHC complexes on the cell surface will take advantage of the enhanced specificity and therapeutic potency offered by mAbs.

Cancers of the central nervous system are the most prevalent childhood solid tumors, accounting for >20% of cancer incidence in children aged 0-14 (American Cancer Society Surveillance, Epidemiology, and End Results (SEER) Program. 2014. "Cancer in Children & Adolescents." SEER Registries, National Cancer Institute. American Cancer Society, Surveillance Research). The median survival for children with pediatric glioblastoma was found to be 19 months in a meta-study of 178 patients (Ansari et al., *Indian J Med Paediatr Oncol.* (2012) 33: 155), and for children with diffuse intrinsic pontine gliomas (DIPG), 5-year survival was reported to be <1% (Warren, *Front Oncol.* (2012) 2:205).

Genome-wide sequencing of pediatric high grade gliomas has revealed recurring somatic heterozygous mutations in multiple genes involved in chromatin assembly and modification. In most pediatric gliomas sequenced, mutations in mutant histone genes H3F3A (encoding H3.3) or HIST1H3B and HIST1H3C (encoding H3.1) were found to be heterozygous and conserved at a few hotspots, suggesting a selective advantage conferred by these mutations, such as a gain-of-function in cells harboring these mutations (Filbin and Suva, *Annu. Rev. Pathol. Mech. Dis.* 2016. 11:497-521). One study (Wu et al., *Nat Genet* (2012) 44: 251) reported that 78% (39/50) of DIPGs and 22% (8/36) of non-brain-stem-pediatric glioblastomas were characterized by a K27M mutation in H3F3A (encoding mutant histone H3.3) or the related HIST1H3B (encoding mutant histone H3.1). Another study (Schwartzentruber et al., *Nature* (2012) 482: 226) found that 20% (10/49) of pediatric glioblastomas were characterized by the K27M mutation in H3F3A. The K27 position is located in a mutant histone tail that is subject to extensive posttranslational modification. The H3.3-K27M mutation leads to de-repression of genes targeted by polycomb repressive complex 2 (PRC2, a mutant histone methyltransferase) by sequestration of PRC2, and a global reduction of trimethylation in position H3-K27 (Lewis et al., *Science* (2013) 340:857). H3.3-K27M expression has been found to synergize with p53 loss and PDGFRA activation in neural progenitor cells derived from human embryonic stem cells, resulting in neoplastic transformation (Funato et al., (2014) *Science* 346:1529). The functional association of H3.3-K27M with tumorigenesis and the high prevalence of this mutation in well-defined cancer indications make the mutated H3 proteins very attractive cancer targets.

Recent advances in using phage display to generate mAbs have made it possible to select agents with exquisite specificity against defined epitopes from large antibody repertoires. A number of such mAbs specific for solid tumor antigens, in the context of HLA-A01 and HLA-A02, have been successfully selected from phage display libraries (Noy et al., *Expert Rev. Anticancer Ther.* 5(3):523-536, 2005; Chames et al., *Proc. Natl. Acad. Sci. USA* 97:7969-7974, 2000; Held et al., *Eur. J. Immunol.* 34:2919-2929, 2004; Lev et al., *Cancer Res.* 62:3184-3194, 2002; Klechevsky et al., *Cancer Res.* 68(15):6360-6367, 2008). More recently, a human mAb specific for human WT1/HLA-A02 complex, a well-described T cell epitope, has been shown to inhibit multiple cancer cell lines and primary cancer cells via Fc-mediated effector cell function (Dao et al., *Sci. Transl. Med.* 5:176ra33, 2013; Veomett et al., *Clin. Cancer Res.* doi:10.1158/1078-0432, 2014) in cellular assays and in in vivo models.

The disclosures of all publications, patents, patent applications and published patent applications referred to herein are hereby incorporated herein by reference in their entirety.

BRIEF SUMMARY OF THE INVENTION

The present application in one aspect provides constructs (such as isolated constructs) that bind to a complex comprising a histone H3 peptide and an MHC class I protein (referred to herein as a "histone H3/MHC class I complex," or "HMC"). In some embodiments, the constructs ("anti- HMC constructs") comprise an antibody moiety (referred to herein as an "anti-HMC antibody moiety") that specifically binds to a complex comprising a histone H3 peptide and an MHC class I protein.

Thus, in some embodiments, there is provided an anti-HMC construct (such as an isolated anti-HMC construct) comprising an antibody moiety that specifically binds to a complex comprising a histone H3 peptide and an MHC class I protein. In some embodiments, the histone H3/MHC class I complex is present on a cell surface. In some embodiments, the histone H3/MHC class I complex is present on the surface of an immune cell, such as a T cell.

In some embodiments, the anti-HMC construct comprises an antibody moiety that specifically binds to a complex comprising a histone H3 peptide and an MHC class I protein, wherein the MHC class I protein is HLA-A. In some embodiments, the MHC class I protein is HLA-A02. In some embodiments, the MHC class I protein is the HLA-A*02:01 subtype of the HLA-A02 allele.

In some embodiments, according to any of the anti-HMC constructs (such as isolated anti-HMC constructs) described above, the anti-HMC construct comprises an antibody moiety that specifically binds to a complex comprising a histone H3 peptide and an MHC class I protein, wherein the antibody moiety cross-reacts with a complex comprising the histone H3 peptide and a second MHC class I protein having a different HLA allele than the MHC class I protein. In some embodiments, the antibody moiety cross-reacts with a complex comprising a variant of the histone H3 peptide comprising one amino acid substitution (such as a conservative amino acid substitution) and the MHC class I protein.

In some embodiments, according to any of the anti-HMC constructs (such as isolated anti-HMC construct) described above, the anti-HMC construct comprises an antibody moiety that specifically binds to a complex comprising a histone H3 peptide and an MHC class I protein, wherein the histone H3 peptide is about 8 to about 12 (such as about any of 8, 9, 10, 11, or 12) amino acids in length. In some embodiments, the histone H3 peptide is derived from the region corresponding to amino acids 26-35 of any one of SEQ ID NOs: 1-4. In some embodiments, the histone H3 peptide comprises an amino acid sequence selected from the group consisting of SEQ ID NOs: 5-24. In some embodiments, the histone H3 peptide has the amino acid sequence RMSAPSTGGV (SEQ ID NO: 7). In some embodiments, the anti-HMC construct cross-reacts with a complex comprising a variant of the histone H3 peptide having the amino acid sequence of RMSAPATGGV (SEQ ID NO: 8) and the MHC class I protein. In some embodiments, the histone H3 peptide has the amino acid sequence RMSAPATGGV (SEQ ID NO: 8). In some embodiments, the isolated anti-HMC construct cross-reacts with a complex comprising a histone H3 peptide having the amino acid sequence of RKSAPSTGGV (SEQ ID NO: 5) and the MHC class I protein and/or cross-reacts with a complex comprising a histone H3 peptide having the amino acid sequence of RKSAPATGGV (SEQ ID NO: 6) and the MHC class I protein. In some embodiments, the isolated anti-HMC construct does not cross-react with a complex comprising a histone H3 peptide having the amino acid sequence of RKSAPSTGGV (SEQ ID NO: 5) and the MHC class I protein and/or does not cross-react with a complex comprising a histone H3 peptide having the amino acid sequence of RKSAPATGGV (SEQ ID NO: 6) and the MHC class I protein.

In some embodiments, according to any of the anti-HMC constructs (such as isolated anti-HMC constructs) described above, the anti-HMC construct comprises an antibody moiety that specifically binds to a complex comprising a histone H3 peptide and an MHC class I protein, wherein the antibody moiety is a full-length antibody, a Fab, a Fab', a (Fab')2, an Fv, or a single chain Fv (scFv). In some embodiments, the antibody moiety is fully human, semi-synthetic with human antibody framework regions, or humanized.

In some embodiments, according to any of the anti-HMC constructs (such as isolated anti-HMC constructs) described above, the anti-HMC construct comprises an antibody moiety that specifically binds to a complex comprising a histone H3 peptide and an MHC class I protein, wherein the antibody moiety binds to the histone H3/MHC class I complex with an equilibrium dissociation constant ($K_d$) between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the isolated anti-HMC construct binds to the histone H3/MHC class I complex with a $K_d$ between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values).

In some embodiments, the anti-HMC construct comprises an antibody moiety that specifically binds to a complex comprising a histone H3 peptide and an MHC class I protein, wherein the antibody moiety comprises: i) a heavy chain variable domain comprising a heavy chain complementarity determining region (HC-CDR) 1 comprising the amino acid sequence of SEQ ID NO: 158, or a variant thereof comprising up to about 3 (such as about any of 1, 2, or 3) amino acid substitutions, an HC-CDR2 comprising the amino acid sequence of SEQ ID NO: 159, or a variant thereof comprising up to about 3 (such as about any of 1, 2, or 3) amino acid substitutions, and an HC-CDR3 comprising the amino acid sequence of SEQ ID NO: 160 or 161, or a variant thereof comprising up to about 3 (such as about any of 1, 2, or 3) amino acid substitutions; and ii) a light chain variable domain comprising a light chain complementarity determining region (LC-CDR) 1 comprising the amino acid sequence of SEQ ID NO: 162, or a variant thereof comprising up to about 3 (such as about any of 1, 2, or 3) amino acid substitutions, and an LC-CDR3 comprising the amino acid sequence of SEQ ID NO: 163, or a variant thereof comprising up to about 3 (such as about any of 1, 2, or 3) amino acid substitutions.

In some embodiments, the anti-HMC construct comprises an antibody moiety that specifically binds to a complex comprising a histone H3 peptide and an MHC class I protein, wherein the antibody moiety comprises: i) a heavy chain variable domain comprising an HC-CDR1 comprising (and in some embodiments consisting of) the amino acid sequence of any one of SEQ ID NOs: 99-107, or a variant thereof comprising up to about 5 (such as about any of 1, 2, 3, 4, or 5) amino acid substitutions, an HC-CDR2 comprising (and in some embodiments consisting of) the amino acid sequence of any one of SEQ ID NOs: 108-116, or a variant thereof comprising up to about 5 (such as about any of 1, 2, 3, 4, or 5) amino acid substitutions, and an HC-CDR3 comprising (and in some embodiments consisting of) the amino acid sequence of any one of SEQ ID NOs: 117-128, or a variant thereof comprising up to about 5 (such as about any of 1, 2, 3, 4, or 5) amino acid substitutions; and ii) a light chain variable domain comprising an LC-CDR1 comprising (and in some embodiments consisting of) the amino acid sequence of any one of SEQ ID NOs: 129-138, or a variant thereof comprising up to about 5 (such as about any of 1, 2, 3, 4, or 5) amino acid substitutions, an LC-CDR2 comprising (and in some embodiments consisting of) the amino acid sequence of any one of SEQ ID NOs: 139-147, or a variant thereof comprising up to about 3 (such as about any of 1, 2, or 3) amino acid substitutions, and an LC-CDR3 comprising (and in some embodiments consisting of) the amino acid sequence of any one of SEQ ID NOs: 148-157, or a variant thereof comprising up to about 5 (such as about any of 1, 2, 3, 4, or 5) amino acid substitutions.

In some embodiments, the anti-HMC construct comprises an antibody moiety that specifically binds to a complex comprising a histone H3 peptide and an MHC class I protein, wherein the antibody moiety comprises: i) a heavy chain variable domain comprising an HC-CDR1 comprising (and in some embodiments consisting of) the amino acid sequence of any one of SEQ ID NOs: 99-107, an HC-CDR2 comprising (and in some embodiments consisting of) the amino acid sequence of any one of SEQ ID NOs: 108-116, and an HC-CDR3 comprising (and in some embodiments consisting of) the amino acid sequence of any one of SEQ ID NOs: 117-128; or a variant thereof comprising up to about 5 (such as about any of 1, 2, 3, 4, or 5) amino acid substitutions in the HC-CDR regions; and ii) a light chain variable domain comprising an LC-CDR1 comprising (and in some embodiments consisting of) the amino acid sequence of any one of SEQ ID NOs: 129-138, an LC-CDR2 comprising (and in some embodiments consisting of) the amino acid sequence of any one of SEQ ID NOs: 139-147, and an LC-CDR3 comprising (and in some embodiments consisting of) the amino acid sequence of any one of SEQ ID NOs: 148-157; or a variant thereof comprising up to about 5 (such as about any of 1, 2, 3, 4, or 5) amino acid substitutions in the LC-CDR regions.

In some embodiments, the anti-HMC construct comprises an antibody moiety that specifically binds to a complex comprising a histone H3 peptide and an MHC class I protein, wherein the antibody moiety comprises a) a heavy chain variable domain comprising (and in some embodiments consisting of) the amino acid sequence of any one of SEQ ID NOs: 75-86 or a variant thereof having at least about 95% (such as at least about any of 95%, 96%, 97%, 98%, or 99%) sequence identify to any one of SEQ ID NOs: 75-86; and b) a light chain variable domain comprising (and in some embodiments consisting of) the amino acid sequence of any one of SEQ ID NOs: 87-98 or a variant thereof having at least about 95% (such as at least about any of 95%, 96%, 97%, 98%, or 99%) sequence identity to any one of SEQ ID NOs: 87-98. In some embodiments, the antibody moiety comprises a heavy chain variable domain comprising (and in some embodiments consisting of) the amino acid sequence of any one of SEQ ID NOs: 75-86 and a light chain variable domain comprising (and in some embodiments consisting of) the amino acid sequence of any one of SEQ ID NOs: 87-98.

In some embodiments, the anti-HMC construct comprises a first antibody moiety that competes for binding to a target histone H3/MHC class I complex with a second antibody moiety according to any of the antibody moieties described above. In some embodiments, the first antibody moiety binds to the same, or substantially the same, epitope as the second antibody moiety. In some embodiments, binding of the first antibody moiety to the target histone H3/MHC class I complex inhibits binding of the second antibody moiety to the target histone H3/MHC class I complex by at least about 70% (such as by at least about any of 75%, 80%, 85%, 90%, 95%, 98% or 99%), or vice versa. In some embodiments, the first antibody moiety and the second antibody moiety cross-compete for binding to the target histone H3/MHC class I complex, i.e., each of the first and second antibody moieties competes with the other for binding to the target histone H3/MHC class I complex.

In some embodiments, according to any of the anti-HMC constructs described above (such as isolated anti-HMC constructs), the isolated anti-HMC construct is a full-length antibody. In some embodiments, the isolated anti-HMC construct is monospecific. In some embodiments, the isolated anti-HMC construct is multi-specific. In some embodiments, the isolated anti-HMC construct is bispecific. In some embodiments, the isolated anti-HMC molecule is a tandem scFv, a diabody (Db), a single chain diabody (scDb), a dual-affinity retargeting (DART) antibody, a dual variable domain (DVD) antibody, a knob-into-hole (KiH) antibody, a dock and lock (DNL) antibody, a chemically cross-linked antibody, a heteromultimeric antibody, or a heteroconjugate antibody. In some embodiments, the isolated anti-HMC construct is a tandem scFv comprising two scFvs linked by a peptide linker. In some embodiments, the peptide linker comprises (and in some embodiments consists of) the amino acid sequence of SEQ ID NO: 48.

In some embodiments, according to any of the anti-HMC constructs described above (such as isolated anti-HMC constructs), the anti-HMC construct comprises an antibody moiety that specifically binds to a complex comprising a histone H3 peptide and an MHC class I protein, wherein the isolated anti-HMC construct further comprises a second antigen-binding moiety that specifically binds to a second antigen. In some embodiments, the second antigen-binding moiety is an antibody moiety. In some embodiments, the second antigen is an antigen on the surface of a T cell. In some embodiments, the T cell is selected from the group consisting of a cytotoxic T cell, a helper T cell, and a natural killer T cell. In some embodiments, the second antigen is selected from the group consisting of CD3γ, CD3δ, CD3ε, CD3ζ, CD28, OX40, GITR, CD137, CD27, CD40L, and HVEM. In some embodiments, the second antigen is CD3ε, and the isolated anti-HMC construct is a tandem scFv comprising an N-terminal scFv specific for the histone H3/MHC class I complex and a C-terminal scFv specific for CD3ε. In some embodiments, the second antigen is an antigen on the surface of a natural killer cell, a neutrophil, a monocyte, a macrophage, or a dendritic cell.

In some embodiments, according to any of the anti-HMC constructs (such as isolated anti-HMC constructs) described above, the anti-HMC construct comprises an antibody moiety that specifically binds to a complex comprising a histone H3 peptide and an MHC class I protein, wherein the isolated anti-HMC construct is a chimeric antigen receptor (CAR). In some embodiments, the chimeric antigen receptor comprises an extracellular domain comprising the antibody moiety, a transmembrane domain, and an intracellular signaling domain. In some embodiments, the intracellular signaling domain comprises a CD3ζ intracellular signaling sequence and a co-stimulatory signaling sequence. In some embodiments, the co-stimulatory signaling sequence is a CD28 or 4-1BB intracellular signaling sequence. In some embodiments, the the intracellular signaling domain comprises a CD3ζ intracellular signaling sequence and a CD28 and/or 4-1BB intracellular signaling sequence.

In some embodiments, according to any of the anti-HMC constructs (such as isolated anti-HMC constructs) described above, the anti-HMC construct comprises an antibody moiety that specifically binds to a complex comprising a histone H3 peptide and an MHC class I protein, wherein the isolated anti-HMC construct is a a chimeric antibody/T cell receptor (abTCR). In some embodiments, the anti-HMC abTCR comprises an extracellular domain comprising the antibody moiety and a T cell receptor (TCR) module (TCRM) comprising TCR transmembrane domains. In some embodiments, the TCRM is capable of recruiting at least one TCR-associated signaling module. In some embodiments, the TCR-associated signaling module is selected from the group consisting of CD3δε, CD3γε, and ζζ. In some embodiments, the antibody moiety comprises: a) a first polypeptide chain comprising a first antigen-binding domain comprising $V_H$ and $C_H1$ antibody domains; and b) a second polypeptide chain comprising a second antigen-binding domain comprising $V_L$ and $C_L$ antibody domains, wherein the $V_H$ and $C_H1$ domains of the first antigen-binding domain and the $V_L$ and $C_L$ domains of the second antigen-binding domain form a Fab-like antigen-binding module that specifically binds to the HMC.

In some embodiments, according to any of the anti-HMC constructs (such as isolated anti-HMC constructs) described above, the anti-HMC construct comprises an antibody moiety that specifically binds to a complex comprising a histone H3 peptide and an MHC class I protein, wherein the isolated anti-HMC construct is an immunoconjugate comprising the antibody moiety and an effector molecule. In some embodiments, the effector molecule is a therapeutic agent selected from the group consisting of a drug, a toxin, a radioisotope, a protein, a peptide, and a nucleic acid. In some embodiments, the therapeutic agent is a drug or a toxin. In some embodiments, the effector molecule is a label.

In yet other embodiments, there is provided a host cell expressing or associated with an anti-HMC construct, or polypeptide component thereof. In some embodiments, there is provided a nucleic acid encoding an anti-HMC construct, or polypeptide component thereof. In some embodiments, there is provided a vector comprising the nucleic acid. In some embodiments, there is provided an effector cell expressing or associated with an anti-HMC construct. In some embodiments, the effector cell is a T cell.

In yet other embodiments, there is provided a pharmaceutical composition comprising an anti-HMC construct (such as an isolated anti-HMC construct), a host cell, a nucleic acid, a vector, or an effector cell according to any of the embodiments described above. In some embodiments, the pharmaceutical composition further comprises a pharmaceutically acceptable carrier.

In some embodiments, there is provided a method of detecting a cell presenting a complex comprising a histone H3 peptide and an MHC class I protein on its surface, comprising contacting the cell with an anti-HMC construct (such as an isolated anti-HMC construct) according to any of the embodiments described above comprising a) an antibody moiety that specifically binds to a complex comprising the histone H3 peptide and the MHC class I protein and b) a label, and detecting the presence of the label on the cell.

In some embodiments, there is provided a method of treating an individual having a histone H3-related disease (such as cancer, e.g., pediatric high grade glioma, such as DIPG), comprising administering to the individual an effective amount of a pharmaceutical composition comprising an anti-HMC construct (such as an isolated anti-HMC construct) according to any of the embodiments described above. In some embodiments, the pharmaceutical composition further comprises a cell (such as an effector cell) associated with the isolated anti-HMC construct. In some embodiments, there is provided a method of treating an individual having a histone H3-related disease (such as cancer, e.g., pediatric high grade glioma, such as DIPG), comprising administering to the individual an effective amount of an effector cell expressing any of the anti-HMC CARs or anti-HMC abTCRs described above. In some embodiments, the effector cell is a T cell. In some embodiments, the histone H3-related disease is a K27M-H3.3-positive disease or a K27M-H3.1-positive disease (such as K27M-H3.3- or K27M-H3.1-positive cancer). In some embodiments, the histone H3-related disease is cancer. In some embodiments, the cancer is pediatric glioma. In some embodiments, the pediatric glioma is high-grade glioma (HGG) or diffuse intrinsic pontine glioma (DIPG). In some embodiments, the individual is human.

In some embodiments, there is provided a method of diagnosing an individual having a histone H3-related disease (such as cancer, e.g., pediatric high grade glioma, such as DIPG), comprising: a) administering an effective amount of an isolated anti-HMC construct comprising a label according to any of the embodiments described above to the individual; and b) determining the level of the label in the individual, wherein a level of the label above a threshold level indicates that the individual has the histone H3-related disease. In some embodiments, there is provided a method of diagnosing an individual having a histone H3-related disease, comprising: a) contacting a sample derived from the individual with an isolated anti-HMC construct comprising a label according to any of the embodiments described above; and b) determining the number of cells bound with the isolated anti-HMC construct in the sample, wherein a value for the number of cells bound with the isolated anti-HMC construct above a threshold level indicates that the individual has the histone H3-related disease. In some embodiments, the histone H3-related disease is a K27M-H3.3-positive disease or a K27M-H3.1-positive disease. In some embodiments, the histone H3-related disease is cancer. In some embodiments, the cancer is pediatric glioma. In some embodiments, the pediatric glioma is high-grade glioma (HGG) or diffuse intrinsic pontine glioma (DIPG). In some embodiments, the individual is human.

Also provided are methods of making any of the constructs described herein, articles of manufacture, and kits that are suitable for the methods described herein.

DETAILED DESCRIPTION OF THE INVENTION

Figure 1A:
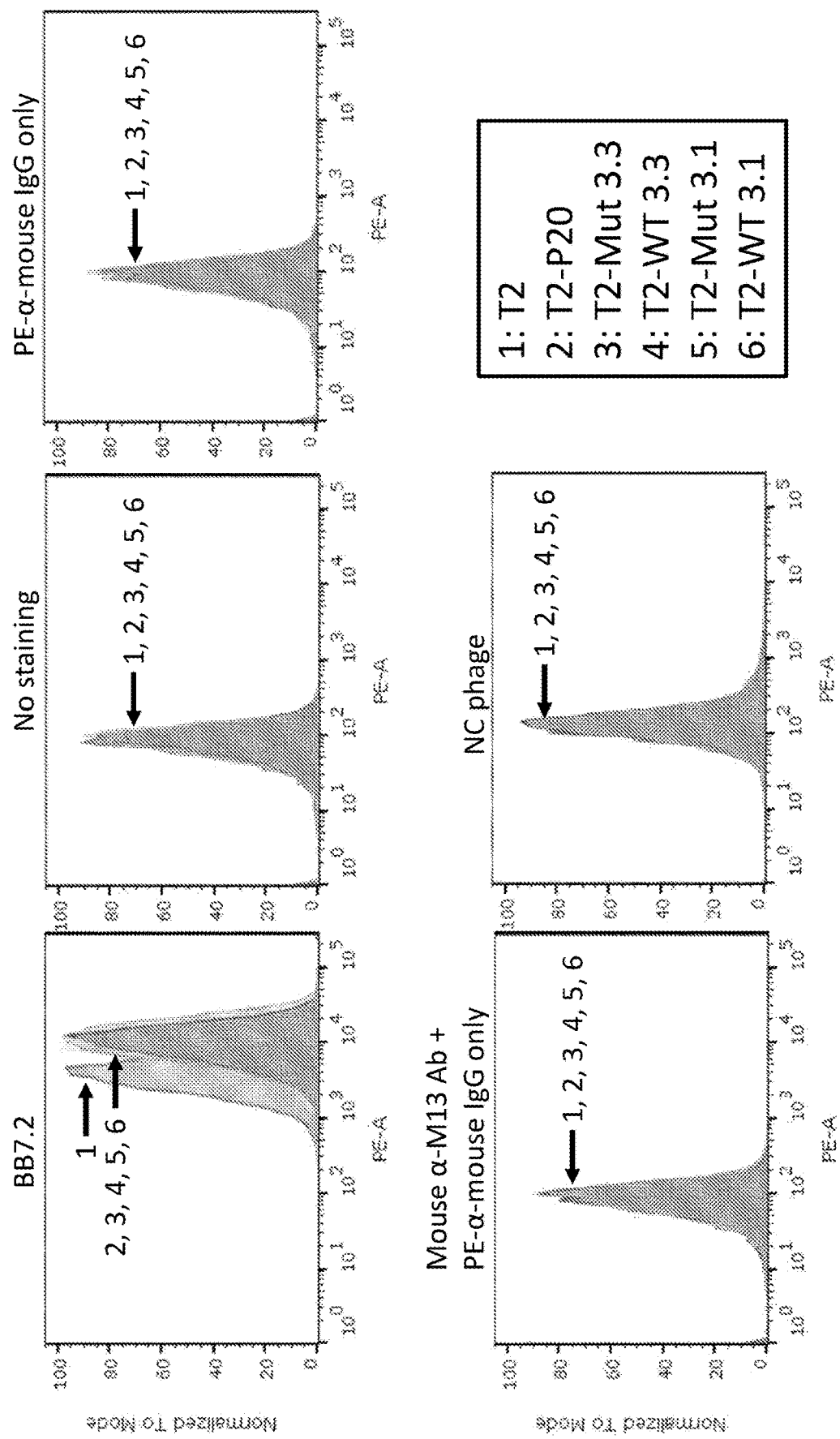
FIG. 1A shows FACS histogram plots for binding of antibody BB7.2 (α-HLA-A02 antibody) to T2 cells (T2), T2 cells loaded with endogenous peptide mixture P20 (T2-P20), T2 cells loaded with K27M-H3.3 26-35 peptide (T2-Mut 3.3), T2 cells loaded with WT-H3.3 26-35 peptide (T2-WT 3.3), T2 cells loaded with K27M-H3.1 26-35 peptide (T2-Mut 3.1), or T2 cells loaded with WT-H3.1 26-35 peptide (T2-WT 3.1) under the indicated staining conditions.

The present application provides isolated constructs (referred to herein as "anti-HMC constructs") that comprise an antibody moiety (referred to herein as an "anti-HMC antibody moiety") that specifically binds to a complex comprising a histone H3 peptide and an MHC class I protein (referred to herein as a "histone H3/MHC class I complex," or "HMC").

Analysis of H3.1 and H3.3 wildtype and K27M mutant peptides using HLA peptide binding prediction tools (Bimas, Parker et al. (1994) *J. Immunol.* 152:163; IEDB, Paul et al, (2016) *Curr. Protoc. Immunol.* 114:18.19.1; SYFPEITHI, Rammensee et al. (1999) *Immunogenetics.* 50:213; NetMHC and NetTepi, Andreatta and Nielsen (2016) *Bioinformatics.* 32:511; Rankpep, Reche and Reinherz (2007) *Methods Mol. Biol.* 409:185) suggests a higher affinity of the K27M mutant peptides for HLA-A*02:01 as compared to the wild type peptides. Thus cells heterozygous for wildtype and K27M mutant histone H3 would be expected to preferentially present MHC/K27M mutant H3 peptide complexes, making antibodies specific for these complexes ideal candidates for use in therapeutics agents to treat cancers characterized by these mutations.

The anti-HMC constructs specifically recognize histone H3/MHC class I complexes. In some embodiments, the histone H3/MHC class I complex is on the surface of cells expressing histone H3. Anti-HMC constructs may specifically bind to the N-terminal portion, the C-terminal portion, or the middle portion of the histone H3 peptide in the complex, and/or cross-react with at least one complex comprising the histone H3 peptide and a different subtype of the MHC class I protein (e.g., the anti-HMC construct binds to both a histone H3 peptide/HLA-A*02:01 complex and a histone H3 peptide/HLA-A*02:02 complex). The anti-HMC constructs allow for specific targeting of HMC-presenting cells (i.e., cells presenting on their surface a histone H3 peptide bound to an MHC molecule), such as cancer cells expressing histone H3 (including, for example, cancer cells expressing a mutant histone H3). This strategy provides a significant technical advantage over using antibodies directed against the histone H3 protein, which may not bind any histone H3 peptides in the context of MHC and would therefore be unable to specifically target HMC-presenting cells. Furthermore, when fused to a detectable moiety, the anti-HMC antibody moiety allows for diagnosis and prognosis of a cancer characterized by aberrant expression of a histone H3 protein, or expression of a mutant histone H3 protein, such as a mutant histone H3 protein comprising a K27M mutation (referred to herein as "K27M-H3"), with high sensitivity to changes in the number and distribution of HMC-presenting cells.

Using phage display technology, we generated multiple monoclonal antigen-binding antibody fragments that are specific and high affinity against mutant histone K27M-H3.3 26-35 peptide/HLA-A*02:01 complex. Flow cytometry assays demonstrated that the antibodies specifically recognized mutant histone H3 peptide-pulsed T2 cells. The data presented herein demonstrate that antibodies against histone H3 peptides (such as mutant histone H3 peptides) in the context of an HLA complex can be effective therapeutic agents for a cancer characterized by aberrant expression of a histone H3 protein, or expression of a mutant histone H3 protein (such as K27M-H3, including K27M-H3.3 and K27M-H3.1).

The present application thus provides constructs (such as isolated constructs) comprising an antibody moiety that specifically binds to a complex comprising a histone H3 peptide and an MHC class I protein. The construct can be, for example, a full-length anti-HMC antibody, a multispecific anti-HMC molecule (such as a bispecific anti-HMC antibody), an anti-HMC chimeric antigen receptor ("CAR"), or an anti-HMC immunoconjugate.

In another aspect, there are provided nucleic acids encoding the anti-HMC constructs or the anti-HMC antibody moiety portion of the constructs.

In another aspect, there are provided compositions comprising an anti-HMC construct comprising an antibody moiety that specifically binds to a complex comprising a histone H3-peptide and an MHC class I protein. The composition can be a pharmaceutical composition comprising an anti-HMC construct or an effector cell expressing or associated with the anti-HMC construct (for example a T cell expressing an anti-HMC CAR or anti-HMC abTCR).

Also provided are methods of making and using the anti-HMC constructs (or cells expressing or associated with the anti-HMC constructs) for treatment or diagnostic purposes, as well as kits and articles of manufacture useful for such methods.

Definitions

As used herein, "treatment" or "treating" is an approach for obtaining beneficial or desired results, including clinical results. For purposes of this invention, beneficial or desired clinical results include, but are not limited to, one or more of the following: alleviating one or more symptoms resulting from the disease, diminishing the extent of the disease, stabilizing the disease (e.g., preventing or delaying the worsening of the disease), preventing or delaying the spread of the disease, preventing or delaying the recurrence of the disease, delay or slowing the progression of the disease, ameliorating the disease state, providing a remission (partial or total) of the disease, decreasing the dose of one or more other medications required to treat the disease, delaying the progression of the disease, increasing or improving the quality of life, increasing weight gain, and/or prolonging survival. Also encompassed by "treatment" is a reduction of pathological consequence of a disease. The methods of the invention contemplate any one or more of these aspects of treatment.

The term "refractory" or "resistant" refers to a disease that has not responded to treatment.

"Activation", as used herein in relation to a cell expressing CD3, refers to the state of the cell that has been sufficiently stimulated to induce a detectable increase in downstream effector functions of the CD3 signaling pathway, including, without limitation, cellular proliferation and cytokine production.

The term "antibody moiety" includes full-length antibodies and antigen-binding fragments thereof. A full-length antibody comprises two heavy chains and two light chains. The variable regions of the light and heavy chains are responsible for antigen binding. The variables region in both chains generally contain three highly variable loops called the complementarity determining regions (CDRs) (light chain (LC) CDRs including LC-CDR1, LC-CDR2, and LC-CDR3, heavy chain (HC) CDRs including HC-CDR1, HC-CDR2, and HC-CDR3). CDR boundaries for the antibodies and antigen-binding fragments disclosed herein may be defined or identified by the conventions of Kabat, Chothia, or Al-Lazikani (Al-Lazikani 1997; Chothia 1985;

Chothia 1987; Chothia 1989; Kabat 1987; Kabat 1991). The three CDRs of the heavy or light chains are interposed between flanking stretches known as framework regions (FRs), which are more highly conserved than the CDRs and form a scaffold to support the hypervariable loops. The constant regions of the heavy and light chains are not involved in antigen binding, but exhibit various effector functions. Antibodies are assigned to classes based on the amino acid sequence of the constant region of their heavy chain. The five major classes or isotypes of antibodies are IgA, IgD, IgE, IgG, and IgM, which are characterized by the presence of α, δ, ε, γ, and heavy chains, respectively. Several of the major antibody classes are divided into subclasses such as IgG1 (γ1 heavy chain), IgG2 (γ2 heavy chain), IgG3 (γ3 heavy chain), IgG4 (γ4 heavy chain), IgA1 (α1 heavy chain), or IgA2 (α2 heavy chain).

The term "antigen-binding fragment" as used herein refers to an antibody fragment including, for example, a diabody, a Fab, a Fab', a F(ab')2, an Fv fragment, a disulfide stabilized Fv fragment (dsFv), a (dsFv)2, a bispecific dsFv (dsFv-dsFv'), a disulfide stabilized diabody (ds diabody), a single-chain antibody molecule (scFv), an scFv dimer (bivalent diabody), a multispecific antibody formed from a portion of an antibody comprising one or more CDRs, a camelized single domain antibody, a nanobody, a domain antibody, a bivalent domain antibody, or any other antibody fragment that binds to an antigen but does not comprise a complete antibody structure. An antigen-binding fragment is capable of binding to the same antigen to which the parent antibody or a parent antibody fragment (e.g., a parent scFv) binds. In some embodiments, an antigen-binding fragment may comprise one or more CDRs from a particular human antibody grafted to a framework region from one or more different human antibodies.

The term "epitope" as used herein refers to the specific group of atoms or amino acids on an antigen to which an antibody or antibody moiety binds. Two antibodies or antibody moieties may bind the same epitope within an antigen if they exhibit competitive binding for the antigen.

A "Fab-like antigen-binding module" refers to an antibody moiety that comprises a first polypeptide chain and a second polypeptide chain, wherein the first and second polypeptide chains comprise a $V_L$ antibody domain, a $C_L$ antibody domain, a $V_H$ antibody domain, and a $C_H1$ antibody domain. The $V_L$ and $C_L$ antibody domains may be on one chain with the $V_H$ and $C_H1$ antibody domains on the other chain, or the $V_L$ and $C_H1$ antibody domains may be on one chain with the $V_H$ and $C_L$ antibody domains on the other chain. In some embodiments, the first and second polypeptide chains are linked, such as by a peptide linkage, or by another chemical linkage, such as a disulfide linkage.

As used herein, a first antibody moiety "competes" for binding to a target HMC with a second antibody moiety when the first antibody moiety inhibits target HMC binding of the second antibody moiety by at least about 50% (such as at least about any of 55%, 60%, 65%, 70%, 75%, 80%, 85%, 90%, 95%, 98% or 99%) in the presence of an equimolar concentration of the first antibody moiety, or vice versa. A high throughput process for "binning" antibodies based upon their cross-competition is described in PCT Publication No. WO 03/48731.

As use herein, the term "specifically binds" or "is specific for" refers to measurable and reproducible interactions, such as binding between a target and an antibody or antibody moiety, that is determinative of the presence of the target in the presence of a heterogeneous population of molecules, including biological molecules. For example, an antibody or antibody moiety that specifically binds to a target (which can be an epitope) is an antibody or antibody moiety that binds this target with greater affinity, avidity, more readily, and/or with greater duration than its bindings to other targets. In some embodiments, an antibody or antibody moiety that specifically binds to an antigen reacts with one or more antigenic determinants of the antigen (for example a histone H3 peptide/MHC class I protein complex) with a binding affinity that is at least about 10 times its binding affinity for other targets.

The term "T cell receptor," or "TCR," refers to a heterodimeric receptor composed of αβ or γδ chains that pair on the surface of a T cell. Each α, β, γ, and δ chain is composed of two Ig-like domains: a variable domain (V) that confers antigen recognition through the complementarity determining regions (CDR), followed by a constant domain (C) that is anchored to cell membrane by a connecting peptide and a transmembrane (TM) region. The TM region associates with the invariant subunits of the CD3 signaling apparatus. Each of the V domains has three CDRs. These CDRs interact with a complex between an antigenic peptide bound to a protein encoded by the major histocompatibility complex (pMHC) (Davis and Bjorkman (1988) Nature, 334, 395-402; Davis et al. (1998) Annu Rev Immunol, 16, 523-544; Murphy (2012), xix, 868 p.).

The term "TCR-associated signaling molecule" refers to a molecule having a cytoplasmic immunoreceptor tyrosine-based activation motif (ITAM) that is part of the TCR-CD3 complex. TCR-associated signaling molecules include CD3γε, CD3δε, and ζζ, and are essential for the signaling capacity of the TCR.

The term "module" when referring to a portion of a protein is meant to include structurally and/or functionally related portions of one or more polypeptides which make up the protein. For example, a transmembrane module of a dimeric receptor may refer to the portions of each polypeptide chain of the receptor that span the membrane. A module may also refer to related portions of a single polypeptide chain. For example, a transmembrane module of a monomeric receptor may refer to portions of the single polypeptide chain of the receptor that span the membrane. A module may also include only a single portion of a polypeptide.

An "isolated" anti-HMC construct as used herein refers to an anti-HMC construct that (1) is not associated with proteins found in nature, (2) is free of other proteins from the same source, (3) is expressed by a cell from a different species, or, (4) does not occur in nature.

The term "isolated nucleic acid" as used herein is intended to mean genomic nucleic acid, cDNA, or nucleic acid of synthetic origin or some combination thereof, which by virtue of its origin the "isolated nucleic acid" (1) is not associated with all or a portion of a polynucleotide in which the "isolated nucleic acid" is found in nature, (2) is operably linked to a polynucleotide which it is not linked to in nature, or (3) does not occur in nature as part of a larger sequence.

As used herein, the term "CDR" or "complementarity determining region" is intended to mean the non-contiguous antigen combining sites found within the variable region of both heavy and light chain polypeptides. These particular regions have been described by Kabat et al., J. Biol. Chem. 252:6609-6616 (1977); Kabat et al., U.S. Dept. of Health and Human Services, "Sequences of proteins of immunological interest" (1991); by Chothia et al., J. Mol. Biol. 196:901-917 (1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues which encompass the CDRs as defined by each of the above cited references are set forth below in Table 1 as a comparison.

TABLE 1

CDR DEFINITIONS

|  | Kabat[1] | Chothia[2] | MacCallum[3] |
|---|---|---|---|
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra The term "chimeric antibodies" refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit a biological activity of this invention (see U.S. Pat. No. 4,816,567; and Morrison et al., Proc. Natl. Acad. Sci. USA, 81:6851-6855 (1984)).

The term "semi-synthetic" in reference to an antibody or antibody moiety means that the antibody or antibody moiety has one or more naturally occurring sequences and one or more non-naturally occurring (i.e., synthetic) sequences.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the heavy and light chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

"Single-chain Fv," also abbreviated as "sFv" or "scFv," are antibody fragments that comprise the $V_H$ and $V_L$ antibody domains connected into a single polypeptide chain. In some embodiments, the scFv polypeptide further comprises a polypeptide linker between the $V_H$ and $V_L$ domains which enables the scFv to form the desired structure for antigen binding. For a review of scFv, see Pluckthun in *The Pharmacology of Monoclonal Antibodies*, vol. 113, Rosenburg and Moore eds., Springer-Verlag, New York, pp. 269-315 (1994).

The term "diabodies" refers to small antibody fragments prepared by constructing scFv fragments (see preceding paragraph) typically with short linkers (such as about 5 to about 10 residues) between the $V_H$ and $V_L$ domains such that inter-chain but not intra-chain pairing of the V domains is achieved, resulting in a bivalent fragment, i.e., fragment having two antigen-binding sites. Bispecific diabodies are heterodimers of two "crossover" scFv fragments in which the $V_H$ and $V_L$ domains of the two antibodies are present on different polypeptide chains. Diabodies are described more fully in, for example, EP 404,097; WO 93/11161; and Hollinger et al., *Proc. Natl. Acad. Sci. USA*, 90:6444-6448 (1993).

"Humanized" forms of non-human (e.g., rodent) antibodies are chimeric antibodies that contain minimal sequence derived from the non-human antibody. For the most part, humanized antibodies are human immunoglobulins (recipient antibody) in which residues from a hypervariable region (HVR) of the recipient are replaced by residues from a hypervariable region of a non-human species (donor antibody) such as mouse, rat, rabbit or non-human primate having the desired antibody specificity, affinity, and capability. In some instances, framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

"Percent (%) amino acid sequence identity" or "homology" with respect to the polypeptide and antibody sequences identified herein is defined as the percentage of amino acid residues in a candidate sequence that are identical with the amino acid residues in the polypeptide being compared, after aligning the sequences considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, Megalign (DNASTAR), or MUSCLE software. Those skilled in the art can determine appropriate parameters for measuring alignment, including any algorithms needed to achieve maximal alignment over the full-length of the sequences being compared. For purposes herein, however, % amino acid sequence identity values are generated using the sequence comparison computer program MUSCLE (Edgar, R. C., *Nucleic Acids Research* 32(5):1792-1797, 2004; Edgar, R. C., *BMC Bioinformatics* 5(1):113, 2004).

The terms "Fc receptor" or "FcR" are used to describe a receptor that binds to the Fc region of an antibody. In some embodiments, an FcR of this invention is one that binds an IgG antibody (a γ receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daëron, *Annu. Rev. Immunol.* 15:203-234 (1997)). The term includes allotypes, such as FcγRIIIA allotypes: FcγRIIIA-Phe158, FcγRIIIA-Val158, FcγRIIA-R131 and/or FcγRIIA-H131. FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

The term "FcRn" refers to the neonatal Fc receptor (FcRn). FcRn is structurally similar to major histocompatibility complex (MHC) and consists of an α-chain noncovalently bound to β2-microglobulin. The multiple functions of the neonatal Fc receptor FcRn are reviewed in Ghetie and Ward (2000) *Annu. Rev. Immunol.* 18, 739-766. FcRn plays a role in the passive delivery of immunoglobulin IgGs from mother to young and the regulation of serum IgG levels. FcRn can act as a salvage receptor, binding and transporting pinocytosed IgGs in intact form both within and across cells, and rescuing them from a default degradative pathway.

The "$C_H1$ domain" of a human IgG Fc region (also referred to as "C1" of "H1" domain) usually extends from about amino acid 118 to about amino acid 215 (EU numbering system).

"Hinge region" is generally defined as stretching from Glu216 to Pro230 of human IgG1 (Burton, *Molec. Immunol.* 22:161-206 (1985)). Hinge regions of other IgG isotypes may be aligned with the IgG1 sequence by placing the first and last cysteine residues forming inter-heavy chain S—S bonds in the same positions.

The "CH2 domain" of a human IgG Fc region (also referred to as "C2" of "H2" domain) usually extends from about amino acid 231 to about amino acid 340. The CH2 domain is unique in that it is not closely paired with another domain. Rather, two N-linked branched carbohydrate chains are interposed between the two CH2 domains of an intact native IgG molecule. It has been speculated that the carbohydrate may provide a substitute for the domain-domain pairing and help stabilize the CH2 domain. Burton, *Molec Immunol.* 22:161-206 (1985).

The "CH3 domain" (also referred to as "C2" or "H3" domain) comprises the stretch of residues C-terminal to a CH2 domain in an Fc region (i.e. from about amino acid residue 341 to the C-terminal end of an antibody sequence, typically at amino acid residue 446 or 447 of an IgG).

A "functional Fc fragment" possesses an "effector function" of a native sequence Fc region. Exemplary "effector functions" include C1q binding; complement dependent cytotoxicity (CDC); Fc receptor binding; antibody-dependent cell-mediated cytotoxicity (ADCC); phagocytosis; down regulation of cell surface receptors (e.g. B cell receptor; BCR), etc. Such effector functions generally require the Fc region to be combined with a binding domain (e.g. an antibody variable domain) and can be assessed using various assays known in the art.

An antibody with a variant IgG Fc with "altered" FcR binding affinity or ADCC activity is one which has either enhanced or diminished FcR binding activity (e.g., FcγR or FcRn) and/or ADCC activity compared to a parent polypeptide or to a polypeptide comprising a native sequence Fc region. The variant Fc which "exhibits increased binding" to an FcR binds at least one FcR with higher affinity (e.g., lower apparent $K_d$ or $IC_{50}$ value) than the parent polypeptide or a native sequence IgG Fc. According to some embodiments, the improvement in binding compared to a parent polypeptide is about 3 fold, such as about any of 5, 10, 25, 50, 60, 100, 150, 200, or up to 500 fold, or about 25% to 1000% improvement in binding. The polypeptide variant which "exhibits decreased binding" to an FcR, binds at least one FcR with lower affinity (e.g., higher apparent $K_d$ or higher $IC_{50}$ value) than parent polypeptide. The decrease in binding compared to a parent polypeptide may be about 40% or more decrease in binding.

"Antibody-dependent cell-mediated cytotoxicity" or "ADCC" refers to a form of cytotoxicity in which secreted Ig bound to Fc receptors (FcRs) present on certain cytotoxic cells (e.g. Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are absolutely required for such killing. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *PNAS* (USA) 95:652-656 (1998).

The polypeptide comprising a variant Fc region which "exhibits increased ADCC" or mediates antibody-dependent cell-mediated cytotoxicity (ADCC) in the presence of human effector cells more effectively than polypeptide having wild type IgG Fc or a parent polypeptide is one which in vitro or in vivo is substantially more effective at mediating ADCC, when the amounts of polypeptide with variant Fc region and the polypeptide with wild type Fc region (or the parent polypeptide) in the assay are essentially the same. Generally, such variants will be identified using any in vitro ADCC assay known in the art, such as assays or methods for determining ADCC activity, e.g. in an animal model etc. In some embodiments, the variant is from about 5 fold to about 100 fold, e.g. from about 25 to about 50 fold, more effective at mediating ADCC than the wild type Fc (or parent polypeptide).

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass) which are bound to their cognate antigen. To assess complement activation, a CDC assay, e.g. as described in Gazzano-Santoro et al., *J. Immunol. Methods* 202:163 (1996), may be performed. Polypeptide variants with altered Fc region amino acid sequences and increased or decreased C1q binding capability are described in U.S. Pat. No. 6,194,551B1 and WO99/51642. The contents of those patent publications are specifically incorporated herein by reference. See, also, Idusogie et al. *J. Immunol.* 164: 4178-4184 (2000).

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared times 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

An "effective amount" of an anti-HMC construct or composition as disclosed herein, is an amount sufficient to carry out a specifically stated purpose. An "effective amount" can be determined empirically and by known methods relating to the stated purpose.

The term "therapeutically effective amount" refers to an amount of an anti-HMC construct or composition as disclosed herein, effective to "treat" a disease or disorder in an individual. In the case of cancer, the therapeutically effective amount of the anti-HMC construct or composition as disclosed herein can reduce the number of cancer cells; reduce the tumor size or weight; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the anti-HMC construct or composition as disclosed herein can prevent growth and/or kill existing cancer cells, it can be cytostatic and/or cytotoxic. In some embodiments, the therapeutically effective amount is a growth inhibitory amount. In some embodiments, the therapeutically effective amount is an amount that extends the survival of a patient. In some embodiments, the therapeutically effective amount is an amount that improves progression free survival of a patient.

As used herein, by "pharmaceutically acceptable" or "pharmacologically compatible" is meant a material that is not biologically or otherwise undesirable, e.g., the material may be incorporated into a pharmaceutical composition administered to a patient without causing any significant undesirable biological effects or interacting in a deleterious manner with any of the other components of the composition in which it is contained. Pharmaceutically acceptable carriers or excipients have preferably met the required standards of toxicological and manufacturing testing and/or are included on the Inactive Ingredient Guide prepared by the U.S. Food and Drug administration.

The term "label" when used herein refers to a detectable compound or composition which can be conjugated directly or indirectly to the anti-HMC antibody moiety. The label may be detectable by itself (e.g., radioisotope labels or fluorescent labels) or, in the case of an enzymatic label, may catalyze chemical alteration of a substrate compound or composition which is detectable.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancers of types other than X.

As used herein and in the appended claims, the singular forms "a," "or," and "the" include plural referents unless the context clearly dictates otherwise.

Anti-HMC Constructs

In one aspect, the present invention provides histone H3/MHC class I complex-specific constructs (anti-HMC constructs) that comprise an antibody moiety that specifically binds to a complex comprising a histone H3 peptide and an MHC class I protein ("histone H3/MHC class I complex," or "HMC"). In some embodiments, the anti-HMC construct is an isolated anti-HMC construct. The specificity of the anti-HMC construct derives from an anti-HMC antibody moiety, such as a full-length antibody or antigen-binding fragment thereof, that specifically binds to the HMC. In some embodiments, reference to a moiety (such as an antibody moiety) that specifically binds to a complex comprising a histone H3 peptide and an MHC class I protein means that the moiety binds to the HMC with a) an affinity that is at least about 10 (including for example at least about any of 10, 20, 30, 40, 50, 75, 100, 200, 300, 400, 500, 750, 1000 or more) times its binding affinity for each of full-length histone H3, free histone H3 peptide, MHC class I protein not bound to a peptide, and/or MHC class I protein bound to a non-histone H3 peptide; or b) a $K_d$ no more than about 1/10 (such as no more than about any of 1/10, 1/20, 1/30, 1/40, 1/50, 1/75, 1/100, 1/200, 1/300, 1/400, 1/500, 1/750, 1/1000 or less) times its $K_d$ for binding to each of full-length histone H3, free histone H3 peptide, MHC class I protein not bound to a peptide, and/or MHC class I protein bound to a non-histone H3 peptide. Binding affinity can be determined by methods known in the art, such as ELISA, fluorescence activated cell sorting (FACS) analysis, or radioimmunoprecipitation assay (RIA). $K_d$ can be determined by methods known in the art, such as surface plasmon resonance (SPR) assay utilizing, for example, Biacore instruments, or kinetic exclusion assay (KinExA) utilizing, for example, Sapidyne instruments. In some embodiments, a moiety (such as an antibody moiety) that specifically binds to a complex comprising a histone H3 peptide and an MHC class I protein cross-reacts with a complex comprising a variant of the histone H3 peptide comprising at least one amino acid substitution (such as 1, 2, or 3 amino acid substitutions) compared to the histone H3 peptide and the MHC class I protein. In some embodiments, the variant of the histone H3 peptide comprises only 1 amino acid substitution compared to the histone H3 peptide. For example, in some embodiments, the moiety (such as antibody moiety) cross-reacts with two or more complexes, each individually comprising a histone H3 peptide comprising (such as consisting of) the amino acid sequence of any one of SEQ ID NOs: 5-8 and the MHC class I protein. In some embodiments, the moiety (such as antibody moiety) cross-reacts with a complex comprising a wild-type sequence of the histone H3 peptide and the MHC class I protein and a complex comprising a mutant sequence of the histone H3 peptide and the MHC class I protein. For example, in some embodiments, the moiety (such as antibody moiety) cross-reacts with a complex comprising a histone H3 peptide comprising (such as consisting of) the amino acid sequence of SEQ ID NO: 5 or 6 (wild-type histone H3 peptides) and the MHC class I protein and a complex comprising a histone H3 peptide comprising (such as consisting of) the amino acid sequence of SEQ ID NO: 7 or 8 (mutant histone H3 peptides) and the MHC class I protein. In some embodiments, the moiety (such as antibody moiety) binds to a complex comprising the mutant histone H3 peptide and the MHC class I protein with greater affinity than it binds to a complex comprising the wild-type histone H3 peptide and the MHC class I protein. In other embodiments, a moiety (such as an antibody moiety) that specifically binds to a complex comprising a histone H3 peptide and an MHC class I protein does not cross-react with a complex comprising a wild-type sequence of the histone H3 peptide and the MHC class I protein and a complex comprising a mutant sequence of the histone H3 peptide and the MHC class I protein. For example, in some embodiments, the moiety (such as antibody moiety) a) binds to a complex comprising a histone H3 peptide comprising (such as consisting of) the amino acid sequence of SEQ ID NO: 5 or 6 (wild-type histone H3 peptides) and the MHC class I protein and does not bind (or binds with a much lower affinity towards) a complex comprising a histone H3 peptide comprising (such as consisting of) the amino acid sequence of SEQ ID NO: 7 or 8 (mutant histone H3 peptides) and the MHC class I protein; or b) binds to a complex comprising a histone H3 peptide comprising (such as consisting of) the amino acid sequence of SEQ ID NO: 7 or 8 (mutant histone H3 peptides) and the MHC class I protein and does not bind (or binds with a much lower affinity towards) a complex comprising a histone H3 peptide comprising (such as consisting of) the amino acid sequence of SEQ ID NO: 5 or 6 (wild-type histone H3 peptides) and the MHC class I protein. In some embodiments, the mutant histone H3 peptide is a K27M-H3 26-35 peptide, such as K27M-H3.3 26-35 (SEQ ID NO: 7) or K27M-H3.1 26-35 (SEQ ID NO: 8). In some embodiments, the wild-type histone H3 peptide is a WT H3 26-35 peptide, such as WT H3.3 26-35 (SEQ ID NO: 5) or WT H3.1 (SEQ ID NO: 6).

Contemplated anti-HMC constructs include, for example, full-length anti-HMC antibodies, multi-specific (such as bispecific) anti-HMC molecules, anti-HMC chimeric antigen receptors (CARs), and anti-HMC immunoconjugates.

For example, in some embodiments, there is provided an anti-HMC construct (such as an isolated anti-HMC construct) comprising an anti-HMC antibody moiety that specifically binds to a complex comprising a histone H3 peptide and an MHC class I protein. In some embodiments, the histone H3 peptide comprises (such as consists of) the amino acid sequence of any one of SEQ ID NOs: 5-24. In some embodiments, the histone H3 peptide is WT histone H3.3 26-35 (SEQ ID NO: 5), WT histone H3.1 26-35 (SEQ ID NO: 6), mutant histone K27M-H3.3 26-35 (SEQ ID NO: 7), or mutant histone K27M-H3.1 26-35 (SEQ ID NO: 8). In some embodiments, the MHC class I protein is HLA-A02. In some embodiments, the MHC class I protein is HLA-A*02:01 (GenBank Accession No.: AAO20853). In some embodiments, the anti-HMC construct is non-naturally occurring. In some embodiments, the anti-HMC construct is a full-length antibody. In some embodiments, the anti-HMC construct is a multi-specific (such as bispecific) molecule. In some embodiments, the anti-HMC construct is a chimeric receptor (e.g., a CAR or abTCR). In some embodiments, the anti-HMC construct is an immunoconjugate. In some embodiments, the anti-HMC construct binds the HMC with a $K_d$ between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the anti-HMC construct cross-reacts with at least one (such as at least any of 2, 3, 4, 5, or 6) complex comprising the MHC class I protein and a variant of the histone H3 peptide having one amino acid substitution (such as a conservative amino acid substitution). In some embodiments, the anti-HMC construct cross-reacts with at least one (such as at least any of 2, 3, 4, or 5) complex comprising the histone H3 peptide and a different subtype of the MHC class I protein.

In some embodiments, there is provided an anti-HMC construct comprising an anti-HMC antibody moiety that specifically binds to a complex comprising a histone H3 peptide comprising (such as consisting of) the amino acid sequence of any one of SEQ ID NOs: 5-24 and HLA-A*02:01. In some embodiments, the histone H3 peptide is mutant histone K27M-H3.3 26-35 (SEQ ID NO: 7) or mutant histone K27M-H3.1 26-35 (SEQ ID NO: 8). In some embodiments, the histone H3 peptide is WT H3.3 26-35 (SEQ ID NO: 5) or WT H3.1 26-35 (SEQ ID NO: 6). In some embodiments, the anti-HMC construct is non-naturally occurring. In some embodiments, the anti-HMC construct is a full-length antibody. In some embodiments, the anti-HMC construct is a multi-specific (such as bispecific) molecule. In some embodiments, the anti-HMC construct is a chimeric receptor (e.g., a CAR or abTCR). In some embodiments, the anti-HMC construct is an immunoconjugate. In some embodiments, the anti-HMC construct binds the HMC with a $K_d$ between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the anti-HMC construct cross-reacts with at least one (such as at least any of 2, 3, 4, 5, or 6) complex comprising the MHC class I protein and a variant of the histone H3 peptide having one amino acid substitution (such as a conservative amino acid substitution). In some embodiments, the anti-HMC construct cross-reacts with at least one (such as at least any of 2, 3, 4, or 5) complex comprising the histone H3 peptide and a different subtype of the MHC class I protein.

In some embodiments, there is provided an anti-HMC construct comprising an anti-HMC antibody moiety that specifically binds to a complex comprising a histone H3 peptide and an MHC class I protein, wherein the anti-HMC antibody moiety comprises: i) a heavy chain variable domain sequence comprising an HC-CDR1 comprising the amino acid sequence of SEQ ID NO: 158, or a variant thereof comprising up to about 3 (for example about any of 1, 2, or 3) amino acid substitutions, an HC-CDR2 comprising the amino acid sequence of SEQ ID NO: 159, or a variant thereof comprising up to about 3 (for example about any of 1, 2, or 3) amino acid substitutions, and/or an HC-CDR3 comprising the amino acid sequence of SEQ ID NO: 160 or 161; or a variant thereof comprising up to about 3 (for example about any of 1, 2, or 3) amino acid substitutions; and ii) a light chain variable domain comprising an LC-CDR1 comprising the amino acid sequence of SEQ ID NO: 162, or a variant thereof comprising up to about 3 (for example about any of 1, 2, or 3) amino acid substitutions, and/or an LC-CDR3 comprising the amino acid sequence of SEQ ID NO: 163, or a variant thereof comprising up to about 3 (for example about any of 1, 2, or 3) amino acid substitutions. In some embodiments, the anti-HMC construct is non-naturally occurring. In some embodiments, the anti-HMC construct is a full-length antibody. In some embodiments, the anti-HMC construct is a multi-specific (such as bispecific) molecule. In some embodiments, the anti-HMC construct is a chimeric receptor (e.g., a CAR or abTCR). In some embodiments, the anti-HMC construct is an immunoconjugate. In some embodiments, the anti-HMC construct binds the HMC with a $K_d$ between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the anti-HMC construct cross-reacts with at least one (such as at least any of 2, 3, 4, 5, or 6) complex comprising the MHC class I protein and a variant of the histone H3 peptide having one amino acid substitution (such as a conservative amino acid substitution). In some embodiments, the anti-HMC construct cross-reacts with at least one (such as at least any of 2, 3, 4, or 5) complex comprising the histone H3 peptide and a different subtype of the MHC class I protein.

In some embodiments, there is provided an anti-HMC construct comprising an anti-HMC antibody moiety that specifically binds to a complex comprising a histone H3 peptide and an MHC class I protein, wherein the anti-HMC antibody moiety comprises: i) a heavy chain variable domain sequence comprising an HC-CDR1 comprising (and in some embodiments consisting of) the amino acid sequence of any one of SEQ ID NOs: 99-107; or a variant thereof comprising up to about 5 (for example about any of 1, 2, 3, 4, or 5) amino acid substitutions; an HC-CDR2 comprising (and in some embodiments consisting of) the amino acid sequence of any one of SEQ ID NOs: 108-116; or a variant thereof comprising up to about 5 (for example about any of 1, 2, 3, 4, or 5) amino acid substitutions; and an HC-CDR3 comprising (and in some embodiments consisting of) the amino acid sequence of any one of SEQ ID NOs: 117-128; or a variant thereof comprising up to about 5 (for example about any of 1, 2, 3, 4, or 5) amino acid substitutions; and ii) a light chain variable domain sequence comprising an LC-CDR1 comprising (and in some embodiments consisting of) the amino acid sequence of any one of SEQ ID NOs: 129-138; or a variant thereof comprising up to about 5 (for example about any of 1, 2, 3, 4, or 5) amino acid substitutions; an LC-CDR2 comprising (and in some embodiments consisting of) the amino acid sequence of any one of SEQ ID NOs: 139-147; or a variant thereof comprising up to about 3 (for example about any of 1, 2, or 3) amino acid substitutions; and an LC-CDR3 comprising (and in some embodiments consisting of) the amino acid sequence of any one of SEQ ID NOs: 148-157; or a variant thereof comprising up to about 5 (for example about any of 1, 2, 3, 4, or 5) amino acid substitutions. In some embodiments, there is provided an anti-HMC construct comprising an anti-HMC antibody moiety that specifically binds to a complex comprising a histone H3 peptide and an MHC class I protein, wherein the anti-HMC antibody moiety comprises: i) a heavy chain variable domain sequence comprising an HC-CDR1 comprising (and in some embodiments consisting of) the amino acid sequence of any one of SEQ ID NOs: 99-107; an HC-CDR2 comprising (and in some embodiments consisting of) the amino acid sequence of any one of SEQ ID NOs: 108-116; and an HC-CDR3 comprising (and in some embodiments consisting of) the amino acid sequence of any one of SEQ ID NOs: 117-128; or a variant thereof comprising up to about 5 (for example about any of 1, 2, 3, 4, or 5) amino acid substitutions in the HC-CDR sequences; and ii) a light chain variable domain sequence comprising an LC-CDR1 comprising (and in some embodiments consisting of) the amino acid sequence of any one of SEQ ID NOs: 129-138; an LC-CDR2 comprising (and in some embodiments consisting of) the amino acid sequence of any one of SEQ ID NOs: 139-147; and an LC-CDR3 comprising (and in some embodiments consisting of) the amino acid sequence of any one of SEQ ID NOs: 148-157; or a variant thereof comprising up to about 5 (for example about any of 1, 2, 3, 4, or 5) amino acid substitutions in the LC-CDR sequences. In some embodiments, the anti-HMC construct is non-naturally occurring. In some embodiments, the anti-HMC construct is a full-length antibody. In some embodiments, the anti-HMC construct is a multi-specific (such as bispecific) molecule. In some embodiments, the anti-HMC construct is a chimeric receptor (e.g., a CAR or abTCR). In some embodiments, the anti-HMC construct is an immunoconjugate. In some embodiments, the anti-HMC construct binds the HMC with a $K_d$ between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the anti-HMC construct cross-reacts with at least one (such as at least any of 2, 3, 4, 5, or 6) complex comprising the MHC class I protein and a variant of the histone H3 peptide having one amino acid substitution (such as a conservative amino acid substitution). In some embodiments, the anti-HMC construct cross-reacts with at least one (such as at least any of 2, 3, 4, or 5) complex comprising the histone H3 peptide and a different subtype of the MHC class I protein.

In some embodiments, there is provided an anti-HMC construct comprising an anti-HMC antibody moiety that specifically binds to a complex comprising a histone H3 peptide and an MHC class I protein, wherein the anti-HMC antibody moiety comprises a heavy chain variable domain comprising (and in some embodiments consisting of) the amino acid sequence of any one of SEQ ID NOs: 75-86, or a variant thereof having at least about 95% (for example at least about any of 96%, 97%, 98%, or 99%) sequence identity, and a light chain variable domain comprising (and in some embodiments consisting of) the amino acid sequence of any one of SEQ ID NOs: 87-98, or a variant thereof having at least about 95% (for example at least about any of 96%, 97%, 98%, or 99%) sequence identity. In some embodiments, the anti-HMC construct is non-naturally occurring. In some embodiments, the anti-HMC construct is a full-length antibody. In some embodiments, the anti-HMC construct is a multi-specific (such as bispecific) molecule. In some embodiments, the anti-HMC construct is a chimeric receptor (e.g., a CAR or abTCR). In some embodiments, the anti-HMC construct is an immunoconjugate. In some embodiments, the anti-HMC construct binds the HMC with a $K_d$ between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the anti-HMC construct cross-reacts with at least one (such as at least any of 2, 3, 4, 5, or 6) complex comprising the MHC class I protein and a variant of the histone H3 peptide having one amino acid substitution (such as a conservative amino acid substitution). In some embodiments, the anti-HMC construct cross-reacts with at least one (such as at least any of 2, 3, 4, or 5) complex comprising the histone H3 peptide and a different subtype of the MHC class I protein.

In some embodiments, there is provided an anti-HMC construct comprising a first anti-HMC antibody moiety that competes for binding to a target histone H3/MHC class I complex with a second anti-HMC antibody moiety according to any of the anti-HMC antibody moieties described herein. In some embodiments, the first anti-HMC antibody moiety binds to the same, or substantially the same, epitope as the second anti-HMC antibody moiety. In some embodiments, binding of the first anti-HMC antibody moiety to the target histone H3/MHC class I complex inhibits binding of the second anti-HMC antibody moiety to the target histone H3/MHC class I complex by at least about 70% (such as by at least about any of 75%, 80%, 85%, 90%, 95%, 98% or 99%), or vice versa. In some embodiments, the first anti-HMC antibody moiety and the second anti-HMC antibody moiety cross-compete for binding to the target histone H3/MHC class I complex, i.e., each of the first and second antibody moieties competes with the other for binding to the target histone H3/MHC class I complex.

For example, in some embodiments, there is provided an anti-HMC construct comprising an anti-HMC antibody moiety that competes for binding to a target histone H3/MHC class I complex with an antibody moiety comprising i) a heavy chain variable domain sequence comprising an HC-CDR1 comprising the amino acid sequence of SEQ ID NO: 158, or a variant thereof comprising up to about 3 (for example about any of 1, 2, or 3) amino acid substitutions, an HC-CDR2 comprising the amino acid sequence of SEQ ID NO: 159, or a variant thereof comprising up to about 3 (for example about any of 1, 2, or 3) amino acid substitutions, and/or an HC-CDR3 comprising the amino acid sequence of SEQ ID NO: 160 or 161; or a variant thereof comprising up to about 3 (for example about any of 1, 2, or 3) amino acid substitutions; and ii) a light chain variable domain comprising an LC-CDR1 comprising the amino acid sequence of SEQ ID NO: 162, or a variant thereof comprising up to about 3 (for example about any of 1, 2, or 3) amino acid substitutions, and/or an LC-CDR3 comprising the amino acid sequence of SEQ ID NO: 163, or a variant thereof comprising up to about 3 (for example about any of 1, 2, or 3) amino acid substitutions.

In some embodiments, there is provided an anti-HMC construct comprising an anti-HMC antibody moiety that competes for binding to a target histone H3/MHC class I complex with an antibody moiety comprising i) a heavy chain variable domain sequence comprising an HC-CDR1 comprising (and in some embodiments consisting of) the amino acid sequence of any one of SEQ ID NOs: 99-107; or a variant thereof comprising up to about 5 (for example about any of 1, 2, 3, 4, or 5) amino acid substitutions; an HC-CDR2 comprising (and in some embodiments consisting of) the amino acid sequence of any one of SEQ ID NOs: 108-116; or a variant thereof comprising up to about 5 (for example about any of 1, 2, 3, 4, or 5) amino acid substitutions; and an HC-CDR3 comprising (and in some embodiments consisting of) the amino acid sequence of any one of SEQ ID NOs: 117-128; or a variant thereof comprising up to about 5 (for example about any of 1, 2, 3, 4, or 5) amino acid substitutions; and ii) a light chain variable domain sequence comprising an LC-CDR1 comprising (and in some embodiments consisting of) the amino acid sequence of any one of SEQ ID NOs: 129-138; or a variant thereof comprising up to about 5 (for example about any of 1, 2, 3, 4, or 5) amino acid substitutions; an LC-CDR2 comprising (and in some embodiments consisting of) the amino acid sequence of any one of SEQ ID NOs: 139-147; or a variant thereof comprising up to about 3 (for example about any of 1, 2, or 3) amino acid substitutions; and an LC-CDR3 comprising (and in some embodiments consisting of) the amino acid sequence of any one of SEQ ID NOs: 148-157; or a variant thereof comprising up to about 5 (for example about any of 1, 2, 3, 4, or 5) amino acid substitutions. In some embodiments, there is provided an anti-HMC construct comprising an anti-HMC antibody moiety that competes for binding to a target histone H3/MHC class I complex with an antibody moiety comprising i) a heavy chain variable domain sequence comprising an HC-CDR1 comprising (and in some embodiments consisting of) the amino acid sequence of any one of SEQ ID NOs: 99-107; an HC-CDR2 comprising (and in some embodiments consisting of) the amino acid sequence of any one of SEQ ID NOs: 108-116; and an HC-CDR3 comprising (and in some embodiments consisting of) the amino acid sequence of any one of SEQ ID NOs: 117-128; or a variant thereof comprising up to about 5 (for example about any of 1, 2, 3, 4, or 5) amino acid substitutions in the HC-CDR sequences; and ii) a light chain variable domain sequence comprising an LC-CDR1 comprising (and in some embodiments consisting of) the amino acid sequence of any one of SEQ ID NOs: 129-138; an LC-CDR2 comprising (and in some embodiments consisting of) the amino acid sequence of any one of SEQ ID NOs: 139-147; and an LC-CDR3 comprising (and in some embodiments consisting of) the amino acid sequence of any one of SEQ ID NOs: 148-157; or a variant thereof comprising up to about 5 (for example about any of 1, 2, 3, 4, or 5) amino acid substitutions in the LC-CDR sequences.

In some embodiments, there is provided an anti-HMC construct comprising an anti-HMC antibody moiety that competes for binding to a target histone H3/MHC class I complex with an antibody moiety comprising a heavy chain variable domain comprising (and in some embodiments consisting of) the amino acid sequence of any one of SEQ ID NOs: 75-86, or a variant thereof having at least about 95% (for example at least about any of 96%, 97%, 98%, or 99%) sequence identity, and a light chain variable domain comprising (and in some embodiments consisting of) the amino acid sequence of any one of SEQ ID NOs: 87-98, or a variant thereof having at least about 95% (for example at least about any of 96%, 97%, 98%, or 99%) sequence identity. In some embodiments, there is provided an anti-HMC construct comprising an anti-HMC antibody moiety that competes for binding to a target histone H3/MHC class I complex with an antibody moiety comprising a heavy chain variable domain comprising (and in some embodiments consisting of) the amino acid sequence of any one of SEQ ID NOs: 75-86, and a light chain variable domain comprising (and in some embodiments consisting of) the amino acid sequence of any one of SEQ ID NOs: 87-98.

The different aspects are discussed in various sections below in further detail.

Anti-HMC Antibody Moiety

The anti-HMC constructs comprise an anti-HMC antibody moiety that specifically binds to a complex comprising a histone H3 peptide and an MHC class I protein.

In some embodiments, the anti-HMC antibody moiety specifically binds to an HMC present on the surface of a cell. In some embodiments, the cell is a cancer cell. In some embodiments, the cancer cell is in a solid tumor. In some embodiments, the cancer cell is a metastatic cancer cell.

In some embodiments, the histone H3 peptide is an MHC class I-restricted peptide. In some embodiments, the histone H3 peptide is from about 8 to about 12 (such as about any of 8, 9, 10, 11, or 12) amino acids in length.

In some embodiments, the histone H3 peptide comprises (and in some embodiments consists of) the amino acid sequence of any one of SEQ ID NOs: 5-24.

In some embodiments, the histone H3 peptide comprises (and in some embodiments consists of) the sequence of amino acids 26-35 of mutant histone K27M-H3.3 (RMSAP-STGGV, SEQ ID NO: 7; also referred to herein as "K27M-H3.3 26"). In some embodiments, the histone H3 peptide comprises (and in some embodiments consists of) the sequence of amino acids 26-35 of mutant histone K27M-H3.1 (RMSAPATGGV, SEQ ID NO: 8; also referred to herein as "K27M-H3.1 26").

In some embodiments, the MHC class I protein is HLA-A, HLA-B, HLA-C, HLA-E, HLA-F, or HLA-G. In some embodiments, the MHC class I protein is HLA-A. In some embodiments, the HLA-A is HLA-A02. In some embodiments, the HLA-A02 is HLA-A*02:01.

In some embodiments, the anti-HMC antibody moiety is a full-length antibody. In some embodiments, the anti-HMC antibody moiety is an antigen-binding fragment, for example an antigen-binding fragment selected from the group consisting of a Fab, a Fab', a F(ab')2, an Fv fragment, a disulfide stabilized Fv fragment (dsFv), and a single-chain antibody molecule (scFv). In some embodiments, the anti-HMC antibody moiety is an scFv. In some embodiments, the anti-HMC antibody moiety is human, humanized, or semi-synthetic.

In some embodiments, the anti-HMC antibody moiety specifically binds to the N-terminal portion of the histone H3 peptide in the complex. In some embodiments, the anti-HMC antibody moiety specifically binds to the C-terminal portion of the histone H3 peptide in the complex. In some embodiments, the anti-HMC antibody moiety specifically binds to the middle portion of the histone H3 peptide in the complex.

In some embodiments, the anti-HMC antibody moiety (or the anti-HMC construct comprising the anti-HMC antibody moiety) binds to the complex comprising the histone H3 peptide and the MHC class I protein with an affinity that is at least about 10 (including for example at least about any of 10, 20, 30, 40, 50, 75, 100, 200, 300, 400, 500, 750, 1000 or more) times its binding affinity for each of full-length histone H3, free histone H3 peptide, MHC class I protein not bound to a peptide, and/or MHC class I protein bound to a non-histone H3 peptide. In some embodiments, the anti-HMC antibody moiety (or the anti-HMC construct comprising the anti-HMC antibody moiety) binds to the complex comprising the histone H3 peptide and the MHC class I protein with a $K_d$ no more than about 1/10 (such as no more than about any of 1/10, 1/20, 1/30, 1/40, 1/50, 1/75, 1/100, 1/200, 1/300, 1/400, 1/500, 1/750, 1/1000 or less) times its $K_d$ for binding to each of full-length histone H3, free histone H3 peptide, MHC class I protein not bound to a peptide, and/or MHC class I protein bound to a non-histone H3 peptide. In some embodiments, the anti-HMC antibody moiety (or the anti-HMC construct comprising the anti-HMC antibody moiety) cross-reacts with a complex comprising a variant of the histone H3 peptide comprising at least one amino acid substitution (such as 1, 2, or 3 amino acid substitutions) compared to the histone H3 peptide and the MHC class I protein. In some embodiments, the variant of the histone H3 peptide comprises only 1 amino acid substitution compared to the histone H3 peptide. For example, in some embodiments, the anti-HMC antibody moiety (or the anti-HMC construct comprising the anti-HMC antibody moiety) cross-reacts with two or more complexes, each individually comprising a histone H3 peptide comprising (such as consisting of) the amino acid sequence of any one of SEQ ID NOs: 5-8 and the MHC class I protein.

In some embodiments, the anti-HMC antibody moiety (or the anti-HMC construct comprising the anti-HMC antibody moiety) cross-reacts with a complex comprising a wild-type sequence of the histone H3 peptide and the MHC class I protein and a complex comprising a mutant sequence of the histone H3 peptide and the MHC class I protein. For example, in some embodiments, the anti-HMC antibody moiety (or the anti-HMC construct comprising the anti-HMC antibody moiety) cross-reacts with a complex comprising a histone H3 peptide comprising (such as consisting of) the amino acid sequence of SEQ ID NO: 5 or 6 (wild-type histone H3 peptides) and the MHC class I protein and a complex comprising a histone H3 peptide comprising (such as consisting of) the amino acid sequence of SEQ ID NO: 7 or 8 (mutant histone H3 peptides) and the MHC class I protein. In some embodiments, the anti-HMC antibody moiety (or the anti-HMC construct comprising the anti-HMC antibody moiety) binds to a complex comprising the mutant histone H3 peptide and the MHC class I protein with greater affinity than it binds to a complex comprising the wild-type histone H3 peptide and the MHC class I protein. In some embodiments, the anti-HMC antibody moiety (or the anti-HMC construct comprising the anti-HMC antibody moiety) binds to the complex comprising the mutant histone H3 peptide and the MHC class I protein with an affinity that is at least about 1/2 (including for example at least about any of 1, 2, 3, 4, 5, 6, 7, 8, 9, or more) times its binding affinity for a complex comprising the wild-type histone H3 peptide and the MHC class I protein. In other embodiments, the anti-HMC antibody moiety (or the anti-HMC construct comprising the anti-HMC antibody moiety) does not cross-react with a complex comprising a wild-type sequence of the histone H3 peptide and the MHC class I protein and a complex comprising a mutant sequence of the histone H3 peptide and the MHC class I protein. For example, in some embodiments, the anti-HMC antibody moiety (or the anti-HMC construct comprising the anti-HMC antibody moiety) a) binds to a complex comprising a histone H3 peptide comprising (such as consisting of) the amino acid sequence of SEQ ID NO: 5 or 6 (wild-type histone H3 peptides) and the MHC class I protein and does not bind (or binds with a much lower affinity towards) a complex comprising a histone H3 peptide comprising (such as consisting of) the amino acid sequence of SEQ ID NO: 7 or 8 (mutant histone H3 peptides) and the MHC class I protein; or b) binds to a complex comprising a histone H3 peptide comprising (such as consisting of) the amino acid sequence of SEQ ID NO: 7 or 8 (mutant histone H3 peptides) and the MHC class I protein and does not bind (or binds with a much lower affinity towards) a complex comprising a histone H3 peptide comprising (such as consisting of) the amino acid sequence of SEQ ID NO: 5 or 6 (wild-type histone H3 peptides) and the MHC class I protein. In some embodiments, the mutant histone H3 peptide is a K27M-H3 26-35 peptide, such as K27M-H3.3 26-35 (SEQ ID NO: 7) or K27M-H3.1 26-35 (SEQ ID NO: 8). In some embodiments, the wild-type histone H3 peptide is a WT H3 26-35 peptide, such as WT H3.3 26-35 (SEQ ID NO: 5) or WT H3.1 (SEQ ID NO: 6).

In some embodiments, the anti-HMC antibody moiety (or the anti-HMC construct comprising the anti-HMC antibody moiety) binds to the complex comprising the histone H3 peptide and the MHC class I protein with a $K_d$ between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the anti-HMC antibody moiety (or the anti-HMC construct comprising the anti-HMC antibody moiety) binds to the complex comprising the histone H3 peptide and the MHC class I protein with a $K_d$ between about 1 pM to about 250 pM (such as about any of 1, 10, 25, 50, 75, 100, 150, 200, or 250 pM, including any ranges between these values). In some embodiments, the anti-HMC antibody moiety (or the anti-HMC construct comprising the anti-HMC antibody moiety) binds to the complex comprising the histone H3 peptide and the MHC class I protein with a $K_d$ between about 1 nM to about 500 nM (such as about any of 1, 10, 25, 50, 75, 100, 150, 200, 250, 300, 350, 400, 450, or 500 nM, including any ranges between these values).

In some embodiments, the anti-HMC antibody moiety specifically binds to a complex comprising a histone H3 peptide and an MHC class I protein, wherein the anti-HMC antibody moiety cross-reacts with at least one complex comprising the histone H3 peptide and an allelic variant of the MHC class I protein. In some embodiments, the allelic variant has up to about 10 (such as about any of 1, 2, 3, 4, 5, 6, 7, 8, 9, or 10) amino acid substitutions when compared to the MHC class I protein. In some embodiments, the allelic variant is the same serotype as the MHC class I protein. In some embodiments, the allelic variant is a different serotype than the MHC class I protein. In some embodiments, the anti-HMC antibody moiety does not cross-react with any complex comprising the histone H3 peptide and an allelic variant of the MHC class I protein. In some embodiments, the anti-HMC antibody moiety cross-reacts with at least one (such as at least any of 2, 3, 4, or 5) complex comprising the histone H3 peptide and a different subtype of the MHC class I protein. In some embodiments, the histone H3 peptide is a K27M-H3 26-35 peptide, such as K27M-H3.3 26-35 (SEQ ID NO: 7) or K27M-H3.1 26-35 (SEQ ID NO: 8). In some embodiments, the histone H3 peptide is a WT H3 26-35 peptide, such as WT H3.3 26-35 (SEQ ID NO: 5) or WT H3.1 26-35 (SEQ ID NO: 6).

In some embodiments, the anti-HMC antibody moiety specifically binds to a complex comprising a histone H3 peptide and an MHC class I protein, wherein the anti-HMC antibody moiety cross-reacts with at least one complex comprising the MHC class I protein and a variant of the histone H3 peptide having one amino acid substitution (such as a conservative amino acid substitution). In some embodiments, the anti-HMC antibody moiety does not cross-react with any complex comprising the MHC class I protein and a variant of the histone H3 peptide. In some embodiments, the histone H3 peptide is a K27M-H3 26-35 peptide, such as K27M-H3.3 26-35 (SEQ ID NO: 7) or K27M-H3.1 26-35 (SEQ ID NO: 8).

For example, in some embodiments, the anti-HMC antibody moiety specifically binds to a complex comprising a histone H3 peptide comprising (such as consisting of) the amino acid sequence of any one of SEQ ID NOs: 5-8 and an MHC class I protein (such as HLA-A02, for example HLA-A*02:01), wherein the anti-HMC antibody moiety further binds to at least one (including at least about any of 2, 3, 4, 5, 6, 7, 8, 9, or more) complex comprising an alanine-substituted histone H3 peptide of any one of SEQ ID NOs: 9-24 and an MHC class I protein (such as HLA-A02, for example HLA-A*02:01).

In some embodiments, the anti-HMC antibody moiety specifically binds to a complex comprising a histone H3 peptide comprising the amino acid sequence of any one of SEQ ID NOs: 5-8 and HLA-A*02:01, wherein the anti-HMC antibody moiety cross-reacts with at least one (including at least about any of 2, 3, 4, 5, or 6) of: a complex comprising the histone H3 peptide and HLA-A*02:02 (GenBank Accession No.: AFL91480), a complex comprising the histone H3 peptide and HLA-A*02:03 (GenBank Accession No.: AAA03604), a complex comprising the histone H3 peptide and HLA-A*02:05 (GenBank Accession No.: AAA03603), a complex comprising the histone H3 peptide and HLA-A*02:06 (GenBank Accession No.: CCB78868), a complex comprising the histone H3 peptide and HLA-A*02:07 (GenBank Accession No.: ACR55712), and a complex comprising the histone H3 peptide and HLA-A*02:11 (GenBank Accession No.: CAB56609).

In some embodiments, the anti-HMC antibody moiety specifically binds to one or more of: a complex comprising K27M-H3.3 26 (SEQ ID NO: 7) and an MHC class I protein (such as HLA-A02, for example HLA-A*02:01); and a complex comprising K27M-H3.1 26 (SEQ ID NO: 8) and an MHC class I protein (such as HLA-A02, for example HLA-A*02:01). In some embodiments, the anti-HMC antibody moiety cross-reacts with one or more of: a complex comprising WT H3.3 26 (SEQ ID NO: 5) and an MHC class I protein (such as HLA-A02, for example HLA-A*02:01); and a complex comprising WT H3.1 26 (SEQ ID NO: 6) and an MHC class I protein (such as HLA-A02, for example HLA-A*02:01). In some embodiments, the anti-HMC antibody moiety does not cross-react with one or more of: a complex comprising WT H3.3 26 (SEQ ID NO: 5) and an MHC class I protein (such as HLA-A02, for example HLA-A*02:01); and a complex comprising WT H3.1 26 (SEQ ID NO: 6) and an MHC class I protein (such as HLA-A02, for example HLA-A*02:01).

In some embodiments, the anti-HMC antibody moiety is a semi-synthetic antibody moiety comprising fully human sequences and one or more synthetic regions. In some embodiments, the anti-HMC antibody moiety is a semi-synthetic antibody moiety comprising a fully human light chain variable domain and a semi-synthetic heavy chain variable domain comprising fully human FR1, HC-CDR1, FR2, HC-CDR2, FR3, and FR4 regions and a synthetic HC-CDR3. In some embodiments, the semi-synthetic heavy chain variable domain comprises a fully synthetic HC-CDR3 having a sequence from about 5 to about 25 (such as about any of 5, 6, 7, 8, 9, 10, 11, 12, 13, 14, 15, 16, 17, 18, 19, 20, 21, 22, 23, 24, or 25) amino acids in length. In some embodiments, the semi-synthetic heavy chain variable domain or the synthetic HC-CDR3 is obtained from a semi-synthetic library (such as a semi-synthetic human library) comprising fully synthetic HC-CDR3s having a sequence from about 5 to about 25 (such as about any of 5, 6, 7, 8, 9, 10, 11, 12, 13, 14, 15, 16, 17, 18, 19, 20, 21, 22, 23, 24, or 25) amino acids in length, wherein each amino acid in the sequence is randomly selected from the standard human amino acids, minus cysteine. In some embodiments, the synthetic HC-CDR3 is from about 7 to about 15 (such as about any of 7, 8, 9, 10, 11, 12, 13, 14, or 15) amino acids in length.

The anti-HMC antibody moieties in some embodiments comprise specific sequences or certain variants of such sequences. In some embodiments, the amino acid substitutions in the variant sequences do not substantially reduce the ability of the anti-HMC antibody moiety to bind the HMC. For example, alterations that do not substantially reduce HMC binding affinity may be made. Alterations that substantially improve HMC binding affinity or affect some other property, such as specificity and/or cross-reactivity with related variants of the HMC, are also contemplated.

In some embodiments, the anti-HMC antibody moiety comprises i) a heavy chain variable domain comprising an HC-CDR3 comprising the amino acid sequence of SEQ ID NO: 160 or 161, or a variant thereof comprising up to about 3 (for example about any of 1, 2, or 3) amino acid substitutions; and ii) a light chain variable domain comprising an LC-CDR3 comprising the amino acid sequence of SEQ ID NO: 163, or a variant thereof comprising up to about 3 (for example about any of 1, 2, or 3) amino acid substitutions.

In some embodiments, the anti-HMC antibody moiety comprises i) a heavy chain variable domain comprising an HC-CDR3 comprising the amino acid sequence of SEQ ID NO: 160 or 161; and ii) a light chain variable domain comprising an LC-CDR3 comprising the amino acid sequence of SEQ ID NO: 163.

In some embodiments, the anti-HMC antibody moiety comprises i) a heavy chain variable domain comprising an HC-CDR1 comprising the amino acid sequence of SEQ ID NO: 158, or a variant thereof comprising up to about 3 (for example about any of 1, 2, or 3) amino acid substitutions, an HC-CDR2 comprising the amino acid sequence of SEQ ID NO: 159, or a variant thereof comprising up to about 3 (for example about any of 1, 2, or 3) amino acid substitutions, and/or an HC-CDR3 comprising the amino acid sequence of SEQ ID NO: 160 or 161, or a variant thereof comprising up to about 3 (for example about any of 1, 2, or 3) amino acid substitutions; and ii) a light chain variable domain comprising an LC-CDR1 comprising the amino acid sequence of SEQ ID NO: 162, or a variant thereof comprising up to about 3 (for example about any of 1, 2, or 3) amino acid substitutions, and/or an LC-CDR3 comprising the amino acid sequence of SEQ ID NO: 163, or a variant thereof comprising up to about 3 (for example about any of 1, 2, or 3) amino acid substitutions.

In some embodiments, the anti-HMC antibody moiety comprises i) a heavy chain variable domain comprising an HC-CDR1 comprising the amino acid sequence of SEQ ID NO: 158, or a variant thereof comprising up to about 3 (for example about any of 1, 2, or 3) amino acid substitutions, an HC-CDR2 comprising the amino acid sequence of SEQ ID NO: 159, or a variant thereof comprising up to about 3 (for example about any of 1, 2, or 3) amino acid substitutions, and/or an HC-CDR3 comprising the amino acid sequence of SEQ ID NO: 160 or 161; and ii) a light chain variable domain comprising an LC-CDR1 comprising the amino acid sequence of SEQ ID NO: 162, or a variant thereof comprising up to about 3 (for example about any of 1, 2, or 3) amino acid substitutions, and/or an LC-CDR3 comprising the amino acid sequence of SEQ ID NO: 163.

In some embodiments, the anti-HMC antibody moiety comprises i) a heavy chain variable domain comprising an HC-CDR1 comprising the amino acid sequence of SEQ ID NO: 158, an HC-CDR2 comprising the amino acid sequence of SEQ ID NO: 159, and/or an HC-CDR3 comprising the amino acid sequence of SEQ ID NO: 160 or 161; or a variant thereof comprising up to about 3 (such as about any of 1, 2, or 3) amino acid substitutions in the HC-CDR sequences; and ii) a light chain variable domain comprising an LC-CDR1 comprising the amino acid sequence of SEQ ID NO: 162, and/or an LC-CDR3 comprising the amino acid sequence of SEQ ID NO: 163; or a variant thereof comprising up to about 3 (such as about any of 1, 2, or 3) amino acid substitutions in the LC-CDR sequences.

In some embodiments, the anti-HMC antibody moiety comprises i) a heavy chain variable domain comprising an HC-CDR1 comprising the amino acid sequence of SEQ ID NO: 158, an HC-CDR2 comprising the amino acid sequence of SEQ ID NO: 159, and/or an HC-CDR3 comprising the amino acid sequence of SEQ ID NO: 160 or 161; and ii) a light chain variable domain comprising an LC-CDR1 comprising the amino acid sequence of SEQ ID NO: 162, and/or an LC-CDR3 comprising the amino acid sequence of SEQ ID NO: 163. The sequences of the CDRs noted herein are provided in Table 2 below.

TABLE 2

| | | |
|---|---|---|
| HC-CDR1 consensus | SEQ ID NO: 158 | $X_1X_2X_3FX_4X_5Y$ wherein $X_1$ = A or G, $X_2$ = G or Y, $X_3$ = S or T, $X_4$ = S or T, and $X_5$ = any AA |
| HC-CDR2 consensus | SEQ ID NO: 159 | $IX_1X_2X_3X_4GX_5X_6$ wherein $X_1$ = any AA, $X_2$ = A or P, $X_3$ = any AA, $X_4$ = any AA, $X_5$ = any AA, and $X_6$ = A or T |
| HC-CDR3 consensus 1 | SEQ ID NO: 160 | $ARGX_1D$ wherein $X_1$ = F or Y |
| HC-CDR3 consensus 2 | SEQ ID NO: 161 | $ARX_1X_2EX_3GX_4PX_5D$ wherein $X_1$ = any AA, $X_2$ = W or Y, $X_3$ = any AA, $X_4$ = F or Y, and $X_5$ = F or Y |
| LC-CDR1 consensus | SEQ ID NO: 162 | $X_1X_2NX_3GX_4$ wherein $X_1$ = S or T, $X_2$ = any AA, $X_3$ = I, L, or N, and $X_4$ = A, S, or T |
| LC-CDR3 consensus | SEQ ID NO: 163 | $X_1X_2X_3DX_4SL$ wherein $X_1$ = A or Q, $X_2$ = A or S, $X_3$ = W or Y, and $X_4$ = any AA |

In some embodiments, the anti-HMC antibody moiety comprises i) a heavy chain variable domain comprising an HC-CDR3 comprising the amino acid sequence of any one of SEQ ID NOs: 117-128, or a variant thereof comprising up to about 5 (such as about any of 1, 2, 3, 4, or 5) amino acid substitutions; and ii) a light chain variable domain comprising an LC-CDR3 comprising the amino acid sequence of any one of SEQ ID NOs: 148-157, or a variant thereof comprising up to about 5 (such as about any of 1, 2, 3, 4, or 5) amino acid substitutions.

In some embodiments, the anti-HMC antibody moiety comprises i) a heavy chain variable domain comprising an HC-CDR3 comprising the amino acid sequence of any one of SEQ ID NOs: 117-128; and ii) a light chain variable domain comprising an LC-CDR3 comprising the amino acid sequence of any one of SEQ ID NOs: 148-157.

In some embodiments, the anti-HMC antibody moiety comprises i) a heavy chain variable domain comprising an HC-CDR1 comprising the amino acid sequence of any one of SEQ ID NOs: 99-107, or a variant thereof comprising up to about 5 (such as about any of 1, 2, 3, 4, or 5) amino acid substitutions, an HC-CDR2 comprising the amino acid sequence of any one of SEQ ID NOs: 108-116, or a variant thereof comprising up to about 5 (such as about any of 1, 2, 3, 4, or 5) amino acid substitutions, and/or an HC-CDR3 comprising the amino acid sequence of any one of SEQ ID NOs: 117-128, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 129-138, or a variant thereof comprising up to about 5 (such as about any of 1, 2, 3, 4, or 5) amino acid substitutions, an LC-CDR2 comprising the amino acid sequence of any one of SEQ ID NOs: 139-147, or a variant thereof comprising up to about 3 (such as about any of 1, 2, or 3) amino acid substitutions, and/or an LC-CDR3 comprising the amino acid sequence of any one of SEQ ID NOs: 148-157, or a variant thereof comprising up to about 5 (such as about any of 1, 2, 3, 4, or 5) amino acid substitutions.

In some embodiments, the anti-HMC antibody moiety comprises i) a heavy chain variable domain comprising an HC-CDR1 comprising the amino acid sequence of any one of SEQ ID NOs: 99-107, or a variant thereof comprising up to about 5 (such as about any of 1, 2, 3, 4, or 5) amino acid substitutions, an HC-CDR2 comprising the amino acid sequence of any one of SEQ ID NOs: 108-116, or a variant thereof comprising up to about 5 (such as about any of 1, 2, 3, 4, or 5) amino acid substitutions, and/or an HC-CDR3 comprising the amino acid sequence of any one of SEQ ID NOs: 117-128; and ii) a light chain variable domain comprising an LC-CDR1 comprising the amino acid sequence of any one of SEQ ID NOs: 129-138, or a variant thereof comprising up to about 5 (such as about any of 1, 2, 3, 4, or 5) amino acid substitutions, an LC-CDR2 comprising the amino acid sequence of any one of SEQ ID NOs: 139-147, or a variant thereof comprising up to about 3 (such as about any of 1, 2, or 3) amino acid substitutions, and/or an LC-CDR3 comprising the amino acid sequence of any one of SEQ ID NOs: 148-157.

In some embodiments, the anti-HMC antibody moiety comprises i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; or a variant thereof comprising up to about 5 (such as about any of 1, 2, 3, 4, or 5) amino acid substitutions in the LC-CDR sequences.

In some embodiments, the anti-HMC antibody moiety comprises i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; or a variant thereof comprising up to about 5 (such as about any of 1, 2, 3, 4, or 5) amino acid substitutions, wherein the amino acid substitutions are in HC-CDR1 or HC-CDR2; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; or a variant thereof comprising up to about 5 (such as about any of 1, 2, 3, 4, or 5) amino acid substitutions, wherein the amino acid substitutions are in HC-CDR1 or HC-CDR2.

In some embodiments, the anti-HMC antibody moiety comprises i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157. The sequences of the HC-CDRs from putative anti-HMC antibody clones are provided in Table 3 below and the LC-CDRs from the clones are provided in Table 4 below.

TABLE 3

| Clone # | HC-CDR1 | HC-CDR2 | HC-CDR3 |
|---|---|---|---|
| 5 | GYSFTSYW SEQ ID NO: 99 | IYPGDSDT SEQ ID NO: 108 | ARGYDG SEQ ID NO: 117 |
| 10 | GYSFTSYW SEQ ID NO: 99 | IYPGDSDT SEQ ID NO: 108 | ARGFDN SEQ ID NO: 118 |
| 13 | GYSFTSYW SEQ ID NO: 99 | IYPGDSDT SEQ ID NO: 108 | ARGYDV SEQ ID NO: 119 |
| 16 | GYSFTSYW SEQ ID NO: 99 | IYPGDSDT SEQ ID NO: 108 | ARGYDS SEQ ID NO: 120 |
| 31 | GLTFDRYA SEQ ID NO: 100 | ITGDGYYT SEQ ID NO: 109 | ARLSGIGRSSYDG SEQ ID NO: 121 |
| 32 | GYTFTSYT SEQ ID NO: 101 | ISPYNGNT SEQ ID NO: 110 | ARSWEHGFPYDE SEQ ID NO: 122 |
| 33 | AGTFNRYS SEQ ID NO: 102 | IIPIIGVA SEQ ID NO: 111 | ARQEYSYAMDY SEQ ID NO: 123 |
| 34 | GGTFSSYA SEQ ID NO: 103 | IIPIFGTA SEQ ID NO: 112 | ARSYWTFEYSIDS SEQ ID NO: 124 |
| 35 | GYTFTSYG SEQ ID NO: 104 | ISAYNGNT SEQ ID NO: 113 | ARYYESGYPFDW SEQ ID NO: 125 |
| 36 | GYTFTGYY SEQ ID NO: 105 | FDPEDGET SEQ ID NO: 114 | ARSSWWSPVTYYDI SEQ ID NO: 126 |
| 37 | GYTVTSYG SEQ ID NO: 106 | ISAYNGDT SEQ ID NO: 115 | ARSSLPFGVVPNAFDI SEQ ID NO: 127 |
| 38 | GYTFTDYY SEQ ID NO: 107 | INPHSGGT SEQ ID NO: 116 | AREDYSGSGSSDA SEQ ID NO: 128 |

TABLE 4

| Clone # | LC-CDR1 | LC-CDR2 | LC-CDR3 |
|---|---|---|---|
| 5 | QSLVYSNGNTY SEQ ID NO: 129 | EVS SEQ ID NO: 139 | MQGTHWPPT SEQ ID NO: 148 |
| 10 | QSLVYSNGNTY SEQ ID NO: 129 | KVS SEQ ID NO: 140 | MQGTYWPYT SEQ ID NO: 149 |
| 13 | QSLIYSNGNTY SEQ ID NO: 130 | KVS SEQ ID NO: 140 | MQGTHWPPT SEQ ID NO: 148 |

TABLE 4-continued

| Clone # | LC-CDR1 | LC-CDR2 | LC-CDR3 |
|---|---|---|---|
| 16 | QSLIYSNGNTY SEQ ID NO: 130 | KVS SEQ ID NO: 140 | MQGTHWPPT SEQ ID NO: 148 |
| 31 | SGINVGTYR SEQ ID NO: 131 | YKSDSDK SEQ ID NO: 141 | MIWHSSA SEQ ID NO: 150 |
| 32 | SSNLGAGYD SEQ ID NO: 132 | FNN SEQ ID NO: 142 | QSYDSSLSASV SEQ ID NO: 151 |
| 33 | SSNIGAGYD SEQ ID NO: 133 | GNN SEQ ID NO: 143 | QSYDTSLTPV SEQ ID NO: 152 |
| 34 | SLNLGAGYD SEQ ID NO: 134 | ANT SEQ ID NO: 144 | QSYDNSLSGYV SEQ ID NO: 153 |
| 35 | TFNIGSNT SEQ ID NO: 135 | SNN SEQ ID NO: 145 | AAWDDSLSGHVV SEQ ID NO: 154 |
| 36 | SLRSYY SEQ ID NO: 136 | AKS SEQ ID NO: 146 | NSRDSSGNR SEQ ID NO: 155 |
| 37 | SSNIGSNT SEQ ID NO: 137 | SNN SEQ ID NO: 145 | AAWDDSLNGYV SEQ ID NO: 156 |
| 38 | NIGSKS SEQ ID NO: 138 | YDN SEQ ID NO: 147 | QVWNSSSDHYV SEQ ID NO: 157 |

In some embodiments, the anti-HMC antibody moiety comprises a heavy chain variable domain comprising the amino acid sequence of any one of SEQ ID NOs: 75-86, or a variant thereof having at least about 95% (including for example at least about any of 96%, 97%, 98%, or 99%) sequence identity, and a light chain variable domain comprising the amino acid sequence of any one of SEQ ID NOs: 87-98, or a variant thereof having at least about 95% (including for example at least any of 96%, 97%, 98%, or 99%) sequence identity.

In some embodiments, the anti-HMC antibody moiety comprises a heavy chain variable domain comprising the amino acid sequence of any one of SEQ ID NOs: 75-86 and a light chain variable domain comprising the amino acid sequence of any one of SEQ ID NOs: 87-98.

The heavy and light chain variable domains can be combined in various pair-wise combinations to generate a number of anti-HMC antibody moieties.

For example, in some embodiments, the anti-HMC antibody moiety comprises heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (for example about any of 1, 2, 3, 4, or 5) amino acid substitutions, individually, in HC-CDR1, HC-CDR2, HC-CDR3, LC-CDR1, and/or LC-CDR3, and/or up to about 3 (for example about any of 1, 2, or 3) amino acid substitutions in LC-CDR2. For example, in some embodiments, the heavy chain comprises an HC-CDR1 comprising the amino acid sequence of SEQ ID NO: 99, an HC-CDR2 comprising the amino acid sequence of SEQ ID NO: 108, and an HC-CDR3 comprising the amino acid sequence of SEQ ID NO 117, and the light chain comprises an LC-CDR1 comprising the amino acid sequence of SEQ ID NO: 129, an LC-CDR2 comprising the amino acid sequence of SEQ ID NO: 139, and an LC-CDR3 comprising the amino acid sequence of SEQ ID NO: 148.

In some embodiments, the anti-HMC antibody moiety comprises heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (such as about any of 1, 2, 3, 4, or 5) amino acid substitutions in the HC-CDR sequences and/or up to about 5 (such as about any of 1, 2, 3, 4, or 5) amino acid substitutions in the LC-CDR sequences.

In some embodiments, the anti-HMC antibody moiety comprises heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively. The sequences of the heavy chain variable domains and light chain variable domains from putative anti-HMC antibody clones are provided in Table 5 below.

TABLE 5

| Clone # | Heavy chain variable domain (SEQ ID NO) | Light chain variable domain (SEQ ID NO) |
|---|---|---|
| 5 | 75 | 87 |
| 10 | 76 | 88 |
| 13 | 77 | 89 |
| 16 | 78 | 90 |

TABLE 5-continued

| Clone # | Heavy chain variable domain (SEQ ID NO) | Light chain variable domain (SEQ ID NO) |
|---|---|---|
| 31 | 79 | 91 |
| 32 | 80 | 92 |
| 33 | 81 | 93 |
| 34 | 82 | 94 |
| 35 | 83 | 95 |
| 36 | 84 | 96 |
| 37 | 85 | 97 |
| 38 | 86 | 98 |

In some embodiments, the anti-HMC antibody moiety comprises heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively; or variants thereof having, individually, at least about 95% (for example at least about any of 96%, 97%, 98%, or 99%) sequence identity. In some embodiments, the anti-HMC antibody moiety comprises heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively.

In some embodiments, the anti-HMC antibody moiety competes for binding to a target histone H3/MHC class I complex with a second anti-HMC antibody moiety according to any of the anti-HMC antibody moieties described herein. In some embodiments, the anti-HMC antibody moiety binds to the same, or substantially the same, epitope as the second anti-HMC antibody moiety. In some embodiments, binding of the anti-HMC antibody moiety to the target histone H3/MHC class I complex inhibits binding of the second anti-HMC antibody moiety to the target histone H3/MHC class I complex by at least about 70% (such as by at least about any of 75%, 80%, 85%, 90%, 95%, 98% or 99%), or vice versa. In some embodiments, the anti-HMC antibody moiety and the second anti-HMC antibody moiety cross-compete for binding to the target histone H3/MHC class I complex, i.e., each of the antibody moieties competes with the other for binding to the target histone H3/MHC class I complex.

For example, in some embodiments, the anti-HMC antibody moiety competes for binding to a target histone H3/MHC class I complex with an antibody moiety comprising i) a heavy chain variable domain sequence comprising an HC-CDR1 comprising the amino acid sequence of SEQ ID NO: 158, or a variant thereof comprising up to about 3 (for example about any of 1, 2, or 3) amino acid substitutions, an HC-CDR2 comprising the amino acid sequence of SEQ ID NO: 159, or a variant thereof comprising up to about 3 (for example about any of 1, 2, or 3) amino acid substitutions, and/or an HC-CDR3 comprising the amino acid sequence of SEQ ID NO: 160 or 161; or a variant thereof comprising up to about 3 (for example about any of 1, 2, or 3) amino acid substitutions; and ii) a light chain variable domain comprising an LC-CDR1 comprising the amino acid sequence of SEQ ID NO: 162, or a variant thereof comprising up to about 3 (for example about any of 1, 2, or 3) amino acid substitutions, and/or an LC-CDR3 comprising the amino acid sequence of SEQ ID NO: 163, or a variant thereof comprising up to about 3 (for example about any of 1, 2, or 3) amino acid substitutions.

In some embodiments, the anti-HMC antibody moiety competes for binding to a target histone H3/MHC class I complex with an antibody moiety comprising i) a heavy chain variable domain sequence comprising an HC-CDR1 comprising (and in some embodiments consisting of) the amino acid sequence of any one of SEQ ID NOs: 99-107; or a variant thereof comprising up to about 5 (for example about any of 1, 2, 3, 4, or 5) amino acid substitutions; an HC-CDR2 comprising (and in some embodiments consisting of) the amino acid sequence of any one of SEQ ID NOs: 108-116; or a variant thereof comprising up to about 5 (for example about any of 1, 2, 3, 4, or 5) amino acid substitutions; and an HC-CDR3 comprising (and in some embodiments consisting of) the amino acid sequence of any one of SEQ ID NOs: 117-128; or a variant thereof comprising up to about 5 (for example about any of 1, 2, 3, 4, or 5) amino acid substitutions; and ii) a light chain variable domain sequence comprising an LC-CDR1 comprising (and in some embodiments consisting of) the amino acid sequence of any one of SEQ ID NOs: 129-138; or a variant thereof comprising up to about 5 (for example about any of 1, 2, 3, 4, or 5) amino acid substitutions; an LC-CDR2 comprising (and in some embodiments consisting of) the amino acid sequence of any one of SEQ ID NOs: 139-147; or a variant thereof comprising up to about 3 (for example about any of 1, 2, or 3) amino acid substitutions; and an LC-CDR3 comprising (and in some embodiments consisting of) the amino acid sequence of any one of SEQ ID NOs: 148-157; or a variant thereof comprising up to about 5 (for example about any of 1, 2, 3, 4, or 5) amino acid substitutions.

In some embodiments, the anti-HMC antibody moiety competes for binding to a target histone H3/MHC class I complex with an antibody moiety comprising i) a heavy chain variable domain sequence comprising an HC-CDR1 comprising (and in some embodiments consisting of) the amino acid sequence of any one of SEQ ID NOs: 99-107; an HC-CDR2 comprising (and in some embodiments consisting of) the amino acid sequence of any one of SEQ ID NOs: 108-116; and an HC-CDR3 comprising (and in some embodiments consisting of) the amino acid sequence of any one of SEQ ID NOs: 117-128; or a variant thereof comprising up to about 5 (for example about any of 1, 2, 3, 4, or 5) amino acid substitutions in the HC-CDR sequences; and ii) a light chain variable domain sequence comprising an LC-CDR1 comprising (and in some embodiments consisting of) the amino acid sequence of any one of SEQ ID NOs: 129-138; an LC-CDR2 comprising (and in some embodiments consisting of) the amino acid sequence of any one of SEQ ID NOs: 139-147; and an LC-CDR3 comprising (and in some embodiments consisting of) the amino acid sequence of any one of SEQ ID NOs: 148-157; or a variant thereof comprising up to about 5 (for example about any of 1, 2, 3, 4, or 5) amino acid substitutions in the LC-CDR sequences.

In some embodiments, the anti-HMC antibody moiety competes for binding to a target histone H3/MHC class I complex with an antibody moiety comprising a heavy chain variable domain comprising (and in some embodiments consisting of) the amino acid sequence of any one of SEQ ID NOs: 75-86, or a variant thereof having at least about 95% (for example at least about any of 96%, 97%, 98%, or 99%) sequence identity, and a light chain variable domain comprising (and in some embodiments consisting of) the amino acid sequence of any one of SEQ ID NOs: 87-98, or a variant thereof having at least about 95% (for example at least about any of 96%, 97%, 98%, or 99%) sequence identity.

In some embodiments, the anti-HMC antibody moiety competes for binding to a target histone H3/MHC class I complex with an antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (for example about any of 1, 2, 3, 4, or 5) amino acid substitutions, individually, in HC-CDR1, HC-CDR2, HC-CDR3, LC-CDR1, and/or LC-CDR3, and/or up to about 3 (for example about any of 1, 2, or 3) amino acid substitutions in LC-CDR2.

In some embodiments, the anti-HMC antibody moiety competes for binding to a target histone H3/MHC class I complex with an antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (such as about any of 1, 2, 3, 4, or 5) amino acid substitutions in the HC-CDR sequences and/or up to about 5 (such as about any of 1, 2, 3, 4, or 5) amino acid substitutions in the LC-CDR sequences.

In some embodiments, the anti-HMC antibody moiety competes for binding to a target histone H3/MHC class I complex with an antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively.

In some embodiments, the anti-HMC antibody moiety competes for binding to a target histone H3/MHC class I complex with an antibody moiety comprising heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively; or variants thereof having, individually, at least about 95% (for example at least about any of 96%, 97%, 98%, or 99%) sequence identity. In some embodiments, the anti-HMC antibody moiety competes for binding to a target histone H3/MHC class I complex with an antibody moiety comprising heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively.

Full-Length Anti-HMC Antibodies

The anti-HMC constructs in some embodiments are full-length antibodies comprising an anti-HMC antibody moiety (also referred to herein as a "full-length anti-HMC antibody"). In some embodiments, the full-length antibody is a monoclonal antibody.

In some embodiments, the full-length anti-HMC antibody comprises an Fc sequence from an immunoglobulin, such as IgA, IgD, IgE, IgG, and IgM. In some embodiments, the full-length anti-HMC antibody comprises an Fc sequence of IgG, such as any of IgG, IgG2, IgG3, or IgG4. In some embodiments, the full-length anti-HMC antibody comprises an Fc sequence of a human immunoglobulin. In some embodiments, the full-length anti-HMC antibody comprises an Fc sequence of a mouse immunoglobulin. In some embodiments, the full-length anti-HMC antibody comprises an Fc sequence that has been altered or otherwise changed so that it has enhanced antibody dependent cellular cytotoxicity (ADCC) or complement dependent cytotoxicity (CDC) effector function.

Thus, for example, in some embodiments, there is provided a full-length anti-HMC antibody comprising a) an anti-HMC antibody moiety that specifically binds to a complex comprising a histone H3 peptide and an MHC class I protein, and b) an Fc region. In some embodiments, the histone H3 peptide is mutant histone K27M-H3.3 26-35 (SEQ ID NO: 7) or mutant histone K27M-H3.1 26-35 (SEQ ID NO: 8). In some embodiments, the histone H3 peptide is WT H3.3 26-35 (SEQ ID NO: 5) or WT H3.1 26-35 (SEQ ID NO: 6). In some embodiments, the MHC class I protein is HLA-A02. In some embodiments, the MHC class I protein is HLA-A*02:01. In some embodiments, the Fc region comprises an IgG1 Fc sequence. In some embodiments, the Fc region comprises a human IgG1 Fc sequence. In some embodiments, the Fc region comprises a mouse IgG1 Fc sequence. In some embodiments, the anti-HMC antibody moiety cross-reacts with at least one (such as at least any of 2, 3, 4, 5, or 6) complex comprising the MHC class I protein and a variant of the histone H3 peptide having one amino acid substitution (such as a conservative amino acid substitution). In some embodiments, the anti-HMC antibody moiety cross-reacts with at least one (such as at least any of 2, 3, 4, or 5) complex comprising the histone H3 peptide and a different subtype of the MHC class I protein.

In some embodiments, there is provided a full-length anti-HMC antibody comprising a) an anti-HMC antibody moiety that specifically binds to a complex comprising a histone H3 peptide selected from mutant histone K27M-H3.3 26-35 (SEQ ID NO: 7), mutant histone K27M-H3.1 26-35 (SEQ ID NO: 8), WT H3.3 26-35 (SEQ ID NO: 5), or WT H3.1 26-35 (SEQ ID NO: 6) peptide and HLA-A*02:01, and b) an Fc region. In some embodiments, the histone H3 peptide is mutant histone K27M-H3.3 26-35 (SEQ ID NO: 7). In some embodiments, the histone H3 peptide is mutant histone K27M-H3.1 26-35 (SEQ ID NO: 8). In some embodiments, the histone H3 peptide is WT H3.3 26-35 (SEQ ID NO: 5). In some embodiments, the histone H3 peptide is WT H3.1 26-35 (SEQ ID NO: 6). In some embodiments, the Fc region comprises an IgG1 Fc sequence. In some embodiments, the Fc region comprises a human IgG1 Fc sequence. In some embodiments, the Fc region comprises a mouse IgG1 Fc sequence. In some embodiments, the anti-HMC antibody moiety cross-reacts with at least one (such as at least any of 2, 3, 4, 5, or 6) complex comprising the MHC class I protein and a variant of the histone H3 peptide having one amino acid substitution (such as a conservative amino acid substitution). In some embodiments, the anti-HMC antibody moiety cross-reacts with at least one (such as at least any of 2, 3, 4, or 5) complex comprising the histone H3 peptide and a different subtype of the MHC class I protein.

In some embodiments, there is provided a full-length anti-HMC antibody comprising a) an anti-HMC antibody moiety that specifically binds to a complex comprising a histone H3 peptide and an MHC class I protein comprising i) a heavy chain variable domain sequence comprising an HC-CDR1 comprising the amino acid sequence of SEQ ID NO: 158, or a variant thereof comprising up to about 3 (for example about any of 1, 2, or 3) amino acid substitutions, an HC-CDR2 comprising the amino acid sequence of SEQ ID NO: 159, or a variant thereof comprising up to about 3 (for example about any of 1, 2, or 3) amino acid substitutions, and/or an HC-CDR3 comprising the amino acid sequence of SEQ ID NO: 160 or 161; or a variant thereof comprising up to about 3 (for example about any of 1, 2, or 3) amino acid substitutions; and ii) a light chain variable domain comprising an LC-CDR1 comprising the amino acid sequence of SEQ ID NO: 162, or a variant thereof comprising up to about 3 (for example about any of 1, 2, or 3) amino acid substitutions, and/or an LC-CDR3 comprising the amino acid sequence of SEQ ID NO: 163, or a variant thereof comprising up to about 3 (for example about any of 1, 2, or 3) amino acid substitutions, and b) an Fc region. In some embodiments, the Fc region comprises an IgG1 Fc sequence. In some embodiments, the Fc region comprises a human IgG1 Fc sequence. In some embodiments, the Fc region comprises a mouse IgG1 Fc sequence.

In some embodiments, there is provided a full-length anti-HMC antibody comprising a) an anti-HMC antibody moiety that specifically binds to a complex comprising a histone H3 peptide and an MHC class I protein comprising i) a heavy chain variable domain sequence comprising an HC-CDR1 comprising the amino acid sequence of SEQ ID NO: 158, an HC-CDR2 comprising the amino acid sequence of SEQ ID NO: 159, and/or an HC-CDR3 comprising the amino acid sequence of SEQ ID NO: 160 or 161; and ii) a light chain variable domain comprising an LC-CDR1 comprising the amino acid sequence of SEQ ID NO: 162, and/or an LC-CDR3 comprising the amino acid sequence of SEQ ID NO: 163, and b) an Fc region. In some embodiments, the Fc region comprises an IgG1 Fc sequence. In some embodiments, the Fc region comprises a human IgG1 Fc sequence. In some embodiments, the Fc region comprises a mouse IgG1 Fc sequence.

In some embodiments, there is provided a full-length anti-HMC antibody comprising a) an anti-HMC antibody moiety that specifically binds to a complex comprising a histone H3 peptide and an MHC class I protein comprising i) a heavy chain variable domain comprising an HC-CDR1 comprising the amino acid sequence of any one of SEQ ID NOs: 99-107, or a variant thereof comprising up to about 5 (such as about any of 1, 2, 3, 4, or 5) amino acid substitutions, an HC-CDR2 comprising the amino acid sequence of any one of SEQ ID NOs: 108-116, or a variant thereof comprising up to about 5 (such as about any of 1, 2, 3, 4, or 5) amino acid substitutions, and/or an HC-CDR3 comprising the amino acid sequence of any one of SEQ ID NOs: 117-128, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 129-138, or a variant thereof comprising up to about 5 (such as about any of 1, 2, 3, 4, or 5) amino acid substitutions, an LC-CDR2 comprising the amino acid sequence of any one of SEQ ID NOs: 139-147, or a variant thereof comprising up to about 3 (such as about any of 1, 2, or 3) amino acid substitutions, and/or an LC-CDR3 comprising the amino acid sequence of any one of SEQ ID NOs: 148-157, or a variant thereof comprising up to about 5 (such as about any of 1, 2, 3, 4, or 5) amino acid substitutions. In some embodiments, the Fc region comprises an IgG1 Fc sequence. In some embodiments, the Fc region comprises a human IgG1 Fc sequence. In some embodiments, the Fc region comprises a mouse IgG1 Fc sequence.

In some embodiments, there is provided a full-length anti-HMC antibody comprising a) an anti-HMC antibody moiety that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; or a variant thereof comprising up to about 5 (such as about any of 1, 2, 3, 4, or 5) amino acid substitutions in the LC-CDR sequences; and b) an Fc region. In some embodiments, the Fc region comprises an IgG1 Fc sequence. In some embodiments, the Fc region comprises a human IgG1 Fc sequence. In some embodiments, the Fc region comprises a mouse IgG1 Fc sequence.

In some embodiments, there is provided a full-length anti-HMC antibody comprising a) an anti-HMC antibody moiety that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; and b) an Fc region. In some embodiments, the Fc region comprises an IgG1 Fc sequence. In some embodiments, the Fc region comprises a human IgG1 Fc sequence. In some embodiments, the Fc region comprises a mouse IgG1 Fc sequence.

In some embodiments, there is provided a full-length anti-HMC antibody comprising a) an anti-HMC antibody moiety that specifically binds to a complex comprising a histone H3 peptide and an MHC class I protein comprising a heavy chain variable domain comprising the amino acid sequence of any one of SEQ ID NOs: 75-86, or a variant thereof having at least about 95% (for example at least about any of 96%, 97%, 98%, or 99%) sequence identity, and a light chain variable domain comprising the amino acid sequence of any one of SEQ ID NOs: 87-98, or a variant thereof having at least about 95% (including for example at least about any of 96%, 97%, 98%, or 99%) sequence identity; and b) an Fc region. In some embodiments, the Fc region comprises an IgG1 Fc sequence. In some embodiments, the Fc region comprises a human IgG1 Fc sequence. In some embodiments, the Fc region comprises a mouse IgG1 Fc sequence.

In some embodiments, there is provided a full-length anti-HMC antibody comprising a) an anti-HMC antibody moiety that specifically binds to a complex comprising a histone H3 peptide and an MHC class I protein comprising a heavy chain variable domain comprising the amino acid sequence of any one of SEQ ID NOs: 75-86 and a light chain variable domain comprising the amino acid sequence of any one of SEQ ID NOs: 87-98; and b) an Fc region. In some embodiments, the Fc region comprises an IgG1 Fc sequence. In some embodiments, the Fc region comprises a human IgG1 Fc sequence. In some embodiments, the Fc region comprises a mouse IgG1 Fc sequence.

For example, in some embodiments, the full-length anti-HMC antibody moiety comprises heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (for example about any of 1, 2, 3, 4, or 5) amino acid substitutions, individually, in HC-CDR1, HC-CDR2, HC-CDR3, LC-CDR1, and/or LC-CDR3, and/or up to about 3 (for example about any of 1, 2, or 3) amino acid substitutions in LC-CDR2.

In some embodiments, the full-length anti-HMC antibody moiety comprises heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (such as about any of 1, 2, 3, 4, or 5) amino acid substitutions in the HC-CDR sequences and/or up to about 5 (such as about any of 1, 2, 3, 4, or 5) amino acid substitutions in the LC-CDR sequences.

In some embodiments, the full-length anti-HMC antibody moiety comprises heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively.

In some embodiments, the full-length anti-HMC antibody moiety comprises heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively; or variants thereof having, individually, at least about 95% (for example at least about any of 96%, 97%, 98%, or 99%) sequence identity. In some embodiments, the full-length anti-HMC antibody moiety comprises heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively.

In some embodiments, the full-length anti-HMC antibody binds to a complex comprising a histone H3 peptide and an MHC class I protein with a $K_d$ between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the full-length anti-HMC antibody binds to a complex comprising a histone H3 peptide and an MHC class I protein with a $K_d$ between about 1 pM to about 250 pM (such as about any of 1, 10, 25, 50, 75, 100, 150, 200, or 250 pM, including any ranges between these values).

Multi-Specific Anti-HMC Molecules

The anti-HMC constructs in some embodiments comprise a multi-specific anti-HMC molecule comprising an anti-HMC antibody moiety and a second binding moiety (such as a second antigen-binding moiety). In some embodiments, the multi-specific anti-HMC molecule comprises an anti-HMC antibody moiety and a second antigen-binding moiety.

Multi-specific molecules are molecules that have binding specificities for at least two different antigens or epitopes (e.g., bispecific antibodies have binding specificities for two antigens or epitopes). Multi-specific molecules with more than two valencies and/or specificities are also contemplated. For example, trispecific antibodies can be prepared. Tutt et al. *J. Immunol.* 147: 60 (1991). It is to be appreciated that one of skill in the art could select appropriate features of individual multi-specific molecules described herein to combine with one another to form a multi-specific anti-HMC molecule of the invention.

Thus, for example, in some embodiments, there is provided a multi-specific (e.g., bispecific) anti-HMC molecule comprising a) an anti-HMC antibody moiety that specifically binds to a complex comprising a histone H3 peptide and an MHC class I protein, and b) a second binding moiety (such as an antigen-binding moiety). In some embodiments, the second binding moiety specifically binds to a complex comprising a different histone H3 peptide bound to the MHC class I protein. In some embodiments, the second scFv specifically binds to a complex comprising the histone H3 peptide bound to a different MHC class I protein. In some embodiments, the second binding moiety specifically binds to a different epitope on the complex comprising the histone H3 peptide and the MHC class I protein. In some embodiments, the second binding moiety specifically binds to a different antigen. In some embodiments, the second binding moiety specifically binds to an antigen on the surface of a cell, such as a cytotoxic cell. In some embodiments, the second binding moiety specifically binds to an antigen on the surface of a lymphocyte, such as a T cell, an NK cell, a neutrophil, a monocyte, a macrophage, or a dendritic cell. In some embodiments, the second binding moiety specifically binds to an effector T cell, such as a cytotoxic T cell (also known as cytotoxic T lymphocyte (CTL) or T killer cell).

In some embodiments, there is provided a multi-specific anti-HMC molecule comprising a) an anti-HMC antibody moiety that specifically binds to a complex comprising a histone H3 peptide and an MHC class I protein, and b) a second antigen-binding moiety that binds specifically to CD3. In some embodiments, the second antigen-binding moiety specifically binds to CD3ε. In some embodiments, the second antigen-binding moiety specifically binds to an agonistic epitope of CD3ε. The term "agonistic epitope", as used herein, means (a) an epitope that, upon binding of the multi-specific molecule, optionally upon binding of several multi-specific molecules on the same cell, allows said multi-specific molecules to activate T cell receptor (TCR) signaling and induce T cell activation, and/or (b) an epitope that is solely composed of amino acid residues of the epsilon chain of CD3 and is accessible for binding by the multi-specific molecule, when presented in its natural context on T cells (i.e. surrounded by the TCR, the CD3γ chain, etc.), and/or (c) an epitope that, upon binding of the multi-specific molecule, does not lead to stabilization of the spatial position of CD3ε relative to CD3γ.

In some embodiments, there is provided a multi-specific anti-HMC molecule comprising a) an anti-HMC antibody moiety that specifically binds to a complex comprising a histone H3 peptide and an MHC class I protein, and b) a second antigen-binding moiety that binds specifically to an antigen on the surface of an effector cell, including for example CD3γ, CD3δ, CD3ε, CD3ζ, CD28, CD16a, CD56, CD68, and GDS2D.

In some embodiments, there is provided a multi-specific anti-HMC molecule comprising a) an anti-HMC antibody moiety that specifically binds to a complex comprising a histone H3 peptide and an MHC class I protein, and b) a second antigen-binding moiety that binds specifically to a component of the complement system, such as C1q. C1q is a subunit of the C1 enzyme complex that activates the serum complement system.

In some embodiments, the second antigen-binding moiety specifically binds to an Fc receptor. In some embodiments, the second antigen-binding moiety specifically binds to an Fcγ receptor (FcγR). The FcγR may be an FcγRIII present on the surface of natural killer (NK) cells or one of FcγRI, FcγRIIA, FcγRIIB1, FcγRIIB2, and FcγRIIIB present on the surface of macrophages, monocytes, neutrophils and/or dendritic cells. In some embodiments, the second antigen-binding moiety is an Fc region or functional fragment thereof. A "functional fragment" as used in this context refers to a fragment of an antibody Fc region that is still capable of binding to an FcR, in particular to an FcγR, with sufficient specificity and affinity to allow an FcγR bearing effector cell, in particular a macrophage, a monocyte, a neutrophil and/or a dendritic cell, to kill the target cell by cytotoxic lysis or phagocytosis. A functional Fc fragment is capable of competitively inhibiting the binding of the original, full-length Fc portion to an FcR such as the activating FcγRI. In some embodiments, a functional Fc fragment retains at least 30%, 40%, 50%, 60%, 70%, 80%, 90% or 95% of its affinity to an activating FcγR. In some embodiments, the Fc region or functional fragment thereof is an enhanced Fc region or functional fragment thereof. The term "enhanced Fc region", as used herein, refers to an Fc region that is modified to enhance Fc receptor-mediated effector-functions, in particular antibody-dependent cell-mediated cytotoxicity (ADCC), complement-dependent cytotoxicity (CDC), and antibody-mediated phagocytosis. This can be achieved as known in the art, for example by altering the Fc region in a way that leads to an increased affinity for an activating receptor (e.g. FcγRIIIA (CD16A) expressed on natural killer (NK) cells) and/or a decreased binding to an inhibitory receptor (e.g. FcγRIIB 1/B2 (CD32B)). In yet other embodiments, the second antigen-binding moiety is an antibody or antigen-binding fragment thereof that specifically binds to an FcR, in particular to an FcγR, with sufficient specificity and affinity to allow an FcγR bearing effector cell, in particular a macrophage, a monocyte, a neutrophil and/or a dendritic cell, to kill the target cell by cytotoxic lysis or phagocytosis.

In some embodiments, the multi-specific anti-HMC molecule allows killing of HMC-presenting target cells and/or can effectively redirect CTLs to lyse HMC-presenting target cells. In some embodiments, the multi-specific (e.g., bispecific) anti-HMC molecule of the present invention shows an in vitro $EC_{50}$ ranging from 10 to 500 ng/ml, and is able to induce redirected lysis of about 50% of the target cells through CTLs at a ratio of CTLs to target cells of from about 1:1 to about 50:1 (such as from about 1:1 to about 15:1, or from about 2:1 to about 10:1).

In some embodiments, the multi-specific (e.g., bispecific) anti-HMC molecule is capable of cross-linking a stimulated or unstimulated CTL and the target cell in such a way that the target cell is lysed. This offers the advantage that no generation of target-specific T cell clones or common antigen presentation by dendritic cells is required for the multi-specific anti-HMC molecule to exert its desired activity. In some embodiments, the multi-specific anti-HMC molecule of the present invention is capable of redirecting CTLs to lyse the target cells in the absence of other activating signals. In some embodiments, the second antigen-binding moiety of the multi-specific anti-HMC molecule specifically binds to CD3 (e.g., specifically binds to CD3ε), and signaling through CD28 and/or IL-2 is not required for redirecting CTLs to lyse the target cells.

Methods for measuring the preference of the multi-specific anti-HMC molecule to simultaneously bind to two antigens (e.g., antigens on two different cells) are within the normal capabilities of a person skilled in the art. For example, when the second binding moiety specifically binds to CD3, the multi-specific anti-HMC molecule may be contacted with a mixture of CD3+/histone H3− cells and CD3−/histone H3+ cells. The number of multi-specific anti-HMC molecule-positive single cells and the number of cells cross-linked by multi-specific anti-HMC molecules may then be assessed by microscopy or fluorescence-activated cell sorting (FACS) as known in the art.

For example, in some embodiments, there is provided a multi-specific anti-HMC molecule comprising a) an anti-HMC antibody moiety that specifically binds to a complex comprising a histone H3 peptide and an MHC class I protein, and b) a second antigen-binding moiety. In some embodiments, the histone H3 peptide is mutant histone K27M-H3.3 26-35 (SEQ ID NO: 7) or mutant histone K27M-H3.1 26-35 (SEQ ID NO: 8). In some embodiments, the histone H3 peptide is WT H3.3 26-35 (SEQ ID NO: 5) or WT H3.1 26-35 (SEQ ID NO: 6). In some embodiments, the MHC class I protein is HLA-A02. In some embodiments, the MHC class I protein is HLA-A*02:01. In some embodiments, the second antigen-binding moiety specifically binds to a complex comprising a different histone H3 peptide bound to the MHC class I protein. In some embodiments, the second antigen-binding moiety specifically binds to a complex comprising the histone H3 peptide bound to a different MHC class I protein. In some embodiments, the second antigen-binding moiety specifically binds to a different epitope on the complex comprising the histone H3 peptide and the MHC class I protein. In some embodiments, the second antigen-binding moiety specifically binds to another antigen. In some embodiments, the second antigen-binding moiety specifically binds to an antigen on the surface of a cell, such as an HMC-presenting cell. In some embodiments, the second antigen-binding moiety specifically binds to an antigen on the surface of a cell that does not express histone H3. In some embodiments, the second antigen-binding moiety specifically binds to an antigen on the surface of a cytotoxic cell. In some embodiments, the second antigen-binding moiety specifically binds to an antigen on the surface of a lymphocyte, such as a T cell, an NK cell, a neutrophil, a monocyte, a macrophage, or a dendritic cell. In some embodiments, the second antigen-binding moiety specifically binds to an antigen on the surface of an effector T cell, such as a cytotoxic T cell. In some embodiments, the second antigen-binding moiety specifically binds to an antigen on the surface of an effector cell, including for example CD3γ, CD3δ, CD3ε, CD3ζ, CD28, CD16a, CD56, CD68, and GDS2D. In some embodiments, the anti-HMC antibody moiety is human, humanized, or semi-synthetic. In some embodiments, the second antigen-binding moiety is an antibody moiety. In some embodiments, the second antigen-binding moiety is a human, humanized, or semi-synthetic antibody moiety. In some embodiments, the multi-specific anti-HMC molecule further comprises at least one (such as at least about any of 2, 3, 4, 5, or more) additional antigen-binding moieties. In some embodiments, the anti-HMC antibody moiety cross-reacts with at least one (such as at least any of 2, 3, 4, 5, or 6) complex comprising the MHC class I protein and a variant of the histone H3 peptide having one amino acid substitution (such as a conservative amino acid substitution). In some embodiments, the anti-HMC antibody moiety cross-reacts with at least one (such as at least any of 2, 3, 4, or 5) complex comprising the histone H3 peptide and a different subtype of the MHC class I protein.

In some embodiments, there is provided a multi-specific anti-HMC molecule comprising a) an anti-HMC antibody moiety that specifically binds to a complex comprising a histone H3 peptide selected from histone H3 peptide selected from mutant histone K27M-H3.3 26-35 (SEQ ID NO: 7), mutant histone K27M-H3.1 26-35 (SEQ ID NO: 8), WT H3.3 26-35 (SEQ ID NO: 5), or WT H3.1 26-35 (SEQ ID NO: 6) peptide and HLA-A*02:01, and b) a second antigen-binding moiety. In some embodiments, the histone H3 peptide is mutant histone K27M-H3.3 26-35 (SEQ ID NO: 7). In some embodiments, the histone H3 peptide is mutant histone K27M-H3.1 26-35 (SEQ ID NO: 8). In some embodiments, the histone H3 peptide is WT H3.3 26-35 (SEQ ID NO: 5). In some embodiments, the histone H3 peptide is WT H3.1 26-35 (SEQ ID NO: 6).

In some embodiments, there is provided a multi-specific anti-HMC molecule comprising a) an anti-HMC antibody moiety that specifically binds to a complex comprising a histone H3 peptide and an MHC class I protein comprising i) a heavy chain variable domain sequence comprising an HC-CDR1 comprising the amino acid sequence of SEQ ID NO: 158, or a variant thereof comprising up to about 3 (for example about any of 1, 2, or 3) amino acid substitutions, an HC-CDR2 comprising the amino acid sequence of SEQ ID NO: 159, or a variant thereof comprising up to about 3 (for example about any of 1, 2, or 3) amino acid substitutions, and/or an HC-CDR3 comprising the amino acid sequence of SEQ ID NO: 160 or 161, or a variant thereof comprising up to about 3 (for example about any of 1, 2, or 3) amino acid substitutions; and ii) a light chain variable domain comprising an LC-CDR1 comprising the amino acid sequence of SEQ ID NO: 162, or a variant thereof comprising up to about 3 (for example about any of 1, 2, or 3) amino acid substitutions, and/or an LC-CDR3 comprising the amino acid sequence of SEQ ID NO: 163, or a variant thereof comprising up to about 3 (for example about any of 1, 2, or 3) amino acid substitutions, and b) a second antigen-binding moiety.

In some embodiments, there is provided a multi-specific anti-HMC molecule comprising a) an anti-HMC antibody moiety that specifically binds to a complex comprising a histone H3 peptide and an MHC class I protein comprising i) a heavy chain variable domain sequence comprising an HC-CDR1 comprising the amino acid sequence of SEQ ID NO: 158, an HC-CDR2 comprising the amino acid sequence of SEQ ID NO: 159, and/or an HC-CDR3 comprising the amino acid sequence of SEQ ID NO: 160 or 161; and ii) a light chain variable domain comprising an LC-CDR1 comprising the amino acid sequence of SEQ ID NO: 162, and/or an LC-CDR3 comprising the amino acid sequence of SEQ ID NO: 163, and b) a second antigen-binding moiety.

In some embodiments, there is provided a multi-specific anti-HMC molecule comprising a) an anti-HMC antibody moiety that specifically binds to a complex comprising a histone H3 peptide and an MHC class I protein comprising i) a heavy chain variable domain comprising an HC-CDR1 comprising the amino acid sequence of any one of SEQ ID NOs: 99-107, or a variant thereof comprising up to about 5 (such as about any of 1, 2, 3, 4, or 5) amino acid substitutions, an HC-CDR2 comprising the amino acid sequence of any one of SEQ ID NOs: 108-116, or a variant thereof comprising up to about 5 (such as about any of 1, 2, 3, 4, or 5) amino acid substitutions, and/or an HC-CDR3 comprising the amino acid sequence of any one of SEQ ID NOs: 117-128, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 129-138, or a variant thereof comprising up to about 5 (such as about any of 1, 2, 3, 4, or 5) amino acid substitutions, an LC-CDR2 comprising the amino acid sequence of any one of SEQ ID NOs: 139-147, or a variant thereof comprising up to about 3 (such as about any of 1, 2, or 3) amino acid substitutions, and/or an LC-CDR3 comprising the amino acid sequence of any one of SEQ ID NOs: 148-157, or a variant thereof comprising up to about 5 (such as about any of 1, 2, 3, 4, or 5) amino acid substitutions; and b) a second antigen-binding moiety.

In some embodiments, there is provided a multi-specific anti-HMC molecule comprising a) an anti-HMC antibody moiety that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; or a variant thereof comprising up to about 5 (such as about any of 1, 2, 3, 4, or 5) amino acid substitutions in the LC-CDR sequences; and b) a second antigen-binding moiety.

In some embodiments, there is provided a multi-specific anti-HMC molecule comprising a) an anti-HMC antibody moiety that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; and b) a second antigen-binding moiety.

In some embodiments, there is provided a multi-specific anti-HMC molecule comprising a) an anti-HMC antibody moiety comprising a heavy chain variable domain comprising the amino acid sequence of any one of SEQ ID NOs: 75-86, or a variant thereof having at least about 95% (for example at least about any of 96%, 97%, 98%, or 99%) sequence identity, and a light chain variable domain comprising the amino acid sequence of any one of SEQ ID NOs: 87-98, or a variant thereof having at least about 95% (including for example at least about any of 96%, 97%, 98%, or 99%) sequence identity; and b) a second scFv.

In some embodiments, there is provided a multi-specific anti-HMC molecule comprising a) an anti-HMC antibody moiety comprising a heavy chain variable domain comprising the amino acid sequence of any one of SEQ ID NOs: 75-86 and a light chain variable domain comprising the amino acid sequence of any one of SEQ ID NOs: 87-98; and b) a second antigen-binding moiety.

In some embodiments, the multi-specific anti-HMC molecule is, for example, a diabody (Db), a single-chain diabody (scDb), a tandem scDb (Tandab), a linear dimeric scDb (LD-scDb), a circular dimeric scDb (CD-scDb), a di-diabody, a tandem scFv, a tandem di-scFv (e.g., a bispecific T cell engager), a tandem tri-scFv, a tri(a)body, a bispecific Fab2, a di-miniantibody, a tetrabody, an scFv-Fc-scFv fusion, a dual-affinity retargeting (DART) antibody, a dual variable domain (DVD) antibody, an IgG-scFab, an scFab-ds-scFv, an Fv2-Fc, an IgG-scFv fusion, a dock and lock (DNL) antibody, a knob-into-hole (KiH) antibody (bispecific IgG prepared by the KiH technology), a DuoBody (bispecific IgG prepared by the Duobody technology), a heteromultimeric antibody, or a heteroconjugate antibody. In some embodiments, the multi-specific anti-HMC molecule is a tandem scFv (e.g., a tandem di-scFv, such as a bispecific T cell engager).

Tandem scFv

The multi-specific anti-HMC molecule in some embodiments is a tandem scFv comprising a first scFv comprising an anti-HMC antibody moiety and a second scFv (also referred to herein as a "tandem scFv multi-specific anti-HMC antibody"). In some embodiments, the tandem scFv multi-specific anti-HMC antibody further comprises at least one (such as at least about any of 2, 3, 4, 5, or more) additional scFv.

In some embodiments, there is provided a tandem scFv multi-specific (e.g., bispecific) anti-HMC antibody comprising a) a first scFv that specifically binds to a complex comprising a histone H3 peptide and an MHC class I protein, and b) a second scFv. In some embodiments, the histone H3 peptide is mutant histone K27M-H3.3 26-35 (SEQ ID NO: 7) or mutant histone K27M-H3.1 26-35 (SEQ ID NO: 8). In some embodiments, the histone H3 peptide is WT H3.3 26-35 (SEQ ID NO: 5) or WT H3.1 26-35 (SEQ ID NO: 6). In some embodiments, the MHC class I protein is HLA-A02. In some embodiments, the MHC class I protein is HLA-A*02:01. In some embodiments, the second scFv specifically binds to a complex comprising a different histone H3 peptide bound to the MHC class I protein. In some embodiments, the second scFv specifically binds to a complex comprising the histone H3 peptide bound to a different MHC class I protein. In some embodiments, the second scFv specifically binds to a different epitope on the complex comprising the histone H3 peptide and the MHC class I protein. In some embodiments, the second scFv specifically binds to another antigen. In some embodiments, the second scFv specifically binds to an antigen on the surface of a cell, such as an HMC-presenting cell. In some embodiments, the second scFv specifically binds to an antigen on the surface of a cell that does not express histone H3. In some embodiments, the second scFv specifically binds to an antigen on the surface of a cytotoxic cell. In some embodiments, the second scFv specifically binds to an antigen on the surface of a lymphocyte, such as a T cell, an NK cell, a neutrophil, a monocyte, a macrophage, or a dendritic cell. In some embodiments, the second scFv specifically binds to an antigen on the surface of an effector T cell, such as a cytotoxic T cell. In some embodiments, the second scFv specifically binds to an antigen on the surface of an effector cell, including for example CD3γ, CD3δ, CD3ε, CD3ζ, CD28, CD16a, CD56, CD68, and GDS2D. In some embodiments, the first scFv is human, humanized, or semi-synthetic. In some embodiments, the second scFv is human, humanized, or semi-synthetic. In some embodiments, both the first scFv and the second scFv are human, humanized, or semi-synthetic. In some embodiments, the tandem scFv multi-specific anti-HMC antibody further comprises at least one (such as at least about any of 2, 3, 4, 5, or more) additional scFv. In some embodiments, the anti-HMC antibody moiety cross-reacts with at least one (such as at least any of 2, 3, 4, 5, or 6) complex comprising the MHC class I protein and a variant of the histone H3 peptide having one amino acid substitution (such as a conservative amino acid substitution). In some embodiments, the anti-HMC antibody moiety cross-reacts with at least one (such as at least any of 2, 3, 4, or 5) complex comprising the histone H3 peptide and a different subtype of the MHC class I protein.

In some embodiments, there is provided a tandem scFv multi-specific (e.g., bispecific) anti-HMC antibody comprising a) a first scFv that specifically binds to a complex comprising a histone H3 peptide selected from mutant histone K27M-H3.3 26-35 (SEQ ID NO: 7), mutant histone K27M-H3.1 26-35 (SEQ ID NO: 8), WT H3.3 26-35 (SEQ ID NO: 5), or WT H3.1 26-35 (SEQ ID NO: 6) peptide and HLA-A*02:01, and b) a second scFv. In some embodiments, the histone H3 peptide is mutant histone K27M-H3.3 26-35 (SEQ ID NO: 7). In some embodiments, the histone H3 peptide is mutant histone K27M-H3.1 26-35 (SEQ ID NO: 8). In some embodiments, the histone H3 peptide is WT H3.3 26-35 (SEQ ID NO: 5). In some embodiments, the histone H3 peptide is WT H3.1 26-35 (SEQ ID NO: 6).

In some embodiments, there is provided a tandem scFv multi-specific (e.g., bispecific) anti-HMC antibody comprising a) a first scFv that specifically binds to a complex comprising a histone H3 peptide and an MHC class I protein comprising i) a heavy chain variable domain sequence comprising an HC-CDR1 comprising the amino acid sequence of SEQ ID NO: 158, or a variant thereof comprising up to about 3 (for example about any of 1, 2, or 3) amino acid substitutions, an HC-CDR2 comprising the amino acid sequence of SEQ ID NO: 159, or a variant thereof comprising up to about 3 (for example about any of 1, 2, or 3) amino acid substitutions, and/or an HC-CDR3 comprising the amino acid sequence of SEQ ID NO: 160 or 161, or a variant thereof comprising up to about 3 (for example about any of 1, 2, or 3) amino acid substitutions; and ii) a light chain variable domain comprising an LC-CDR1 comprising the amino acid sequence of SEQ ID NO: 162, or a variant thereof comprising up to about 3 (for example about any of 1, 2, or 3) amino acid substitutions, and/or an LC-CDR3 comprising the amino acid sequence of SEQ ID NO: 163, or a variant thereof comprising up to about 3 (for example about any of 1, 2, or 3) amino acid substitutions, and b) a second scFv.

In some embodiments, there is provided a tandem scFv multi-specific (e.g., bispecific) anti-HMC antibody comprising a) a first scFv that specifically binds to a complex comprising a histone H3 peptide and an MHC class I protein comprising i) a heavy chain variable domain sequence comprising an HC-CDR1 comprising the amino acid sequence of SEQ ID NO: 158, an HC-CDR2 comprising the amino acid sequence of SEQ ID NO: 159, and/or an HC-CDR3 comprising the amino acid sequence of SEQ ID NO: 160 or 161; and ii) a light chain variable domain comprising an LC-CDR1 comprising the amino acid sequence of SEQ ID NO: 162, and/or an LC-CDR3 comprising the amino acid sequence of SEQ ID NO: 163, and b) a second scFv.

In some embodiments, there is provided a tandem scFv multi-specific (e.g., bispecific) anti-HMC antibody comprising a) a first scFv that specifically binds to a complex comprising a histone H3 peptide and an MHC class I protein comprising i) a heavy chain variable domain comprising an HC-CDR1 comprising the amino acid sequence of any one of SEQ ID NOs: 99-107, or a variant thereof comprising up to about 5 (such as about any of 1, 2, 3, 4, or 5) amino acid substitutions, an HC-CDR2 comprising the amino acid sequence of any one of SEQ ID NOs: 108-116, or a variant thereof comprising up to about 5 (such as about any of 1, 2, 3, 4, or 5) amino acid substitutions, and/or an HC-CDR3 comprising the amino acid sequence of any one of SEQ ID NOs: 117-128, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 129-138, or a variant thereof comprising up to about 5 (such as about any of 1, 2, 3, 4, or 5) amino acid substitutions, an LC-CDR2 comprising the amino acid sequence of any one of SEQ ID NOs: 139-147, or a variant thereof comprising up to about 3 (such as about any of 1, 2, or 3) amino acid substitutions, and/or an LC-CDR3 comprising the amino acid sequence of any one of SEQ ID NOs: 148-157, or a variant thereof comprising up to about 5 (such as about any of 1, 2, 3, 4, or 5) amino acid substitutions; and b) a second scFv.

In some embodiments, there is provided a tandem scFv multi-specific (e.g., bispecific) anti-HMC antibody comprising a) a first scFv that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; or a variant thereof comprising up to about 5 (such as about any of 1, 2, 3, 4, or 5) amino acid substitutions in the LC-CDR sequences; and b) a second scFv.

In some embodiments, there is provided a tandem scFv multi-specific (e.g., bispecific) anti-HMC antibody comprising a) a first scFv that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; and b) a second scFv.

In some embodiments, there is provided a tandem scFv multi-specific (e.g., bispecific) anti-HMC antibody comprising a) a first scFv comprising a heavy chain variable domain comprising the amino acid sequence of any one of SEQ ID NOs: 75-86, or a variant thereof having at least about 95% (for example at least about any of 96%, 97%, 98%, or 99%) sequence identity, and a light chain variable domain comprising the amino acid sequence of any one of SEQ ID NOs: 87-98, or a variant thereof having at least about 95% (including for example at least about any of 96%, 97%, 98%, or 99%) sequence identity; and b) a second scFv.

In some embodiments, there is provided a tandem scFv multi-specific (e.g., bispecific) anti-HMC antibody comprising a) a first scFv comprising a heavy chain variable domain comprising the amino acid sequence of any one of SEQ ID NOs: 75-86 and a light chain variable domain comprising the amino acid sequence of any one of SEQ ID NOs: 87-98; and b) a second scFv.

In some embodiments, there is provided a tandem scFv multi-specific (e.g., bispecific) anti-HMC antibody comprising a) a first scFv that specifically binds to a complex comprising a histone H3 peptide and an MHC class I protein, and b) a second scFv, wherein the tandem scFv multi-specific anti-HMC antibody is a tandem di-scFv or a tandem tri-scFv. In some embodiments, the tandem scFv multi-specific anti-HMC antibody is a tandem di-scFv. In some embodiments, the tandem scFv multi-specific anti-HMC antibody is a bispecific T-cell engager.

For example, in some embodiments, there is provided a tandem di-scFv bispecific anti-HMC antibody comprising a) a first scFv that specifically binds to a complex comprising a histone H3 peptide and an MHC class I protein, and b) a second scFv that specifically binds to an antigen on the surface of a T cell. In some embodiments, the histone H3 peptide is mutant histone K27M-H3.3 26-35 (SEQ ID NO: 7) or mutant histone K27M-H3.1 26-35 (SEQ ID NO: 8). In some embodiments, the histone H3 peptide is WT H3.3 26-35 (SEQ ID NO: 5) or WT H3.1 26-35 (SEQ ID NO: 6). In some embodiments, the MHC class I protein is HLA-A02. In some embodiments, the MHC class I protein is HLA-A*02:01. In some embodiments, the second scFv specifically binds to an antigen on the surface of an effector T cell, such as a cytotoxic T cell. In some embodiments, the second scFv specifically binds to an antigen selected, for example, from the group consisting of CD3γ, CD3δ, CD3ε, CD3ζ, CD28, OX40, GITR, CD137, CD27, CD40L, and HVEM. In some embodiments, the second scFv specifically binds to an agonistic epitope on an antigen on the surface of a T cell, wherein the binding of the second scFv to the antigen enhances T cell activation. In some embodiments, the first scFv is human, humanized, or semi-synthetic. In some embodiments, the second scFv is human, humanized, or semi-synthetic. In some embodiments, both the first scFv and the second scFv are human, humanized, or semi-synthetic.

In some embodiments, there is provided a tandem di-scFv bispecific anti-HMC antibody comprising a) a first scFv that specifically binds to a complex comprising a histone H3 peptide selected from mutant histone K27M-H3.3 26-35 (SEQ ID NO: 7), mutant histone K27M-H3.1 26-35 (SEQ ID NO: 8), WT H3.3 26-35 (SEQ ID NO: 5), or WT H3.1 26-35 (SEQ ID NO: 6) peptide and HLA-A*02:01, and b) a second scFv that specifically binds to an antigen on the surface of a T cell. In some embodiments, the histone H3 peptide is mutant histone K27M-H3.3 26-35 (SEQ ID NO: 7). In some embodiments, the histone H3 peptide is mutant histone K27M-H3.1 26-35 (SEQ ID NO: 8). In some embodiments, the histone H3 peptide is WT H3.3 26-35 (SEQ ID NO: 5). In some embodiments, the histone H3 peptide is WT H3.1 26-35 (SEQ ID NO: 6).

In some embodiments, there is provided a tandem di-scFv bispecific anti-HMC antibody comprising a) a first scFv that specifically binds to a complex comprising a histone H3 peptide and an MHC class I protein comprising i) a heavy chain variable domain sequence comprising an HC-CDR1 comprising the amino acid sequence of SEQ ID NO: 158, or a variant thereof comprising up to about 3 (for example about any of 1, 2, or 3) amino acid substitutions, an HC-CDR2 comprising the amino acid sequence of SEQ ID NO: 159, or a variant thereof comprising up to about 3 (for example about any of 1, 2, or 3) amino acid substitutions, and/or an HC-CDR3 comprising the amino acid sequence of SEQ ID NO: 160 or 161, or a variant thereof comprising up to about 3 (for example about any of 1, 2, or 3) amino acid substitutions; and ii) a light chain variable domain comprising an LC-CDR1 comprising the amino acid sequence of SEQ ID NO: 162, or a variant thereof comprising up to about 3 (for example about any of 1, 2, or 3) amino acid substitutions, and/or an LC-CDR3 comprising the amino acid sequence of SEQ ID NO: 163, or a variant thereof comprising up to about 3 (for example about any of 1, 2, or 3) amino acid substitutions, and b) a second scFv that specifically binds to an antigen on the surface of a T cell.

In some embodiments, there is provided a tandem di-scFv bispecific anti-HMC antibody comprising a) a first scFv that specifically binds to a complex comprising a histone H3 peptide and an MHC class I protein comprising i) a heavy chain variable domain sequence comprising an HC-CDR1 comprising the amino acid sequence of SEQ ID NO: 158, an HC-CDR2 comprising the amino acid sequence of SEQ ID NO: 159, and/or an HC-CDR3 comprising the amino acid sequence of SEQ ID NO: 160 or 161; and ii) a light chain variable domain comprising an LC-CDR1 comprising the amino acid sequence of SEQ ID NO: 162, and/or an LC-CDR3 comprising the amino acid sequence of SEQ ID NO: 163, and b) a second scFv that specifically binds to an antigen on the surface of a T cell.

In some embodiments, there is provided a tandem di-scFv bispecific anti-HMC antibody comprising a) a first scFv that specifically binds to a complex comprising a histone H3 peptide and an MHC class I protein comprising i) a heavy chain variable domain comprising an HC-CDR1 comprising the amino acid sequence of any one of SEQ ID NOs: 99-107, or a variant thereof comprising up to about 5 (such as about any of 1, 2, 3, 4, or 5) amino acid substitutions, an HC-CDR2 comprising the amino acid sequence of any one of SEQ ID NOs: 108-116, or a variant thereof comprising up to about 5 (such as about any of 1, 2, 3, 4, or 5) amino acid substitutions, and/or an HC-CDR3 comprising the amino acid sequence of any one of SEQ ID NOs: 117-128, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 129-138, or a variant thereof comprising up to about 5 (such as about any of 1, 2, 3, 4, or 5) amino acid substitutions, an LC-CDR2 comprising the amino acid sequence of any one of SEQ ID NOs: 139-147, or a variant thereof comprising up to about 3 (such as about any of 1, 2, or 3) amino acid substitutions, and/or an LC-CDR3 comprising the amino acid sequence of any one of SEQ ID NOs: 148-157, or a variant thereof comprising up to about 5 (such as about any of 1, 2, 3, 4, or 5) amino acid substitutions; and b) a second scFv that specifically binds to an antigen on the surface of a T cell.

In some embodiments, there is provided a tandem di-scFv bispecific anti-HMC antibody comprising a) a first scFv that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; or a variant thereof comprising up to about 5 (such as about any of 1, 2, 3, 4, or 5) amino acid substitutions in the LC-CDR sequences, and b) a second scFv that specifically binds to an antigen on the surface of a T cell.

In some embodiments, there is provided a tandem di-scFv bispecific anti-HMC antibody comprising a) a first scFv that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; and b) a second scFv that specifically binds to an antigen on the surface of a T cell.

In some embodiments, there is provided a tandem di-scFv bispecific anti-HMC antibody comprising a) a first scFv comprising a heavy chain variable domain comprising the amino acid sequence of any one of SEQ ID NOs: 75-86, or a variant thereof having at least about 95% (for example at least about any of 96%, 97%, 98%, or 99%) sequence identity, and a light chain variable domain comprising the amino acid sequence of any one of SEQ ID NOs: 87-98, or a variant thereof having at least about 95% (for example at least about any of 96%, 97%, 98%, or 99%) sequence identity, and b) a second scFv that specifically binds to an antigen on the surface of a T cell.

In some embodiments, there is provided a tandem di-scFv bispecific anti-HMC antibody comprising a) a first scFv comprising a heavy chain variable domain comprising the amino acid sequence of any one of SEQ ID NOs: 75-86 and a light chain variable domain comprising the amino acid sequence of any one of SEQ ID NOs: 87-98, and b) a second scFv that specifically binds to an antigen on the surface of a T cell.

In some embodiments, there is provided a tandem di-scFv bispecific anti-HMC antibody comprising a) a first scFv that specifically binds to a complex comprising a histone H3 peptide and an MHC class I protein, and b) a second scFv that specifically binds to CD3ε. In some embodiments, the histone H3 peptide is mutant histone K27M-H3.3 26-35 (SEQ ID NO: 7) or mutant histone K27M-H3.1 26-35 (SEQ ID NO: 8). In some embodiments, the histone H3 peptide is WT H3.3 26-35 (SEQ ID NO: 5) or WT H3.1 26-35 (SEQ ID NO: 6). In some embodiments, the MHC class I protein is HLA-A02. In some embodiments, the MHC class I protein is HLA-A*02:01. In some embodiments, the first scFv is fused to the second scFv through linkage with a peptide linker. In some embodiments, the peptide linker is between about 5 to about 20 (such as about any of 5, 10, 15, or 20, including any ranges between these values) amino acids in length. In some embodiments, the peptide linker comprises (and in some embodiments consists of) the amino acid sequence SRGGGGSGGGGSGGGGSLEMA (SEQ ID NO: 46). In some embodiments, the first scFv is human, humanized, or semi-synthetic. In some embodiments, the second scFv is human, humanized, or semi-synthetic. In some embodiments, both the first scFv and the second scFv are human, humanized, or semi-synthetic.

In some embodiments, there is provided a tandem di-scFv bispecific anti-HMC antibody comprising a) a first scFv that specifically binds to a complex comprising a histone H3 peptide selected from mutant histone K27M-H3.3 26-35 (SEQ ID NO: 7), mutant histone K27M-H3.1 26-35 (SEQ ID NO: 8), WT H3.3 26-35 (SEQ ID NO: 5), or WT H3.1 26-35 (SEQ ID NO: 6) peptide and HLA-A*02:01, and b) a second scFv that specifically binds to CD3ε. In some embodiments, the histone H3 peptide is mutant histone K27M-H3.3 26-35 (SEQ ID NO: 7). In some embodiments, the histone H3 peptide is mutant histone K27M-H3.1 26-35 (SEQ ID NO: 8). In some embodiments, the histone H3 peptide is WT H3.3 26-35 (SEQ ID NO: 5). In some embodiments, the histone H3 peptide is WT H3.1 26-35 (SEQ ID NO: 6). In some embodiments, the first scFv is fused to the second scFv through linkage with a peptide linker. In some embodiments, the peptide linker is between about 5 to about 20 (such as about any of 5, 10, 15, or 20, including any ranges between these values) amino acids in length. In some embodiments, the peptide linker comprises (and in some embodiments consists of) the amino acid sequence of SEQ ID NO: 46. In some embodiments, the first scFv is human, humanized, or semi-synthetic. In some embodiments, the second scFv is human, humanized, or semi-synthetic. In some embodiments, both the first scFv and the second scFv are human, humanized, or semi-synthetic.

In some embodiments, there is provided a tandem di-scFv bispecific anti-HMC antibody comprising a) a first scFv that specifically binds to a complex comprising a histone H3 peptide and an MHC class I protein comprising i) a heavy chain variable domain sequence comprising an HC-CDR1 comprising the amino acid sequence of SEQ ID NO: 158, or a variant thereof comprising up to about 3 (for example about any of 1, 2, or 3) amino acid substitutions, an HC-CDR2 comprising the amino acid sequence of SEQ ID NO: 159, or a variant thereof comprising up to about 3 (for example about any of 1, 2, or 3) amino acid substitutions, and/or an HC-CDR3 comprising the amino acid sequence of SEQ ID NO: 160 or 161, or a variant thereof comprising up to about 3 (for example about any of 1, 2, or 3) amino acid substitutions; and ii) a light chain variable domain comprising an LC-CDR1 comprising the amino acid sequence of SEQ ID NO: 162, or a variant thereof comprising up to about 3 (for example about any of 1, 2, or 3) amino acid substitutions, and/or an LC-CDR3 comprising the amino acid sequence of SEQ ID NO: 163, or a variant thereof comprising up to about 3 (for example about any of 1, 2, or 3) amino acid substitutions, and b) a second scFv that specifically binds to CD3ε. In some embodiments, there is provided a tandem di-scFv bispecific anti-HMC antibody comprising a) a first scFv that specifically binds to a complex comprising a histone H3 peptide and an MHC class I protein comprising i) a heavy chain variable domain sequence comprising an HC-CDR1 comprising the amino acid sequence of SEQ ID NO: 158, an HC-CDR2 comprising the amino acid sequence of SEQ ID NO: 159, and/or an HC-CDR3 comprising the amino acid sequence of SEQ ID NO: 160 or 161; and ii) a light chain variable domain comprising an LC-CDR1 comprising the amino acid sequence of SEQ ID NO: 162, and/or an LC-CDR3 comprising the amino acid sequence of SEQ ID NO: 163, and b) a second scFv that specifically binds to CD3ε. In some embodiments, the first scFv is fused to the second scFv through linkage with a peptide linker. In some embodiments, the peptide linker is between about 5 to about 20 (such as about any of 5, 10, 15, or 20, including any ranges between these values) amino acids in length. In some embodiments, the peptide linker comprises (and in some embodiments consists of) the amino acid sequence of SEQ ID NO: 46. In some embodiments, the first scFv is human, humanized, or semi-synthetic. In some embodiments, the second scFv is human, humanized, or semi-synthetic. In some embodiments, both the first scFv and the second scFv are human, humanized, or semi-synthetic.

In some embodiments, there is provided a tandem di-scFv bispecific anti-HMC antibody comprising a) a first scFv that specifically binds to a complex comprising a histone H3 peptide and an MHC class I protein comprising i) a heavy chain variable domain comprising an HC-CDR1 comprising the amino acid sequence of any one of SEQ ID NOs: 99-107, or a variant thereof comprising up to about 5 (such as about any of 1, 2, 3, 4, or 5) amino acid substitutions, an HC-CDR2 comprising the amino acid sequence of any one of SEQ ID NOs: 108-116, or a variant thereof comprising up to about 5 (such as about any of 1, 2, 3, 4, or 5) amino acid substitutions, and/or an HC-CDR3 comprising the amino acid sequence of any one of SEQ ID NOs: 117-128, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 129-138, or a variant thereof comprising up to about 5 (such as about any of 1, 2, 3, 4, or 5) amino acid substitutions, an LC-CDR2 comprising the amino acid sequence of any one of SEQ ID NOs: 139-147, or a variant thereof comprising up to about 3 (such as about any of 1, 2, or 3) amino acid substitutions, and/or an LC-CDR3 comprising the amino acid sequence of any one of SEQ ID NOs: 148-157, or a variant thereof comprising up to about 5 (such as about any of 1, 2, 3, 4, or 5) amino acid substitutions, and b) a second scFv that specifically binds to CD3ε. In some embodiments, here is provided a tandem di-scFv bispecific anti-HMC antibody comprising a) a first scFv that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; or a variant thereof comprising up to about 5 (such as about any of 1, 2, 3, 4, or 5) amino acid substitutions in the LC-CDR sequences, and b) a second scFv that specifically binds to CD3ε. In some embodiments, there is provided a tandem di-scFv bispecific anti-HMC antibody comprising a) a first scFv that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; and b) a second scFv that specifically binds to CD3ε. In some embodiments, the first scFv is fused to the second scFv through linkage with a peptide linker. In some embodiments, the peptide linker is between about 5 to about 20 (such as about any of 5, 10, 15, or 20, including any ranges between these values) amino acids in length. In some embodiments, the peptide linker comprises (and in some embodiments consists of) the amino acid sequence of SEQ ID NO: 46. In some embodiments, the first scFv is human, humanized, or semi-synthetic. In some embodiments, the second scFv is human, humanized, or semi-synthetic. In some embodiments, both the first scFv and the second scFv are human, humanized, or semi-synthetic.

In some embodiments, there is provided a tandem di-scFv bispecific anti-HMC antibody comprising a) a first scFv comprising a heavy chain variable domain comprising the amino acid sequence of any one of SEQ ID NOs: 75-86, or a variant thereof having at least about 95% (for example at least about any of 96%, 97%, 98%, or 99%) sequence identity, and a light chain variable domain comprising the amino acid sequence of any one of SEQ ID NOs: 87-98, or a variant thereof having at least about 95% (for example at least about any of 96%, 97%, 98%, or 99%) sequence identity, and b) a second scFv that specifically binds to CD3ε. In some embodiments, there is provided a tandem di-scFv bispecific anti-HMC antibody comprising a) a first scFv comprising a heavy chain variable domain comprising the amino acid sequence of any one of SEQ ID NOs: 75-86 and a light chain variable domain comprising the amino acid sequence of any one of SEQ ID NOs: 87-98, and b) a second scFv that specifically binds to CD3ε. In some embodiments, the first scFv is fused to the second scFv through linkage with a peptide linker. In some embodiments, the peptide linker is between about 5 to about 20 (such as about any of 5, 10, 15, or 20, including any ranges between these values) amino acids in length. In some embodiments, the peptide linker comprises (and in some embodiments consists of) the amino acid sequence of SEQ ID NO: 46. In some embodiments, the first scFv is human, humanized, or semi-synthetic. In some embodiments, the second scFv is human, humanized, or semi-synthetic. In some embodiments, both the first scFv and the second scFv are human, humanized, or semi-synthetic.

In some embodiments, the tandem di-scFv bispecific anti-HMC antibody binds to a complex comprising a histone H3 peptide and an MHC class I protein with a $K_d$ between about 0.1 pM to about 500 nM (such as about any of 0.1 pM, 1.0 pM, 10 pM, 50 pM, 100 pM, 500 pM, 1 nM, 10 nM, 50 nM, 100 nM, or 500 nM, including any ranges between these values). In some embodiments, the tandem di-scFv bispecific anti-HMC antibody binds to a complex comprising a histone H3 peptide and an MHC class I protein with a $K_d$ between about 1 nM to about 500 nM (such as about any of 1, 10, 25, 50, 75, 100, 150, 200, 250, 300, 350, 400, 450, or 500 nM, including any ranges between these values).

For example, in some embodiments, the multi-specific anti-HMC molecule (such as di-scFv) comprises an anti-HMC antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (for example about any of 1, 2, 3, 4, or 5) amino acid substitutions, individually, in HC-CDR1, HC-CDR2, HC-CDR3, LC-CDR1, and/or LC-CDR3, and/or up to about 3 (for example about any of 1, 2, or 3) amino acid substitutions in LC-CDR2.

In some embodiments, the multi-specific anti-HMC molecule (such as di-scFv) comprises an anti-HMC antibody moiety comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (such as about any of 1, 2, 3, 4, or 5) amino acid substitutions in the HC-CDR sequences and/or up to about 5 (such as about any of 1, 2, 3, 4, or 5) amino acid substitutions in the LC-CDR sequences.

In some embodiments, the multi-specific anti-HMC molecule (such as di-scFv) comprises an anti-HMC antibody moiety comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively.

In some embodiments, the multi-specific anti-HMC molecule (such as di-scFv) comprises an anti-HMC antibody moiety comprising heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively; or variants thereof having, individually, at least about 95% (for example at least about any of 96%, 97%, 98%, or 99%) sequence identity. In some embodiments, the multi-specific anti-HMC molecule comprises an anti-HMC antibody moiety comprising heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively.

Chimeric Receptors and Effector Cells

The anti-HMC construct in some embodiments is a chimeric receptor comprising an anti-HMC antibody moiety (also referred to herein as an "anti-HMC chimeric receptor"). Also provided is an effector cell (e.g., T cell) comprising a chimeric receptor comprising an anti-HMC antibody moiety (also referred to herein as an "anti-HMC chimeric receptor effector cell", e.g., "anti-HMC chimeric receptor T cell").

Chimeric Antigen Receptor

In some embodiments, the chimeric receptor is a chimeric antigen receptor (CAR), and the anti-HMC chimeric receptor is an anti-HMC CAR. In some embodiments, the anti-HMC CAR comprises a) an extracellular domain comprising an anti-HMC antibody moiety that specifically binds to a complex comprising a histone H3 peptide and an MHC class I protein and b) an intracellular signaling domain. A transmembrane domain may be present between the extracellular domain and the intracellular domain.

Between the extracellular domain and the transmembrane domain of the anti-HMC CAR, or between the intracellular domain and the transmembrane domain of the anti-HMC CAR, there may be a spacer domain. The spacer domain can be any oligo- or polypeptide that functions to link the transmembrane domain to the extracellular domain or the intracellular domain in the polypeptide chain. A spacer domain may comprise up to about 300 amino acids, including for example about 10 to about 100, or about 25 to about 50 amino acids.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the α, β, δ, γ, or ζ chain of the T-cell receptor, CD28, CD3ε, CD3ζ, CD45, CD4, CD5, CD8, CD9, CD16, CD22, CD33, CD37, CD64, CD80, CD86, CD134, CD137, or CD154. In some embodiments, the transmembrane domain may be synthetic, in which case it may comprise predominantly hydrophobic residues such as leucine and valine. In some embodiments, a triplet of phenylalanine, tryptophan and valine may be found at each end of a synthetic transmembrane domain. In some embodiments, a short oligo- or polypeptide linker, having a length of, for example, between about 2 and about 10 (such as about any of 2, 3, 4, 5, 6, 7, 8, 9, or 10) amino acids in length may form the linkage between the transmembrane domain and the intracellular signaling domain of the anti-HMC CAR. In some embodiments, the linker is a glycine-serine doublet.

In some embodiments, the transmembrane domain that naturally is associated with one of the sequences in the intracellular domain of the anti-HMC CAR is used (e.g., if an anti-HMC CAR intracellular domain comprises a CD28 co-stimulatory sequence, the transmembrane domain of the anti-HMC CAR is derived from the CD28 transmembrane domain). In some embodiments, the transmembrane domain can be selected or modified by amino acid substitution to avoid binding of such domains to the transmembrane domains of the same or different surface membrane proteins to minimize interactions with other members of the receptor complex.

The intracellular signaling domain of the anti-HMC CAR is responsible for activation of at least one of the normal effector functions of the immune cell in which the anti-HMC CAR has been placed in. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term "intracellular signaling sequence" is thus meant to include any truncated portion of the intracellular signaling domain sufficient to transduce the effector function signal.

Examples of intracellular signaling domains for use in the anti-HMC CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of intracellular signaling sequence: those that initiate antigen-dependent primary activation through the TCR (primary signaling sequences) and those that act in an antigen-independent manner to provide a secondary or co-stimulatory signal (co-stimulatory signaling sequences).

Primary signaling sequences regulate primary activation of the TCR complex either in a stimulatory way, or in an inhibitory way. Primary signaling sequences that act in a stimulatory manner may contain signaling motifs which are known as immunoreceptor tyrosine-based activation motifs or ITAMs. The anti-HMC CAR constructs in some embodiments comprise one or more ITAMs.

Examples of ITAM containing primary signaling sequences that are of particular use in the invention include those derived from TCRζ, FcRγ, FcRβ, CD3γ, CD3δ, CD3ε, CD5, CD22, CD79a, CD79b, and CD66d.

In some embodiments, the anti-HMC CAR comprises a primary signaling sequence derived from CD3ζ. For example, the intracellular signaling domain of the CAR can comprise the CD3ζ intracellular signaling sequence by itself or combined with any other desired intracellular signaling sequence(s) useful in the context of the anti-HMC CAR of the invention. For example, the intracellular domain of the anti-HMC CAR can comprise a CD3ζ intracellular signaling sequence and a costimulatory signaling sequence. The costimulatory signaling sequence can be a portion of the intracellular domain of a costimulatory molecule including, for example, CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, and the like.

In some embodiments, the intracellular signaling domain of the anti-HMC CAR comprises the intracellular signaling sequence of CD3ζ and the intracellular signaling sequence of CD28. In some embodiments, the intracellular signaling domain of the anti-HMC CAR comprises the intracellular signaling sequence of CD3ζ and the intracellular signaling sequence of 4-1BB. In some embodiments, the intracellular signaling domain of the anti-HMC CAR comprises the intracellular signaling sequence of CD3ζ and the intracellular signaling sequences of CD28 and 4-1BB.

Thus, for example, in some embodiments, there is provided an anti-HMC CAR comprising a) an extracellular domain comprising an anti-HMC antibody moiety that specifically binds to a complex comprising a histone H3 peptide and an MHC class I protein, b) a transmembrane domain, and c) an intracellular signaling domain. In some embodiments, the histone H3 peptide is mutant histone K27M-H3.3 26-35 (SEQ ID NO: 7) or mutant histone K27M-H3.1 26-35 (SEQ ID NO: 8). In some embodiments, the histone H3 peptide is WT H3.3 26-35 (SEQ ID NO: 5) or WT H3.1 26-35 (SEQ ID NO: 6). In some embodiments, the MHC class I protein is HLA-A02. In some embodiments, the MHC class I protein is HLA-A*02:01. In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 and/or 4-1BB intracellular signaling sequence. In some embodiments, the intracellular domain comprises a CD3ζ intracellular signaling sequence and a CD28 and/or 4-1BB intracellular signaling sequence. In some embodiments, the anti-HMC antibody moiety cross-reacts with at least one (such as at least any of 2, 3, 4, 5, or 6) complex comprising the MHC class I protein and a variant of the histone H3 peptide having one amino acid substitution (such as a conservative amino acid substitution). In some embodiments, the anti-HMC antibody moiety cross-reacts with at least one (such as at least any of 2, 3, 4, or 5) complex comprising the histone H3 peptide and a different subtype of the MHC class I protein.

In some embodiments, there is provided an anti-HMC CAR comprising a) an extracellular domain comprising an anti-HMC antibody moiety that specifically binds to a complex comprising a histone H3 peptide selected from mutant histone K27M-H3.3 26-35 (SEQ ID NO: 7), mutant histone K27M-H3.1 26-35 (SEQ ID NO: 8), WT H3.3 26-35 (SEQ ID NO: 5), or WT H3.1 26-35 (SEQ ID NO: 6) peptide and HLA-A*02:01, b) a transmembrane domain, and c) an intracellular signaling domain. In some embodiments, the histone H3 peptide is mutant histone K27M-H3.3 26-35 (SEQ ID NO: 7). In some embodiments, the histone H3 peptide is mutant histone K27M-H3.1 26-35 (SEQ ID NO: 8). In some embodiments, the histone H3 peptide is WT H3.3 26-35 (SEQ ID NO: 5). In some embodiments, the histone H3 peptide is WT H3.1 26-35 (SEQ ID NO: 6). In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 and/or 4-1BB intracellular signaling sequence. In some embodiments, the intracellular domain comprises a CD3ζ intracellular signaling sequence and a CD28 and/or 4-1BB intracellular signaling sequence.

In some embodiments, there is provided an anti-HMC CAR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of SEQ ID NO: 158, or a variant thereof comprising up to about 3 (for example about any of 1, 2, or 3) amino acid substitutions, an HC-CDR2 comprising the amino acid sequence of SEQ ID NO: 159, or a variant thereof comprising up to about 3 (for example about any of 1, 2, or 3) amino acid substitutions, and/or an HC-CDR3 comprising the amino acid sequence of SEQ ID NO: 160 or 161, or a variant thereof comprising up to about 3 (for example about any of 1, 2, or 3) amino acid substitutions; and ii) a light chain variable domain comprising an LC-CDR1 comprising the amino acid sequence of SEQ ID NO: 162, or a variant thereof comprising up to about 3 (for example about any of 1, 2, or 3) amino acid substitutions, and/or an LC-CDR3 comprising the amino acid sequence of SEQ ID NO: 163, or a variant thereof comprising up to about 3 (for example about any of 1, 2, or 3) amino acid substitutions, b) a transmembrane domain, and c) an intracellular signaling domain. In some embodiments, there is provided an anti-HMC CAR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of SEQ ID NO: 158, an HC-CDR2 comprising the amino acid sequence of SEQ ID NO: 159, and/or an HC-CDR3 comprising the amino acid sequence of SEQ ID NO: 160 or 161; and ii) a light chain variable domain comprising an LC-CDR1 comprising the amino acid sequence of SEQ ID NO: 162, and/or an LC-CDR3 comprising the amino acid sequence of SEQ ID NO: 163; b) an intracellular signaling domain. In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 and/or 4-1BB intracellular signaling sequence. In some embodiments, the intracellular domain comprises a CD3ζ intracellular signaling sequence and a CD28 and/or 4-1BB intracellular signaling sequence.

In some embodiments, there is provided an anti-HMC CAR comprising a) an extracellular domain comprising an anti-HMC antibody moiety that specifically binds to a complex comprising a histone H3 peptide and an MHC class I protein comprising i) a heavy chain variable domain comprising an HC-CDR1 comprising the amino acid sequence of any one of SEQ ID NOs: 99-107, or a variant thereof comprising up to about 5 (such as about any of 1, 2, 3, 4, or 5) amino acid substitutions, an HC-CDR2 comprising the amino acid sequence of any one of SEQ ID NOs: 108-116, or a variant thereof comprising up to about 5 (such as about any of 1, 2, 3, 4, or 5) amino acid substitutions, and/or an HC-CDR3 comprising the amino acid sequence of any one of SEQ ID NOs: 117-128, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 129-138, or a variant thereof comprising up to about 5 (such as about any of 1, 2, 3, 4, or 5) amino acid substitutions, an LC-CDR2 comprising the amino acid sequence of any one of SEQ ID NOs: 139-147, or a variant thereof comprising up to about 3 (such as about any of 1, 2, or 3) amino acid substitutions, and/or an LC-CDR3 comprising the amino acid sequence of any one of SEQ ID NOs: 148-157, or a variant thereof comprising up to about 5 (such as about any of 1, 2, 3, 4, or 5) amino acid substitutions; b) a transmembrane domain, and c) an intracellular signaling domain. In some embodiments, there is provided an anti-HMC CAR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; or a variant thereof comprising up to about 5 (such as about any of 1, 2, 3, 4, or 5) amino acid substitutions in the LC-CDR sequences; b) a transmembrane domain, and c) an intracellular signaling domain. In some embodiments, there is provided an anti-HMC CAR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; b) an intracellular signaling domain. In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 and/or 4-1BB intracellular signaling sequence. In some embodiments, the intracellular domain comprises a CD3ζ intracellular signaling sequence and a CD28 and/or 4-1BB intracellular signaling sequence.

In some embodiments, there is provided an anti-HMC CAR comprising a) an extracellular domain comprising an anti-HMC antibody moiety that specifically binds to a complex comprising a histone H3 peptide and an MHC class I protein comprising a heavy chain variable domain comprising the amino acid sequence of any one of SEQ ID NOs: 75-86, or a variant thereof having at least about 95% (for example at least about any of 96%, 97%, 98%, or 99%) sequence identity, and a light chain variable domain comprising the amino acid sequence of any one of SEQ ID NOs: 87-98, or a variant thereof having at least about 95% (including for example at least about any of 96%, 97%, 98%, or 99%) sequence identity; b) a transmembrane domain, and c) an intracellular signaling domain. In some embodiments, there is provided an anti-HMC CAR comprising a) an extracellular domain comprising an anti-HMC antibody moiety that specifically binds to a complex comprising a histone H3 peptide and an MHC class I protein comprising a heavy chain variable domain comprising the amino acid sequence of any one of SEQ ID NOs: 75-86 and a light chain variable domain comprising the amino acid sequence of any one of SEQ ID NOs: 87-98; b) an intracellular signaling domain. In some embodiments, the intracellular signaling domain is capable of activating an immune cell. In some embodiments, the intracellular signaling domain comprises a primary signaling sequence and a co-stimulatory signaling sequence. In some embodiments, the primary signaling sequence comprises a CD3ζ intracellular signaling sequence. In some embodiments, the co-stimulatory signaling sequence comprises a CD28 and/or 4-1BB intracellular signaling sequence. In some embodiments, the intracellular domain comprises a CD3ζ intracellular signaling sequence and a CD28 and/or 4-1BB intracellular signaling sequence.

In some embodiments, there is provided an anti-HMC CAR comprising a) an extracellular domain comprising an anti-HMC antibody moiety that specifically binds to a complex comprising a histone H3 peptide and an MHC class I protein, b) a transmembrane domain, and c) an intracellular signaling domain comprising a CD3ζ intracellular signaling sequence and a CD28 and/or 4-1BB intracellular signaling sequence. In some embodiments, the histone H3 peptide is mutant histone K27M-H3.3 26-35 (SEQ ID NO: 7) or mutant histone K27M-H3.1 26-35 (SEQ ID NO: 8). In some embodiments, the histone H3 peptide is WT H3.3 26-35 (SEQ ID NO: 5) or WT H3.1 26-35 (SEQ ID NO: 6). In some embodiments, the MHC class I protein is HLA-A02. In some embodiments, the MHC class I protein is HLA-A*02:01.

In some embodiments, there is provided an anti-HMC CAR comprising a) an extracellular domain comprising an anti-HMC antibody moiety that specifically binds to a complex comprising a histone H3 peptide selected from mutant histone K27M-H3.3 26-35 (SEQ ID NO: 7), mutant histone K27M-H3.1 26-35 (SEQ ID NO: 8), WT H3.3 26-35 (SEQ ID NO: 5), or WT H3.1 26-35 (SEQ ID NO: 6) peptide and HLA-A*02:01, b) a transmembrane domain, and c) an intracellular signaling domain comprising a CD3ζ intracellular signaling sequence and a CD28 and/or 4-1BB intracellular signaling sequence. In some embodiments, the histone H3 peptide is mutant histone K27M-H3.3 26-35 (SEQ ID NO: 7). In some embodiments, the histone H3 peptide is mutant histone K27M-H3.1 26-35 (SEQ ID NO: 8). In some embodiments, the histone H3 peptide is WT H3.3 26-35 (SEQ ID NO: 5). In some embodiments, the histone H3 peptide is WT H3.1 26-35 (SEQ ID NO: 6).

In some embodiments, there is provided an anti-HMC CAR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of SEQ ID NO: 158, or a variant thereof comprising up to about 3 (for example about any of 1, 2, or 3) amino acid substitutions, an HC-CDR2 comprising the amino acid sequence of SEQ ID NO: 159, or a variant thereof comprising up to about 3 (for example about any of 1, 2, or 3) amino acid substitutions, and/or an HC-CDR3 comprising the amino acid sequence of SEQ ID NO: 160 or 161, or a variant thereof comprising up to about 3 (for example about any of 1, 2, or 3) amino acid substitutions; and ii) a light chain variable domain comprising an LC-CDR1 comprising the amino acid sequence of SEQ ID NO: 162, or a variant thereof comprising up to about 3 (for example about any of 1, 2, or 3) amino acid substitutions, and/or an LC-CDR3 comprising the amino acid sequence of SEQ ID NO: 163, or a variant thereof comprising up to about 3 (for example about any of 1, 2, or 3) amino acid substitutions, b) a transmembrane domain, and c) an intracellular signaling domain comprising a CD3ζ intracellular signaling sequence and a CD28 and/or 4-1BB intracellular signaling sequence.

In some embodiments, there is provided an anti-HMC CAR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of SEQ ID NO: 158, an HC-CDR2 comprising the amino acid sequence of SEQ ID NO: 159, and/or an HC-CDR3 comprising the amino acid sequence of SEQ ID NO: 160 or 161; and ii) a light chain variable domain comprising an LC-CDR1 comprising the amino acid sequence of SEQ ID NO: 162, and/or an LC-CDR3 comprising the amino acid sequence of SEQ ID NO: 163, b) a transmembrane domain, and c) an intracellular signaling domain comprising a CD3 intracellular signaling sequence and a CD28 and/or 4-1BB intracellular signaling sequence.

In some embodiments, there is provided an anti-HMC CAR comprising a) an extracellular domain comprising an anti-HMC antibody moiety that specifically binds to a complex comprising a histone H3 peptide and an MHC class I protein comprising i) a heavy chain variable domain comprising an HC-CDR1 comprising the amino acid sequence of any one of SEQ ID NOs: 99-107, or a variant thereof comprising up to about 5 (such as about any of 1, 2, 3, 4, or 5) amino acid substitutions, an HC-CDR2 comprising the amino acid sequence of any one of SEQ ID NOs: 108-116, or a variant thereof comprising up to about 5 (such as about any of 1, 2, 3, 4, or 5) amino acid substitutions, and/or an HC-CDR3 comprising the amino acid sequence of any one of SEQ ID NOs: 117-128, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 129-138, or a variant thereof comprising up to about 5 (such as about any of 1, 2, 3, 4, or 5) amino acid substitutions, an LC-CDR2 comprising the amino acid sequence of any one of SEQ ID NOs: 139-147, or a variant thereof comprising up to about 3 (such as about any of 1, 2, or 3) amino acid substitutions, and/or an LC-CDR3 comprising the amino acid sequence of any one of SEQ ID NOs: 148-157, or a variant thereof comprising up to about 5 (such as about any of 1, 2, 3, 4, or 5) amino acid substitutions; b) a transmembrane domain, and c) an intracellular signaling domain comprising a CD3ζ intracellular signaling sequence and a CD28 and/or 4-1BB intracellular signaling sequence.

In some embodiments, there is provided an anti-HMC CAR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; or a variant thereof comprising up to about 5 (such as about any of 1, 2, 3, 4, or 5) amino acid substitutions in the LC-CDR sequences; b) a transmembrane domain, and c) an intracellular signaling domain comprising a CD3ζ intracellular signaling sequence and a CD28 and/or 4-1BB intracellular signaling sequence.

In some embodiments, there is provided an anti-HMC CAR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; b) a transmembrane domain, and c) an intracellular signaling domain comprising a CD3ζ intracellular signaling sequence and a CD28 and/or 4-1BB intracellular signaling sequence.

In some embodiments, there is provided an anti-HMC CAR comprising a) an extracellular domain comprising an anti-HMC antibody moiety that specifically binds to a complex comprising a histone H3 peptide and an MHC class I protein comprising i) a heavy chain variable domain comprising the amino acid sequence of any one of SEQ ID NOs: 75-86, or a variant thereof having at least about 95% (for example at least about any of 96%, 97%, 98%, or 99%) sequence identity, and a light chain variable domain comprising the amino acid sequence of any one of SEQ ID NOs: 87-98, or a variant thereof having at least about 95% (including for example at least about any of 96%, 97%, 98%, or 99%) sequence identity; b) a transmembrane domain, and c) an intracellular signaling domain comprising a CD3ζ intracellular signaling sequence and a CD28 and/or 4-1BB intracellular signaling sequence.

In some embodiments, there is provided an anti-HMC CAR comprising a) an extracellular domain comprising an anti-HMC antibody moiety that specifically binds to a complex comprising a histone H3 peptide and an MHC class I protein comprising a heavy chain variable domain comprising the amino acid sequence of any one of SEQ ID NOs: 75-86 and a light chain variable domain comprising the amino acid sequence of any one of SEQ ID NOs: 87-98; b) a transmembrane domain, and c) an intracellular signaling domain comprising a CD3 intracellular signaling sequence and a CD28 and/or 4-1BB intracellular signaling sequence.

For example, in some embodiments, the anti-HMC CAR comprises an anti-HMC antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (for example about any of 1, 2, 3, 4, or 5) amino acid substitutions, individually, in HC-CDR1, HC-CDR2, HC-CDR3, LC-CDR1, and/or LC-CDR3, and/or up to about 3 (for example about any of 1, 2, or 3) amino acid substitutions in LC-CDR2.

In some embodiments, the anti-HMC CAR comprises an anti-HMC antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (such as about any of 1, 2, 3, 4, or 5) amino acid substitutions in the HC-CDR sequences and/or up to about 5 (such as about any of 1, 2, 3, 4, or 5) amino acid substitutions in the LC-CDR sequences.

In some embodiments, the anti-HMC CAR comprises an anti-HMC antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively.

In some embodiments, the anti-HMC CAR comprises an anti-HMC antibody moiety comprising heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively; or variants thereof having, individually, at least about 95% (for example at least about any of 96%, 97%, 98%, or 99%) sequence identity. In some embodiments, the anti-HMC CAR comprises an anti-HMC antibody moiety comprising heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively.

Chimeric Antibody/T Cell Receptor

In some embodiments, the chimeric receptor is a chimeric antibody/T cell receptor construct (referred to herein as "abTCR"), and the anti-HMC chimeric receptor is an anti-HMC abTCR. In some embodiments, the anti-HMC abTCR comprises a) an extracellular domain comprising an anti-HMC antibody moiety that specifically binds to a complex comprising a histone H3 peptide and an MHC class I protein and b) a T cell receptor module (TCRM) capable of recruiting at least one TCR-associated signaling module.

In some embodiments, the anti-HMC abTCR comprises a first polypeptide chain and a second polypeptide chain. In some embodiments, the first and second polypeptide chains are linked, such as by a covalent linkage (e.g., peptide or other chemical linkage) or non-covalent linkage. In some embodiments, the anti-HMC abTCR is a heterodimer comprising the first polypeptide chain and the second polypeptide chain. In some embodiments, the first polypeptide chain and the second polypeptide chain are linked by at least one disulfide bond. The specificity of the anti-HMC abTCR derives from an antibody moiety that confers binding specificity to the HMC. In some embodiments, the antibody moiety is a Fab-like antigen-binding module. In some embodiments, the antibody moiety is an Fv-like antigen-binding module. In some embodiments, the antibody moiety is an scFv. The capability of the anti-HMC abTCR to recruit a TCR-associated signaling module derives from a T cell receptor module (TCRM). In some embodiments, the TCRM comprises the transmembrane module of a TCR (such as an $\alpha\beta$TCR or a $\gamma\delta$TCR). In some embodiments, the TCRM further comprises one or both of the connecting peptides or fragments thereof of a TCR. In some embodiments, the anti-HMC abTCR further comprises at least one intracellular domain. In some embodiments, one or more of the at least one intracellular domain of the anti-HMC abTCR comprises a sequence from the intracellular domain of a TCR. In some embodiments, one or more of the at least one intracellular domain of the anti-HMC abTCR comprises a T cell costimulatory signaling sequence. The costimulatory signaling sequence can be a portion of the intracellular domain of a costimulatory molecule including, for example, CD27, CD28, 4-1BB (CD137), OX40, CD30, CD40, ICOS, lymphocyte function-associated antigen-1 (LFA-1), CD2, CD7, LIGHT, NKG2C, B7-H3, a ligand that specifically binds with CD83, and the like. In some embodiments, the antibody moiety is contained in an extracellular domain of the anti-HMC abTCR. In some embodiments, the anti-HMC abTCR further comprises one or more peptide linkers between the antibody moiety and the TCRM to optimize the length of the extracellular domain.

In some embodiments, the antibody moiety is a Fab-like antigen-binding module that specifically binds to a complex comprising a histone H3 peptide and an MHC class I protein, comprising a) a first polypeptide chain comprising a first antigen-binding domain comprising a $V_H$ antibody domain and a $C_H 1$ antibody domain and b) a second polypeptide chain comprising a second antigen-binding domain comprising a $V_L$ antibody domain and a $C_L$ antibody domain. In some embodiments, the first antigen-binding domain comprises the $V_H$ antibody domain amino-terminal to the $C_H 1$ antibody domain and/or the second antigen-binding domain comprises the $V_L$ antibody domain amino-terminal to the $C_L$ antibody domain. In some embodiments, there is a peptide linker between the $V_L$ and $C_L$ antibody domains and/or a peptide linker between the $V_H$ and $C_H 1$ antibody domains. In some embodiments, all of the $V_L$ antibody domain and $V_H$ antibody domain CDRs are derived from the same antibody moiety. In some embodiments, the $V_L$ antibody domain and the $V_H$ antibody domain comprise antibody CDRs derived from more than one antibody moiety. In some embodiments, the first and second polypeptide chains are linked, such as by a covalent linkage (e.g., peptide or other chemical linkage) or non-covalent linkage. In some embodiments, the first and second antigen-binding domains are linked by a disulfide bond. In some embodiments, the first and second antigen-binding domains are linked by a disulfide bond between a residue in the $C_H 1$ domain and a residue in the $C_L$ domain. In some embodiments, the $C_H 1$ domain is derived from an IgG (e.g, IgG1, IgG2, IgG3, or IgG4) heavy chain, optionally human. In some embodiments, the $C_H 1$ domain is a variant comprising one or more modifications (e.g., amino acid substitutions, insertions, and/or deletions) compared to the sequence from which it is derived. In some embodiments, the $C_L$ domain is derived from a kappa or lambda light chain, optionally human. In some embodiments, the $C_L$ domain is a variant comprising one or more modifications (e.g., amino acid substitutions, insertions, and/or deletions) compared to the sequence from which it is derived. In some embodiments, the $C_H1$ and/or $C_L$ domains comprise one or more modifications that do not substantially alter their binding affinities for one another. In some embodiments, the $C_H1$ and/or $C_L$ domains comprise one or more modifications that increase their binding affinities for one another and/or introduce a non-naturally occurring disulfide bond. In some embodiments, the Fab-like antigen-binding module is human, humanized, chimeric, semi-synthetic, or fully synthetic.

In some embodiments, the antibody moiety is a Fab-like antigen-binding module that specifically binds to a complex comprising a histone H3 peptide and an MHC class I protein, comprising a) a first polypeptide chain comprising a first antigen-binding domain comprising a $V_L$ antibody domain and a $C_H1$ antibody domain and b) a second polypeptide chain comprising a second antigen-binding domain comprising a $V_H$ antibody domain and a $C_L$ antibody domain. In some embodiments, the first antigen-binding domain comprises the $V_L$ antibody domain amino-terminal to the $C_H1$ antibody domain and/or the second antigen-binding domain comprises the $V_H$ antibody domain amino-terminal to the $C_L$ antibody domain. In some embodiments, there is a peptide linker between the $V_H$ and $C_L$ antibody domains and/or a peptide linker between the $V_L$ and $C_H1$ antibody domains. In some embodiments, all of the $V_L$ antibody domain and $V_H$ antibody domain CDRs are derived from the same antibody moiety. In some embodiments, the $V_L$ antibody domain and the $V_H$ antibody domain comprise antibody CDRs derived from more than one antibody moiety. In some embodiments, the first and second polypeptide chains are linked, such as by a covalent linkage (e.g., peptide or other chemical linkage) or non-covalent linkage. In some embodiments, the first and second antigen-binding domains are linked by a disulfide bond. In some embodiments, the first and second antigen-binding domains are linked by a disulfide bond between a residue in the $C_H1$ domain and a residue in the $C_L$ domain. In some embodiments, the $C_H1$ domain is derived from an IgG (e.g, IgG1, IgG2, IgG3, or IgG4) heavy chain, optionally human. In some embodiments, the $C_H1$ domain is a variant comprising one or more modifications (e.g., amino acid substitutions, insertions, and/or deletions) compared to the sequence from which it is derived. In some embodiments, the $C_L$ domain is derived from a kappa or lambda light chain, optionally human. In some embodiments, the $C_L$ domain is a variant comprising one or more modifications (e.g., amino acid substitutions, insertions, and/or deletions) compared to the sequence from which it is derived. In some embodiments, the $C_H1$ and/or $C_L$ domains comprise one or more modifications that do not substantially alter their binding affinities for one another. In some embodiments, the $C_H1$ and/or $C_L$ domains comprise one or more modifications that increase their binding affinities for one another and/or introduce a non-naturally occurring disulfide bond. In some embodiments, the Fab-like antigen-binding module is human, humanized, chimeric, semi-synthetic, or fully synthetic.

In some embodiments, the antibody moiety is an Fv-like antigen-binding module that specifically binds to a complex comprising a histone H3 peptide and an MHC class I protein, comprising a) a first polypeptide chain comprising a first antigen-binding domain comprising a $V_H$ antibody domain and optionally a first TCR constant domain from a T cell receptor subunit; and b) a second polypeptide chain comprising a second antigen-binding domain comprising a $V_L$ antibody domain and optionally a second TCR constant domain from a T cell receptor subunit. In some embodiments, the first antigen-binding domain comprises the $V_H$ antibody domain amino-terminal to the first TCR constant domain and/or the second antigen-binding domain comprises the $V_L$ antibody domain amino-terminal to the second TCR constant domain. In some embodiments, there is a peptide linker between the $V_L$ antibody domain and the first TCR constant domain and/or a peptide linker between the $V_H$ antibody domain and the second TCR constant domain. In some embodiments, all of the $V_L$ antibody domain and $V_H$ antibody domain CDRs are derived from the same antibody moiety. In some embodiments, the $V_L$ antibody domain and the $V_H$ antibody domain comprise antibody CDRs derived from more than one antibody moiety. In some embodiments, the first and second polypeptide chains are linked, such as by a covalent linkage (e.g., peptide or other chemical linkage) or non-covalent linkage. In some embodiments, the first and second antigen-binding domains are linked by a disulfide bond. In some embodiments, the first and second antigen-binding domains are linked by a disulfide bond between a residue in the first TCR constant domain and a residue in the second TCR constant domain. In some embodiments, the first TCR constant domain is derived from a TCR α subunit, optionally human, and/or the second TCR constant domain is derived from a TCR β subunit, optionally human. In some embodiments, the first TCR constant domain is derived from a TCR α subunit comprising the amino acid sequence of SEQ ID NO: 51, and/or the second TCR constant domain is derived from a TCR β subunit, comprising the amino acid sequence of SEQ ID NO: 52. In some embodiments, the first TCR constant domain is derived from a TCR δ subunit, optionally human, and/or the second TCR constant domain is derived from a TCR γ subunit, optionally human. In some embodiments, the first TCR constant domain is derived from a TCR δ subunit comprising the amino acid sequence of SEQ ID NO: 53, and/or the second TCR constant domain is derived from a TCR γ subunit, comprising the amino acid sequence of SEQ ID NO: 54. In some embodiments, the first and/or second TCR constant domain is a variant comprising one or more modifications (e.g., amino acid substitutions, insertions, and/or deletions) compared to the sequence from which it is derived. In some embodiments, the first and/or second TCR constant domains comprise one or more modifications that do not substantially alter their binding affinities for one another. In some embodiments, the first and/or second TCR constant domains comprise one or more modifications that increase their binding affinities for one another and/or introduce a non-naturally occurring disulfide bond. In some embodiments, the Fv-like antigen-binding module is human, humanized, chimeric, semi-synthetic, or fully synthetic.

In some embodiments, the antibody moiety is an scFv that specifically binds to a complex comprising a histone H3 peptide and an MHC class I protein, comprising a) a polypeptide chain comprising a $V_H$ antibody domain and a $V_L$ antibody domain. In some embodiments, the scFv comprises the $V_H$ antibody domain amino-terminal to the $V_L$ antibody domain. In some embodiments, the scFv comprises the $V_L$ antibody domain amino-terminal to the $V_H$ antibody domain. In some embodiments, there is a peptide linker between the $V_L$ antibody domain and the $V_H$ antibody domain. In some embodiments, all of the $V_L$ antibody domain and $V_H$ antibody domain CDRs are derived from the same antibody moiety. In some embodiments, the $V_L$ antibody domain and the $V_H$ antibody domain comprise antibody CDRs derived from more than one antibody moiety. In some embodiments, the scFv is human, humanized, chimeric, semi-synthetic, or fully synthetic.

In some embodiments, the TCRM comprises a) a first polypeptide chain comprising a first T cell receptor domain (TCRD) comprising a first transmembrane domain and b) a second polypeptide chain comprising a second TCRD comprising a second transmembrane domain. In some embodiments, the first transmembrane domain is the transmembrane domain of a first TCR subunit and/or the second transmembrane domain is the transmembrane domain of a second TCR subunit. In some embodiments, the first TCR subunit is a TCR α chain (e.g., GenBank Accession No: CCI73895), and the second TCR subunit is a TCR β chain (e.g., GenBank Accession No: CCI73893). In some embodiments, the first TCR subunit is a TCR R chain, and the second TCR subunit is a TCR α chain. In some embodiments, the first TCR subunit is a TCR γ chain (e.g., GenBank Accession No: AGE91788), and the second TCR subunit is a TCR δ chain (e.g., GenBank Accession No: AAQ57272). In some embodiments, the first TCR subunit is a TCR δ chain, and the second TCR subunit is a TCR γ chain. In some embodiments, the first and/or second transmembrane domains comprise (such as consist of), individually, a transmembrane domain contained in any one of the TCR subunit amino acid sequences of SEQ ID NOs: 51-54. In some embodiments, the first and/or second transmembrane domains comprise (such as consist of), individually, any one of the amino acid sequences of SEQ ID NOs: 55-58. In some embodiments, the first TCRD further comprises a first connecting peptide amino-terminal to the transmembrane domain and/or the second TCRD further comprises a second connecting peptide amino-terminal to the transmembrane domain. In some embodiments, the first connecting peptide comprises all or a portion of the connecting peptide of the first TCR subunit and/or the second connecting peptide comprises all or a portion of the connecting peptide of the second TCR subunit. In some embodiments, the first and/or second connecting peptides comprise (such as consist of), individually, all or a portion of a connecting peptide contained in any one of the TCR subunit amino acid sequences of SEQ ID NOs: 51-54. In some embodiments, the first and/or second connecting peptides comprise (such as consist of), individually, any one of the amino acid sequences of SEQ ID NOs: 59-66. In some embodiments, the first TCRD further comprises a first TCR intracellular domain carboxy-terminal to the first transmembrane domain and/or the second TCRD further comprises a second TCR intracellular domain carboxy-terminal to the second transmembrane domain. In some embodiments, the first TCR intracellular domain comprises all or a portion of the intracellular domain of the first TCR subunit and/or the second TCR intracellular domain comprises all or a portion of the intracellular domain of the second TCR subunit. In some embodiments, the first and/or second TCR intracellular domains comprise (such as consist of), individually, all or a portion of an intracellular sequence contained in any one of the TCR subunit amino acid sequences of SEQ ID NOs: 51-54. In some embodiments, the first and/or second TCR intracellular domains comprise (such as consist of), individually, any one of the amino acid sequences of SEQ ID NOs: 67-68. In some embodiments, the first TCRD is a fragment of the first TCR subunit and/or the second TCRD is a fragment of the second TCR chain. In some embodiments, the first and second polypeptide chains are linked, such as by a covalent linkage (e.g., peptide or other chemical linkage) or non-covalent linkage. In some embodiments, the first and second TCRDs are linked by a disulfide bond. In some embodiments, the first and second TCRDs are linked by a disulfide bond between a residue in the first connecting peptide and a residue in the second connecting peptide. In some embodiments, the TCRM is capable of recruiting at least one TCR-associated signaling module selected from the group consisting of CD3δε, CD3γε, and ζζ. In some embodiments, the TCRM is capable of recruiting each of CD3δε, CD3γε, and ζζ to form an octameric anti-HMC abTCR-CD3 complex (i.e., promotes anti-HMC abTCR-CD3 complex formation).

In some embodiments, the anti-HMC abTCR is a molecule comprising a fusion of the antibody moiety (which specifically binds to a complex comprising a histone H3 peptide and an MHC class I protein) to the TCRM. In some embodiments, the anti-HMC abTCR comprises a fusion of the first polypeptide chain of the Fab-like or Fv-like antigen-binding module amino-terminal to the first polypeptide chain of the TCRM, thereby forming a first polypeptide chain of the anti-HMC abTCR, and a fusion of the second polypeptide chain of the Fab-like or Fv-like antigen-binding module amino-terminal to the second polypeptide chain of the TCRM, thereby forming a second polypeptide chain of the anti-HMC abTCR. In some embodiments, the anti-HMC abTCR comprises a fusion of the scFv amino-terminal to the first or second polypeptide chain of the TCRM. In some embodiments, the anti-HMC abTCR further comprises a peptide linker between the first polypeptide chain of the Fab-like or Fv-like antigen-binding module and the first polypeptide chain of the TCRM and/or a peptide linker between the second polypeptide chain of the Fab-like or Fv-like antigen-binding module and the second polypeptide chain of the TCRM. In some embodiments, the anti-HMC abTCR further comprises a peptide linker between the scFv and the first or second polypeptide chain of the TCRM. In some embodiments, the peptide linker is between about 5 to about 70 (such as about any of 5, 10, 15, 20, 25, 30, 35, 40, 45, 50, 55, 60, 65, or 70, including any ranges between these values) amino acids in length. In some embodiments, the first polypeptide chain of the anti-HMC abTCR further comprises an amino-terminal first signal peptide and/or the second polypeptide chain of the anti-HMC abTCR further comprises an amino-terminal second signal peptide. In some embodiments, the first and/or second signal peptides comprise (such as consist of) the amino acid sequence of SEQ ID NO: 73. In some embodiments, the first polypeptide chain of the anti-HMC abTCR further comprises a first accessory intracellular domain carboxy-terminal to the first transmembrane domain and/or the second polypeptide chain of the anti-HMC abTCR further comprises a second accessory intracellular domain carboxy-terminal to the second transmembrane domain. In some embodiments, the first and/or second accessory intracellular domains comprise a TCR costimulatory domain. In some embodiments, the TCR costimulatory domain comprises all or a portion of the amino acid sequence of SEQ ID NO: 74. In some embodiments, the first and second polypeptide chains of the anti-HMC abTCR are linked, such as by a covalent linkage (e.g., peptide or other chemical linkage) or non-covalent linkage. In some embodiments, the anti-HMC abTCR is a heterodimer.

Thus, for example, in some embodiments, there is provided an anti-HMC abTCR comprising a) an extracellular domain comprising an anti-HMC antibody moiety that specifically binds to a complex comprising a histone H3 peptide and an MHC class I protein, and b) a T cell receptor module (TCRM) capable of recruiting at least one TCR-associated signaling module. In some embodiments, the histone H3 peptide is mutant histone K27M-H3.3 26-35 (SEQ ID NO: 7) or mutant histone K27M-H3.1 26-35 (SEQ ID NO: 8). In some embodiments, the histone H3 peptide is WT H3.3 26-35 (SEQ ID NO: 5) or WT H3.1 26-35 (SEQ ID NO: 6). In some embodiments, the antibody moiety is a Fab-like antigen-binding module. In some embodiments, the antibody moiety is an Fv-like antigen-binding module. In some embodiments, the antibody moiety is an scFv. In some embodiments, the MHC class I protein is HLA-A02. In some embodiments, the MHC class I protein is HLA-A*02:01. In some embodiments, the anti-HMC antibody moiety cross-reacts with at least one (such as at least any of 2, 3, 4, 5, or 6) complex comprising the MHC class I protein and a variant of the histone H3 peptide having one amino acid substitution (such as a conservative amino acid substitution). In some embodiments, the anti-HMC antibody moiety cross-reacts with at least one (such as at least any of 2, 3, 4, or 5) complex comprising the histone H3 peptide and a different subtype of the MHC class I protein.

In some embodiments, there is provided an anti-HMC abTCR comprising a) an extracellular domain comprising an anti-HMC antibody moiety that specifically binds to a complex comprising a histone H3 peptide selected from mutant histone K27M-H3.3 26-35 (SEQ ID NO: 7), mutant histone K27M-H3.1 26-35 (SEQ ID NO: 8), WT H3.3 26-35 (SEQ ID NO: 5), or WT H3.1 26-35 (SEQ ID NO: 6) peptide and HLA-A*02:01, and b) a T cell receptor module (TCRM) capable of recruiting at least one TCR-associated signaling module. In some embodiments, the histone H3 peptide is mutant histone K27M-H3.3 26-35 (SEQ ID NO: 7). In some embodiments, the histone H3 peptide is mutant histone K27M-H3.1 26-35 (SEQ ID NO: 8). In some embodiments, the histone H3 peptide is WT H3.3 26-35 (SEQ ID NO: 5). In some embodiments, the histone H3 peptide is WT H3.1 26-35 (SEQ ID NO: 6). In some embodiments, the antibody moiety is a Fab-like antigen-binding module. In some embodiments, the antibody moiety is an Fv-like antigen-binding module. In some embodiments, the antibody moiety is an scFv.

In some embodiments, there is provided an anti-HMC abTCR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of SEQ ID NO: 158, or a variant thereof comprising up to about 3 (for example about any of 1, 2, or 3) amino acid substitutions, an HC-CDR2 comprising the amino acid sequence of SEQ ID NO: 159, or a variant thereof comprising up to about 3 (for example about any of 1, 2, or 3) amino acid substitutions, and/or an HC-CDR3 comprising the amino acid sequence of SEQ ID NO: 160 or 161, or a variant thereof comprising up to about 3 (for example about any of 1, 2, or 3) amino acid substitutions; and ii) a light chain variable domain comprising an LC-CDR1 comprising the amino acid sequence of SEQ ID NO: 162, or a variant thereof comprising up to about 3 (for example about any of 1, 2, or 3) amino acid substitutions, and/or an LC-CDR3 comprising the amino acid sequence of SEQ ID NO: 163, or a variant thereof comprising up to about 3 (for example about any of 1, 2, or 3) amino acid substitutions, and b) a T cell receptor module (TCRM) capable of recruiting at least one TCR-associated signaling module. In some embodiments, there is provided an anti-HMC abTCR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of SEQ ID NO: 158, an HC-CDR2 comprising the amino acid sequence of SEQ ID NO: 159, and/or an HC-CDR3 comprising the amino acid sequence of SEQ ID NO: 160 or 161; and ii) a light chain variable domain comprising an LC-CDR1 comprising the amino acid sequence of SEQ ID NO: 162, and/or an LC-CDR3 comprising the amino acid sequence of SEQ ID NO: 163; and b) a T cell receptor module (TCRM) capable of recruiting at least one TCR-associated signaling module. In some embodiments, the antibody moiety is a Fab-like antigen-binding module. In some embodiments, the antibody moiety is an Fv-like antigen-binding module. In some embodiments, the antibody moiety is an scFv.

In some embodiments, there is provided an anti-HMC abTCR comprising a) an extracellular domain comprising an anti-HMC antibody moiety that specifically binds to a complex comprising a histone H3 peptide and an MHC class I protein comprising i) a heavy chain variable domain comprising an HC-CDR1 comprising the amino acid sequence of any one of SEQ ID NOs: 99-107, or a variant thereof comprising up to about 5 (such as about any of 1, 2, 3, 4, or 5) amino acid substitutions, an HC-CDR2 comprising the amino acid sequence of any one of SEQ ID NOs: 108-116, or a variant thereof comprising up to about 5 (such as about any of 1, 2, 3, 4, or 5) amino acid substitutions, and/or an HC-CDR3 comprising the amino acid sequence of any one of SEQ ID NOs: 117-128, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 129-138, or a variant thereof comprising up to about 5 (such as about any of 1, 2, 3, 4, or 5) amino acid substitutions, an LC-CDR2 comprising the amino acid sequence of any one of SEQ ID NOs: 139-147, or a variant thereof comprising up to about 3 (such as about any of 1, 2, or 3) amino acid substitutions, and/or an LC-CDR3 comprising the amino acid sequence of any one of SEQ ID NOs: 148-157, or a variant thereof comprising up to about 5 (such as about any of 1, 2, 3, 4, or 5) amino acid substitutions; and b) a T cell receptor module (TCRM) capable of recruiting at least one TCR-associated signaling module. In some embodiments, there is provided an anti-HMC abTCR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; or a variant thereof comprising up to about 5 (such as about any of 1, 2, 3, 4, or 5) amino acid substitutions in the LC-CDR sequences; and b) a T cell receptor module (TCRM) capable of recruiting at least one TCR-associated signaling module. In some embodiments, there is provided an anti-HMC abTCR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; and b) a T cell receptor module (TCRM) capable of recruiting at least one TCR-associated signaling module. In some embodiments, the antibody moiety is a Fab-like antigen-binding module. In some embodiments, the antibody moiety is an Fv-like antigen-binding module. In some embodiments, the antibody moiety is an scFv.

In some embodiments, there is provided an anti-HMC abTCR comprising a) an extracellular domain comprising an anti-HMC antibody moiety that specifically binds to a complex comprising a histone H3 peptide and an MHC class I protein comprising a heavy chain variable domain comprising the amino acid sequence of any one of SEQ ID NOs: 75-86, or a variant thereof having at least about 95% (for example at least about any of 96%, 97%, 98%, or 99%) sequence identity, and a light chain variable domain comprising the amino acid sequence of any one of SEQ ID NOs: 87-98, or a variant thereof having at least about 95% (including for example at least about any of 96%, 97%, 98%, or 99%) sequence identity; and b) a T cell receptor module (TCRM) capable of recruiting at least one TCR-associated signaling module. In some embodiments, there is provided an anti-HMC abTCR comprising a) an extracellular domain comprising an anti-HMC antibody moiety that specifically binds to a complex comprising a histone H3 peptide and an MHC class I protein comprising a heavy chain variable domain comprising the amino acid sequence of any one of SEQ ID NOs: 75-86 and a light chain variable domain comprising the amino acid sequence of any one of SEQ ID NOs: 87-98; and b) a T cell receptor module (TCRM) capable of recruiting at least one TCR-associated signaling module. In some embodiments, the antibody moiety is a Fab-like antigen-binding module. In some embodiments, the antibody moiety is an Fv-like antigen-binding module. In some embodiments, the antibody moiety is an scFv.

For example, in some embodiments, the anti-HMC abTCR comprises an anti-HMC antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (for example about any of 1, 2, 3, 4, or 5) amino acid substitutions, individually, in HC-CDR1, HC-CDR2, HC-CDR3, LC-CDR1, and/or LC-CDR3, and/or up to about 3 (for example about any of 1, 2, or 3) amino acid substitutions in LC-CDR2.

In some embodiments, the anti-HMC abTCR comprises an anti-HMC antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (such as about any of 1, 2, 3, 4, or 5) amino acid substitutions in the HC-CDR sequences and/or up to about 5 (such as about any of 1, 2, 3, 4, or 5) amino acid substitutions in the LC-CDR sequences.

In some embodiments, the anti-HMC abTCR comprises an anti-HMC antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively.

In some embodiments, the anti-HMC abTCR comprises an anti-HMC antibody moiety comprising heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively; or variants thereof having, individually, at least about 95% (for example at least about any of 96%, 97%, 98%, or 99%) sequence identity. In some embodiments, the anti-HMC abTCR comprises an anti-HMC antibody moiety comprising heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively.

Also provided herein are effector cells (such as lymphocytes, e.g., T cells) expressing an anti-HMC chimeric receptor, such as an anti-HMC CAR or anti-HMC abTCR.

Also provided is a method of producing an effector cell expressing an anti-HMC CAR or anti-HMC abTCR, the method comprising introducing a vector comprising a nucleic acid encoding the anti-HMC CAR or anti-HMC abTCR into the effector cell. In some embodiments, introducing the vector into the effector cell comprises transducing the effector cell with the vector. In some embodiments, introducing the vector into the effector cell comprises transfecting the effector cell with the vector. Transduction or transfection of the vector into the effector cell can be carried about using any method known in the art.

Immunoconjugates

The anti-HMC constructs in some embodiments comprise an immunoconjugate comprising an anti-HMC antibody moiety attached to an effector molecule (also referred to herein as an "anti-HMC immunoconjugate"). In some embodiments the effector molecule is a therapeutic agent, such as a viral therapeutic agent, which is either cytotoxic, cytostatic or otherwise provides some therapeutic benefit. In some embodiments, the effector molecule is a label, which can generate a detectable signal, either directly or indirectly.

In some embodiments, there is provided an anti-HMC immunoconjugate comprising an anti-HMC antibody moiety and a therapeutic agent (also referred to herein as an "antibody-drug conjugate", or "ADC"). In some embodiments, the therapeutic agent is a toxin that is either cytotoxic, cytostatic or otherwise prevents or reduces the ability of the target cells to divide. The use of ADCs for the local delivery of cytotoxic or cytostatic agents, i.e., drugs to kill or inhibit tumor cells in the treatment of cancer (Syrigos and Epenetos, *Anticancer Research* 19:605-614 (1999); Niculescu-Duvaz and Springer, *Adv. Drg. Del. Rev.* 26:151-172 (1997); U.S. Pat. No. 4,975,278) allows targeted delivery of the drug moiety to target cells, and intracellular accumulation therein, where systemic administration of these unconjugated therapeutic agents may result in unacceptable levels of toxicity to normal cells as well as the target cells sought to be eliminated (Baldwin et al., *Lancet* (Mar. 15, 1986):603-605 (1986); Thorpe, (1985) "Antibody Carriers Of Cytotoxic Agents In Cancer Therapy: A Review," in Monoclonal Antibodies '84: Biological And Clinical Applications, A. Pinchera et al. (eds.), pp. 475-506). Maximal efficacy with minimal toxicity is sought thereby. Importantly, since most normal cells do not present the HMC on their surface, they cannot bind the anti-HMC immunoconjugate, and are protected from the killing effect of the toxin or other therapeutic agents.

Therapeutic agents used in anti-HMC immunoconjugates include, for example, daunomycin, doxorubicin, methotrexate, and vindesine (Rowland et al., *Cancer Immunol. Immunother.* 21:183-187 (1986)). Toxins used in anti-HMC immunoconjugates include bacterial toxins such as diphtheria toxin, plant toxins such as ricin, small molecule toxins such as geldanamycin (Mandler et al., *J. Nat. Cancer Inst.* 92(19):1573-1581 (2000); Mandler et al., *Bioorganic & Med. Chem. Letters* 10:1025-1028 (2000); Mandler et al., *Bioconjugate Chem.* 13:786-791 (2002)), maytansinoids (EP 1391213; Liu et al., *Proc. Natl. Acad. Sci. USA* 93:8618-8623 (1996)), and calicheamicin (Lode et al., *Cancer Res.* 58:2928 (1998); Hinman et al., *Cancer Res.* 53:3336-3342 (1993)). The toxins may exert their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

Enzymatically active toxins and fragments thereof that can be used include, for example, diphtheria A chain, nonbinding active fragments of diphtheria toxin, exotoxin A chain (from *Pseudomonas aeruginosa*), ricin A chain, abrin A chain, modeccin A chain, α-sarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. See, e.g., WO 93/21232 published Oct. 28, 1993.

Anti-HMC immunoconjugates of an anti-HMC antibody moiety and one or more small molecule toxins, such as a calicheamicin, maytansinoids, dolastatins, aurostatins, a trichothecene, and CC1065, and the derivatives of these toxins that have toxin activity, are also contemplated herein.

In some embodiments, there is provided an anti-HMC immunoconjugate comprising a therapeutic agent that has an intracellular activity. In some embodiments, the anti-HMC immunoconjugate is internalized and the therapeutic agent is a cytotoxin that blocks the protein synthesis of the cell, therein leading to cell death. In some embodiments, the therapeutic agent is a cytotoxin comprising a polypeptide having ribosome-inactivating activity including, for example, gelonin, bouganin, saporin, ricin, ricin A chain, bryodin, diphtheria toxin, restrictocin, *Pseudomonas* exotoxin A and variants thereof. In some embodiments, where the therapeutic agent is a cytotoxin comprising a polypeptide having a ribosome-inactivating activity, the anti-HMC immunoconjugate must be internalized upon binding to the target cell in order for the protein to be cytotoxic to the cells.

In some embodiments, there is provided an anti-HMC immunoconjugate comprising a therapeutic agent that acts to disrupt DNA. In some embodiments, the therapeutic agent that acts to disrupt DNA is, for example, selected from the group consisting of enediyne (e.g., calicheamicin and esperamicin) and non-enediyne small molecule agents (e.g., bleomycin, methidiumpropyl-EDTA-Fe(II)).

The present invention further contemplates an anti-HMC immunoconjugate formed between the anti-HMC antibody moiety and a compound with nucleolytic activity (e.g., a ribonuclease or a DNA endonuclease such as a deoxyribonuclease; DNase).

In some embodiments, the anti-HMC immunoconjugate comprises an agent that acts to disrupt tubulin. Such agents may include, for example, rhizoxin/maytansine, paclitaxel, vincristine and vinblastine, colchicine, auristatin dolastatin 10 MMAE, and peloruside A.

In some embodiments, the anti-HMC immunoconjugate comprises an alkylating agent including, for example, Asaley NSC 167780, AZQ NSC 182986, BCNU NSC 409962, Busulfan NSC 750, carboxyphthalatoplatinum NSC 271674, CBDCA NSC 241240, CCNU NSC 79037, CHIP NSC 256927, chlorambucil NSC 3088, chlorozotocin NSC 178248, cis-platinum NSC 119875, clomesone NSC 338947, cyanomorpholinodoxorubicin NSC 357704, cyclodisone NSC 348948, dianhydrogalactitol NSC 132313, fluorodopan NSC 73754, hepsulfam NSC 329680, hycanthone NSC 142982, melphalan NSC 8806, methyl CCNU NSC 95441, mitomycin C NSC 26980, mitozolamide NSC 353451, nitrogen mustard NSC 762, PCNU NSC 95466, piperazine NSC 344007, piperazinedione NSC 135758, pipobroman NSC 25154, porfiromycin NSC 56410, spirohydantoin mustard NSC 172112, teroxirone NSC 296934, tetraplatin NSC 363812, thio-tepa NSC 6396, triethylenemelamine NSC 9706, uracil nitrogen mustard NSC 34462, and Yoshi-864 NSC 102627.

In some embodiments, the anti-HMC immunoconjugate comprises a highly radioactive atom. A variety of radioactive isotopes are available for the production of radioconjugated antibodies. Examples include $^{211}$At, $^{131}$I, $^{125}$I, $^{90}$Y, $^{186}$Re, $^{188}$Re, $^{153}$Sm, $^{212}$Bi, $^{32}$P, $^{212}$Pb and radioactive isotopes of Lu.

In some embodiments, the anti-HMC antibody moiety can be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

In some embodiments, an anti-HMC immunoconjugate may comprise an anti-HMC antibody moiety conjugated to a prodrug-activating enzyme. In some such embodiments, a prodrug-activating enzyme converts a prodrug to an active drug, such as an anti-viral drug. Such anti-HMC immunoconjugates are useful, in some embodiments, in antibody-dependent enzyme-mediated prodrug therapy ("ADEPT"). Enzymes that may be conjugated to an antibody include, but are not limited to, alkaline phosphatases, which are useful for converting phosphate-containing prodrugs into free drugs; arylsulfatases, which are useful for converting sulfate-containing prodrugs into free drugs; proteases, such as serratia protease, thermolysin, subtilisin, carboxypeptidases and cathepsins (such as cathepsins B and L), which are useful for converting peptide-containing prodrugs into free drugs; D-alanylcarboxypeptidases, which are useful for converting prodrugs that contain D-amino acid substituents; carbohydrate-cleaving enzymes such as β-galactosidase and neuraminidase, which are useful for converting glycosylated prodrugs into free drugs; β-lactamase, which is useful for converting drugs derivatized with β-lactams into free drugs; and penicillin amidases, such as penicillin V amidase and penicillin G amidase, which are useful for converting drugs derivatized at their amine nitrogens with phenoxyacetyl or phenylacetyl groups, respectively, into free drugs. In some embodiments, enzymes may be covalently bound to antibody moieties by recombinant DNA techniques well known in the art. See, e.g., Neuberger et al., Nature 312:604-608 (1984).

In some embodiments, the therapeutic portion of the anti-HMC immunoconjugates may be a nucleic acid. Nucleic acids that may be used include, but are not limited to, anti-sense RNA, genes or other polynucleotides, including nucleic acid analogs such as thioguanine and thiopurine.

The present application further provides anti-HMC immunoconjugates comprising an anti-HMC antibody moiety attached to an effector molecule, wherein the effector molecule is a label, which can generate a detectable signal, indirectly or directly. These anti-HMC immunoconjugates can be used for research or diagnostic applications, such as for the in vivo detection of cancer. The label is preferably capable of producing, either directly or indirectly, a detectable signal. For example, the label may be radio-opaque or a radioisotope, such as $^{3}$H, $^{14}$C, $^{32}$P, $^{35}$S, $^{123}$I, $^{125}$I, $^{131}$I; a fluorescent (fluorophore) or chemiluminescent (chromophore) compound, such as fluorescein isothiocyanate, rhodamine or luciferin; an enzyme, such as alkaline phosphatase, β-galactosidase or horseradish peroxidase; an imaging agent; or a metal ion. In some embodiments, the label is a radioactive atom for scintigraphic studies, for example $^{99}$Tc or $^{123}$I, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

In some embodiments, the anti-HMC immunoconjugate is detectable indirectly. For example, a secondary antibody that is specific for the anti-HMC immunoconjugate and contains a detectable label can be used to detect the anti-HMC immunoconjugate.

Thus, for example, in some embodiments, there is provided an anti-HMC immunoconjugate comprising a) an anti-HMC antibody moiety that specifically binds to a complex comprising a histone H3 peptide and an MHC class I protein, and b) an effector molecule. In some embodiments, the histone H3 peptide is mutant histone K27M-H3.3 26-35 (SEQ ID NO: 7) or mutant histone K27M-H3.1 26-35 (SEQ ID NO: 8). In some embodiments, the histone H3 peptide is WT H3.3 26-35 (SEQ ID NO: 5) or WT H3.1 26-35 (SEQ ID NO: 6). In some embodiments, the MHC class I protein is HLA-A02. In some embodiments, the MHC class I protein is HLA-A*02:01. In some embodiments, the effector molecule is covalently attached to the anti-HMC antibody moiety. In some embodiments, the effector molecule is a therapeutic agent selected, for example, from the group consisting of a drug, a toxin, a radioisotope, a protein, a peptide, and a nucleic acid. In some embodiments, the effector molecular is a viral therapeutic agent. In some embodiments, the viral therapeutic agent is a highly radioactive atom selected, for example, from the group consisting of $^{211}$At, $^{131}$I, $^{125}$I, $^{90}$Y, $^{186}$Re, $^{188}$Re, $^{153}$Sm, $^{212}$Bi, $^{32}$P, and $^{212}$Pb. In some embodiments, the effector molecule is a label that can generate a detectable signal, either directly or indirectly. In some embodiments, the label is a radioisotope selected, for example, from the group consisting of $^{3}$H, $^{14}$C, $^{32}$P, $^{123}$I, $^{125}$I, and $^{131}$I. In some embodiments, the anti-HMC antibody moiety is an scFv. In some embodiments, the anti-HMC antibody moiety is human, humanized, or semi-synthetic. In some embodiments, the anti-HMC antibody moiety cross-reacts with at least one (such as at least any of 2, 3, 4, 5, or 6) complex comprising the MHC class I protein and a variant of the histone H3 peptide having one amino acid substitution (such as a conservative amino acid substitution). In some embodiments, the anti-HMC antibody moiety cross-reacts with at least one (such as at least any of 2, 3, 4, or 5) complex comprising the histone H3 peptide and a different subtype of the MHC class I protein.

In some embodiments, there is provided an anti-HMC immunoconjugate comprising a) an anti-HMC antibody moiety that specifically binds to a complex comprising a histone H3 peptide selected from mutant histone K27M-H3.3 26-35 (SEQ ID NO: 7), mutant histone K27M-H3.1 26-35 (SEQ ID NO: 8), WT H3.3 26-35 (SEQ ID NO: 5), or WT H3.1 26-35 (SEQ ID NO: 6) peptide and HLA-A*02:01, and b) an effector molecule. In some embodiments, the histone H3 peptide is mutant histone K27M-H3.3 26-35 (SEQ ID NO: 7). In some embodiments, the histone H3 peptide is mutant histone K27M-H3.1 26-35 (SEQ ID NO: 8). In some embodiments, the histone H3 peptide is WT H3.3 26-35 (SEQ ID NO: 5). In some embodiments, the histone H3 peptide is WT H3.1 26-35 (SEQ ID NO: 6). In some embodiments, the effector molecule is covalently attached to the anti-HMC antibody moiety. In some embodiments, the effector molecule is a therapeutic agent selected, for example, from the group consisting of a drug, a toxin, a radioisotope, a protein, a peptide, and a nucleic acid. In some embodiments, the effector molecular is a viral therapeutic agent. In some embodiments, the viral therapeutic agent is a highly radioactive atom selected, for example, from the group consisting of $^{211}$At, $^{131}$I, $^{125}$I, $^{90}$Y, $^{186}$Re, $^{188}$Re, $^{153}$Sm, $^{212}$Bi, $^{32}$P, and $^{212}$Pb. In some embodiments, the effector molecule is a label that can generate a detectable signal, either directly or indirectly. In some embodiments, the label is a radioisotope selected, for example, from the group consisting of $^{3}$H, $^{14}$C, $^{32}$P, $^{35}$S, $^{123}$I, $^{125}$I, and $^{131}$I. In some embodiments, the anti-HMC antibody moiety is an scFv. In some embodiments, the anti-HMC antibody moiety is human, humanized, or semi-synthetic.

In some embodiments, there is provided an anti-HMC immunoconjugate comprising a) an anti-HMC antibody moiety that specifically binds to a complex comprising a histone H3 peptide and an MHC class I protein comprising i) a heavy chain variable domain sequence comprising an HC-CDR1 comprising the amino acid sequence of SEQ ID NO: 158, or a variant thereof comprising up to about 3 (for example about any of 1, 2, or 3) amino acid substitutions, an HC-CDR2 comprising the amino acid sequence of SEQ ID NO: 159, or a variant thereof comprising up to about 3 (for example about any of 1, 2, or 3) amino acid substitutions, and/or an HC-CDR3 comprising the amino acid sequence of SEQ ID NO: 160 or 161, or a variant thereof comprising up to about 3 (for example about any of 1, 2, or 3) amino acid substitutions; and ii) a light chain variable domain comprising an LC-CDR1 comprising the amino acid sequence of SEQ ID NO: 162, or a variant thereof comprising up to about 3 (for example about any of 1, 2, or 3) amino acid substitutions, and/or an LC-CDR3 comprising the amino acid sequence of SEQ ID NO: 163, or a variant thereof comprising up to about 3 (for example about any of 1, 2, or 3) amino acid substitutions, and b) an effector molecule.

In some embodiments, there is provided an anti-HMC immunoconjugate comprising a) an anti-HMC antibody moiety that specifically binds to a complex comprising a histone H3 peptide and an MHC class I protein comprising i) a heavy chain variable domain sequence comprising an HC-CDR1 comprising the amino acid sequence of SEQ ID NO: 158, an HC-CDR2 comprising the amino acid sequence of SEQ ID NO: 159, and/or an HC-CDR3 comprising the amino acid sequence of SEQ ID NO: 160 or 161; and ii) a light chain variable domain comprising an LC-CDR1 comprising the amino acid sequence of SEQ ID NO: 162, and/or an LC-CDR3 comprising the amino acid sequence of SEQ ID NO: 163, and b) an effector molecule.

In some embodiments, there is provided an anti-HMC immunoconjugate comprising a) an anti-HMC antibody moiety that specifically binds to a complex comprising a histone H3 peptide and an MHC class I protein comprising i) a heavy chain variable domain comprising an HC-CDR1 comprising the amino acid sequence of any one of SEQ ID NOs: 99-107, or a variant thereof comprising up to about 5 (such as about any of 1, 2, 3, 4, or 5) amino acid substitutions, an HC-CDR2 comprising the amino acid sequence of any one of SEQ ID NOs: 108-116, or a variant thereof comprising up to about 5 (such as about any of 1, 2, 3, 4, or 5) amino acid substitutions, and/or an HC-CDR3 comprising the amino acid sequence of any one of SEQ ID NOs: 117-128, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 129-138, or a variant thereof comprising up to about 5 (such as about any of 1, 2, 3, 4, or 5) amino acid substitutions, an LC-CDR2 comprising the amino acid sequence of any one of SEQ ID NOs: 139-147, or a variant thereof comprising up to about 3 (such as about any of 1, 2, or 3) amino acid substitutions, and/or an LC-CDR3 comprising the amino acid sequence of any one of SEQ ID NOs: 148-157, or a variant thereof comprising up to about 5 (such as about any of 1, 2, 3, 4, or 5) amino acid substitutions, and b) an effector molecule.

In some embodiments, there is provided an anti-HMC immunoconjugate comprising a) an anti-HMC antibody moiety that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; or a variant thereof comprising up to about 5 (such as about any of 1, 2, 3, 4, or 5) amino acid substitutions in the LC-CDR sequences, and b) an effector molecule.

In some embodiments, there is provided an anti-HMC immunoconjugate comprising a) an anti-HMC antibody moiety that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157, and b) an effector molecule.

In some embodiments, there is provided an anti-HMC immunoconjugate comprising a) an anti-HMC antibody moiety that specifically binds to a complex comprising a histone H3 peptide and an MHC class I protein comprising a heavy chain variable domain comprising the amino acid sequence of any one of SEQ ID NOs: 75-86, or a variant thereof having at least about 95% (for example at least about any of 96%, 97%, 98%, or 99%) sequence identity, and a light chain variable domain comprising the amino acid sequence of any one of SEQ ID NOs: 87-98, or a variant thereof having at least about 95% (for example at least about any of 96%, 97%, 98%, or 99%) sequence identity, and b) an effector molecule.

In some embodiments, there is provided an anti-HMC immunoconjugate comprising a) an anti-HMC antibody moiety that specifically binds to a complex comprising a histone H3 peptide and an MHC class I protein comprising a heavy chain variable domain comprising the amino acid sequence of any one of SEQ ID NOs: 75-86 and a light chain variable domain comprising the amino acid sequence of any one of SEQ ID NOs: 87-98, b) an effector molecule.

For example, in some embodiments, the anti-HMC immunoconjugate comprises an anti-HMC antibody moiety comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (for example about any of 1, 2, 3, 4, or 5) amino acid substitutions, individually, in HC-CDR1, HC-CDR2, HC-CDR3, LC-CDR1, and/or LC-CDR3, and/or up to about 3 (for example about any of 1, 2, or 3) amino acid substitutions in LC-CDR2.

In some embodiments, the anti-HMC immunoconjugate comprises an anti-HMC antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (such as about any of 1, 2, 3, 4, or 5) amino acid substitutions in the HC-CDR sequences and/or up to about 5 (such as about any of 1, 2, 3, 4, or 5) amino acid substitutions in the LC-CDR sequences.

In some embodiments, the anti-HMC immunoconjugate comprises an anti-HMC antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively.

In some embodiments, the anti-HMC immunoconjugate comprises an anti-HMC antibody moiety comprising heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively; or variants thereof having, individually, at least about 95% (for example at least about any of 96%, 97%, 98%, or 99%) sequence identity. In some embodiments, the anti-HMC immunoconjugate comprises an anti-HMC antibody moiety comprising heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively.

Nucleic Acids

Nucleic acid molecules encoding the anti-HMC constructs or anti-HMC antibody moieties are also contemplated. In some embodiments, there is provided a nucleic acid (or a set of nucleic acids) encoding a full-length anti-HMC antibody. In some embodiments, there is provided a nucleic acid (or a set of nucleic acids) encoding a multi-specific anti-HMC molecule (e.g., a multi-specific anti-HMC antibody, a bispecific anti-HMC antibody, or a bispecific T-cell engager anti-HMC antibody), or polypeptide portion thereof. In some embodiments, there is provided a nucleic acid (or a set of nucleic acids) encoding an anti-HMC CAR or anti-HMC abTCR. In some embodiments, there is provided a nucleic acid (or a set of nucleic acids) encoding an anti-HMC immunoconjugate, or polypeptide portion thereof.

The present application also includes variants to these nucleic acid sequences. For example, the variants include nucleotide sequences that hybridize to the nucleic acid sequences encoding the anti-HMC constructs or anti-HMC antibody moieties of the present application under at least moderately stringent hybridization conditions.

The present invention also provides vectors in which a nucleic acid of the present invention is inserted.

In brief summary, the expression of an anti-HMC construct (e.g., anti-HMC CAR or anti-HMC abTCR) or polypeptide portion thereof by a natural or synthetic nucleic acid encoding the anti-HMC construct or polypeptide portion thereof can be achieved by inserting the nucleic acid into an appropriate expression vector, such that the nucleic acid is operably linked to 5' and 3' regulatory elements, including for example a promoter (e.g., a lymphocyte-specific promoter) and a 3' untranslated region (UTR). The vectors can be suitable for replication and integration in eukaryotic host cells. Typical cloning and expression vectors contain transcription and translation terminators, initiation sequences, and promoters useful for regulation of the expression of the desired nucleic acid sequence.

The nucleic acids of the present invention may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In some embodiments, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers (see, e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In some embodiments, lentivirus vectors are used. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, β-galactosidase, chloramphenicol acetyl transferase, secreted alkaline phosphatase, or the green fluorescent protein gene (e.g., Ui-Tel et al., 2000 *FEBS Letters* 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). In some embodiments, the introduction of a polynucleotide into a host cell is carried out by calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus 1, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

MHC Class I Proteins

MHC class I proteins are one of two primary classes of major histocompatibility complex (MHC) molecules (the other being MHC class II) and are found on nearly every nucleated cell of the body. Their function is to display fragments of proteins from within the cell to T cells; healthy cells will be ignored, while cells containing foreign proteins will be attacked by the immune system. Because MHC class I proteins present peptides derived from cytosolic proteins, the pathway of MHC class I presentation is often called the cytosolic or endogenous pathway. Class I MHC molecules bind peptides generated mainly from degradation of cytosolic proteins by the proteasome. The MHC I:peptide complex is then inserted into the plasma membrane of the cell. The peptide is bound to the extracellular part of the class I MHC molecule. Thus, the function of the class I MHC is to display intracellular proteins to cytotoxic T cells (CTLs). However, class I MHC can also present peptides generated from exogenous proteins, in a process known as cross-presentation.

MHC class I proteins consist of two polypeptide chains, a and β2-microglobulin (β2M). The two chains are linked noncovalently via interaction of b2m and the α3 domain. Only the a chain is polymorphic and encoded by a HLA gene, while the b2m subunit is not polymorphic and encoded by the β-2 microglobulin gene. The α3 domain is plasma membrane-spanning and interacts with the CD8 co-receptor of T-cells. The α3-CD8 interaction holds the MHC I molecule in place while the T cell receptor (TCR) on the surface of the cytotoxic T cell binds its α1-α2 heterodimer ligand, and checks the coupled peptide for antigenicity. The α1 and α2 domains fold to make up a groove for peptides to bind. MHC class I proteins bind peptides that are 8-10 amino acid in length.

The human leukocyte antigen (HLA) genes are the human versions of the MHC genes. The three major MHC class I proteins in humans are HLA-A, HLA-B, and HLA-C, while the 3 minor ones are HLA-E, HLA-F, and HLA-G. HLA-A is ranked among the genes in humans with the fastest-evolving coding sequence. As of December 2013, there were 2432 known HLA-A alleles coding for 1740 active proteins and 117 null proteins. The HLA-A gene is located on the short arm of chromosome 6 and encodes the larger, α-chain, constituent of HLA-A. Variation of HLA-A α-chain is key to HLA function. This variation promotes genetic diversity in the population. Since each HLA has a different affinity for peptides of certain structures, greater variety of HLAs means greater variety of antigens to be 'presented' on the cell surface, enhancing the likelihood that a subset of the population will be resistant to any given foreign invader. This decreases the likelihood that a single pathogen has the capability to wipe out the entire human population. Each individual can express up to two types of HLA-A, one from each of their parents. Some individuals will inherit the same HLA-A from both parents, decreasing their individual HLA diversity; however, the majority of individuals will receive two different copies of HLA-A. This same pattern follows for all HLA groups. In other words, a person can only express either one or two of the 2432 known HLA-A alleles.

All alleles receive at least a four digit classification, e.g., HLA-A*02:12. The A signifies which HLA gene the allele belongs to. There are many HLA-A alleles, so that classification by serotype simplifies categorization. The next pair of digits indicates this assignment. For example, HLA-A*02:02, HLA-A*02:04, and HLA-A*02:324 are all members of the A2 serotype (designated by the *02 prefix). This group is the primary factor responsible for HLA compatibility. All numbers after this cannot be determined by serotyping and are designated through gene sequencing. The second set of digits indicates what HLA protein is produced. These are assigned in order of discovery and as of December 2013 there are 456 different HLA-A02 proteins known (assigned names HLA-A*02:01 to HLA-A*02:456). The shortest possible HLA name includes both of these details. Each extension beyond that signifies a nucleotide change that may or may not change the protein.

In some embodiments, the anti-HMC antibody moiety specifically binds to a complex comprising a histone H3 peptide and an MHC class I protein, wherein the MHC class I protein is HLA-A, HLA-B, HLA-C, HLA-E, HLA-F, or HLA-G. In some embodiments, the MHC class I protein is HLA-A, HLA-B, or HLA-C. In some embodiments, the MHC class I protein is HLA-A. In some embodiments, the MHC class I protein is HLA-B. In some embodiments, the MHC class I protein is HLA-C. In some embodiments, the MHC class I protein is HLA-A01, HLA-A02, HLA-A03, HLA-A09, HLA-A10, HLA-A11, HLA-A19, HLA-A23, HLA-A24, HLA-A25, HLA-A26, HLA-A28, HLA-A29, HLA-A30, HLA-A31, HLA-A32, HLA-A33, HLA-A34, HLA-A36, HLA-A43, HLA-A66, HLA-A68, HLA-A69, HLA-A74, or HLA-A80. In some embodiments, the MHC class I protein is HLA-A02. In some embodiments, the MHC class I protein is any one of HLA-A*02:01-555, such as HLA-A*02:01, HLA-A*02:02, HLA-A*02:03, HLA-A*02:04, HLA-A*02:05, HLA-A*02:06, HLA-A*02:07, HLA-A*02:08, HLA-A*02:09, HLA-A*02:10, HLA-A*02:11, HLA-A*02:12, HLA-A*02:13, HLA-A*02:14, HLA-A*02:15, HLA-A*02:16, HLA-A*02:17, HLA-A*02:18, HLA-A*02:19, HLA-A*02:20, HLA-A*02:21, HLA-A*02:22, or HLA-A*02:24. In some embodiments, the MHC class I protein is HLA-A*02:01. HLA-A*02:01 is expressed in 39-46% of all Caucasians, and therefore represents a suitable choice of MHC class I protein for use in the present invention.

Histone H3 peptides suitable for use in generating anti-HMC antibody moieties can be determined, for example, based on the presence of HLA-A*02:01-binding motifs and cleavage sites for proteasomes and immune-proteasomes using computer prediction models known to those of skill in the art. For predicting MHC binding sites, such models include, but are not limited to, IEDB (Vita et al., The immune epitope database (IEDB) 3.0. *Nucleic Acids Res.* 2014 Oct. 9. pii: gku938), ProPred1 (described in more detail in Singh and Raghava, *ProPred: prediction of HLA-DR binding sites. BIOINFORMATICS* 17(12):1236-1237, 2001), and SYFPEITHI (see Schuler et al. *SYFPEITHI, Database for Searching and T-Cell Epitope Prediction. in Immunoinformatics Methods in Molecular Biology*, vol 409 (1): 75-93, 2007).

Once appropriate peptides have been identified, peptide synthesis may be done in accordance with protocols well known to those of skill in the art. Because of their relatively small size, the peptides of the invention may be directly synthesized in solution or on a solid support in accordance with conventional peptide synthesis techniques. Various automatic synthesizers are commercially available and can be used in accordance with known protocols. The synthesis of peptides in solution phase has become a well-established procedure for large-scale production of synthetic peptides and as such is a suitable alternative method for preparing the peptides of the invention (See for example, Solid Phase Peptide Synthesis by John Morrow Stewart and Martin et al. *Application of Almez-mediated Amidation Reactions to Solution Phase Peptide Synthesis*, Tetrahedron Letters Vol. 39, pages 1517-1520, 1998).

The binding activity of candidate histone H3 peptides can be tested using the antigen-processing-deficient T2 cell line, which increases expression of HLA-A when stabilized by a peptide in the antigen-presenting groove. T2 cells are pulsed with the candidate peptide for a time sufficient to stabilize HLA-A expression on the cell surface, which can be measured using any methods known in the art, such as by immunostaining with a fluorescently labeled monoclonal antibody specific for HLA-A (for example, BB7.2) followed by fluorescence-activated cell-sorting (FACS) analysis.

Histones

Histone proteins are among the most highly conserved proteins in eukaryotes, with the majority of the protein sequences being identical in organisms ranging from yeast to humans (Liu et al., *Cold Spring Harb Perspect Biol.* 2014 April; 6(4): a018689). Histone proteins (H2A, H2B, H3, and H4) form an octameric complex that comprises a nucleosome core around which DNA is wrapped. Post-translational modifications of these proteins determine the structure of the chromatin, regulating transcription and consequently cell determination and differentiation.

Preparation of Anti-HMC Antibodies and Anti-HMC Antibody Moieties

In some embodiments, the anti-HMC antibody or anti-HMC antibody moiety is a monoclonal antibody. Monoclonal antibodies can be prepared, e.g., using hybridoma methods, such as those described by Kohler and Milstein, *Nature*, 256:495 (1975) and Sergeeva et al., *Blood*, 117(16):4262-4272, using the phage display methods described herein and in the Examples below, or using recombinant DNA methods (see, e.g., U.S. Pat. No. 4,816,567).

In a hybridoma method, a hamster, mouse, or other appropriate host animal is typically immunized with an immunizing agent to elicit lymphocytes that produce or are capable of producing antibodies that will specifically bind to the immunizing agent. Alternatively, the lymphocytes can be immunized in vitro. The immunizing agent can include a polypeptide or a fusion protein of the protein of interest, or a complex comprising at least two molecules, such as a complex comprising a histone H3 peptide and an MHC class I protein. Generally, peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell. See, e.g., Goding, Monoclonal Antibodies: Principles and Practice (New York: Academic Press, 1986), pp. 59-103. Immortalized cell lines are usually transformed mammalian cells, particularly myeloma cells of rodent, bovine, and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which prevents the growth of HGPRT-deficient cells.

In some embodiments, the immortalized cell lines fuse efficiently, support stable high-level expression of antibody by the selected antibody-producing cells, and are sensitive to a medium such as HAT medium. In some embodiments, the immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. Kozbor, *J. Immunol.*, 133:3001 (1984); Brodeur et al. Monoclonal Antibody Production Techniques and Applications (Marcel Dekker, Inc.: New York, 1987) pp. 51-63.

The culture medium in which the hybridoma cells are cultured can then be assayed for the presence of monoclonal antibodies directed against the polypeptide. The binding specificity of monoclonal antibodies produced by the hybridoma cells can be determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, *Anal. Biochem.*, 107:220 (1980).

After the desired hybridoma cells are identified, the clones can be sub cloned by limiting dilution procedures and grown by standard methods. Goding, supra. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the sub clones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The anti-HMC antibodies or antibody moieties may also be identified by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al., *Methods in Molecular Biology* 178:1-37 (O'Brien et al., ed., Human Press, Totowa, N.J., 2001) and further described, e.g., in McCafferty et al., *Nature* 348:552-554; Clackson et al., *Nature* 352: 624-628 (1991); Marks et al., *J. Mol. Biol.* 222: 581-597 (1992); Marks and Bradbury, *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of $V_H$ and $V_L$ genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

The antibodies or antigen-binding fragments thereof can be prepared using phage display to screen libraries for antibodies specific to a complex comprising a histone H3 peptide and an MHC class I protein. The library can be a human scFv phage display library having a diversity of at least one×$10^9$ (such as at least about any of 1×$10^9$, 2.5×$10^9$, 5×$10^9$, 7.5×$10^9$, 1×$10^{10}$, 2.5×$10^{10}$, 5×$10^{10}$, 7.5×$10^{10}$, or 1×$10^{11}$) unique human antibody fragments. In some embodiments, the library is a naïve human library constructed from DNA extracted from human PMBCs and spleens from healthy donors, encompassing all human heavy and light chain subfamilies. In some embodiments, the library is a naïve human library constructed from DNA extracted from PBMCs isolated from patients with various diseases, such as patients with autoimmune diseases, cancer patients, and patients with infectious diseases. In some embodiments, the library is a semi-synthetic human library, wherein heavy chain CDR3 is completely randomized, with all amino acids (with the exception of cysteine) equally likely to be present at any given position (see, e.g., Hoet, R. M. et al., *Nat. Biotechnol.* 23(3):344-348, 2005). In some embodiments, the heavy chain CDR3 of the semi-synthetic human library has a length from about 5 to about 24 (such as about any of 5, 6, 7, 8, 9, 10, 11, 12, 13, 14, 15, 16, 17, 18, 19, 20, 21, 22, 23, or 24) amino acids. In some embodiments, the library is a non-human phage display library.

Phage clones that bind to the HMC with high affinity can be selected by iterative binding of phage to the HMC, which is bound to a solid support (such as, for example, beads for solution panning or mammalian cells for cell panning), followed by removal of non-bound phage and by elution of specifically bound phage. In an example of solution panning, the HMC can be biotinylated for immobilization to a solid support. The biotinylated HMC is mixed with the phage library and a solid support, such as streptavidin-conjugated Dynabeads M-280, and then HMC-phage-bead complexes are isolated. The bound phage clones are then eluted and used to infect an appropriate host cell, such as *E. coli* XL1-Blue, for expression and purification. In an example of cell panning, T2 cells (a TAP-deficient, HLA-A*02:01$^+$ lymphoblast cell line) loaded with the histone H3 peptide of the HMC are mixed with the phage library, after which the cells are collected and the bound clones are eluted and used to infect an appropriate host cell for expression and purification. The panning can be performed for multiple (such as about any of 2, 3, 4, 5, 6 or more) rounds with either solution panning, cell panning, or a combination of both, to enrich for phage clones binding specifically to the HMC. Enriched phage clones can be tested for specific binding to the HMC by any methods known in the art, including for example ELISA and FACS.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). Hybridoma cells as described above or HMC-specific phage clones of the invention can serve as a source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy- and light-chain constant domains and/or framework regions in place of the homologous non-human sequences (U.S. Pat. No. 4,816,567; Morrison et al., supra) or by covalently joining to the immunoglobulin coding sequence all or part of the coding sequence for a nonimmunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies can be monovalent antibodies. Methods for preparing monovalent antibodies are known in the art. For example, one method involves recombinant expression of immunoglobulin light chain and modified heavy chain. The heavy chain is truncated generally at any point in the Fc region so as to prevent heavy-chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly Fab fragments, can be accomplished using any method known in the art.

Antibody variable domains with the desired binding specificities (antibody-antigen combining sites) can be fused to immunoglobulin constant-domain sequences. The fusion preferably is with an immunoglobulin heavy-chain constant domain, comprising at least part of the hinge, CH2, and CH3 regions. In some embodiments, the first heavy-chain constant region ($C_H1$) containing the site necessary for light-chain binding is present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies, see, for example, Suresh et al., *Methods in Enzymology*, 121: 210 (1986).

Human and Humanized Antibodies

The anti-HMC antibodies or antibody moieties can be humanized antibodies or human antibodies. Humanized forms of non-human (e.g., murine) antibodies are chimeric immunoglobulins, immunoglobulin chains, or fragments thereof (such as Fv, Fab, Fab', F(ab')$_2$, scFv, or other antigen-binding subsequences of antibodies) that typically contain minimal sequence derived from non-human immunoglobulin. Humanized antibodies include human immunoglobulins (recipient antibody) in which residues from a CDR of the recipient are replaced by residues from a CDR of a non-human species (donor antibody) such as mouse, rat, or rabbit having the desired specificity, affinity, and capacity. In some instances, Fv framework residues of the human immunoglobulin are replaced by corresponding non-human residues. Humanized antibodies can also comprise residues that are found neither in the recipient antibody nor in the imported CDR or framework sequences. In general, the humanized antibody can comprise substantially all of at least one, and typically two, variable domains, in which all or substantially all of the CDR regions correspond to those of a non-human immunoglobulin, and all or substantially all of the FR regions are those of a human immunoglobulin consensus sequence. In some embodiments, the humanized antibody will comprise at least a portion of an immunoglobulin constant region (Fc), typically that of a human immunoglobulin. See, e.g., Jones et al., *Nature*, 321: 522-525 (1986); Riechmann et al., *Nature*, 332: 323-329 (1988); Presta, *Curr. Op. Struct. Biol.*, 2:593-596 (1992).

Generally, a humanized antibody has one or more amino acid residues introduced into it from a source that is non-human. These non-human amino acid residues are often referred to as "import" residues, which are typically taken from an "import" variable domain. According to some embodiments, humanization can be essentially performed following the method of Winter and co-workers (Jones et al., *Nature*, 321: 522-525 (1986); Riechmann et al., *Nature*, 332: 323-327 (1988); Verhoeyen et al., *Science*, 239: 1534-1536 (1988)), by substituting rodent CDRs or CDR sequences for the corresponding sequences of a human antibody. Accordingly, such "humanized" antibodies are antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *PNAS USA*, 90:2551 (1993); Jakobovits et al., *Nature*, 362:255-258 (1993); Bruggemann et al., *Year in Immunol.*, 7:33 (1993); U.S. Pat. Nos. 5,545,806, 5,569,825, 5,591,669; 5,545,807; and WO 97/17852. Alternatively, human antibodies can be made by introducing human immunoglobulin loci into transgenic animals, e.g., mice in which the endogenous immunoglobulin genes have been partially or completely inactivated. Upon challenge, human antibody production is observed that closely resembles that seen in humans in all respects, including gene rearrangement, assembly, and antibody repertoire. This approach is described, for example, in U.S. Pat. Nos. 5,545, 807; 5,545,806; 5,569,825; 5,625,126; 5,633,425; and 5,661,016, and Marks et al., *Bio/Technology*, 10: 779-783 (1992); Lonberg et al., *Nature*, 368: 856-859 (1994); Morrison, *Nature*, 368: 812-813 (1994); Fishwild et al., *Nature Biotechnology*, 14: 845-851 (1996); Neuberger, *Nature Biotechnology*, 14: 826 (1996); Lonberg and Huszar, *Intern. Rev. Immunol.*, 13: 65-93 (1995).

Human antibodies may also be generated by in vitro activated B cells (see U.S. Pat. Nos. 5,567,610 and 5,229, 275) or by using various techniques known in the art, including phage display libraries. Hoogenboom and Winter, *J. Mol. Biol.*, 227:381 (1991); Marks et al., *J. Mol. Biol.*, 222:581 (1991). The techniques of Cole et al. and Boerner et al. are also available for the preparation of human monoclonal antibodies. Cole et al., *Monoclonal Antibodies and Cancer Therapy*, Alan R. Liss, p. 77 (1985) and Boerner et al., *J. Immunol.*, 147(1): 86-95 (1991).

Multi-Specific Antibodies

In some embodiments, the anti-HMC construct is a multi-specific antibody. Suitable methods for making multi-specific (e.g., bispecific) antibodies are well known in the art. For example, the production of bispecific antibodies can based on the co-expression of two immunoglobulin heavy-chain/light-chain pairs, where the two pairs each have different specificities, and upon association result in a heterodimeric antibody (see, e.g., Milstein and Cuello, *Nature*, 305: 537-539 (1983); WO 93/08829, and Traunecker et al., *EMBO J.* 10: 3655 (1991)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829 and in Traunecker et al., *EMBO*, 10: 3655-3659 (1991). Alternatively, the combining of heavy and light chains can be directed by taking advantage of species-restricted pairing (see, e.g., Lindhofer et al., *J. Immunol.*, 155:219-225 (1995)) and the pairing of heavy chains can be directed by use of "knob-into hole" engineering of CH3 domains (see, e.g., U.S. Pat. No. 5,731,168; Ridgway et al., *Protein Eng.*, 9(7):617-621 (1996)). Multi-specific antibodies may also be made by engineering electrostatic steering effects for making antibody Fc-heterodimeric molecules (see, e.g., WO 2009/089004A1). In yet another method, stable bispecific antibodies can be generated by controlled Fab-arm exchange, where two parental antibodies having distinct antigen specificity and matched point mutations in the CH3 domains are mixed in reducing condition to allow for separation, reassembly, and reoxidation to form highly pure bispecific antibodies. Labrigin et al., *Proc. Natl. Acad. Sci.*, 110(13):5145-5150 (2013). Such antibodies, comprising a mixture of heavy-chain/light-chain pairs, are also referred to herein as "heteromultimeric antibodies".

Antibodies or antigen-binding fragments thereof having different specificities can also be chemically cross-linked to generate multi-specific heteroconjugate antibodies. For example, two F(ab')2 molecules, each having specificity for a different antigen, can be chemically linked. Pullarkat et al., *Trends Biotechnol.*, 48:9-21 (1999). Such antibodies have, for example, been proposed to target immune-system cells to unwanted cells (U.S. Pat. No. 4,676,980), and for treatment of HIV infection. WO 91/00360; WO 92/200373; EP 03089. It is contemplated that the antibodies can be prepared in vitro using known methods in synthetic protein chemistry, including those involving crosslinking agents. For example, immunotoxins can be constructed using a disulfide-exchange reaction or by forming a thioether bond. Examples of suitable reagents for this purpose include iminothiolate and methyl-4-mercaptobutyrimidate and those disclosed, for example, in U.S. Pat. No. 4,676,980.

In some embodiments, multi-specific antibodies can be prepared using recombinant DNA techniques. For example, a bispecific antibody can be engineered by fusing two scFvs, such as by fusing them through a peptide linker, resulting in a tandem scFv. One example of a tandem scFv is a bispecific T cell engager. Bispecific T cell engagers are made by linking an anti-CD3 scFv to an scFv specific for a surface antigen of a target cell, such as a tumor-associated antigen (TAA), resulting in the redirection of T cells to the target cells. Mack et al., *Proc. Natl. Acad. Sci.*, 92:7021-7025 (1995); Brischwein et al., *Mol. Immunol.*, 43(8):1129-1143 (2006). By shortening the length of a peptide linker between two variable domains, they can be prevented from self-assembling and forced to pair with domains on a second polypeptide, resulting in a compact bispecific antibody called a diabody (Db). Holliger et al., *Proc. Natl. Acad. Sci.*, 90:6444-6448 (1993). The two polypeptides of a Db each comprise a $V_H$ connected to a $V_L$ by a linker which is too short to allow pairing between the two domains on the same chain. Accordingly, the $V_H$ and $V_L$ domains of one polypeptide are forced to pair with the complementary $V_L$ and $V_H$ domains of another polypeptide, thereby forming two antigen-binding sites. In a modification of this format, the two polypeptides are linked by another peptide linker, resulting in a single chain diabody (scDb). In yet another modification of the Db format, dual-affinity retargeting (DART) bispecific antibodies can be generated by introducing a disulfide linkage between cysteine residues at the C-terminus of each polypeptide, optionally including domains prior to the C-terminal cysteine residues that drive assembly of the desired heterodimeric structure. Veri et al., *Arthritis Rheum.*, 62(7): 1933-1943 (2010). Dual-variable-domain immunoglobulins (DVD-Ig™), in which the target-binding variable domains of two monoclonal antibodies are combined via naturally occurring linkers to yield a tetravalent, bispecific antibody, are also known in the art. Gu and Ghayur, *Methods Enzymol.*, 502:25-41 (2012). In yet another format, Dock and Lock (DNL), bispecific antibodies are prepared by taking advantage of the dimerization of a peptide (DDD2) derived from the regulatory subunit of human cAMP-dependent protein kinase (PKA) with a peptide (AD2) derived from the anchoring domains of human A kinase anchor proteins (AKAPs). Rossi et al., *Proc. Natl. Acad. Sci.*, 103:6841-6846 (2006).

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). This method can also be utilized for the production of antibody homodimers.

Anti-HMC Variants

In some embodiments, amino acid sequence variants of the antibody moieties provided herein are contemplated. For example, it may be desirable to improve the binding affinity and/or other biological properties of the antibody moiety. Amino acid sequence variants of an antibody moiety may be prepared by introducing appropriate modifications into the nucleotide sequence encoding the antibody moiety, or by peptide synthesis. Such modifications include, for example, deletions from, and/or insertions into and/or substitutions of residues within the amino acid sequences of the antibody moiety. Any combination of deletion, insertion, and substitution can be made to arrive at the final construct, provided that the final construct possesses the desired characteristics, e.g., antigen-binding.

In some embodiments, antibody moiety variants having one or more amino acid substitutions are provided. Sites of interest for substitutional mutagenesis include the HVRs and FRs. Amino acid substitutions may be introduced into an antibody moiety of interest and the products screened for a desired activity, e.g., retained/improved antigen binding, decreased immunogenicity, or improved ADCC or CDC.

Conservative substitutions are shown in Table 5 below.

TABLE 5

CONSERVATIVE SUBSTITITIONS

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped into different classes according to common side-chain properties:

a. hydrophobic: Norleucine, Met, Ala, Val, Leu, Ile;
b. neutral hydrophilic: Cys, Ser, Thr, Asn, Gln;
c. acidic: Asp, Glu;

d. basic: His, Lys, Arg;
e. residues that influence chain orientation: Gly, Pro;
f. aromatic: Trp, Tyr, Phe.

Non-conservative substitutions will entail exchanging a member of one of these classes for another class.

An exemplary substitutional variant is an affinity matured antibody moiety, which may be conveniently generated, e.g., using phage display-based affinity maturation techniques. Briefly, one or more CDR residues are mutated and the variant antibody moieties displayed on phage and screened for a particular biological activity (e.g. binding affinity). Alterations (e.g., substitutions) may be made in HVRs, e.g., to improve antibody moiety affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or specificity determining residues (SDRs), with the resulting variant $V_H$ or $V_L$ being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).)

In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody moiety variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In some embodiments, substitutions, insertions, or deletions may occur within one or more HVRs so long as such alterations do not substantially reduce the ability of the antibody moiety to bind antigen. For example, conservative alterations (e.g., conservative substitutions as provided herein) that do not substantially reduce binding affinity may be made in HVRs. Such alterations may be outside of HVR "hotspots" or SDRs. In some embodiments of the variant $V_H$ and $V_L$ sequences provided above, each HVR either is unaltered, or contains no more than one, two or three amino acid substitutions.

A useful method for identification of residues or regions of an antibody moiety that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody moiety with antigen is affected. Further substitutions may be introduced at the amino acid locations demonstrating functional sensitivity to the initial substitutions. Alternatively, or additionally, a crystal structure of an antigen-antibody moiety complex can be determined to identify contact points between the antibody moiety and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody moiety with an N-terminal methionyl residue. Other insertional variants of the antibody moiety include the fusion to the N- or C-terminus of the antibody moiety to an enzyme (e.g. for ADEPT) or a polypeptide which increases the serum half-life of the antibody moiety.

Fc Region Variants

In some embodiments, one or more amino acid modifications may be introduced into the Fc region of a full-length anti-HMC antibody provided herein, thereby generating an Fc region variant. In some embodiments, the Fc region variant has enhanced antibody dependent cellular cytotoxicity (ADCC) effector function, often related to binding to Fc receptors (FcRs). In some embodiments, the Fc region variant has decreased ADCC effector function. There are many examples of changes or mutations to Fc sequences that can alter effector function. For example, WO 00/42072 and Shields et al. *J Biol. Chem.* 9(2): 6591-6604 (2001) describe antibody variants with improved or diminished binding to FcRs. The contents of those publications are specifically incorporated herein by reference.

Antibody-Dependent Cell-Mediated Cytotoxicity (ADCC) is a mechanism of action of therapeutic antibodies against tumor cells. ADCC is a cell-mediated immune defense whereby an effector cell of the immune system actively lyses a target cell (e.g., a cancer cell), whose membrane-surface antigens have been bound by specific antibodies (e.g., an anti-HMC antibody). The typical ADCC involves activation of NK cells by antibodies. An NK cell expresses CD16 which is an Fc receptor. This receptor recognizes, and binds to, the Fc portion of an antibody bound to the surface of a target cell. The most common Fc receptor on the surface of an NK cell is called CD16 or FcγRIII. Binding of the Fc receptor to the Fc region of an antibody results in NK cell activation, release of cytolytic granules and consequent target cell apoptosis. The contribution of ADCC to tumor cell killing can be measured with a specific test that uses NK-92 cells that have been transfected with a high-affinity FcR. Results are compared to wild-type NK-92 cells that do not express the FcR.

In some embodiments, the invention contemplates an anti-HMC construct variant comprising an FC region that possesses some but not all effector functions, which makes it a desirable candidate for applications in which the half-life of the anti-HMC construct in vivo is important yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CytoTox 96™ non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103: 2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In some embodiments, there is provided an anti-HMC construct (e.g., a full-length anti-HMC antibody) variant comprising a variant Fc region comprising one or more amino acid substitutions which improve ADCC. In some embodiments, the variant Fc region comprises one or more amino acid substitutions which improve ADCC, wherein the substitutions are at positions 298, 333, and/or 334 of the variant Fc region (EU numbering of residues). In some embodiments, the anti-HMC construct (e.g., full-length anti-HMC antibody) variant comprises the following amino acid substitution in its variant Fc region: S298A, E333A, and K334A.

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al., *J. Immunol.* 164: 4178-4184 (2000).

In some embodiments, there is provided an anti-HMC construct (e.g., a full-length anti-HMC antibody) variant comprising a variant Fc region comprising one or more amino acid substitutions which increase half-life and/or improve binding to the neonatal Fc receptor (FcRn). Antibodies with increased half-lives and improved binding to FcRn are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. Nos. 5,648,260; 5,624,821; and WO 94/29351 concerning other examples of Fc region variants.

Anti-HMC constructs (such as full-length anti-HMC antibodies) comprising any of the Fc variants described herein, or combinations thereof, are contemplated.

Glycosylation Variants

In some embodiments, an anti-HMC construct provided herein is altered to increase or decrease the extent to which the anti-HMC construct is glycosylated. Addition or deletion of glycosylation sites to an anti-HMC construct may be conveniently accomplished by altering the amino acid sequence of the anti-HMC construct or polypeptide portion thereof such that one or more glycosylation sites is created or removed.

Where the anti-HMC construct comprises an Fc region, the carbohydrate attached thereto may be altered. Native antibodies produced by mammalian cells typically comprise a branched, biantennary oligosaccharide that is generally attached by an N-linkage to Asn297 of the $C_H2$ domain of the Fc region. See, e.g., Wright et al., *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an anti-HMC construct of the invention may be made in order to create anti-HMC construct variants with certain improved properties.

In some embodiments, anti-HMC construct (such as full-length anti-HMC antibody) variants are provided comprising an Fc region wherein a carbohydrate structure attached to the Fc region has reduced fucose or lacks fucose, which may improve ADCC function. Specifically, anti-HMC constructs are contemplated herein that have reduced fusose relative to the amount of fucose on the same anti-HMC construct produced in a wild-type CHO cell. That is, they are characterized by having a lower amount of fucose than they would otherwise have if produced by native CHO cells (e.g., a CHO cell that produce a native glycosylation pattern, such as, a CHO cell containing a native FUT8 gene). In some embodiments, the anti-HMC construct is one wherein less than about 50%, 40%, 30%, 20%, 10%, or 5% of the N-linked glycans thereon comprise fucose. For example, the amount of fucose in such an anti-HMC construct may be from 1% to 80%, from 1% to 65%, from 5% to 65% or from 20% to 40%. In some embodiments, the anti-HMC construct is one wherein none of the N-linked glycans thereon comprise fucose, i.e., wherein the anti-HMC construct is completely without fucose, or has no fucose or is afucosylated. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as α-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Anti-HMC construct (such as full-length anti-HMC antibody) variants are further provided with bisected oligosaccharides, e.g., in which a biantennary oligosaccharide attached to the Fc region of the anti-HMC construct is bisected by GlcNAc. Such anti-HMC construct (such as full-length anti-HMC antibody) variants may have reduced fucosylation and/or improved ADCC function. Examples of such antibody variants are described, e.g., in WO 2003/011878 (Jean-Mairet et al.); U.S. Pat. No. 6,602,684 (Umana et al.); US 2005/0123546 (Umana et al.), and Ferrara et al., *Biotechnology and Bioengineering*, 93(5): 851-861 (2006). Anti-HMC construct (such as full-length anti-HMC antibody) variants with at least one galactose residue in the oligosaccharide attached to the Fc region are also provided. Such anti-HMC construct variants may have improved CDC function. Such antibody variants are described, e.g., in WO 1997/30087 (Patel et al.); WO 1998/58964 (Raju, S.); and WO 1999/22764 (Raju, S.).

In some embodiments, the anti-HMC construct (such as full-length anti-HMC antibody) variants comprising an Fc region are capable of binding to an FcγRIII. In some embodiments, the anti-HMC construct (such as full-length anti-HMC antibody) variants comprising an Fc region have ADCC activity in the presence of human effector cells or have increased ADCC activity in the presence of human effector cells compared to the otherwise same anti-HMC construct (such as full-length anti-HMC antibody) comprising a human wild-type IgG1Fc region.

Cysteine Engineered Variants

In some embodiments, it may be desirable to create cysteine engineered anti-HMC constructs (such as full-length anti-HMC antibodies) in which one or more amino acid residues are substituted with cysteine residues. In some embodiments, the substituted residues occur at accessible sites of the anti-HMC construct. By substituting those residues with cysteine, reactive thiol groups are thereby positioned at accessible sites of the anti-HMC construct and may be used to conjugate the anti-HMC construct to other moieties, such as drug moieties or linker-drug moieties, to create an anti-HMC immunoconjugate, as described further herein. Cysteine engineered anti-HMC constructs (such as full-length anti-HMC antibodies) may be generated as described, e.g., in U.S. Pat. No. 7,521,541.

Derivatives

In some embodiments, an anti-HMC construct provided herein may be further modified to contain additional nonproteinaceous moieties that are known in the art and readily available. The moieties suitable for derivatization of the anti-HMC construct include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the anti-HMC construct may vary, and if more than one polymer are attached, they can be the same or different molecules. In general, the number and/or type of polymers used for derivatization can be determined based on considerations including, but not limited to, the particular properties or functions of the anti-HMC construct to be improved, whether the anti-HMC construct derivative will be used in a therapy under defined conditions, etc.

In some embodiments, conjugates of an anti-HMC construct and nonproteinaceous moiety that may be selectively heated by exposure to radiation are provided. In some embodiments, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the anti-HMC construct-nonproteinaceous moiety are killed.

Chimeric Receptor Effector Cell Preparation

The present invention in one aspect provides effector cells (such as lymphocytes, for example T cells) expressing an anti-HMC chimeric receptor, such as an anti-HMC CAR or anti-HMC abTCR. Exemplary methods of preparing effector cells (such as T cells) expressing the anti-HMC chimeric receptor (anti-HMC chimeric receptor effector cells, such as anti-HMC CAR T cells or anti-HMC abTCR T cells) are provided herein.

In some embodiments, an anti-HMC chimeric receptor (such as anti-HMC CAR or anti-HMC abTCR) effector cell (such as T cell) can be generated by introducing a vector (including for example a lentiviral vector) comprising a sequence encoding an anti-HMC CAR (for example a CAR comprising an anti-HMC antibody moiety and CD28 or 4-1BB and CD3ζ intracellular signaling sequences) or an anti-HMC abTCR into the effector cell (such as T cell). In some embodiments, the anti-HMC chimeric receptor effector cells (such as T cells) of the invention are able to replicate in vivo, resulting in long-term persistence that can lead to sustained control of a histone H3-related disease (such as cancer, e.g., pediatric high grade glioma, such as DIPG).

In some embodiments, the invention relates to administering a genetically modified T cell expressing an anti-HMC CAR or anti-HMC abTCR for the treatment of a patient having a histone H3-related disease (such as cancer, e.g., pediatric high grade glioma, such as DIPG) or at risk of having a histone H3-related disease using lymphocyte infusion. In some embodiments, autologous lymphocyte infusion is used in the treatment. Autologous PBMCs are collected from a patient in need of treatment and T cells are activated and expanded using the methods described herein and known in the art and then infused back into the patient.

In some embodiments, the anti-HMC CAR T cell expresses an anti-HMC CAR comprising an anti-HMC antibody moiety (also referred to herein as an "anti-HMC CAR T cell"). In some embodiments, the anti-HMC CAR T cell expresses an anti-HMC CAR comprising an extracellular domain comprising the anti-HMC antibody moiety and an intracellular domain comprising intracellular signaling sequences of CD3ζ and CD28 and/or 4-1BB. In some embodiments, the anti-HMC abTCR T cell expresses an anti-HMC abTCR comprising an anti-HMC antibody moiety (also referred to herein as an "anti-HMC abTCR T cell"). In some embodiments, the anti-HMC abTCR T cell expresses an anti-HMC abTCR comprising a) an extracellular domain comprising an anti-HMC antibody moiety that specifically binds to a complex comprising a histone H3 peptide and an MHC class I protein and b) a T cell receptor module (TCRM) capable of recruiting at least one TCR-associated signaling module. The anti-HMC chimeric receptor T cells (such as anti-HMC CAR T cells or anti-HMC abTCR T cells) of the invention can undergo robust in vivo T cell expansion and can establish HMC-specific memory cells that persist at high levels for an extended amount of time in blood and bone marrow. In some embodiments, the anti-HMC chimeric receptor T cells of the invention infused into a patient can eliminate HMC-presenting cells, such as HMC-presenting disease cells, in vivo in patients having a histone H3-related disease (such as cancer, e.g., pediatric high grade glioma, such as DIPG). In some embodiments, the anti-HMC chimeric receptor T cells of the invention infused into a patient can eliminate HMC-presenting cells, such as HMC-presenting disease cells, in vivo in patients having a histone H3-related disease that is refractory to at least one conventional treatment.

Prior to expansion and genetic modification of the T cells, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In some embodiments of the present invention, any number of T cell lines available in the art may be used. In some embodiments of the present invention, T cells can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In some embodiments, the wash solution lacks calcium and may lack magnesium or may lack many if not all divalent cations. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as $Ca^{2+}$-free, $Mg^{2+}$-free PBS, PlasmaLyte A, or other saline solutions with or without buffer. Alternatively, the undesirable components of the apheresis sample may be removed and the cells directly resuspended in culture media.

In some embodiments, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in some embodiments, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In some embodiments, the time period is about 30 minutes. In some embodiments, the time period ranges from 30 minutes to 36 hours or longer and all integer values there between. In some embodiments, the time period is at least one, 2, 3, 4, 5, or 6 hours. In some embodiments, the time period is 10 to 24 hours. In some embodiments, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such as in isolating tumor infiltrating lymphocytes (TIL) from tumor tissue or from immune-compromised individuals. Further, use of longer incubation times can increase the efficiency of capture of $CD8^+$ T cells. Thus, by simply shortening or lengthening the time T cells are allowed to bind to the CD3/CD28 beads and/or by increasing or decreasing the ratio of beads to T cells, subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In some embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD 14, CD20, CD11b, CD 16, HLA-DR, and CD8. In some embodiments, it may be desirable to enrich for or positively select for regulatory T cells which typically express $CD4^+$, $CD25^+$, CD62Lhi, $GITR^+$, and $FoxP3^+$. Alternatively, in some embodiments, T regulatory cells are depleted by anti-CD25 conjugated beads or other similar methods of selection.

For isolation of a desired population of cells by positive or negative selection, the concentration of cells and surface (e.g., particles such as beads) can be varied. In some embodiments, it may be desirable to significantly decrease the volume in which beads and cells are mixed together (i.e., increase the concentration of cells), to ensure maximum contact of cells and beads. For example, in some embodiments, a concentration of about 2 billion cells/ml is used. In some embodiments, a concentration of about 1 billion cells/ml is used. In some embodiments, greater than about 100 million cells/ml is used. In some embodiments, a concentration of cells of about any of 10, 15, 20, 25, 30, 35, 40, 45, or 50 million cells/ml is used. In some embodiments, a concentration of cells of about any of 75, 80, 85, 90, 95, or 100 million cells/ml is used. In some embodiments, a concentration of about 125 or about 150 million cells/ml is used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of $CD8^+$ T cells that normally have weaker CD28 expression.

In some embodiments of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in some embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

Whether prior to or after genetic modification of the T cells to express a desirable anti-HMC chimeric receptor (such as anti-HMC CAR or anti-HMC abTCR), the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., *Transplant Proc.* 30(8):3975-3977, 1998; Haanen et al., *J. Exp. Med.* 190(9):13191328, 1999; Garland et al., *J. Immunol. Meth.* 227(1-2):53-63, 1999).

Immunoconjugate Preparation

The anti-HMC immunoconjugates may be prepared using any methods known in the art. See, e.g., WO 2009/067800, WO 2011/133886, and U.S. Patent Application Publication No. 2014322129, incorporated by reference herein in their entirety.

The anti-HMC antibody moiety of an anti-HMC immunoconjugate may be "attached to" the effector molecule by any means by which the anti-HMC antibody moiety can be associated with, or linked to, the effector molecule. For example, the anti-HMC antibody moiety of an anti-HMC immunoconjugate may be attached to the effector molecule by chemical or recombinant means. Chemical means for preparing fusions or conjugates are known in the art and can be used to prepare the anti-HMC immunoconjugate. The method used to conjugate the anti-HMC antibody moiety and effector molecule must be capable of joining the binding protein with the effector molecule without interfering with the ability of the binding protein to bind to the antigen on the target cell.

The anti-HMC antibody moiety of an anti-HMC immunoconjugate may be linked indirectly to the effector molecule. For example, the anti-HMC antibody moiety of an anti-HMC immunoconjugate may be directly linked to a liposome containing the effector molecule of one of several types. The effector molecule(s) and/or the anti-HMC antibody moiety may also be bound to a solid surface.

In some embodiments, the anti-HMC antibody moiety of an anti-HMC immunoconjugate and the effector molecule are both proteins and can be conjugated using techniques well known in the art. There are several hundred crosslinkers available that can conjugate two proteins. (See for example "Chemistry of Protein Conjugation and Crosslinking". 1991, Shans Wong, CRC Press, Ann Arbor). The crosslinker is generally chosen based on the reactive functional groups available or inserted on the anti-HMC antibody moiety and/or effector molecule. In addition, if there are no reactive groups, a photoactivatible crosslinker can be used. In certain instances, it may be desirable to include a spacer between the anti-HMC antibody moiety and the effector molecule. Crosslinking agents known to the art include the homobifunctional agents: glutaraldehyde, dimethyladipimidate and Bis(diazobenzidine) and the heterobifunctional agents: m Maleimidobenzoyl-N-Hydroxysuccinimide and Sulfo-m Maleimidobenzoyl-N-Hydroxysuccinimide.

In some embodiments, the anti-HMC antibody moiety of an anti-HMC immunoconjugate may be engineered with specific residues for chemical attachment of the effector molecule. Specific residues used for chemical attachment of molecule known to the art include lysine and cysteine. The crosslinker is chosen based on the reactive functional groups inserted on the anti-HMC antibody moiety, and available on the effector molecule.

An anti-HMC immunoconjugate may also be prepared using recombinant DNA techniques. In such a case a DNA sequence encoding the anti-HMC antibody moiety is fused to a DNA sequence encoding the effector molecule, resulting in a chimeric DNA molecule. The chimeric DNA sequence is transfected into a host cell that expresses the fusion protein. The fusion protein can be recovered from the cell culture and purified using techniques known in the art.

Examples of attaching an effector molecule, which is a label, to the binding protein include the methods described in Hunter, et al., *Nature* 144:945 (1962); David, et al., *Biochemistry* 13:1014 (1974); Pain, et al., *J. Immunol. Meth.* 40:219 (1981); Nygren, *J. Histochem. and Cytochem.* 30:407 (1982); Wensel and Meares, *Radioimmunoimaging And Radioimmunotherapy*, Elsevier, N.Y. (1983); and Colcher et al., "Use Of Monoclonal Antibodies As Radiopharmaceuticals For The Localization Of Human Carcinoma Xenografts In Athymic Mice", *Meth. Enzymol.,* 121:802-16 (1986).

The radio- or other labels may be incorporated in the immunoconjugate in known ways. For example, the peptide may be biosynthesized or may be synthesized by chemical amino acid synthesis using suitable amino acid precursors involving, for example, fluorine-19 in place of hydrogen. Labels such as $^{99}$Tc or $^{123}$I, $^{186}$Re, $^{188}$Re and $^{111}$In can be attached via a cysteine residue in the peptide. Yttrium-90 can be attached via a lysine residue. The IODOGEN method (Fraker et al., *Biochem. Biophys. Res. Commun.* 80:49-57 (1978)) can be used to incorporate iodine-123. "Monoclonal Antibodies in Immunoscintigraphy" (Chatal, CRC Press 1989) describes other methods in detail.

Immunoconjugates of the antibody moiety and a cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene tnaminepentaacetic acid (MX-DTPA) is an exemplary chelating agent for conjugation of radionucleotide to the antibody. See, e.g., WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208,020) may be used.

The anti-HMC immunoconjugates of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Pharmaceutical Compositions

Also provided herein are compositions (such as pharmaceutical compositions, also referred to herein as formulations) comprising an anti-HMC construct. In some embodiments, the composition further comprises a cell (such as an effector cell, e.g., a T cell) associated with the anti-HMC construct. In some embodiments, there is provided a pharmaceutical composition comprising an anti-HMC construct and a pharmaceutically acceptable carrier. In some embodiments, the pharmaceutical composition further comprises a cell (such as an effector cell, e.g., a T cell) associated with the anti-HMC construct.

Suitable formulations of the anti-HMC constructs are obtained by mixing an anti-HMC construct having the desired degree of purity with optional pharmaceutically acceptable carriers, excipients or stabilizers (*Remington's Pharmaceutical Sciences* 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propylparaben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as olyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary formulations are described in WO98/56418, expressly incorporated herein by reference. Lyophilized formulations adapted for subcutaneous administration are described in WO97/04801. Such lyophilized formulations may be reconstituted with a suitable diluent to a high protein concentration and the reconstituted formulation may be administered subcutaneously to the individual to be treated herein. Lipofectins or liposomes can be used to deliver the anti-HMC constructs of this invention into cells.

The formulation herein may also contain one or more active compounds in addition to the anti-HMC construct as necessary for the particular indication being treated, preferably those with complementary activities that do not adversely affect each other. For example, it may be desirable to further provide an anti-neoplastic agent, a growth inhibitory agent, a cytotoxic agent, or a chemotherapeutic agent in addition to the anti-HMC construct. Such molecules are suitably present in combination in amounts that are effective for the purpose intended. The effective amount of such other agents depends on the amount of anti-HMC construct present in the formulation, the type of disease or disorder or treatment, and other factors discussed above. These are generally used in the same dosages and with administration routes as described herein or about from 1 to 99% of the heretofore employed dosages.

The anti-HMC constructs may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980). Sustained-release preparations may be prepared.

Sustained-release preparations of the anti-HMC constructs can be prepared. Suitable examples of sustained-release preparations include semipermeable matrices of solid hydrophobic polymers containing the antibody (or fragment thereof), which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydro gels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization of anti-HMC constructs depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

In some embodiments, the anti-HMC construct is formulated in a buffer comprising a citrate, NaCl, acetate, succinate, glycine, polysorbate 80 (Tween 80), or any combination of the foregoing. In some embodiments, the anti-HMC construct is formulated in a buffer comprising about 100 mM to about 150 mM glycine. In some embodiments, the anti-HMC construct is formulated in a buffer comprising about 50 mM to about 100 mM NaCl. In some embodiments, the anti-HMC construct is formulated in a buffer comprising about 10 mM to about 50 mM acetate. In some embodiments, the anti-HMC construct is formulated in a buffer comprising about 10 mM to about 50 mM succinate. In some embodiments, the anti-HMC construct is formulated in a buffer comprising about 0.005% to about 0.02% polysorbate 80. In some embodiments, the anti-HMC construct is formulated in a buffer having a pH between about 5.1 and 5.6. In some embodiments, the anti-HMC construct is formulated in a buffer comprising 10 mM citrate, 100 mM NaCl, 100 mM glycine, and 0.01% polysorbate 80, wherein the formulation is at pH 5.5.

The formulations to be used for in vivo administration must be sterile. This is readily accomplished by, e.g., filtration through sterile filtration membranes.

Methods for Treatment Using Anti-HMC Constructs

The anti-HMC constructs and/or compositions of the invention can be administered to individuals (e.g., mammals such as humans) to treat a histone H3-related disease, including, for example, a disease characterized by aberrant expression of histone H3 or expression of a mutant histone H3 (such as K27M-H3, including K27M-H3.3 and K27M-H3.1). Examples of histone H3-related disease include, without limitation, cancer, e.g., pediatric high grade glioma, such as DIPG. The present application thus in some embodiments provides a method of treating a histone H3-related disease in an individual comprising administering to the individual an effective amount of a composition (such as a pharmaceutical composition) comprising an anti-HMC construct comprising an anti-HMC antibody moiety, such as any one of the anti-HMC constructs described herein. In some embodiments, the composition further comprises a cell (such as an effector cell) associated with the anti-HMC construct. In some embodiments, the histone H3-related disease is a K27M-H3-positive disease, such as a K27M-H3.3-positive disease or a K27M-H3.1-positive disease (such as cancer, e.g., pediatric high grade glioma, such as DIPG). In some embodiments, the K27M-H3-positive disease is a K27M-H3.3-positive disease. In some embodiments, the K27M-H3-positive disease is a K27M-H3.1-positive disease.

For example, in some embodiments, there is provided a method of treating a histone H3-related disease (such as cancer, e.g., pediatric high grade glioma, such as DIPG) in an individual comprising administering to the individual an effective amount of a composition comprising an anti-HMC construct comprising an anti-HMC antibody moiety that specifically binds to a complex comprising a histone H3 peptide and an MHC class I protein. In some embodiments, the histone H3 peptide comprises (such as consists of) the amino acid sequence of any one of SEQ ID NOs: 5-24. In some embodiments, the histone H3 peptide is mutant histone K27M-H3.3 26-35 (SEQ ID NO: 7) or mutant histone K27M-H3.1 26-35 (SEQ ID NO: 8). In some embodiments, the histone H3 peptide is WT H3.3 26-35 (SEQ ID NO: 5) or WT H3.1 26-35 (SEQ ID NO: 6). In some embodiments, the MHC class I protein is HLA-A02. In some embodiments, the MHC class I protein is HLA-A*02:01. In some embodiments, the anti-HMC construct is non-naturally occurring. In some embodiments, the anti-HMC construct is a full-length antibody. In some embodiments, the anti-HMC construct is a multi-specific (such as bispecific) molecule. In some embodiments, the anti-HMC construct is a chimeric receptor (e.g., a CAR or abTCR). In some embodiments, the anti-HMC construct is an immunoconjugate. In some embodiments, the composition further comprises a cell (such as an effector cell) associated with the anti-HMC construct. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease (such as cancer, e.g., pediatric high grade glioma, such as DIPG) in an individual comprising administering to the individual an effective amount of a composition comprising an anti-HMC construct comprising an anti-HMC antibody moiety that specifically binds to a complex comprising a histone H3 peptide selected from mutant histone K27M-H3.3 26-35 (SEQ ID NO: 7), mutant histone K27M-H3.1 26-35 (SEQ ID NO: 8), WT H3.3 26-35 (SEQ ID NO: 5), or WT H3.1 26-35 (SEQ ID NO: 6) peptide and HLA-A*02:01. In some embodiments, the histone H3 peptide is mutant histone K27M-H3.3 26-35 (SEQ ID NO: 7). In some embodiments, the histone H3 peptide is mutant histone K27M-H3.1 26-35 (SEQ ID NO: 8). In some embodiments, the histone H3 peptide is WT H3.3 26-35 (SEQ ID NO: 5). In some embodiments, the histone H3 peptide is WT H3.1 26-35 (SEQ ID NO: 6). In some embodiments, the anti-HMC construct is non-naturally occurring. In some embodiments, the anti-HMC construct is a full-length antibody. In some embodiments, the anti-HMC construct is a multi-specific (such as bispecific) molecule. In some embodiments, the anti-HMC construct is a chimeric receptor (e.g., a CAR or abTCR). In some embodiments, the anti-HMC construct is an immunoconjugate. In some embodiments, the composition further comprises a cell (such as an effector cell) associated with the anti-HMC construct. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease (such as cancer, e.g., pediatric high grade glioma, such as DIPG) in an individual comprising administering to the individual an effective amount of a composition comprising an anti-HMC construct comprising an anti-HMC antibody moiety that specifically binds to a complex comprising a histone H3 peptide and an MHC class I protein, wherein the anti-HMC antibody moiety comprises: i) a heavy chain variable domain sequence comprising an HC-CDR1 comprising the amino acid sequence of SEQ ID NO: 158, or a variant thereof comprising up to about 3 (for example about any of 1, 2, or 3) amino acid substitutions, an HC-CDR2 comprising the amino acid sequence of SEQ ID NO: 159, or a variant thereof comprising up to about 3 (for example about any of 1, 2, or 3) amino acid substitutions, and/or an HC-CDR3 comprising the amino acid sequence of SEQ ID NO: 160 or 161, or a variant thereof comprising up to about 3 (for example about any of 1, 2, or 3) amino acid substitutions; and ii) a light chain variable domain comprising an LC-CDR1 comprising the amino acid sequence of SEQ ID NO: 162, or a variant thereof comprising up to about 3 (for example about any of 1, 2, or 3) amino acid substitutions, and/or an LC-CDR3 comprising the amino acid sequence of SEQ ID NO: 163, or a variant thereof comprising up to about 3 (for example about any of 1, 2, or 3) amino acid substitutions. In some embodiments, there is provided a method of treating a histone H3-related disease in an individual comprising administering to the individual an effective amount of a composition comprising an anti-HMC construct comprising an anti-HMC antibody moiety that specifically binds to a complex comprising a histone H3 peptide and an MHC class I protein, wherein the anti-HMC antibody moiety comprises: i) a heavy chain variable domain sequence comprising an HC-CDR1 comprising the amino acid sequence of SEQ ID NO: 158, an HC-CDR2 comprising the amino acid sequence of SEQ ID NO: 159, and/or an HC-CDR3 comprising the amino acid sequence of SEQ ID NO: 160 or 161; and ii) a light chain variable domain comprising an LC-CDR1 comprising the amino acid sequence of SEQ ID NO: 162, and/or an LC-CDR3 comprising the amino acid sequence of SEQ ID NO: 163. In some embodiments, the anti-HMC construct is non-naturally occurring. In some embodiments, the anti-HMC construct is a full-length antibody. In some embodiments, the anti-HMC construct is a multi-specific (such as bispecific) molecule. In some embodiments, the anti-HMC construct is a chimeric receptor (e.g., a CAR or abTCR). In some embodiments, the anti-HMC construct is an immunoconjugate. In some embodiments, the composition further comprises a cell (such as an effector cell) associated with the anti-HMC construct. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease (such as cancer, e.g., pediatric high grade glioma, such as DIPG) in an individual comprising administering to the individual an effective amount of a composition comprising an anti-HMC construct comprising an anti-HMC antibody moiety that specifically binds to a complex comprising a histone H3 peptide and an MHC class I protein, wherein the anti-HMC antibody moiety comprises: i) a heavy chain variable domain sequence comprising an HC-CDR1 comprising the amino acid sequence of any one of SEQ ID NOs: 99-107, or a variant thereof comprising up to about 5 (for example about any of 1, 2, 3, 4, or 5) amino acid substitutions; an HC-CDR2 comprising the amino acid sequence of any one of SEQ ID NOs: 108-116, or a variant thereof comprising up to about 5 (for example about any of 1, 2, 3, 4, or 5) amino acid substitutions; and/or an HC-CDR3 comprising the amino acid sequence of any one of SEQ ID NOs: 117-128; or a variant thereof comprising up to about 5 (for example about any of 1, 2, 3, 4, or 5) amino acid substitutions; and ii) a light chain variable domain sequence comprising an LC-CDR1 comprising the amino acid sequence of any one of SEQ ID NOs: 129-138, or a variant thereof comprising up to about 5 (for example about any of 1, 2, 3, 4, or 5) amino acid substitutions; an LC-CDR2 comprising the amino acid sequence of any one of SEQ ID NOs: 139-147, or a variant thereof comprising up to about 3 (for example about any of 1, 2, or 3) amino acid substitutions; and/or an LC-CDR3 comprising the amino acid sequence of any one of SEQ ID NOs: 148-157; or a variant thereof comprising up to about 5 (for example about any of 1, 2, 3, 4, or 5) amino acid substitutions. In some embodiments, there is provided a method of treating a histone H3-related disease in an individual comprising administering to the individual an effective amount of a composition comprising an anti-HMC construct comprising an anti-HMC antibody moiety that specifically binds to a complex comprising a histone H3 peptide and an MHC class I protein, wherein the anti-HMC antibody moiety comprises: i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; or a variant thereof comprising up to about 5 (for example about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; or a variant thereof comprising up to about 5 (for example about any of 1, 2, 3, 4, or 5) amino acid substitutions in the LC-CDR sequences. In some embodiments, there is provided a method of treating a histone H3-related disease in an individual comprising administering to the individual an effective amount of a composition comprising an anti-HMC construct comprising an anti-HMC antibody moiety that specifically binds to a complex comprising a histone H3 peptide and an MHC class I protein, wherein the anti-HMC antibody moiety comprises: i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157. In some embodiments, the anti-HMC construct is non-naturally occurring. In some embodiments, the anti-HMC construct is a full-length antibody. In some embodiments, the anti-HMC construct is a multi-specific (such as bispecific) molecule. In some embodiments, the anti-HMC construct is a chimeric receptor (e.g., a CAR or abTCR). In some embodiments, the anti-HMC construct is an immunoconjugate. In some embodiments, the composition further comprises a cell (such as an effector cell) associated with the anti-HMC construct. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease (such as cancer, e.g., pediatric high grade glioma, such as DIPG) in an individual comprising administering to the individual an effective amount of a composition comprising an anti-HMC construct comprising an anti-HMC antibody moiety that specifically binds to a complex comprising a histone H3 peptide and an MHC class I protein, wherein the anti-HMC antibody moiety comprises a heavy chain variable domain comprising the amino acid sequence of any one of SEQ ID NOs: 75-86, or a variant thereof having at least about 95% (for example at least about any of 96%, 97%, 98%, or 99%) sequence identity, and a light chain variable domain comprising the amino acid sequence of any one of SEQ ID NOs: 87-98, or a variant thereof having at least about 95% (for example at least about any of 96%, 97%, 98%, or 99%) sequence identity. In some embodiments, there is provided a method of treating a histone H3-related disease in an individual comprising administering to the individual an effective amount of a composition comprising an anti-HMC construct comprising an anti-HMC antibody moiety that specifically binds to a complex comprising a histone H3 peptide and an MHC class I protein, wherein the anti-HMC antibody moiety comprises a heavy chain variable domain comprising the amino acid sequence of any one of SEQ ID NOs: 75-86 and a light chain variable domain comprising the amino acid sequence of any one of SEQ ID NOs: 87-98. In some embodiments, the anti-HMC construct is non-naturally occurring. In some embodiments, the anti-HMC construct is a full-length antibody. In some embodiments, the anti-HMC construct is a multi-specific (such as bispecific) molecule. In some embodiments, the anti-HMC construct is a chimeric receptor (e.g., a CAR or abTCR). In some embodiments, the anti-HMC construct is an immunoconjugate. In some embodiments, the composition further comprises a cell (such as an effector cell) associated with the anti-HMC construct. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

For example, in some embodiments, the anti-HMC construct contained in a composition administered to an individual in a method of treating a histone H3-related disease (such as cancer, e.g., pediatric high grade glioma, such as DIPG) comprises an anti-HMC antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (for example about any of 1, 2, 3, 4, or 5) amino acid substitutions, individually, in HC-CDR1, HC-CDR2, HC-CDR3, LC-CDR1, and/or LC-CDR3, and/or up to about 3 (for example about any of 1, 2, or 3) amino acid substitutions in LC-CDR2. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, the anti-HMC construct contained in a composition administered to an individual in a method of treating a histone H3-related disease (such as cancer, e.g., pediatric high grade glioma, such as DIPG) comprises an anti-HMC antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, or SEQ ID NOs: 106, 115, 127, 137, 145, and 156, respectively, or SEQ ID NOs: 107, 116, 128, 138, 147, and 157, respectively; or variants thereof comprising up to about 5 (such as about any of 1, 2, 3, 4, or 5) amino acid substitutions in the HC-CDR sequences and/or up to about 5 (such as about any of 1, 2, 3, 4, or 5) amino acid substitutions in the LC-CDR sequences. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, the anti-HMC construct contained in a composition administered to an individual in a method of treating a histone H3-related disease (such as cancer, e.g., pediatric high grade glioma, such as DIPG) comprises an anti-HMC antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, the anti-HMC construct contained in a composition administered to an individual in a method of treating a histone H3-related disease (such as cancer, e.g., pediatric high grade glioma, such as DIPG) comprises an anti-HMC antibody moiety comprising heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively; or variants thereof having, individually, at least about 95% (for example at least about any of 96%, 97%, 98%, or 99%) sequence identity. In some embodiments, the anti-HMC antibody moiety comprises heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments of any of the methods for treating a histone H3-related disease described above, the anti-HMC construct is conjugated to a cell (such as an immune cell, e.g., a T cell) prior to being administered to the individual. Thus, for example, there is provided a method of treating a histone H3-related disease (such as cancer, e.g., pediatric high grade glioma, such as DIPG) in an individual comprising a) conjugating any one of the anti-HMC constructs described herein to a cell (such as an immune cell, e.g., a T cell) to form an anti-HMC construct/cell conjugate, and b) administering to the individual an effective amount of a composition comprising the anti-HMC construct/cell conjugate. In some embodiments, the cell is derived from the individual. In some embodiments, the cell is not derived from the individual. In some embodiments, the anti-HMC construct is conjugated to the cell by covalent linkage to a molecule on the surface of the cell. In some embodiments, the anti-HMC construct is conjugated to the cell by non-covalent linkage to a molecule on the surface of the cell. In some embodiments, the anti-HMC construct is conjugated to the cell by insertion of a portion of the anti-HMC construct into the outer membrane of the cell. In some embodiments, the anti-HMC construct is non-naturally occurring. In some embodiments, the anti-HMC construct is a full-length antibody. In some embodiments, the anti-HMC construct is a multi-specific (such as bispecific) molecule. In some embodiments, the anti-HMC construct is a chimeric receptor (e.g., a CAR or abTCR). In some embodiments, the anti-HMC construct is an immunoconjugate. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, the individual is a mammal (e.g., human, non-human primate, rat, mouse, cow, horse, pig, sheep, goat, dog, cat, etc.). In some embodiments, the individual is a human. In some embodiments, the individual is a clinical patient, a clinical trial volunteer, an experimental animal, etc. In some embodiments, the individual is younger than about 60 years old (including for example younger than about any of 50, 40, 30, 25, 20, 15, or 10 years old). In some embodiments, the individual is older than about 60 years old (including for example older than about any of 70, 80, 90, or 100 years old). In some embodiments, the individual is diagnosed with a histone H3-related disease. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

The present application in some embodiments provides a method of delivering an anti-HMC construct (such as any one of the anti-HMC constructs described herein) to a cell presenting on its surface a complex comprising a histone H3 peptide and an MHC class I protein in an individual, the method comprising administering to the individual a composition comprising the anti-HMC construct. In some embodiments, the anti-HMC construct to be delivered is associated with a cell (such as an effector cell, e.g., a T cell). In some embodiments, the histone H3 peptide is a K27M-H3.3 26-35 peptide. In some embodiments, the histone H3 peptide is a K27M-H3.1 26-35 peptide.

Diagnostic methods for K27M-H3-positive diseases are known in the art. Such methods include, but are not limited to, e.g., sequencing of cancer cells (such as by Sanger sequencing, next generation sequencing, or deep sequencing), immunohistochemistry, PCR, and fluorescent in situ hybridization (FISH).

In some embodiments, the anti-HMC constructs and/or compositions of the invention are administered in combination with a second, third, or fourth agent (including, e.g., an antiviral drug) to treat a histone H3-related disease. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG. In some embodiments, the anti-HMC construct is administered in combination with an agent that increases the expression of MHC class I proteins and/or enhances the surface presentation of mutant histone H3 peptides by MHC class I proteins. In some embodiments, the agent includes, for example, IFN receptor agonists, Hsp90 inhibitors, enhancers of p53 expression, and chemotherapeutic agents. In some embodiments, the agent is an IFN receptor agonist including, for example, IFNγ, IFNβ, and IFNα. In some embodiments, the agent is an Hsp90 inhibitor including, for example, tanespimycin (17-AAG), alvespimycin (17-DMAG), retaspimycin (IPI-504), IPI-493, CNF2024/BIIB021, MPC-3100, Debio 0932 (CUDC-305), PU-H71, Ganetespib (STA-9090), NVP-AUY922 (VER-52269), HSP990, KW-2478, AT13387, SNX-5422, DS-2248, and XL888. In some embodiments, the agent is an enhancer of p53 expression including, for example, 5-fluorouracil and nutlin-3. In some embodiments, the agent is a chemotherapeutic agent including, for example, topotecan, etoposide, cisplatin, paclitaxel, and vinblastine.

In some embodiments, there is provided a method of treating a histone H3-related disease (such as cancer, e.g., pediatric high grade glioma, such as DIPG) in an individual, wherein the cells expressing the mutant histone H3 do not normally present, or present at relatively low levels, an MHC class I complex comprising a peptide derived from the mutant histone H3 protein on their surface, the method comprising administering to the individual a composition comprising an anti-HMC construct in combination with an agent that increases the expression of MHC class I proteins and/or enhances the surface presentation of mutant histone H3 peptides by MHC class I proteins. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG. In some embodiments, the agent includes, for example, IFN receptor agonists, Hsp90 inhibitors, enhancers of p53 expression, and chemotherapeutic agents. In some embodiments, the agent is an IFN receptor agonist including, for example, IFNγ, IFNβ, and IFNα. In some embodiments, the agent is an Hsp90 inhibitor including, for example, tanespimycin (17-AAG), alvespimycin (17-DMAG), retaspimycin (IPI-504), IPI-493, CNF2024/BIIB021, MPC-3100, Debio 0932 (CUDC-305), PU-H71, Ganetespib (STA-9090), NVP-AUY922 (VER-52269), HSP990, KW-2478, AT13387, SNX-5422, DS-2248, and XL888. In some embodiments, the agent is an enhancer of p53 expression including, for example, 5-fluorouracil and nutlin-3. In some embodiments, the agent is a chemotherapeutic agent including, for example, topotecan, etoposide, cisplatin, paclitaxel, and vinblastine.

Cancer treatments can be evaluated, for example, by tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

In some embodiments, the efficacy of treatment is measured as the percentage tumor growth inhibition (% TGI), calculated using the equation 100−(T/C×100), where T is the mean relative tumor volume of the treated tumor, and C is the mean relative tumor volume of a non-treated tumor. In some embodiments, the % TGI is about 10%, about 20%, about 30%, about 40%, about 50%, about 60%, about 70%, about 80%, about 90%, about 91%, about 92%, about 93%, about 94%, about 95%, or more than 95%.

Dosing and Method of Administering the Anti-HMC Construct Compositions

The dose of the anti-HMC construct compositions administered to an individual (such as a human) may vary with the particular composition, the mode of administration, and the type of disease being treated. In some embodiments, the amount of the composition is effective to result in an undetectable viral load. In some embodiments, the amount of the anti-HMC construct composition is sufficient to result in a complete response in the individual. In some embodiments, the amount of the anti-HMC construct composition is sufficient to result in a partial response in the individual. In some embodiments, the amount of the anti-HMC construct composition administered (for example when administered alone) is sufficient to produce an overall response rate of more than about any of 20%, 25%, 30%, 35%, 40%, 45%, 50%, 55%, 60%, 64%, 65%, 70%, 75%, 80%, 85%, or 90% among a population of individuals treated with the anti-HMC construct composition. Responses of an individual to the treatment of the methods described herein can be determined, for example, based on RECIST levels.

In some embodiments, the amount of the composition is sufficient to prolong overall survival of the individual. In some embodiments, the amount of the composition (for example when administered along) is sufficient to produce clinical benefit of more than about any of 50%, 60%, 70%, or 77% among a population of individuals treated with the anti-HMC construct composition.

In some embodiments, the amount of the composition, alone or in combination with a second, third, and/or fourth agent, is an amount sufficient to decrease the size of a tumor, decrease the number of cancer cells, or decrease the growth rate of a tumor by at least about any of 10%, 20%, 30%, 40%, 50%, 60%, 70%, 80%, 90%, 95% or 100% compared to the corresponding tumor size, number of cancer cells, or tumor growth rate in the same subject prior to treatment or compared to the corresponding activity in other subjects not receiving the treatment. Standard methods can be used to measure the magnitude of this effect, such as in vitro assays with purified enzyme, cell-based assays, animal models, or human testing.

In some embodiments, the amount of the anti-HMC construct (e.g., full-length anti-HMC antibody, multi-specific anti-HMC molecule, anti-HMC CAR, anti-HMC abTCR, or anti-HMC immunoconjugate) in the composition is below the level that induces a toxicological effect (i.e., an effect above a clinically acceptable level of toxicity) or is at a level where a potential side effect can be controlled or tolerated when the composition is administered to the individual.

In some embodiments, the amount of the composition is close to a maximum tolerated dose (MTD) of the composition following the same dosing regimen. In some embodiments, the amount of the composition is more than about any of 80%, 90%, 95%, or 98% of the MTD.

In some embodiments, the amount of an anti-HMC construct (e.g., full-length anti-HMC antibody, multi-specific anti-HMC molecule, anti-HMC CAR, anti-HMC abTCR, or anti-HMC immunoconjugate) in the composition is included in a range of about 0.001 µg to about 1000 µg.

In some embodiments of any of the above aspects, the effective amount of an anti-HMC construct (e.g., full-length anti-HMC antibody, multi-specific anti-HMC molecule, anti-HMC CAR, anti-HMC abTCR, or anti-HMC immunoconjugate) in the composition is in the range of about 0.1 µg/kg to about 100 mg/kg of total body weight.

The anti-HMC construct compositions can be administered to an individual (such as human) via various routes, including, for example, intravenous, intra-arterial, intraperitoneal, intrapulmonary, oral, nasal, inhalation, intravesicular, intramuscular, intra-tracheal, subcutaneous, intraocular, intrathecal, intracranial, intracerebral, intracerebroventricular, transmucosal, and transdermal. In some embodiments, sustained continuous release formulation of the composition may be used. In some embodiments, the composition is administered intravenously. In some embodiments, the composition is administered intraarterially. In some embodiments, the composition is administered intraperitoneally. In some embodiments, the composition is administered intrathecally. In some embodiments, the composition is administered intracranially. In some embodiments, the composition is administered intracerebrally. In some embodiments, the composition is administered intracerebroventricularly. In some embodiments, the composition is administered nasally.

Anti-HMC Chimeric Receptor Effector Cell Therapy

The present application also provides methods of using an anti-HMC chimeric receptor (such as an anti-HMC CAR or anti-HMC abTCR) to redirect the specificity of an effector cell (such as a primary T cell) to a complex comprising a histone H3 peptide and an MHC class I protein. Thus, the present invention also provides a method of stimulating an effector cell-mediated response (such as a T cell-mediated immune response) to a target cell population or tissue comprising HMC-presenting cells in a mammal, comprising the step of administering to the mammal an effector cell (such as a T cell) that expresses an anti-HMC CAR or anti-HMC abTCR.

Anti-HMC chimeric receptor effector cells (such as anti-HMC CAR T cells or anti-HMC abTCR T cells) expressing the anti-HMC chimeric receptor can be infused to a recipient in need thereof. The infused cell is able to kill HMC-presenting cells in the recipient. In some embodiments, unlike antibody therapies, anti-HMC chimeric receptor effector cells (such as T cells) are able to replicate in vivo resulting in long-term persistence that can lead to sustained tumor control.

In some embodiments, the anti-HMC chimeric receptor effector cells are anti-HMC CAR T cells or anti-HMC abTCR T cells that can undergo robust in vivo T cell expansion and can persist for an extended amount of time. In some embodiments, the anti-HMC CAR T cells or anti-HMC abTCR T cells of the invention develop into specific memory T cells that can be reactivated to inhibit any additional tumor formation or growth.

The anti-HMC chimeric receptor T cells (such as anti-HMC CAR T cells or anti-HMC abTCR T cells) of the invention may also serve as a type of vaccine for ex vivo immunization and/or in vivo therapy in a mammal. In some embodiments, the mammal is a human.

With respect to ex vivo immunization, of least one of the following occurs in vitro prior to administering the cell into a mammal: i) expansion of the cells, ii) introducing a nucleic acid encoding an anti-HMC CAR or anti-HMC abTCR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing an anti-HMC CAR or anti-HMC abTCR disclosed herein. The anti-HMC CAR cell or anti-HMC abTCR cell can be administered to a mammalian recipient to provide a therapeutic benefit. The mammalian recipient may be a human and the anti-HMC CAR or anti-HMC abTCR cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting T cells from peripheral blood mononuclear cells (PBMC); and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

The anti-HMC chimeric receptor effector cells (such as anti-HMC CAR T cells or anti-HMC abTCR T cells) of the present invention may be administered either alone, or as a pharmaceutical composition in combination with diluents and/or with other components such as IL-2 or other cytokines or cell populations. Briefly, pharmaceutical compositions of the present invention may comprise anti-HMC chimeric receptor effector cells (such as T cells), in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. In some embodiments, anti-HMC chimeric receptor effector cell (such as T cell) compositions are formulated for administration by intravenous, intrathecal, intracranial, intracerebral, or intracerebroventricular route.

The precise amount of the anti-HMC chimeric receptor effector cell (such as anti-HMC CAR T cell or anti-HMC abTCR T cell) compositions of the present invention to be administered can be determined by a physician with consideration of individual differences in age, weight, tumor size, extent of infection or metastasis, and condition of the patient (subject). In some embodiments, a pharmaceutical composition comprising the anti-HMC chimeric receptor effector cells (such as T cells) is administered at a dosage of about $10^4$ to about $10^9$ cells/kg body weight, such any of about $10^4$ to about $10^5$, about $10^5$ to about $10^6$, about $10^6$ to about $10^7$, about $10^7$ to about $10^8$, or about $10^8$ to about $10^9$ cells/kg body weight, including all integer values within those ranges. Anti-HMC chimeric receptor effect cell (such as T cell) compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regimen for a particular patient can readily be determined by one skilled in the art of medicine by monitoring the patient for signs of disease and adjusting the treatment accordingly.

In some embodiments, it may be desired to administer activated anti-HMC chimeric receptor T cells (such as anti-HMC CAR T cells or anti-HMC abTCR T cells) to a subject and then subsequently redraw blood (or have an apheresis performed), activate T cells therefrom according to the present invention, and reinfuse the patient with these activated and expanded T cells. This process can be carried out multiple times every few weeks. In some embodiments, T cells can be activated from blood draws of from 10 cc to 400 cc. In some embodiments, T cells are activated from blood draws of 20 cc, 30 cc, 40 cc, 50 cc, 60 cc, 70 cc, 80 cc, 90 cc, or 100 cc.

The administration of the anti-HMC chimeric receptor effector cells (such as anti-HMC CAR T cells or anti-HMC abTCR T cells) may be carried out in any convenient manner, including by injection, ingestion, transfusion, implantation or transplantation. The compositions described herein may be administered to a patient subcutaneously, intradermally, intratumorally, intranodally, intramedullary, intramuscularly, intrathecally, intracranially, intracerebrally, intracerebroventricularly, by intravenous (i.v.) injection, or intraperitoneally. In some embodiments, the anti-HMC chimeric receptor effector cell (such as T cell) compositions of the present invention are administered to a patient by intradermal or subcutaneous injection. In some embodiments, the anti-HMC chimeric receptor effector cell (such as T cell) compositions of the present invention are administered by i.v. injection. In some embodiments, the anti-HMC chimeric receptor effector cell (such as T cell) compositions of the present invention are administered by intrathecal injection. In some embodiments, the anti-HMC chimeric receptor effector cell (such as T cell) compositions of the present invention are administered by intracranial injection. In some embodiments, the anti-HMC chimeric receptor effector cell (such as T cell) compositions of the present invention are administered by intracerebral injection. In some embodiments, the anti-HMC chimeric receptor effector cell (such as T cell) compositions of the present invention are administered by intracerebroventricular injection. The compositions of anti-HMC chimeric receptor effector cells (such as T cells) may be injected directly into a tumor, lymph node, or site of infection.

Thus, for example, in some embodiments, there is provided a method of treating a histone H3-related disease in an individual comprising administering to the individual an effective amount of a composition comprising an effector cell (such as a T cell) expressing an anti-HMC CAR comprising a) an extracellular domain comprising an anti-HMC antibody moiety that specifically binds to a complex comprising a histone H3 peptide and an MHC class I protein, b) a transmembrane domain, and c) an intracellular signaling domain comprising a CD3ζ intracellular signaling sequence and a CD28 and/or 4-1BB intracellular signaling sequence. In some embodiments, the histone H3 peptide is mutant histone K27M-H3.3 26-35 (SEQ ID NO: 7) or mutant histone K27M-H3.1 26-35 (SEQ ID NO: 8). In some embodiments, the histone H3 peptide is WT H3.3 26-35 (SEQ ID NO: 5) or WT H3.1 26-35 (SEQ ID NO: 6). In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG. In some embodiments, the MHC class I protein is HLA-A02. In some embodiments, the MHC class I protein is HLA-A*02:01. In some embodiments, the individual is human.

In some embodiments, there is provided a method of treating a histone H3-related disease in an individual comprising administering to the individual an effective amount of a composition comprising an effector cell (such as a T cell) expressing an anti-HMC CAR comprising a) an extracellular domain comprising an anti-HMC antibody moiety that specifically binds to a complex comprising a histone H3 peptide selected from mutant histone K27M-H3.3 26-35 (SEQ ID NO: 7), mutant histone K27M-H3.1 26-35 (SEQ ID NO: 8), WT H3.3 26-35 (SEQ ID NO: 5), or WT H3.1 26-35 (SEQ ID NO: 6) peptide and HLA-A*02:01, b) a transmembrane domain, and c) an intracellular signaling domain comprising a CD3 intracellular signaling sequence and a CD28 and/or 4-1BB intracellular signaling sequence. In some embodiments, the histone H3 peptide is mutant histone K27M-H3.3 26-35 (SEQ ID NO: 7). In some embodiments, the histone H3 peptide is mutant histone K27M-H3.1 26-35 (SEQ ID NO: 8). In some embodiments, the histone H3 peptide is WT H3.3 26-35 (SEQ ID NO: 5). In some embodiments, the histone H3 peptide is WT H3.1 26-35 (SEQ ID NO: 6). In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease in an individual comprising administering to the individual an effective amount of a composition comprising an effector cell (such as a T cell) expressing an anti-HMC CAR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of SEQ ID NO: 158, or a variant thereof comprising up to about 3 (for example about any of 1, 2, or 3) amino acid substitutions, an HC-CDR2 comprising the amino acid sequence of SEQ ID NO: 159, or a variant thereof comprising up to about 3 (for example about any of 1, 2, or 3) amino acid substitutions, and/or an HC-CDR3 comprising the amino acid sequence of SEQ ID NO: 160 or 161, or a variant thereof comprising up to about 3 (for example about any of 1, 2, or 3) amino acid substitutions; and ii) a light chain variable domain comprising an LC-CDR1 comprising the amino acid sequence of SEQ ID NO: 162, or a variant thereof comprising up to about 3 (for example about any of 1, 2, or 3) amino acid substitutions, and/or an LC-CDR3 comprising the amino acid sequence of SEQ ID NO: 163, or a variant thereof comprising up to about 3 (for example about any of 1, 2, or 3) amino acid substitutions, b) a transmembrane domain, and c) an intracellular signaling domain comprising a CD3 intracellular signaling sequence and a CD28 and/or 4-1BB intracellular signaling sequence. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease in an individual comprising administering to the individual an effective amount of a composition comprising an effector cell (such as a T cell) expressing an anti-HMC CAR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of SEQ ID NO: 158, an HC-CDR2 comprising the amino acid sequence of SEQ ID NO: 159, and/or an HC-CDR3 comprising the amino acid sequence of SEQ ID NO: 160 or 161; and ii) a light chain variable domain comprising an LC-CDR1 comprising the amino acid sequence of SEQ ID NO: 162, and/or an LC-CDR3 comprising the amino acid sequence of SEQ ID NO: 163, b) a transmembrane domain, and c) an intracellular signaling domain comprising a CD3ζ intracellular signaling sequence and a CD28 and/or 4-1BB intracellular signaling sequence. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease in an individual comprising administering to the individual an effective amount of a composition comprising an effector cell (such as a T cell) expressing an anti-HMC CAR comprising a) an extracellular domain comprising an anti-HMC antibody moiety that specifically binds to a complex comprising a histone H3 peptide and an MHC class I protein comprising i) a heavy chain variable domain comprising an HC-CDR1 comprising the amino acid sequence of any one of SEQ ID NOs: 99-107, or a variant thereof comprising up to about 5 (such as about any of 1, 2, 3, 4, or 5) amino acid substitutions, an HC-CDR2 comprising the amino acid sequence of any one of SEQ ID NOs: 108-116, or a variant thereof comprising up to about 5 (such as about any of 1, 2, 3, 4, or 5) amino acid substitutions, and/or an HC-CDR3 comprising the amino acid sequence of any one of SEQ ID NOs: 117-128, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 129-138, or a variant thereof comprising up to about 5 (such as about any of 1, 2, 3, 4, or 5) amino acid substitutions, an LC-CDR2 comprising the amino acid sequence of any one of SEQ ID NOs: 139-147, or a variant thereof comprising up to about 3 (such as about any of 1, 2, or 3) amino acid substitutions, and/or an LC-CDR3 comprising the amino acid sequence of any one of SEQ ID NOs: 148-157, or a variant thereof comprising up to about 5 (such as about any of 1, 2, 3, 4, or 5) amino acid substitutions; b) a transmembrane domain, and c) an intracellular signaling domain comprising a CD3ζ intracellular signaling sequence and a CD28 and/or 4-1BB intracellular signaling sequence. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease in an individual comprising administering to the individual an effective amount of a composition comprising an effector cell (such as a T cell) expressing an anti-HMC CAR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; or a variant thereof comprising up to about 5 (such as about any of 1, 2, 3, 4, or 5) amino acid substitutions in the LC-CDR sequences; b) a transmembrane domain, and c) an intracellular signaling domain comprising a CD3ζ intracellular signaling sequence and a CD28 and/or 4-1BB intracellular signaling sequence. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease in an individual comprising administering to the individual an effective amount of a composition comprising an effector cell (such as a T cell) expressing an anti-HMC CAR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; b) a transmembrane domain, and c) an intracellular signaling domain comprising a CD3ζ intracellular signaling sequence and a CD28 and/or 4-1BB intracellular signaling sequence. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease in an individual comprising administering to the individual an effective amount of a composition comprising an effector cell (such as a T cell) expressing an anti-HMC CAR comprising a) an extracellular domain comprising an anti-HMC antibody moiety that specifically binds to a complex comprising a histone H3 peptide and an MHC class I protein comprising i) a heavy chain variable domain comprising the amino acid sequence of any one of SEQ ID NOs: 75-86, or a variant thereof having at least about 95% (for example at least about any of 96%, 97%, 98%, or 99%) sequence identity, and a light chain variable domain comprising the amino acid sequence of any one of SEQ ID NOs: 87-98, or a variant thereof having at least about 95% (including for example at least about any of 96%, 97%, 98%, or 99%) sequence identity; b) a transmembrane domain, and c) an intracellular signaling domain comprising a CD3ζ intracellular signaling sequence and a CD28 and/or 4-1BB intracellular signaling sequence. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease in an individual comprising administering to the individual an effective amount of a composition comprising an effector cell (such as a T cell) expressing an anti-HMC CAR comprising a) an extracellular domain comprising an anti-HMC antibody moiety that specifically binds to a complex comprising a histone H3 peptide and an MHC class I protein comprising a heavy chain variable domain comprising the amino acid sequence of any one of SEQ ID NOs: 75-86 and a light chain variable domain comprising the amino acid sequence of any one of SEQ ID NOs: 87-98; b) a transmembrane domain, and c) an intracellular signaling domain comprising a CD3ζ intracellular signaling sequence and a CD28 and/or 4-1BB intracellular signaling sequence. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

For example, in some embodiments, the anti-HMC CAR comprises an anti-HMC antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (for example about any of 1, 2, 3, 4, or 5) amino acid substitutions, individually, in HC-CDR1, HC-CDR2, HC-CDR3, LC-CDR1, and/or LC-CDR3, and/or up to about 3 (for example about any of 1, 2, or 3) amino acid substitutions in LC-CDR2.

In some embodiments, the anti-HMC CAR comprises an anti-HMC antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (such as about any of 1, 2, 3, 4, or 5) amino acid substitutions in the HC-CDR sequences and/or up to about 5 (such as about any of 1, 2, 3, 4, or 5) amino acid substitutions in the LC-CDR sequences.

In some embodiments, the anti-HMC CAR comprises an anti-HMC antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively.

In some embodiments, the anti-HMC CAR comprises an anti-HMC antibody moiety comprising heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively; or variants thereof having, individually, at least about 95% (for example at least about any of 96%, 97%, 98%, or 99%) sequence identity. In some embodiments, the anti-HMC antibody moiety comprises heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively.

In some embodiments, there is provided a method of treating a histone H3-related disease in an individual comprising administering to the individual an effective amount of a composition comprising an effector cell (such as a T cell) expressing an anti-HMC abTCR comprising a) an extracellular domain comprising an anti-HMC antibody moiety that specifically binds to a complex comprising a histone H3 peptide and an MHC class I protein and b) a T cell receptor module (TCRM) capable of recruiting at least one TCR-associated signaling module. In some embodiments, the histone H3 peptide is mutant histone K27M-H3.3 26-35 (SEQ ID NO: 7) or mutant histone K27M-H3.1 26-35 (SEQ ID NO: 8). In some embodiments, the histone H3 peptide is WT H3.3 26-35 (SEQ ID NO: 5) or WT H3.1 26-35 (SEQ ID NO: 6). In some embodiments, the MHC class I protein is HLA-A02. In some embodiments, the MHC class I protein is HLA-A*02:01. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease in an individual comprising administering to the individual an effective amount of a composition comprising an effector cell (such as a T cell) expressing an anti-HMC abTCR comprising a) an extracellular domain comprising an anti-HMC antibody moiety that specifically binds to a complex comprising a histone H3 peptide selected from mutant histone K27M-H3.3 26-35 (SEQ ID NO: 7), mutant histone K27M-H3.1 26-35 (SEQ ID NO: 8), WT H3.3 26-35 (SEQ ID NO: 5), or WT H3.1 26-35 (SEQ ID NO: 6) peptide and HLA-A*02:01, b) a transmembrane domain, and c) an intracellular signaling domain comprising a CD3 intracellular signaling sequence and a CD28 and/or 4-1BB intracellular signaling sequence. In some embodiments, the histone H3 peptide is mutant histone K27M-H3.3 26-35 (SEQ ID NO: 7). In some embodiments, the histone H3 peptide is mutant histone K27M-H3.1 26-35 (SEQ ID NO: 8). In some embodiments, the histone H3 peptide is WT H3.3 26-35 (SEQ ID NO: 5). In some embodiments, the histone H3 peptide is WT H3.1 26-35 (SEQ ID NO: 6). In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease in an individual comprising administering to the individual an effective amount of a composition comprising an effector cell (such as a T cell) expressing an anti-HMC abTCR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of SEQ ID NO: 158, or a variant thereof comprising up to about 3 (for example about any of 1, 2, or 3) amino acid substitutions, an HC-CDR2 comprising the amino acid sequence of SEQ ID NO: 159, or a variant thereof comprising up to about 3 (for example about any of 1, 2, or 3) amino acid substitutions, and/or an HC-CDR3 comprising the amino acid sequence of SEQ ID NO: 160 or 161, or a variant thereof comprising up to about 3 (for example about any of 1, 2, or 3) amino acid substitutions; and ii) a light chain variable domain comprising an LC-CDR1 comprising the amino acid sequence of SEQ ID NO: 162, or a variant thereof comprising up to about 3 (for example about any of 1, 2, or 3) amino acid substitutions, and/or an LC-CDR3 comprising the amino acid sequence of SEQ ID NO: 163, or a variant thereof comprising up to about 3 (for example about any of 1, 2, or 3) amino acid substitutions, b) a transmembrane domain, and c) an intracellular signaling domain comprising a CD3 intracellular signaling sequence and a CD28 and/or 4-1BB intracellular signaling sequence. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease in an individual comprising administering to the individual an effective amount of a composition comprising an effector cell (such as a T cell) expressing an anti-HMC abTCR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of SEQ ID NO: 158, an HC-CDR2 comprising the amino acid sequence of SEQ ID NO: 159, and/or an HC-CDR3 comprising the amino acid sequence of SEQ ID NO: 160 or 161; and ii) a light chain variable domain comprising an LC-CDR1 comprising the amino acid sequence of SEQ ID NO: 162, and/or an LC-CDR3 comprising the amino acid sequence of SEQ ID NO: 163, b) a transmembrane domain, and c) an intracellular signaling domain comprising a CD3ζ intracellular signaling sequence and a CD28 and/or 4-1BB intracellular signaling sequence. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease in an individual comprising administering to the individual an effective amount of a composition comprising an effector cell (such as a T cell) expressing an anti-HMC abTCR comprising a) an extracellular domain comprising an anti-HMC antibody moiety that specifically binds to a complex comprising a histone H3 peptide and an MHC class I protein comprising i) a heavy chain variable domain comprising an HC-CDR1 comprising the amino acid sequence of any one of SEQ ID NOs: 99-107, or a variant thereof comprising up to about 5 (such as about any of 1, 2, 3, 4, or 5) amino acid substitutions, an HC-CDR2 comprising the amino acid sequence of any one of SEQ ID NOs: 108-116, or a variant thereof comprising up to about 5 (such as about any of 1, 2, 3, 4, or 5) amino acid substitutions, and/or an HC-CDR3 comprising the amino acid sequence of any one of SEQ ID NOs: 117-128, or a variant thereof comprising up to about 5 (such as about any of 1, 2, 3, 4, or 5) amino acid substitutions; and ii) a light chain variable domain comprising an LC-CDR1 comprising the amino acid sequence of any one of SEQ ID NOs: 129-138, or a variant thereof comprising up to about 5 (such as about any of 1, 2, 3, 4, or 5) amino acid substitutions, an LC-CDR2 comprising the amino acid sequence of any one of SEQ ID NOs: 139-147, or a variant thereof comprising up to about 3 (such as about any of 1, 2, or 3) amino acid substitutions, and/or an LC-CDR3 comprising the amino acid sequence of any one of SEQ ID NOs: 148-157, or a variant thereof comprising up to about 5 (such as about any of 1, 2, 3, 4, or 5) amino acid substitutions; b) a transmembrane domain, and c) an intracellular signaling domain comprising a CD3ζ intracellular signaling sequence and a CD28 and/or 4-1BB intracellular signaling sequence. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease in an individual comprising administering to the individual an effective amount of a composition comprising an effector cell (such as a T cell) expressing an anti-HMC abTCR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; or a variant thereof comprising up to about 5 (such as about any of 1, 2, 3, 4, or 5) amino acid substitutions in the HC-CDR sequences; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; or a variant thereof comprising up to about 5 (such as about any of 1, 2, 3, 4, or 5) amino acid substitutions in the LC-CDR sequences; b) a transmembrane domain, and c) an intracellular signaling domain comprising a CD3ζ intracellular signaling sequence and a CD28 and/or 4-1BB intracellular signaling sequence. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease in an individual comprising administering to the individual an effective amount of a composition comprising an effector cell (such as a T cell) expressing an anti-HMC abTCR comprising a) an extracellular domain comprising an anti-HMC antibody moiety that specifically binds to a complex comprising a histone H3 peptide and an MHC class I protein comprising i) a heavy chain variable domain sequence comprising an HC-CDR1 comprising the amino acid sequence of any one of SEQ ID NOs: 99-107; an HC-CDR2 comprising the amino acid sequence of any one of SEQ ID NOs: 108-116; and/or an HC-CDR3 comprising the amino acid sequence of any one of SEQ ID NOs: 117-128; and ii) a light chain variable domain sequence comprising an LC-CDR1 comprising the amino acid sequence of any one of SEQ ID NOs: 129-138; an LC-CDR2 comprising the amino acid sequence of any one of SEQ ID NOs: 139-147; and/or an LC-CDR3 comprising the amino acid sequence of any one of SEQ ID NOs: 148-157; b) a transmembrane domain, and c) an intracellular signaling domain comprising a CD3ζ intracellular signaling sequence and a CD28 and/or 4-1BB intracellular signaling sequence. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease in an individual comprising administering to the individual an effective amount of a composition comprising an effector cell (such as a T cell) expressing an anti-HMC abTCR comprising a) an extracellular domain comprising an anti-HMC antibody moiety that specifically binds to a complex comprising a histone H3 peptide and an MHC class I protein comprising i) a heavy chain variable domain comprising the amino acid sequence of any one of SEQ ID NOs: 75-86, or a variant thereof having at least about 95% (for example at least about any of 96%, 97%, 98%, or 99%) sequence identity, and a light chain variable domain comprising the amino acid sequence of any one of SEQ ID NOs: 87-98, or a variant thereof having at least about 95% (including for example at least about any of 96%, 97%, 98%, or 99%) sequence identity; b) a transmembrane domain, and c) an intracellular signaling domain comprising a CD3ζ intracellular signaling sequence and a CD28 and/or 4-1BB intracellular signaling sequence. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

In some embodiments, there is provided a method of treating a histone H3-related disease in an individual comprising administering to the individual an effective amount of a composition comprising an effector cell (such as a T cell) expressing an anti-HMC abTCR comprising a) an extracellular domain comprising an anti-HMC antibody moiety that specifically binds to a complex comprising a histone H3 peptide and an MHC class I protein comprising a heavy chain variable domain comprising the amino acid sequence of any one of SEQ ID NOs: 75-86 and a light chain variable domain comprising the amino acid sequence of any one of SEQ ID NOs: 87-98; b) a transmembrane domain, and c) an intracellular signaling domain comprising a CD3ζ intracellular signaling sequence and a CD28 and/or 4-1BB intracellular signaling sequence. In some embodiments, the individual is human. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

For example, in some embodiments, the anti-HMC abTCR comprises an anti-HMC antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (for example about any of 1, 2, 3, 4, or 5) amino acid substitutions, individually, in HC-CDR1, HC-CDR2, HC-CDR3, LC-CDR1, and/or LC-CDR3, and/or up to about 3 (for example about any of 1, 2, or 3) amino acid substitutions in LC-CDR2.

In some embodiments, the anti-HMC abTCR comprises an anti-HMC antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively; or variants thereof comprising up to about 5 (such as about any of 1, 2, 3, 4, or 5) amino acid substitutions in the HC-CDR sequences and/or up to about 5 (such as about any of 1, 2, 3, 4, or 5) amino acid substitutions in the LC-CDR sequences.

In some embodiments, the anti-HMC abTCR comprises an anti-HMC antibody moiety comprising heavy chain and light chain variable domains comprising HC-CDR1, HC-CDR2, HC-CDR3, LC-CDR1, LC-CDR2, and LC-CDR3 comprising the amino acid sequences of SEQ ID NOs: 99, 108, 117, 129, 139, and 148, respectively, SEQ ID NOs: 99, 108, 118, 129, 140, and 149, respectively, SEQ ID NOs: 99, 108, 119, 130, 140, and 148, respectively, SEQ ID NOs: 99, 108, 120, 130, 140, and 148, respectively, SEQ ID NOs: 100, 109, 121, 131, 141, and 150, respectively, SEQ ID NOs: 101, 110, 122, 132, 142, and 151, respectively, SEQ ID NOs: 102, 111, 123, 133, 143, and 152, respectively, SEQ ID NOs: 103, 112, 124, 134, 144, and 153, respectively, SEQ ID NOs: 104, 113, 125, 135, 145, and 154, respectively, SEQ ID NOs: 105, 114, 126, 136, 146, and 155, respectively, SEQ ID NOs: 106, 115, 127, 137, 145, and 156, respectively, or SEQ ID NOs: 107, 116, 128, 138, 147, and 157, respectively.

In some embodiments, the anti-HMC abTCR comprises an anti-HMC antibody moiety comprising heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively; or variants thereof having, individually, at least about 95% (for example at least about any of 96%, 97%, 98%, or 99%) sequence identity. In some embodiments, the anti-HMC antibody moiety comprises heavy chain and light chain variable domains comprising the amino acid sequence of SEQ ID NOs: 75 and 87, respectively, SEQ ID NOs: 76 and 88, respectively, SEQ ID NOs: 77 and 89, respectively, SEQ ID NOs: 78 and 90, respectively, SEQ ID NOs: 79 and 91, respectively, SEQ ID NOs: 80 and 92, respectively, SEQ ID NOs: 81 and 93, respectively, SEQ ID NOs: 82 and 94, respectively, SEQ ID NOs: 83 and 95, respectively, SEQ ID NOs: 84 and 96, respectively, SEQ ID NOs: 85 and 97, respectively, or SEQ ID NOs: 86 and 98, respectively.

Cancers

The anti-HMC constructs and anti-HMC CAR cells in some embodiments can be useful for treating histone H3-related cancer. Cancers that may be treated using any of the methods described herein include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the anti-HMC constructs and anti-HMC chimeric receptor effector cells of the invention include, but are not limited to, carcinoma, blastoma, sarcoma, melanoma, neuroendocrine tumors, and glioma, and certain leukemia or lymphoid malignancies, benign and malignant tumors, and malignancies e.g., sarcomas, carcinomas, melanomas, and gliomas. Adult tumors/cancers and pediatric tumors/cancers are also included.

Solid tumors contemplated for treatment by any of the methods described herein include CNS tumors, such as glioma (e.g., brainstem glioma and mixed gliomas), glioblastoma (also known as glioblastoma multiforme), astrocytoma (such as high-grade astrocytoma), pediatric glioma or glioblastoma (such as pediatric high-grade glioma (HGG) and diffuse intrinsic pontine glioma (DIPG)), CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases.

In some embodiments, the histone H3-related cancer is pediatric glioma. In some embodiments, the pediatric glioma is a low-grade glioma. In some embodiments, the pediatric glioma is a high-grade glioma (HGG). In some embodiments, the pediatric glioma is glioblastoma multiforme. In some embodiments, the pediatric glioma is diffuse intrinsic pontine glioma (DIPG). In some embodiments, the DIPG is grade II. In some embodiments, the DIPG is grade III. In some embodiments, the DIPG is grade IV.

Additional solid tumors contemplated for treatment include fibrosarcoma, myxosarcoma, liposarcoma, chondrosarcoma (such as clear-cell chondrosarcoma), chondroblastoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer (e.g., cervical carcinoma and pre-invasive cervical dysplasia), cancer of the anus, anal canal, or anorectum, vaginal cancer, cancer of the vulva (e.g., squamous cell carcinoma, intraepithelial carcinoma, adenocarcinoma, and fibrosarcoma), penile cancer, oropharyngeal cancer, head cancers (e.g., squamous cell carcinoma), neck cancers (e.g., squamous cell carcinoma), testicular cancer (e.g., seminoma, teratoma, embryonal carcinoma, teratocarcinoma, choriocarcinoma, sarcoma, Leydig cell tumor, fibroma, fibroadenoma, adenomatoid tumors, and lipoma), bladder carcinoma, melanoma, cancer of the uterus (e.g., endometrial carcinoma), and urothelial cancers (e.g., squamous cell carcinoma, transitional cell carcinoma, adenocarcinoma, ureter cancer, and urinary bladder cancer).

Hematologic cancers contemplated for treatment by any of the methods described herein include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Cancer treatments can be evaluated, for example, by tumor regression, tumor weight or size shrinkage, time to progression, duration of survival, progression free survival, overall response rate, duration of response, quality of life, protein expression and/or activity. Approaches to determining efficacy of the therapy can be employed, including for example, measurement of response through radiological imaging.

Methods for Diagnosis and Imaging Using Anti-HMC Constructs

Labeled anti-HMC antibody moieties and derivatives and analogs thereof, which specifically bind to an HMC on the surface of a cell, can be used for diagnostic purposes to detect, diagnose, or monitor a histone H3-related disease. For example, the anti-HMC antibody moieties of the invention can be used in in situ, in vivo, ex vivo, and in vitro diagnostic assays or imaging assays. In some embodiments, the histone H3-related disease is a K27M-H3.3-positive disease. In some embodiments, the histone H3-related disease is a K27M-H3.1-positive disease. In some embodiments, the K27M-H3.3- or K27M-H3.1-positive disease is cancer, e.g., pediatric high grade glioma, such as DIPG.

Additional embodiments of the invention include methods of diagnosing a histone H3-related disease in an individual (e.g., a mammal such as a human). The methods comprise detecting HMC-presenting cells in the individual. In some embodiments, the histone H3-related disease is a K27M-H3-positive disease, such as a K27M-H3.3-positive or K27M-H3.1-positive disease. In some embodiments, the K27M-H3.3- or K27M-H3.1-positive disease is cancer, e.g., pediatric high grade glioma, such as DIPG. In some embodiments, there is provided a method of diagnosing a histone H3-related disease in an individual (e.g., a mammal, such as a human) comprising (a) administering an effective amount of a labeled anti-HMC antibody moiety according to any of the embodiments described above to the individual; and (b) determining the level of the label in the individual, such that a level of the label above a threshold level indicates that the individual has the histone H3-related disease. The threshold level can be determined by various methods, including, for example, by detecting the label according to the method of diagnosing described above in a first set of individuals that have the histone H3-related disease and a second set of individuals that do not have the histone H3-related disease, and setting the threshold to a level that allows for discrimination between the first and second sets. In some embodiments, the threshold level is zero, and the method comprises determining the presence or absence of the label in the individual. In some embodiments, the method further comprises waiting for a time interval following the administering of step (a) to permit the labeled anti-HMC antibody moiety to preferentially concentrate at sites in the individual where the HMC is expressed (and for unbound labeled anti-HMC antibody moiety to be cleared). In some embodiments, the method further comprises subtracting a background level of the label. Background level can be determined by various methods, including, for example, by detecting the label in the individual prior to administration of the labeled anti-HMC antibody moiety, or by detecting the label according to the method of diagnosing described above in an individual that does not have the histone H3-related disease.

Anti-HMC antibody moieties of the invention can be used to assay levels of HMC-presenting cell in a biological sample using methods known to those of skill in the art. Suitable antibody labels are known in the art and include enzyme labels, such as, glucose oxidase; radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), samarium ($^{153}$Sm), lutetium ($^{177}$Lu), gadolinium ($^{159}$Gd), promethium ($^{149}$Pm), lanthanum ($^{140}$La), ytterbium ($^{175}$Yb) holmium ($^{166}$Ho), yttrium ($^{90}$Y), scandium ($^{47}$Sc), rhenium ($^{186}$Re, $^{188}$Re), praseodymium ($^{142}$Pr), rhodium ($^{105}$Rh), and ruthenium ($^{97}$Ru); luminol; fluorescent labels, such as fluorescein and rhodamine; and biotin.

Techniques known in the art may be applied to labeled anti-HMC antibody moieties of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003). Aside from the above assays, various in vivo and ex vivo assays are available to the skilled practitioner. For example, one can expose cells within the body of the subject to an anti-HMC antibody moiety which is optionally labeled with a detectable label, e.g., a radioactive isotope, and binding of the anti-HMC antibody moiety to the cells can be evaluated, e.g., by external scanning for radioactivity or by analyzing a sample (e.g., a biopsy or other biological sample) derived from a subject previously exposed to the anti-HMC antibody moiety.

Articles of Manufacture and Kits

In some embodiments of the invention, there is provided an article of manufacture containing materials useful for the treatment of a histone H3-related disease, for delivering an anti-HMC construct to a cell presenting an HMC on its surface, or for isolation or detection of HMC-presenting cells in an individual. In some embodiments, the histone H3-related disease is a K27M-H3-positive disease, such as a K27M-H3.3-positive or K27M-H3.1 positive disease. In some embodiments, the K27M-H3.3- or K27M-H3.1-positive disease is cancer, e.g., pediatric high grade glioma, such as DIPG. The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a histone H3-related disease, and may have a sterile access port (for example the container may be an intravenous solution bag or a vial having a stopper pierceable by a hypodermic injection needle). At least one active agent in the composition is an anti-HMC construct of the invention. The label or package insert indicates that the composition is used for treating the particular condition. The label or package insert will further comprise instructions for administering the anti-HMC construct composition to the patient. Articles of manufacture and kits comprising combinatorial therapies described herein are also contemplated.

Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating a histone H3-related disease. In some embodiments, the histone H3-related disease is a K27M-H3-positive disease, such as a K27M-H3.3-positive or K27M-H3.1 positive disease. In some embodiments, the K27M-H3.3- or K27M-H3.1-positive disease is cancer, e.g., pediatric high grade glioma, such as DIPG.

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

Kits are also provided that are useful for various purposes, e.g., for treatment of a histone H3-related disease, for delivering an anti-HMC construct to a cell presenting an HMC on its surface, or for isolation or detection of HMC-presenting cells in an individual, optionally in combination with the articles of manufacture. In some embodiments, the histone H3-related disease is a K27M-H3-positive disease, such as a K27M-H3.3-positive or K27M-H3.1 positive disease. In some embodiments, the K27M-H3.3- or K27M-H3.1-positive disease is cancer, e.g., pediatric high grade glioma, such as DIPG. Kits of the invention include one or more containers comprising an anti-HMC construct composition (or unit dosage form and/or article of manufacture), and in some embodiments, further comprise another agent (such as the agents described herein) and/or instructions for use in accordance with any of the methods described herein. The kit may further comprise a description of selection of individuals suitable for treatment. Instructions supplied in the kits of the invention are typically written instructions on a label or package insert (e.g., a paper sheet included in the kit), but machine-readable instructions (e.g., instructions carried on a magnetic or optical storage disk) are also acceptable.

For example, in some embodiments, the kit comprises a composition comprising an anti-HMC construct (e.g., a full-length anti-HMC antibody, a multi-specific anti-HMC molecule (such as a bispecific anti-HMC antibody), or an anti-HMC immunoconjugate). In some embodiments, the kit comprises a) a composition comprising an anti-HMC construct, and b) an effective amount of at least one other agent, wherein the other agent increases the expression of MHC class I proteins and/or enhances the surface presentation of mutant histone H3 peptides by MHC class I proteins (e.g., IFNγ, IFNβ, IFNα, or Hsp90 inhibitor). In some embodiments, the kit comprises a) a composition comprising an anti-HMC construct, and b) instructions for administering the anti-HMC construct composition to an individual for treatment of a histone H3-related disease. In some embodiments, the kit comprises a) a composition comprising an anti-HMC construct, b) an effective amount of at least one other agent, wherein the other agent increases the expression of MHC class I proteins and/or enhances the surface presentation of mutant histone H3 peptides by MHC class I proteins (e.g., IFNγ, IFNβ, IFNα, or Hsp90 inhibitor), and c) instructions for administering the anti-HMC construct composition and the other agent(s) to an individual for treatment of an histone H3-related disease. In some embodiments, the histone H3-related disease is a K27M-H3-positive disease, such as a K27M-H3.3-positive or K27M-H3.1 positive disease. In some embodiments, the K27M-H3.3- or K27M-H3.1-positive disease is cancer, e.g., pediatric high grade glioma, such as DIPG. The anti-HMC construct and the other agent(s) can be present in separate containers or in a single container. For example, the kit may comprise one distinct composition or two or more compositions wherein one composition comprises an anti-HMC construct and another composition comprises another agent.

In some embodiments, the kit comprises a) a composition comprising an anti-HMC construct (e.g., a full-length anti-HMC antibody, a multi-specific anti-HMC molecule (such as a bispecific anti-HMC antibody), or an anti-HMC immunoconjugate), and b) instructions for combining the anti-HMC construct with cells (such as cells, e.g., immune cells, derived from an individual) to form a composition comprising anti-HMC construct/cell conjugates and administering the anti-HMC construct/cell conjugate composition to the individual for treatment of a histone H3-related disease. In some embodiments, the kit comprises a) a composition comprising an anti-HMC construct, and b) a cell (such as a cytotoxic cell). In some embodiments, the kit comprises a) a composition comprising an anti-HMC construct, b) a cell (such as a cytotoxic cell), and c) instructions for combining the anti-HMC construct with the cell to form a composition comprising anti-HMC construct/cell conjugates and administering the anti-HMC construct/cell conjugate composition to an individual for the treatment of a histone H3-related disease. In some embodiments, the kit comprises a composition comprising an anti-HMC construct in association with a cell (such as a cytotoxic cell). In some embodiments, the kit comprises a) a composition comprising an anti-HMC construct in association with a cell (such as a cytotoxic cell), and b) instructions for administering the composition to an individual for the treatment of a histone H3-related disease. In some embodiments, the association is by conjugation of the anti-HMC construct to a molecule on the surface of the cell. In some embodiments, the association is by insertion of a portion of the anti-HMC construct into the outer membrane of the cell. In some embodiments, the histone H3-related disease is a K27M-H3-positive disease, such as a K27M-H3.3-positive or K27M-H3.1 positive disease. In some embodiments, the K27M-H3.3- or K27M-H3.1-positive disease is cancer, e.g., pediatric high grade glioma, such as DIPG.

In some embodiments, the kit comprises a nucleic acid (or set of nucleic acids) encoding an anti-HMC construct (e.g., a full-length anti-HMC antibody, a multi-specific anti-HMC molecule (such as a bispecific anti-HMC antibody), an anti-HMC CAR, an anti-HMC abTCR, or an anti-HMC immunoconjugate) or polypeptide portions thereof. In some embodiments, the kit comprises a) a nucleic acid (or set of nucleic acids) encoding an anti-HMC construct or polypeptide portions thereof, and b) a host cell (such as an effector cell) for expressing the nucleic acid (or set of nucleic acids). In some embodiments, the kit comprises a) a nucleic acid (or set of nucleic acids) encoding an anti-HMC construct or polypeptide portions thereof, and b) instructions for i) expressing the anti-HMC construct in a host cell (such as an effector cell, e.g., a T cell), ii) preparing a composition comprising the anti-HMC construct or the host cell expressing the anti-HMC construct, and iii) administering the composition comprising the anti-HMC construct or the host cell expressing the anti-HMC construct to an individual for the treatment of a histone H3-related disease. In some embodiments, the host cell is derived from the individual. In some embodiments, the kit comprises a) a nucleic acid (or set of nucleic acids) encoding an anti-HMC construct or polypeptide portions thereof, b) a host cell (such as an effector cell) for expressing the nucleic acid (or set of nucleic acids), and c) instructions for i) expressing the anti-HMC construct in the host cell, ii) preparing a composition comprising the anti-HMC construct or the host cell expressing the anti-HMC construct, and iii) administering the composition comprising the anti-HMC construct or the host cell expressing the anti-HMC construct to an individual for the treatment of a histone H3-related disease. In some embodiments, the histone H3-related disease is a K27M-H3-positive disease, such as a K27M-H3.3-positive or K27M-H3.1 positive disease. In some embodiments, the K27M-H3.3- or K27M-H3.1-positive disease is cancer, e.g., pediatric high grade glioma, such as DIPG.

In some embodiments, the kit comprises a nucleic acid encoding an anti-HMC CAR or anti-HMC abTCR. In some embodiments, the kit comprises a vector comprising a nucleic acid encoding an anti-HMC CAR or anti-HMC abTCR. In some embodiments, the kit comprises a) a vector comprising a nucleic acid encoding an anti-HMC CAR or anti-HMC abTCR, and b) instructions for i) introducing the vector into effector cells, such as T cells derived from an individual, ii) preparing a composition comprising the anti-HMC CAR or anti-HMC abTCR effector cells, and iii) administering the anti-HMC CAR or anti-HMC abTCR effector cell composition to the individual for treatment of a histone H3-related disease. In some embodiments, the histone H3-related disease is a K27M-H3-positive disease, such as a K27M-H3.3-positive or K27M-H3.1 positive disease. In some embodiments, the K27M-H3.3- or K27M-H3.1-positive disease is cancer, e.g., pediatric high grade glioma, such as DIPG.

The kits of the invention are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The instructions relating to the use of the anti-HMC construct compositions generally include information as to dosage, dosing schedule, and route of administration for the intended treatment. The containers may be unit doses, bulk packages (e.g., multi-dose packages) or subunit doses. For example, kits may be provided that contain sufficient dosages of an anti-HMC construct (e.g., a full-length anti-HMC antibody, a multi-specific anti-HMC molecule (such as a bispecific anti-HMC antibody), an anti-HMC CAR, an anti-HMC abTCR, or an anti-HMC immunoconjugate) as disclosed herein to provide effective treatment of an individual for an extended period, such as any of a week, 8 days, 9 days, 10 days, 11 days, 12 days, 13 days, 2 weeks, 3 weeks, 4 weeks, 6 weeks, 8 weeks, 3 months, 4 months, 5 months, 7 months, 8 months, 9 months, or more. Kits may also include multiple unit doses of the anti-HMC construct and pharmaceutical compositions and instructions for use and packaged in quantities sufficient for storage and use in pharmacies, for example, hospital pharmacies and compounding pharmacies.

EXEMPLARY EMBODIMENTS

Embodiment 1

An isolated anti-HMC construct comprising an antibody moiety that specifically binds to a complex comprising a histone H3 peptide and a major histocompatibility (MHC) class I protein ("HMC").

Embodiment 2

The isolated anti-HMC construct of embodiment 1, wherein the histone H3/MHC class I complex is present on a cell surface.

Embodiment 3

The isolated anti-HMC construct of embodiment 1, wherein the histone H3/MHC class I complex is present on the surface of a T cell.

Embodiment 4

The isolated anti-HMC construct of any one of embodiments 1-3, wherein the MHC class I protein is human leukocyte antigen (HLA)-A.

Embodiment 5

The isolated anti-HMC construct of embodiment 4, wherein the MHC class I protein is HLA-A02.

Embodiment 6

The isolated anti-HMC construct of embodiment 5, wherein the MHC class I protein is selected from the group consisting of HLA-A*02:01, HLA-A*02:02, HLA-A*02:06, HLA-A*02:07, and HLA-A*02:11.

Embodiment 7

The isolated anti-HMC construct of embodiment 6, wherein the MHC class I protein is HLA-A*02:01.

Embodiment 8

The isolated anti-HMC construct of any one of embodiments 1-7, wherein the antibody moiety cross-reacts with a complex comprising the histone H3 peptide and a second MHC class I protein having a different HLA allele than the MHC class I protein.

Embodiment 9

The isolated anti-HMC construct of any one of embodiments 1-8, wherein the histone H3 peptide is 8 to 12 amino acids in length.

Embodiment 10

The isolated anti-HMC construct of any one of embodiments 1-9, wherein the histone H3 peptide comprises amino acids 26-35 of any one of SEQ ID NOs: 1-4.

Embodiment 11

The isolated anti-HMC construct of any one of embodiments 1-10, wherein the histone H3 peptide comprises an amino acid sequence selected from the group consisting of SEQ ID NOs: 5-24.

Embodiment 12

The isolated anti-HMC construct of embodiment 10, wherein the histone H3 peptide has the amino acid sequence of RMSAPATGGV (SEQ ID NO: 7).

Embodiment 13

The isolated anti-HMC construct of embodiment 12, wherein the isolated anti-HMC construct cross-reacts with a complex comprising a variant of the histone H3 peptide having the amino acid sequence of RMSAPSTGGV (SEQ ID NO: 7) and the MHC class I protein.

Embodiment 14

The isolated anti-HMC construct of embodiment 10, wherein the histone H3 peptide has the amino acid sequence of RMSAPSTGGV (SEQ ID NO: 7).

Embodiment 15

The isolated anti-HMC construct of embodiment 14, wherein the isolated anti-HMC construct does not cross-react with a complex comprising a histone H3 peptide having the amino acid sequence of RKSAPATGGV (SEQ ID NO: 5) or RKSAPSTGGV (SEQ ID NO: 6) and the MHC class I protein.

Embodiment 16

The isolated anti-HMC construct of any one of embodiments 1-15, wherein the antibody moiety is human, humanized, synthetic, or semi-synthetic.

Embodiment 17

The isolated anti-HMC construct of any one of embodiments 1-16, wherein the antibody moiety is a full-length antibody, a Fab, a Fab', a (Fab')2, an Fv, or a single chain Fv (scFv).

Embodiment 18

The isolated anti-HMC construct of any one of embodiments 1-17, wherein the antibody moiety binds to the histone H3/MHC class I complex with an equilibrium dissociation constant (Kd) from about 0.1 pM to about 500 nM.

Embodiment 19

The isolated anti-HMC construct of any one of embodiments 1-18, wherein the isolated anti-HMC construct binds to the histone H3/MHC class I complex with a Kd from about 0.1 pM to about 500 nM.

Embodiment 20

The isolated anti-HMC construct of any one of embodiments 1-19, wherein the antibody moiety comprises:
i) a heavy chain variable domain comprising a heavy chain complementarity determining region (HC-CDR) 1 comprising the amino acid sequence of SEQ ID NO: 158, or a variant thereof comprising up to about 3 amino acid substitutions, an HC-CDR2 comprising the amino acid sequence of SEQ ID NO: 159, or a variant thereof comprising up to about 3 amino acid substitutions, and an HC-CDR3 comprising the amino acid sequence of SEQ ID NO: 160 or 161, or a variant thereof comprising up to about 3 amino acid substitutions; and
ii) a light chain variable domain comprising a light chain complementarity determining region (LC-CDR) 1 comprising the amino acid sequence of SEQ ID NO: 162, or a variant thereof comprising up to about 3 amino acid substitutions, and an LC-CDR3 comprising the amino acid sequence of SEQ ID NO: 163, or a variant thereof comprising up to about 3 amino acid substitutions.

Embodiment 21

The isolated anti-HMC construct of any one of embodiments 1-19, wherein the antibody moiety comprises:
i) a heavy chain variable domain comprising an HC-CDR1 comprising the amino acid sequence of any one of SEQ ID NOs: 99-107, or a variant thereof comprising up to about 5 amino acid substitutions, an HC-CDR2 comprising the amino acid sequence of any one of SEQ ID NOs: 108-116, or a variant thereof comprising up to about 5 amino acid substitutions, and an HC-CDR3 comprising the amino acid sequence of any one of SEQ ID NOs: 117-128; or a variant thereof comprising up to about 5 amino acid substitutions; and
ii) a light chain variable domain comprising an LC-CDR1 comprising the amino acid sequence of any one of SEQ ID NOs: 129-138, or a variant thereof comprising up to about 5 amino acid substitutions, an LC-CDR2 comprising the amino acid sequence of any one of SEQ ID NOs: 139-147, or a variant thereof comprising up to about 3 amino acid substitutions, and an LC-CDR3 comprising the amino acid sequence of any one of SEQ ID NOs: 148-157; or a variant thereof comprising up to about 5 amino acid substitutions.

Embodiment 22

The isolated anti-HMC construct of any one of embodiments 1-19, wherein the antibody moiety comprises:
i) a heavy chain (HC) variable domain comprising an HC-CDR1 comprising the amino acid sequence of any one of SEQ ID NOs: 99-107, an HC-CDR2 comprising the amino acid sequence of any one of SEQ ID NOs: 108-116, and an HC-CDR3 comprising the amino acid sequence of any one of SEQ ID NOs: 117-128; or a variant thereof comprising up to about 5 amino acid substitutions in the HC-CDR regions; and
ii) a light chain (LC) variable domain comprising an LC-CDR1 comprising the amino acid sequence of any one of SEQ ID NOs: 129-138, an LC-CDR2 comprising the amino acid sequence of any one of SEQ ID NOs: 139-147, and an LC-CDR3 comprising the amino acid sequence of any one of SEQ ID NOs: 148-157; or a variant thereof comprising up to about 5 amino acid substitutions in the LC-CDR regions.

Embodiment 23

The isolated anti-HMC construct of embodiment 21 or 22, wherein the antibody moiety comprises a) a heavy chain variable domain comprising the amino acid sequence of any one of SEQ ID NOs: 75-86, or a variant thereof having at least about 95% sequence identify to any one of SEQ ID NOs: 75-86; and b) a light chain variable domain comprising the amino acid sequence of any one of SEQ ID NOs: 87-98, or a variant thereof having at least about 95% sequence identity to any one of SEQ ID NOs: 87-98.

Embodiment 24

The isolated anti-HMC construct of embodiment 23, wherein the antibody moiety comprises a heavy chain variable domain comprising the amino acid sequence of any one of SEQ ID NOs: 75-86 and a light chain variable domain comprising the amino acid sequence of any one of SEQ ID NOs: 87-98.

Embodiment 25

The isolated anti-HMC construct of any one of embodiments 1-24, wherein the isolated anti-HMC construct is a full-length antibody.

Embodiment 26

The isolated anti-HMC construct of any one of embodiments 1-25, wherein the isolated anti-HMC construct is monospecific.

Embodiment 27

The isolated anti-HMC construct of any one of embodiments 1-25, wherein the isolated anti-HMC construct is multispecific.

Embodiment 28

The isolated anti-HMC construct of embodiment 27, wherein the isolated anti-HMC construct is bispecific.

Embodiment 29

The isolated anti-HMC construct of embodiment 27 or 28, wherein the isolated anti-HMC construct is a tandem scFv, a diabody (Db), a single chain diabody (scDb), a dual-affinity retargeting (DART) antibody, a dual variable domain (DVD) antibody, a knob-into-hole (KiH) antibody, a dock and lock (DNL) antibody, a chemically cross-linked antibody, a heteromultimeric antibody, or a heteroconjugate antibody.

Embodiment 30

The isolated anti-HMC construct of embodiment 29, wherein the isolated anti-HMC construct is a tandem scFv comprising two scFvs linked by a peptide linker.

Embodiment 31

The isolated anti-HMC construct of embodiment 30, wherein the peptide linker comprises the amino acid sequence of SEQ ID NO: 46.

Embodiment 32

The isolated anti-HMC construct of any one of embodiments 27-31, wherein the isolated anti-HMC construct further comprises a second antibody moiety that specifically binds to a second antigen.

Embodiment 33

The isolated anti-HMC construct of embodiment 32, wherein the second antigen is an antigen on the surface of a T cell.

Embodiment 34

The isolated anti-HMC construct of embodiment 33, wherein the second antigen is selected from the group consisting of CD3γ, CD3δ, CD3ε, CD3ζ, CD28, OX40, GITR, CD137, CD27, CD40L and HVEM.

Embodiment 35

The isolated anti-HMC construct of embodiment 33, wherein the second antigen is CD3ε, and wherein the isolated anti-HMC construct is a tandem scFv comprising an N-terminal scFv specific for the histone H3/MHC class I complex and a C-terminal scFv specific for CD3ε.

Embodiment 36

The isolated anti-HMC construct of embodiment 33, wherein the T cell is selected from the group consisting of a cytotoxic T cell, a helper T cell, and a natural killer T cell.

Embodiment 37

The isolated anti-HMC construct of embodiment 32, wherein the second antigen is an antigen on the surface of a natural killer cell, a neutrophil, a monocyte, a macrophage or a dendritic cell.

Embodiment 38

The isolated anti-HMC construct of any one of embodiments 1-24, wherein the isolated anti-HMC construct is a chimeric antigen receptor (CAR).

Embodiment 39

The isolated anti-HMC construct of embodiment 38, wherein the chimeric antigen receptor comprises an extracellular domain comprising the antibody moiety, a transmembrane domain, and an intracellular signaling domain comprising a CD3ζ intracellular signaling sequence and a CD28 and/or 4-1BB intracellular signaling sequence.

Embodiment 40

The isolated anti-HMC construct of any one of embodiments 1-24, wherein the isolated anti-HMC construct is a chimeric antibody/T cell receptor (abTCR) comprising an extracellular domain comprising the antibody moiety and a T cell receptor (TCR) module (TCRM) comprising TCR transmembrane domains.

Embodiment 41

The isolated anti-HMC construct of embodiment 40, wherein the TCRM is capable of recruiting at least one TCR-associated signaling module.

Embodiment 42

The isolated anti-HMC construct of embodiment 41, wherein the TCR-associated signaling module is selected from the group consisting of CD3δε, CD3γε, and ζζ.

Embodiment 43

The isolated anti-HMC construct of any one of embodiments 40-42, wherein the antibody moiety comprises:
a) a first polypeptide chain comprising a first antigen-binding domain comprising $V_H$ and $C_H1$ antibody domains; and
b) a second polypeptide chain comprising a second antigen-binding domain comprising $V_L$ and $C_L$ antibody domains,
wherein the $V_H$ and $C_H1$ domains of the first antigen-binding domain and the $V_L$ and $C_L$ domains of the second antigen-binding domain form a Fab-like antigen-binding module that specifically binds to the HMC.

Embodiment 44

The isolated anti-HMC construct of any one of embodiments 1-24, wherein the isolated anti-HMC construct is an immunoconjugate comprising the antibody moiety and an effector molecule.

Embodiment 45

The isolated anti-HMC construct of embodiment 44, wherein the effector molecule is a therapeutic agent selected from the group consisting of a drug, a toxin, a radioisotope, a protein, a peptide, and a nucleic acid.

Embodiment 46

The isolated anti-HMC construct of embodiment 45, wherein the therapeutic agent is a drug or a toxin.

Embodiment 47

The isolated anti-HMC construct of embodiment 44, wherein the effector molecule is a label.

Embodiment 48

A host cell expressing the isolated anti-HMC construct of any one of embodiments 1-47.

Embodiment 49

A nucleic acid encoding one or more polypeptides contained in the isolated anti-HMC construct of any one of embodiments 1-47.

Embodiment 50

A vector comprising the nucleic acid of embodiment 49.

Embodiment 51

An effector cell expressing the isolated anti-HMC construct of any one of embodiments 38-43.

Embodiment 52

The effector cell of embodiment 51, wherein the effector cell is a T cell.

Embodiment 53

A pharmaceutical composition comprising the isolated anti-HMC construct of any one of embodiments 1-46, the nucleic acid of embodiment 49, the vector of embodiment 50, or the effector cell of embodiment 51 or 52.

Embodiment 54

A method for detecting a cell presenting a complex comprising a histone H3 peptide and an MHC class I protein on its surface, comprising contacting the cell with the isolated anti-HMC construct of embodiment 47 and detecting the presence of the label on the cell.

Embodiment 55

A method for treating an individual having a histone H3-related disease, comprising administering to the individual an effective amount of the pharmaceutical composition of embodiment 53.

Embodiment 56

A method for treating an individual having a histone H3-related disease, comprising administering to the individual an effective amount of the effector cell of embodiment 51 or 52.

Embodiment 57

A method of diagnosing an individual having a histone H3-related disease, comprising:
a) administering an effective amount of the isolated anti-HMC construct of embodiment 47 to the individual; and
b) determining the level of the label in the individual, wherein a level of the label above a threshold level indicates that the individual has the histone H3-related disease.

Embodiment 58

A method of diagnosing an individual having a histone H3-related disease, comprising:
a) contacting a sample derived from the individual with the isolated anti-HMC construct of embodiment 47; and
b) determining the number of cells bound with the isolated anti-HMC construct in the sample, wherein a value for the number of cells bound with the isolated anti-HMC construct above a threshold level indicates that the individual has the histone H3-related disease.

Embodiment 59

The method of any one of embodiments 55-58, wherein the histone H3-related disease is a K27M-H3.3-positive disease or a K27M-H3.1-positive disease.

Embodiment 60

The method of any one of embodiments 55-59, wherein the histone H3-related disease is cancer.

Embodiment 61

The method of embodiment 60, wherein the cancer is pediatric glioma.

Embodiment 62

The method of embodiment 61, wherein the pediatric glioma is high-grade glioma (HGG) or diffuse intrinsic pontine glioma (DIPG).

Embodiment 63

The method of any one of embodiments 55-62, wherein the individual is human.

EXAMPLES

Those skilled in the art will recognize that several embodiments are possible within the scope and spirit of this invention. The invention will now be described in greater detail by reference to the following non-limiting examples. The following examples further illustrate the invention but, of course, should not be construed as in any way limiting its scope.

Materials

Cell Samples, Cell Lines, and Antibodies

The cell lines include: liver adenocarcinoma cell line SK-HEP-1 (ATCC HTB-52; HLA-A2$^+$, K27M-H3.3$^-$), breast adenocarcinoma cell line MCF-7 (ATCC HTB-22; HLA-A2$^+$, K27M-H3.3$^-$), cervical adenocarcinoma cell line HeLa (ATCC CCL-2; HLA-A2$^+$, K27M-H3.3$^-$), K27M-H3.3 DIPG cell lines SF7761 and SF8628 (Hashizume, R., et al. *Journal of neuro-oncology*, 110(3), 305-313; HLA-A2$^+$, K27M-H3.3$^+$), and lymphoblast cell line T2 (ATCC CRL-1992; HLA-A2$^+$, K27M-H3.3$^-$). T2 is a TAP-deficient cell line. The cell lines were cultured in RPMI 1640 supplemented with 5% FCS, penicillin, streptomycin, 2 mmol/L glutamine, and 2-mercaptoethanol at 37° C./5% CO$_2$.

All peptides were purchased and synthesized by Genemed Synthesis, Inc. (San Antonio, Tex.) or Elim Biopharm (Hayward, Calif.). Peptides were >90% pure. The peptides were dissolved in DMSO at 10 mg/mL and frozen at −80° C. Recombinant mutant histone H3 peptide/HLA-A*02:01 and control peptide/HLA-A*02:01 complexes were prepared by refolding the peptides with recombinant HLA-A02 (biotinylated at the C-terminus using BirA, Biotin-Protein ligase from Avidity (Aurora, Colo.)) and beta-2 microglobulin (β2M) (~2M). 20 control peptides (P20, SEQ ID NOs: 25-44) that bind HLA-A*02:01 were generated from the following 15 genes: BCR, BTG2, CALR, CD247, CSF2RA, CTSG, DDX5, DMTN, HLA-E, IFI30, IL7, PIM1, PPP2R1B, RPS6KB1, SSR1, and β-globin.

Example 1. Production of Biotinylated Histone H3 Peptide/HLA-A*02:01 Complex Monomers Biotinylated WT H3.3 26-35/HLA-A*02:01 complex monomers and mutant histone K27M-H3.3 26-35/HLA-A*02:01 complex monomers were prepared according to standard protocols (John D. Altman and Mark M. Davis, *Current Protocols in Immunology* 17.3.1-17.3.33, 2003). In brief, DNA encoding full-length human beta-2 microglobulin (P2m) was synthesized by Genewiz and cloned into vector pET-27b. DNA encoding HLA-A*02:01 ECD-BSP (BirA substrate peptide (BSP) fused to the C-terminus of HLA-A*02:01 extracellular domain (ECD)) was also synthesized by Genewiz and cloned into vector pET-27b. The vectors expressing human 2m and HLA-A*02:01 ECD-BSP were transformed into *E. coli* BL21 cells separately, and expressed proteins were isolated as inclusion bodies from bacterial culture. Peptide ligands WT H3.3 26-35 (RKSAPSTGGV, SEQ ID NO: 5) and mutant histone K27M-H3.3 26-35 (RMSAPSTGGV, SEQ ID NO: 7) were individually refolded with human 2m and HLA-A*02:01 ECD-BSP to form WT H3.3 26-35/HLA-A*02:01 complex monomer and mutant histone H3.3 26-35/HLA-A*02:01 complex monomer, respectively. Folded peptide/HLA-A*02:01 monomers were concentrated by ultrafiltration and further purified through size-exclusion chromatography. HiPrep 26/60 Sephacryl S-300 HR was equilibrated with 1.5 column volumes of Hyclone Dulbecco's Phosphate Buffered Saline solution (Thermo Scientific, Cat No. SH3002802). The unpurified sample was loaded and eluted with 1 column volume. The first peak, corresponding to misfolded aggregates, eluted at approximately 111 mL, the peak corresponding to the properly folded MHC complex was observed at 212 mL, and the peak corresponding to free 132M was observed at 267 mL (data not shown). Peptide/HLA-A*02:01 monomers were biotinylated via BirA-mediated enzymatic reaction. Biotinylated peptide/HLA-A*02:01 monomers were stored in PBS at −80° C.

SDS-PAGE of the purified histone H3.3 peptide/MHC complex can be performed to determine protein purity. For example, 1 μg of the protein complex is mixed with 2.5 μL of the NuPAGE LDS Sample Buffer (Life Technologies, NP0008) and brought up to 10 μL with deionized water. The sample is heated at 70° C. for 10 minutes, and then loaded onto the gel. Gel electrophoresis is performed at 180V for 1 hour.

Biotinylated WT H3.1 26-35/HLA-A*02:01 complex monomers and mutant histone K27M-H3.1 26-35/HLA-A*02:01 complex monomers can be prepared as described above, using WT H3.1 26-35 peptide (SEQ ID NO: 6) and K27M-H3.1 26-35 peptide (SEQ ID NO: 8), respectively.

Example 2. Selection and Characterization of scFv Specific for Mutant Histone K27M-H3 26-35/HLA-A*02:01 Complexes A collection of human scFv antibody phage display libraries (diversity=10×10$^{10}$) constructed by Eureka Therapeutics was used for the selection of human mAbs specific to mutant histone K27M-H3.3 26-35/HLA-A*02:01 complexes. 24 human phage scFv libraries were used to pan against the mutant histone K27M-H3.3 26-35/HLA-A*02:01 complex. In order to reduce the conformational change of MHCI complex introduced by immobilizing the protein complex onto plastic surfaces, cell panning was used in place of conventional plate panning. In cell panning, T2 cells loaded with mutant histone K27M-H3.3 26-35 peptide were first mixed with the human scFv phage library. T2 cells are a TAP-deficient, HLA-A*02:01$^+$ lymphoblast cell line. To load peptide, T2 cells were pulsed with peptides (50 μg/ml) in serum-free RPMI1640 medium. After extended washing with PBS, peptide-loaded T2 cells with bound scFv antibody phage were spun down. The bound clones were then eluted and used to infect *E. coli* XL1-Blue cells. The phage clones expressed in bacteria were then purified for the next round of panning. The cell panning was performed for 3 rounds to enrich for scFv phage clones that bound mutant histone K27M-H3.3 26-35/HLA-A*02:01 specifically, and 1,575 clones were randomly selected from among these for ELISA screening.

Streptavidin ELISA plates were coated with monomeric biotinylated mutant histone K27M-H3.3 26-35 peptide/HLA-A*02:01 complex or monomeric biotinylated WT H3.3 26-35 peptide/HLA-A*02:01 complex. Individual phage clones from enriched phage display panning pools against mutant histone K27M-H3.3 26-35 peptide/HLA-A*02:01 complex were incubated in the coated plates. Binding of the phage clones was detected by HRP-conjugated anti-M13 antibodies and developed using HRP substrate. The absorbance was read at 450 nm. 94 positive clones (stronger binding to the monomer with K27M-H3.3 26-35 than to the monomer with WT H3.3 26-35) were identified through ELISA screening of the phage clones enriched from phage panning, and 31 unique clones were identified by DNA sequencing of the ELISA-positive phage clones.

The 31 specific and unique clones were further tested for their binding to HLA-A*02:01/peptide complexes on the cell surface by flow cytometry (FACS analysis) using peptide-loaded live T2 cells. To confirm peptide loading, T2 cells were loaded with H3.3 26-35 WT peptide (T2-WT H3.3), K27M-H3.3 26-35 mutant peptide (T2-Mut H3.3), H3.1 26-35 WT peptide (T2-WT H3.1), K27M-H3.1 26-35 mutant peptide (T2 Mut H3.1), or a control mixture of 20 peptides (P20, SEQ ID NOs: 25-44) (T2-P20), stained with BB7.2, an anti-HLA-A*02 specific antibody, and analyzed by FACS for BB7.2 binding (FIG. 1A). Controls included T2 cells without peptide loading (T2). Peptide binding to MHC complex stabilizes cell-surface MHC complexes and this change in stability can be detected with BB7.2. Therefore, T2 cells loaded with MHC-binding peptide and stained with BB7.2 will have an enhanced fluorescence signal compared to T2 cells without peptide loading. BB7.2 binding data showed the WT and mutant histone H3 peptides and control peptide mixture P20 were able to bind HLA-A*02:01 molecules and form surface peptide/MHC complexes, as indicated by the increase in MFI compared to T2 cells (Table 6). No BB7.2 staining was observed for the negative controls.

Figure 1B:
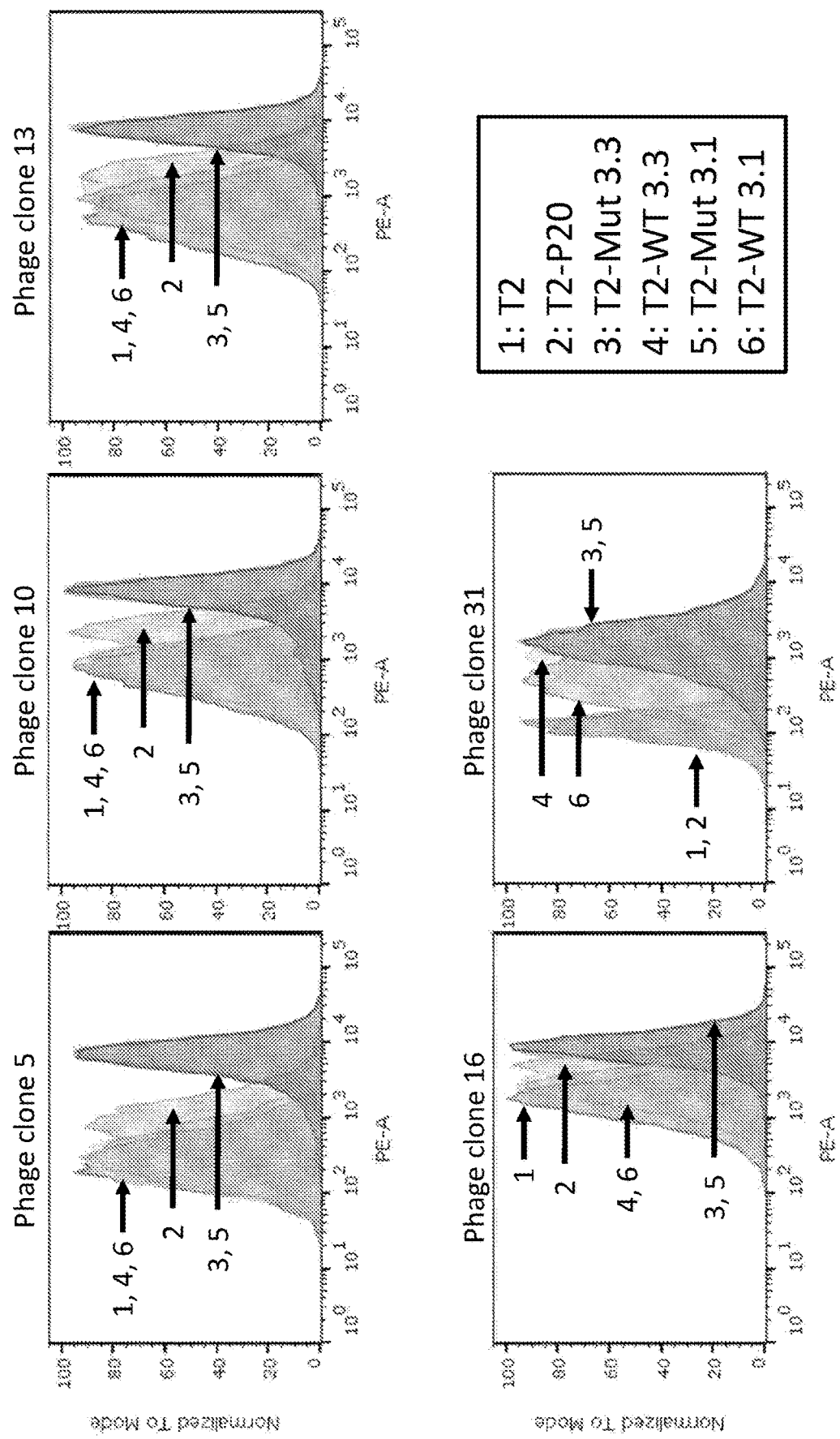
FIG. 1B shows FACS histogram plots for binding of K27M-H3.3 26-35 peptide/HLA-A02-selective phage clones to T2 cells (T2), T2 cells loaded with endogenous peptide mixture P20 (T2-P20), T2 cells loaded with K27M-H3.3 26-35 peptide (T2-Mut 3.3), T2 cells loaded with WT-H3.3 26-35 peptide (T2-WT 3.3), T2 cells loaded with K27M-H3.1 26-35 peptide (T2-Mut 3.1), or T2 cells loaded with WT-H3.1 26-35 peptide (T2-WT 3.1).
Figure 1B:
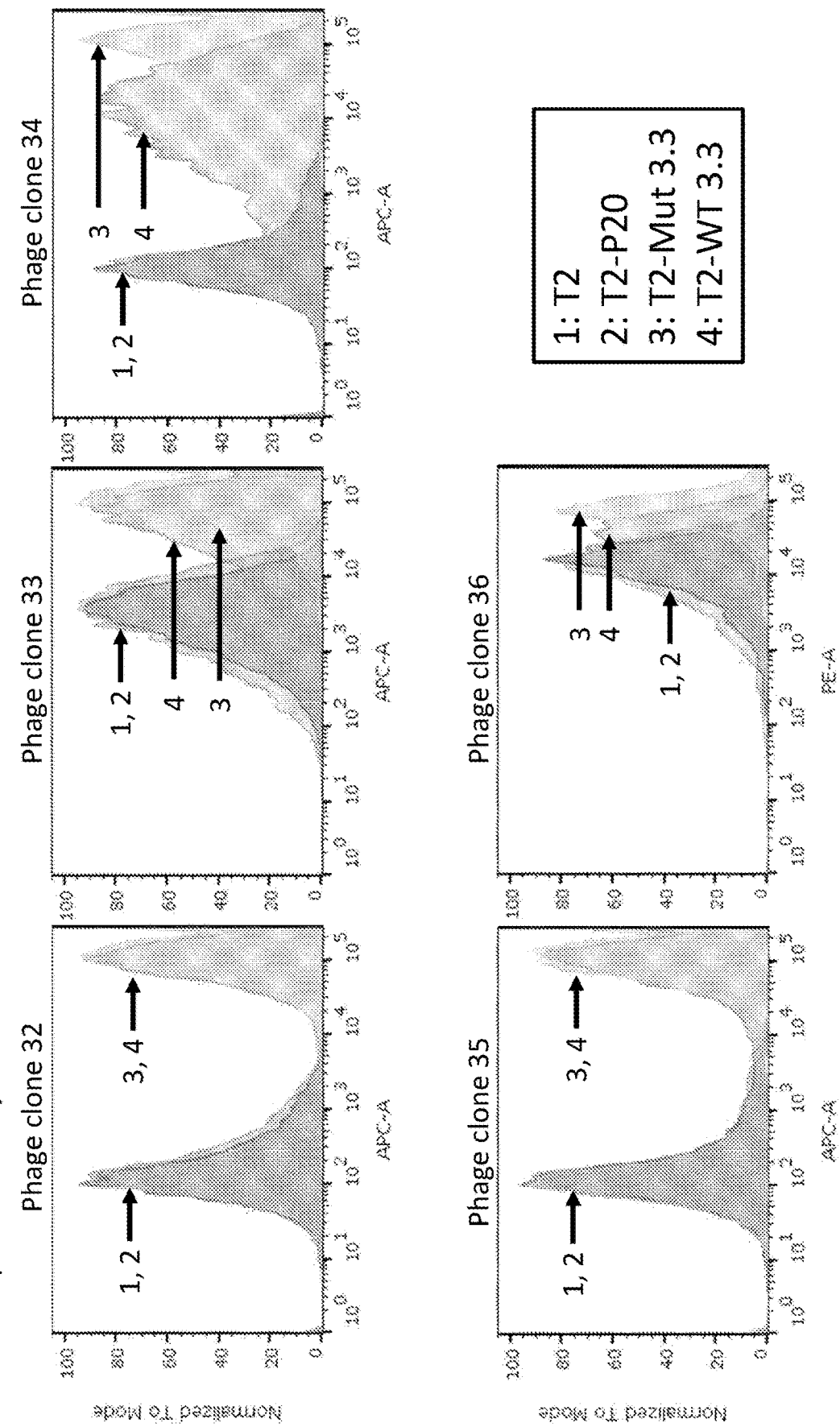
Figure 1B:
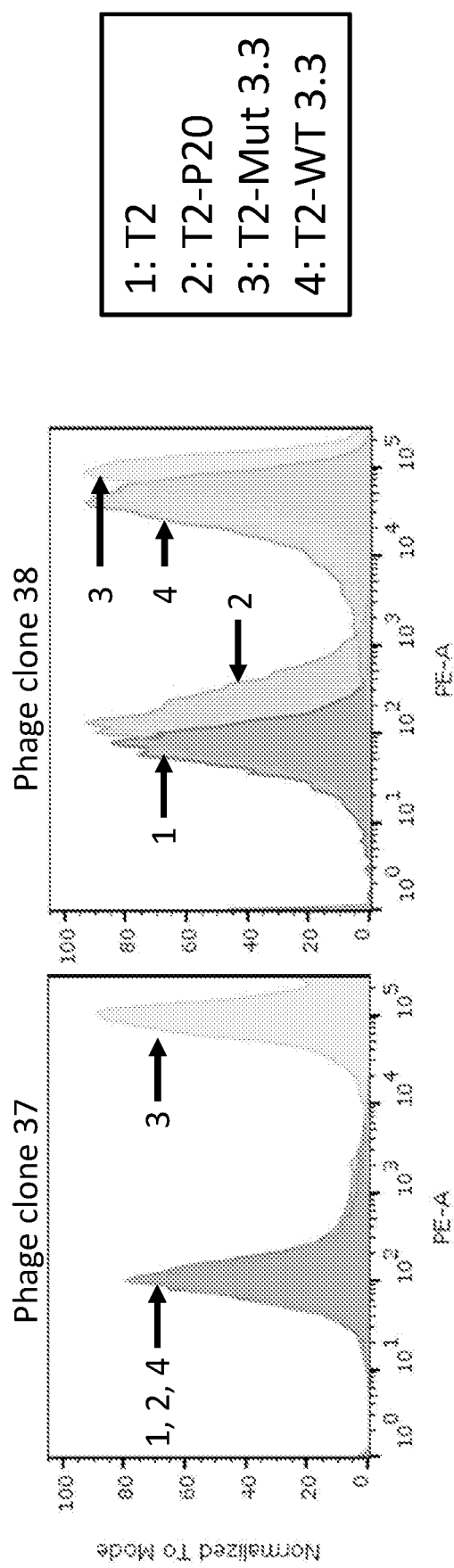

To test for phage binding T2 cells were loaded with H3.3 26-35 WT peptide (T2-WT H3.3), K27M-H3.3 26-35 mutant peptide (T2-Mut H3.3), H3.1 26-35 WT peptide (T2-WT H3.1), K27M-H3.1 26-35 mutant peptide (T2 Mut H3.1), or a control mixture of 20 peptides (P20, SEQ ID NOs: 25-44) (T2-P20), and peptide-loaded T2 cells were first stained with purified scFv phage clones, followed by a second staining with mouse anti-M13 mAb, and a third staining with R-PE conjugated horse anti-mouse IgG from Vector Labs. Each staining step was performed for between 30-60 minutes on ice and the cells were washed twice between stainings. Controls included T2 cells without peptide loading (T2), no staining, secondary antibody staining without phage (PE-α-mouse IgG only), primary and secondary antibody staining without phage (Mouse α-M13 Ab+PE-α-mouse IgG only), and staining with a negative control phage (NC phage). Among the 31 clones tested, 5 (phage clones 5, 10, 13, 16, and 31) specifically recognized mutant H3.3-loaded T2 cells. See FIG. 1B and Table 7. These phage clones did not recognize (or only weakly recognized) T2 cells loaded with control peptide mixture P20 in the context of HLA-A*02:01, or T2 cells without peptide loaded.

A second round of screening was carried out by randomly selecting 660 clones from the phage panning for validation by FACS analysis as described above (R-PE conjugated horse anti-mouse IgG (Vector Labs, Cat. #EI-2007) or APC conjugated anti-mouse IgG (Biolegend, Cat. #405308) was used for the third staining). 52 positive clones were identified (no binding to T2-P20, binding to T2-Mut H3.3), and 7 unique clones were identified by sequencing (phage clones 32, 33, 34, 35, 36, 37, and 38). See FIG. 1B and Table 7.

TABLE 6

BB7.2 Staining
Median MFI (PE-A)

| T2 | T2-P20 | T2-Mut H3.3 | T2-WT H3.3 | T2-Mut H3.1 | T2-WT H3.1 |
|---|---|---|---|---|---|
| 3,597 | 11,272 | 9,650 | 8,648 | 9,533 | 8,701 |

TABLE 7

Phage binding

Median MFI (PE-A)

| Staining | T2 | T2-P20 | T2-Mut H3.3 | T2-WT H3.3 | T2-Mut H3.1 | T2-WT H3.1 |
|---|---|---|---|---|---|---|
| No staining | 80 | 82 | 83 | 82 | 83 | 79 |
| PE-α-mouse IgG only | 82 | 82 | 83 | 83 | 85 | 83 |
| Mouse a-M13 Ab + PE-α-mouse IgG only | 80 | 82 | 83 | 83 | 85 | 86 |
| NC Phage | 122 | 124 | 133 | 128 | 130 | 131 |
| Phage clone 5 | 265 | 703 | 6,300 | 305 | 6,092 | 320 |
| Phage clone 10 | 686 | 2,010 | 7,656 | 849 | 6,987 | 770 |
| Phage clone 13 | 543 | 1,561 | 7,247 | 784 | 7,030 | 761 |
| Phage clone 16 | 1,695 | 4,189 | 7,917 | 2,443 | 8,211 | 2,320 |
| Phage clone 31 | 125 | 128 | 1,491 | 777 | 1,425 | 529 |
| Phage clone 32 | 132 | 146 | 100,422 | 90,819 | — | — |
| Phage clone 33 | 2,888 | 2,862 | 94,487 | 49,085 | — | — |
| Phage clone 34 | 109 | 109 | 95,065 | 8,337 | — | — |
| Phage clone 35 | 125 | 124 | 96,230 | 84,160 | — | — |
| Phage clone 36 | 12,655 | 10,967 | 68,623 | 33,645 | — | — |
| Phage clone 37 | 112 | 112 | 86,763 | 115 | — | — |
| Phage clone 38 | 66 | 128 | 69,889 | 32,935 | — | — |

On average, each nucleated cell in the human body expresses about half a million different peptide/MHC Class I complexes. In order to develop anti-peptide/MHCI-complex antibodies into drugs with high specificity and therapeutic index, it is essential for the antibodies to specifically recognize the target peptide/MHCI complex, but not the MHCI molecule itself, or MHCI molecules bound to other peptides presented on cell surfaces. The phage clones were screened against a mixture of 20 endogenous HLA-A*02:01 peptides, which were derived from proteins normally expressed in multiple types of nucleated human cells, such as globin alpha chain, beta chain, nuclear protein p68, and the like. As reported in Table 7, the mutant histone H3 peptide/HLA-A*02:01-specific antibody phage clones bound mutant histone H3 peptide/HLA-A*02:01 complex and in some cases wild-type histone H3 peptide/HLA-A*02:01 complex, but not HLA-A*02:01 complexes folded with the control endogenous peptides. We conclude that the identified antibodies are specific to mutant histone H3 peptide/HLA-A*02:01 complexes and in some cases wild-type histone H3 peptide/HLA-A*02:01 complexes, and do not recognize HLA-A*02:01 molecules bound to other HLA-A*02:01-restricted peptides.

Selection of human mAbs specific to mutant histone K27M-H3.1 26-35/HLA-A*02:01 complexes can be carried out, for example, as described above, replacing K27M-H3.3 26-35 with K27M-H3.1 26-35 and replacing WT H3.3 26-35 with WT H3.1 26-35.

Example 3. Characterization of FACS-Positive Mutant Histone K27M-H3.3-Specific Phage Clones Cross-Reactivity to Histone H3.1 26-35 Peptide Variants Clones selected from FACS binding analysis against mutant histone K27M-H3.3 26-35-loaded T2 cells are characterized further for cross-reactivity towards wild-type and mutant histone H3.1 26-35/HLA-A*02:01 complexes on live cell surfaces by FACS analysis using histone H3.1 26-35-loaded T2 cells. The histone H3.1 26-35 peptide sequences tested include wild-type histone H3.1 26-35 (RKSAPATGGV, SEQ ID NO: 6) and mutant histone K27M-H3.1 26-25 (RMSAPATGGV, SEQ ID NO: 8).

In brief, T2 cells are loaded with the histone H3.1 26-35 peptide. Controls include T2 cells without peptide loading (T2). The peptide-loaded T2 cells are stained with purified scFv phage clones, followed by a second staining with a mouse anti-M13 mAb and a third staining with R-PE conjugated horse anti-mouse IgG from Vector Labs. Each staining step is performed on ice for 30-60 minutes and the cells are washed twice between each staining.

Similar experiments can be carried out to determine cross-reactivity of K27M-H3.1-specific phage clones towards wild-type and mutant histone H3.3 26-35/HLA-A*02:01 complexes by replacing the H3.1 26-35 peptides with H3.3 26-35 peptides.

Epitope Mapping by Alanine Walking

To investigate with precision the epitope for the mAb recognition, variant histone K27M-H3.3 26-35 peptides with alanine substitutions at positions 1, 2, 3, 5, 6, 7, 8, 9, and 10, or variant K27M-H3.1 26-35 peptides with alanine substitutions at positions 1, 2, 3, 5, 7, 8, 9, and 10 (Table 8) are pulsed onto the surface of T2 cells. Antibody phage clones (K27M-H3.3-specific or K27M-H3.1-specific) are then tested for binding to these peptide-loaded T2 cells by FACS analysis. Controls include T2 cells without peptide loading (T2).

TABLE 8

| Peptide ID | Mutation | Peptide sequence | SEQ ID NO |
|---|---|---|---|
| K27M-H3.3 | — | RMSAPSTGGV | 7 |
| K27M-H3.3 A1 | R26A | AMSAPSTGGV | 9 |
| K27M-H3.3 A2 | M27A | RASAPSTGGV | 10 |
| K27M-H3.3 A3 | S28A | RMAAPSTGGV | 11 |
| K27M-H3.3 A5 | P30A | RMSAASTGGV | 12 |
| K27M-H3.3 A6 | S31A | RMSAPATGGV | 8 |
| K27M-H3.3 A7 | T32A | RMSAPSAGGV | 13 |
| K27M-H3.3 A8 | G33A | RMSAPSTAGV | 14 |
| K27M-H3.3 A9 | G34A | RMSAPSTGAV | 15 |
| K27M-H3.3 A10 | V35A | RMSAPSTGGA | 16 |
| K27M-H3.1 | — | RMSAPATGGV | 8 |
| K27M-H3.1 A1 | R26A | AMSAPATGGV | 17 |
| K27M-H3.1 A2 | M27A | RASAPATGGV | 18 |
| K27M-H3.1 A3 | S28A | RMAAPATGGV | 19 |
| K27M-H3.1 A5 | P30A | RMSAAATGGV | 20 |

TABLE 8-continued

| Peptide ID | Mutation | Peptide sequence | SEQ ID NO |
|---|---|---|---|
| K27M-H3.1 A7 | T32A | RMSAPAAGGV | 21 |
| K27M-H3.1 A8 | G33A | RMSAPATAGV | 22 |
| K27M-H3.1 A9 | G34A | RMSAPATGAV | 23 |
| K27M-H3.1 A10 | V35A | RMSAPATGGA | 24 |

Antibody Binding Specificity Evaluation Against Endogenous Peptide

Phage clones may also be screened against individual endogenous HLA-A*02:01 peptides derived from proteins normally expressed in multiple types of nucleated human cells, such as the peptides contained in P20 (SEQ ID NOs: 25-44). For example, recombinant peptide/HLA-A*02:01 complexes folded with 20 endogenous peptides (SEQ ID NOs: 25-44) separately are coated on streptavidin plates and antibody binding is determined through ELISA analysis. In brief, individual phage clones are incubated on the peptide/HLA-A*02:01 complex-coated plates. Binding of the phage clones is detected by HRP-conjugated anti-M13 antibodies and developed using HRP substrate. The absorbance is read at 450 nm. Alternatively, or in addition, FACS assays, for example as described above, are carried out with endogenous HLA-A*02:01 peptide-loaded T 2 cells.

Example 4. Engineering Bispecific Antibodies

Bispecific antibodies (BsAbs) are generated using scFv sequences of the histone H3/HLA-A*02:01-specific phage clones (such as mutant histone K27M-H3.3/HLA-A*02:01-specific or mutant histone K27M-H3.1/HLA-A*02:01-specific phage clones). The BsAbs are single-chain bispecific antibodies comprising the scFv sequence of a histone H3/HLA-A*02:01-specific phage clone (from N-terminus to C-terminus: light chain variable region (LCVR), scFv linker (SEQ ID NO: 46), heavy chain variable region (HCVR), e.g., phage clone 5 scFv (SEQ ID NO: 45)) fused to an anti-human CD3ε mouse monoclonal scFv at the C-terminal end (SEQ ID NO: 47) (Brischwein, K. et al., *Molecular Immunology* 43:1129-1143, 2006) by a BsAb linker (SEQ ID NO: 48). Exemplary phage clone heavy and light chain variable regions used for generating the BsAbs are listed in Table 9. DNA fragments coding for the anti-histone H3 peptide/HLA-A02 scFv and the anti-human CD3ε scFv are synthesized by Genewiz and subcloned into Eureka's mammalian expression vector pGSN-Hyg using standard DNA techniques. A hexhistamine tag may be inserted at the C-terminal end for antibody purification and detection. Chinese hamster ovary (CHO) cells are transfected with the BsAb expression vector, and then cultured for 7 days for BsAb antibody production. CHO cell supernatants containing secreted anti-histone H3 peptide/MHC BsAb molecules are collected. BsAbs are purified by affinity chromatography, for example by using a HisTrap HP column (GE healthcare) and an AKTA FPLC system. Briefly, CHO cell culture is clarified and loaded onto the column with low imidazole concentration (20 mM), and then an isocratic high imidazole concentration elution buffer (500 mM) is used to elute the bound BsAb proteins. Purity and molecular weight of the purified anti-histone H3 peptide/HLA-A02 BsAbs can be determined under reducing conditions by gel electrophoresis. For example, 4 μg of the protein is mixed with 2.5 μL of the NuPAGE LDS Sample Buffer (Life Technologies, NP0008) and brought up to 10 μL with deionized water. The sample is heated at 70° C. for 10 minutes, and then loaded onto the gel. Gel electrophoresis is performed at 180V for 1 hour.

Antibody aggregation can be assessed by size-exclusion chromatography (SEC). For example, 50 μL of the sample is injected into a SEC column (for example Agilent, BioSEC-3,300A, 4.6×300 mm) while flowing a buffer consisting of Dulbecco's Phosphate Buffered Saline (Fisher Scientific, SH30028.FS) and 0.2M arginine adjusted to pH 7.0. BsAbs with high molecular weight aggregation less than 10% are selected for further characterization.

TABLE 9

| BsAb ID | Phage clone LCVR (SEQ ID NO) | Phage clone HCVR (SEQ ID NO) |
|---------|------------------------------|------------------------------|
| BsAb 5  | 87 | 75 |
| BsAb 10 | 88 | 76 |
| BsAb 13 | 89 | 77 |
| BsAb 16 | 90 | 78 |
| BsAb 31 | 91 | 79 |
| BsAb 32 | 92 | 80 |
| BsAb 33 | 93 | 81 |
| BsAb 34 | 94 | 82 |
| BsAb 35 | 95 | 83 |
| BsAb 36 | 96 | 84 |
| BsAb 37 | 97 | 85 |
| BsAb 38 | 98 | 86 |

BsAb 32 (SEQ ID NO: 164), BsAb 34 (SEQ ID NO: 165), and BsAb 35 (SEQ ID NO: 166) were prepared as described above.

Example 5A. Characterization of Anti-Histone H3 Peptide/HLA-A02 BsAb Antibodies Binding Affinity of Anti-Histone H3 Peptide/HLA-A02 BsAb Antibodies The binding affinity of anti-histone H3 peptide/HLA-A02 (such as anti-K27M-H3.3 26-35/HLA-A02 or anti-K27M-H3.1 26-35/HLA-A02) BsAbs to recombinant target histone H3 peptide/HLA-A*02:01 complex is measured, for example, by Surface Plasma Resonance (BiaCore). For example, the binding parameters between a mutant histone K27M-H3.3 BsAb and the mutant histone K27M-H3.3/HLA-A*02:01 complex are measured, such as by using a His Capture Kit (GE Healthcare, Cat #28995056) on a Biacore X100 (GE Healthcare) according to the manufacturer's protocol for multi-cycle kinetics measurement. All of the proteins used in the assay are diluted using HBS-E buffer. For example, 1 μg/mL of the anti-K27M-H3.3 26-35/HLA-A02 BsAb is immobilized onto a Sensor Chip pre-functionalized with an anti-histidine antibody by flowing the solution through a flow cell at 2 μL/min for 2 minutes. Binding towards the mutant histone K27M-H3.3/A*02:01 complex is analyzed at, for example, 0.19, 0.38, 7.5, 15, and 30 μg/mL, each run consisting of a 3 minute association and 3 minute dissociation at L/min. At the end of the cycles, the surface is regenerated using the regeneration buffer from the His Capture kit. The data are analyzed using 1:1 binding site model with the BiaCore X-100 evaluation software. The binding parameters (association on rate constant $k_a$, dissociation constant $k_d$, and equilibrium dissociation constant $K_d$) are then calculated.

T-Cell Killing Assay with Peptide-Pulsed T2 Cells

Tumor cytotoxicity is assayed by LDH Cytotoxicity Assay (Promega). Human T cells (such as those from AllCells) are activated and expanded with CD3/CD28 Dynabeads (Invitrogen) according to manufacturer's protocol. Activated T cells (ATC) are cultured and maintained in RPMI1640 medium with 10% FBS plus 100 U/ml IL-2, and used at day 7-14. The T cells may be >99% CD3$^+$ by FACS analysis. Activated αβ T cells (effector cells) and target peptide-loaded T2 cells are co-cultured at a 5:1 ratio with 0.2 μg/ml of BsAbs for 16 hours. Peptide-loaded T2 cells are prepared by incubating T2 cells overnight with 50 μg/ml of mutant histone K27M-H3.3 26-35 (RMSAPSTGGV, SEQ ID NO: 7), mutant histone K27M-H3.1 26-35 (RMSAPATGGV, SEQ ID NO: 8), WT H3.3 26-35 (RKSAPSTGGV, SEQ ID NO: 5), WT H3.1 26-35 (RKSAPATGGV, SEQ ID NO: 6), or control peptide mixture P20 (SEQ ID NOs: 25-44). Cytotoxicities are then determined by measuring LDH activity in culture supernatants.

T-Cell Killing Assay with Cell Lines

Target cell cytotoxicity is assayed by LDH Cytotoxicity Assay (Promega). Human T cells (such as from AllCells) are activated and expanded with CD3/CD28 Dynabeads (Invitrogen) according to manufacturer's protocol. Activated T cells (ATC) are cultured and maintained in RPMI1640 medium with 10% FBS plus 100 U/ml IL-2, and used at day 7-14. Activated T cells (effector cells) and target cells are co-cultured at a 5:1 ratio with different concentrations of BsAbs (including for example 0.2, 0.04, 0.008, and 0.0016 μg/ml BsAbs) for 16 hours. Cytotoxicities are then determined by measuring LDH activities in culture supernatants.

Target cells for testing include K27M-H3.3 DIPG cell lines SF7761 and SF8628, as well as parental SK-Hep1, MCF-7 and HeLa cells and SK-Hep1, MCF-7 and HeLa cells transfected with a minigene to stably express mutant histone K27M-H3.3 (SEQ ID NO: 3) (SK-Hep1 K27M-H3.3, MCF-7 K27M-H3.3 and HeLa K27M-H3.3, respectively), mutant histone K27M-H3.1 (SEQ ID NO: 4) (SK-Hep1 K27M-H3.1, MCF-7 K27M-H3.1 and HeLa K27M-H3.1, respectively), WT H3.3 (SEQ ID NO: 1) (SK-Hep1 WT-H3.3, MCF-7 WT-H3.3 and HeLa WT-H3.3, respectively), or WT H3.1 (SEQ ID NO: 2) (SK-Hep1 WT-H3.1, MCF-7 WT-H3.1 and HeLa WT-H3.1, respectively). Additional target cells may be tested by transducing various other cell lines to express mutant histone K27M-H3.3 (SEQ ID NO: 3), mutant histone K27M-H3.1 (SEQ ID NO: 4), WT H3.3 (SEQ ID NO: 1) or WT H3.1 (SEQ ID NO: 2).

Cross-Reactivity of Anti-Histone H3 Peptide/HLA-A02 BsAbs Against Multiple HLA-A02 Alleles Human MHCI molecules consist of 6 class isoforms, HLA-A, -B, -C, -E, -F and G. The HLA-A, -B and -C heavy chain genes are highly polymorphic. For each isoform, the HLA genes are further grouped according to the similarity of heavy chain sequences. For example, HLA-A is divided into different alleles such as HLA-A01, -A02, -A03, etc. For the HLA-A02 allele, there are multiple subtypes, such as HLA-A*02:01, A*02:02, etc. Between the different subtypes of HLA-A02 group, the sequence differences are limited to only several amino acids. So in many cases, peptides that bind to HLA-A*02:01 molecule can also form complexes with multiple subtypes of the HLA-A02 allele. As shown in Table 10 (http://www.allelefrequencies.net/), although HLA-A*02:01 is the dominant HLA-A02 subtype among Caucasian populations, in Asia, A*02:05, A*02:06, A*02:07 and A*02:11 are also common HLA-A02 subtypes. The ability of anti-histone H3/HLA-A02 antibodies to recognize not only target histone H3 peptide (such as mutant histone K27M-H3.3 26-35 or mutant histone K27M-H3.1 26-35) in the context of HLA-A*02:01, but also other subtypes of HLA-A02, will greatly broaden the patient population that might be able to benefit from anti-histone H3 peptide/HLA-A02 antibody drug treatment. To determine cross-reactivity, histone H3 peptide/MHC class I complexes (such as mutant histone K27M-H3.3/MHCI or mutant histone K27M-H3.1/MHCI complexes) with other subtypes of the HLA-A02 allele are generated and the binding affinity of the target histone H3 peptide/HLA-A*02:01-specific (such as mutant histone K27M-H3.3/HLA-A*02:01-specific or mutant histone K27M-H3.1/HLA-A*02:01-specific) antibodies for these other complexes is tested. Binding affinity is determined, for example, using a ForteBio Octet QK. Briefly, 5 μg/mL biotinylated target histone H3 peptide/HLA-A02 MHC complex (such as mutant histone K27M-H3.3 26-35 peptide/HLA-A02 MHC complex or mutant histone K27M-H3.1 26-35 peptide/HLA-A02 MHC complex) having varying HLA subtypes is loaded onto a streptavidin biosensor. After washing off excess antigen, BsAbs are tested at, for example, 10 μg/mL for association and dissociation kinetics. Binding parameters are calculated using a 1:1 binding site, partial fit model.

compared to T2 cells loaded with either of the WT H3 peptides, which showed similar levels of cytotoxicity as T2 cells loaded with the negative control peptide. BsAbs 32 and 35 showed specific killing of T2 cells loaded with H3 peptides as compared to the negative control peptide, but showed less discrimination between the K27M mutant H3 peptides and the WT H3 peptides (see FIG. 2).

T-Cell Killing Assay with Cell Lines

Target cell cytotoxicity is assayed by LDH Cytotoxicity Assay (Promega). Human T cells (such as from AllCells) are activated and expanded with CD3/CD28 Dynabeads (Invitrogen) according to manufacturer's protocol. Activated T cells (ATC) are cultured and maintained in RPMI1640 medium with 10% FBS plus 100 U/ml IL-2, and used at day 7-14. Activated T cells (effector cells) and target cells are co-cultured at a 5:1 ratio with different concentrations of BsAbs (including for example 0.2, 0.04, 0.008, and 0.0016 μg/ml BsAbs) for 16 hours. Cytotoxicities are then determined by measuring LDH activities in culture supernatants.

Target cells for testing include K27M-H3.3 DIPG cell lines SF7761 and SF8628, as well as parental SK-Hep1, MCF-7 and HeLa cells and SK-Hep1, MCF-7 and HeLa

TABLE 10

|  | australia | china | europe | india | north africa | sub-saharan africa | taiwan | us |
|---|---|---|---|---|---|---|---|---|
| A*02:01 | 97.8% | 39.5% | 94.0% | 53.9% | 73.3% | 56.3% | 35.1% | 79.4% |
| A*02:02 | 0.0% | 0.1% | 0.3% | 0.9% | 9.7% | 24.1% | 0.0% | 3.6% |
| A*02:03 | 0.0% | 15.3% | 0.2% | 4.9% | 0.0% | 0.4% | 19.3% | 2.2% |
| A*02:04 | 0.0% | 0.1% | 0.0% | 0.3% | 2.6% | 0.4% | 0.0% | 0.2% |
| A*02:05 | 1.1% | 0.9% | 3.2% | 5.8% | 13.8% | 15.9% | 0.1% | 4.5% |
| A*02:06 | 0.0% | 16.0% | 0.9% | 10.6% | 0.0% | 0.7% | 12.8% | 5.5% |
| A*02:07 | 1.1% | 26.1% | 0.4% | 0.4% | 0.0% | 0.0% | 32.7% | 2.4% |
| A*02:08 | 0.0% | 0.0% | 0.0% | 0.0% | 0.0% | 0.0% | 0.0% | 0.0% |
| A*02:09 | 0.0% | 0.0% | 0.0% | 0.0% | 0.0% | 0.0% | 0.0% | 0.0% |
| A*02:10 | 0.0% | 1.1% | 0.0% | 0.0% | 0.0% | 0.2% | 0.0% | 0.1% |
| A*02:11 | 0.0% | 0.1% | 0.1% | 22.3% | 0.0% | 1.5% | 0.0% | 1.7% |
| other A02 subtypes (A*02:12-A*02:93) | 0.0% | 0.7% | 0.8% | 0.9% | 0.5% | 0.5% | 0.0% | 0.6% |
|  | 100.0% | 100.0% | 100.0% | 100.0% | 100.0% | 100.0% | 100.0% | 100.0% |

Example 5B. Characterization of Anti-Histone H3 Peptide/HLA-A02 BsAb Antibodies

T-Cell Killing Assay with Peptide-Pulsed T2 Cells

Figure 2:
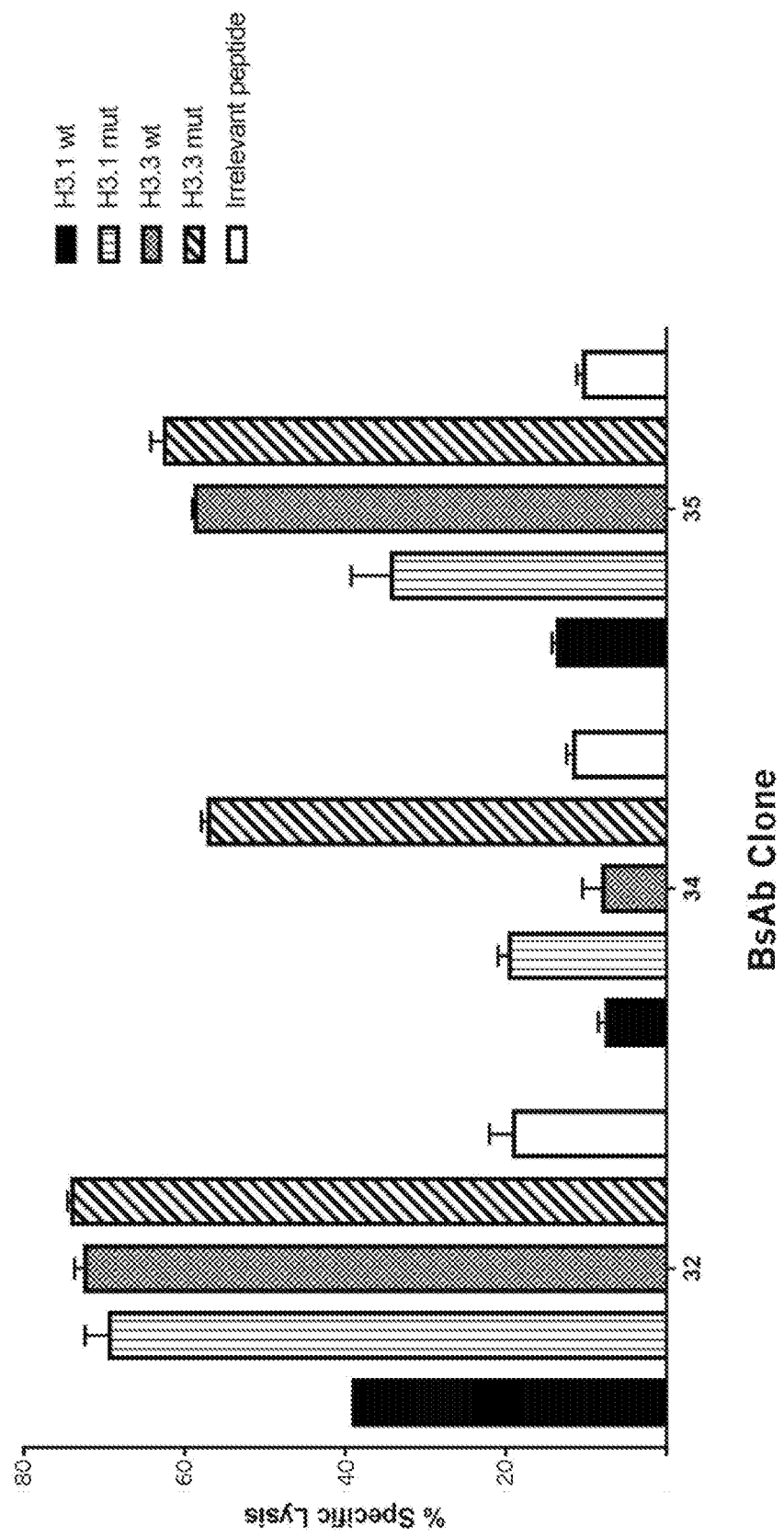
FIG. 2 shows T cell killing of T2 cells loaded with K27M-H3.3 26-35 peptide (H3.3 mut), WT-H3.3 26-35 peptide (H3.3 wt), K27M-H3.1 26-35 peptide (H3.1 mut), WT-H3.1 26-35 peptide (H3.1 wt), or irrelevant peptide, mediated by different BsAbs specific for histone H3 26-35/HLA-A*02:01 and CD3 (BsAbs 32, 34, and 35).

Tumor cytotoxicity was assayed by LDH Cytotoxicity Assay (CytoTox 96® Non-Radioactive Cytotoxicity Assay by Promega). Human T cells (AllCells) were activated and expanded with CD3/CD28 Dynabeads (Invitrogen) according to manufacturer's protocol. Activated T cells (ATC) were cultured and maintained in RPMI1640 medium with 10% FBS plus 100 U/ml IL-2, and used at day 7-14. The T cells were >99% CD3+ by FACS analysis. Peptide-loaded T2 cells were prepared by incubating T2 cells overnight with 50 μg/ml of WT H3.1 26-35 (RKSAPATGGV, SEQ ID NO: 6), mutant histone K27M-H3.1 26-35 (RMSAPATGGV, SEQ ID NO: 8), WT H3.3 26-35 (RKSAPSTGGV, SEQ ID NO: 5), mutant histone K27M-H3.3 26-35 (RMSAPSTGGV, SEQ ID NO: 7), or control HIV peptide (YQYMDDLYV, SEQ ID NO: 167). 5×10$^5$ activated T cells (effector cells) and 1×10$^5$ target peptide-loaded T2 cells were co-cultured (5:1 ratio) with 0.2 μg/ml of BsAbs (BsAb 32, 34, or 35) for 16 hours. Cytotoxicities were then determined by measuring LDH activity in culture supernatants. As shown in FIG. 2, BsAb 34 resulted in specific killing of the T2 cells loaded with the H3.1 and H3.3 K27M mutant peptides as cells transfected with a minigene to stably express mutant histone K27M-H3.3 (SEQ ID NO: 3) (SK-Hep1 K27M-H3.3, MCF-7 K27M-H3.3 and HeLa K27M-H3.3, respectively), mutant histone K27M-H3.1 (SEQ ID NO: 4) (SK-Hep1 K27M-H3.1, MCF-7 K27M-H3.1 and HeLa K27M-H3.1, respectively), WT H3.3 (SEQ ID NO: 1) (SK-Hep1 WT-H3.3, MCF-7 WT-H3.3 and HeLa WT-H3.3, respectively), or WT H3.1 (SEQ ID NO: 2) (SK-Hep1 WT-H3.1, MCF-7 WT-H3.1 and HeLa WT-H3.1, respectively). Additional target cells may be tested by transducing various other cell lines to express mutant histone K27M-H3.3 (SEQ ID NO: 3), mutant histone K27M-H3.1 (SEQ ID NO: 4), WT H3.3 (SEQ ID NO: 1) or WT H3.1 (SEQ ID NO: 2). Cross-reactivity of anti-histone H3 peptide/HLA-A02 BsAbs against multiple HLA-A02 alleles Human MHCI molecules consist of 6 class isoforms, HLA-A, -B, -C, -E, -F and G. The HLA-A, -B and -C heavy chain genes are highly polymorphic. For each isoform, the HLA genes are further grouped according to the similarity of heavy chain sequences. For example, HLA-A is divided into different alleles such as HLA-A01, -A02, -A03, etc. For the HLA-A02 allele, there are multiple subtypes, such as HLA-A*02:01, A*02:02, etc. Between the different subtypes of HLA-A02 group, the sequence differences are limited to only several amino acids. So in many cases, peptides that bind to HLA-A*02:01 molecule can also form complexes with multiple subtypes of the HLA-A02 allele. As shown in Table 10 (http://www.allelefrequencies.net/), although HLA-A*02:01 is the dominant HLA-A02 subtype among Caucasian populations, in Asia, A*02:05, A*02:06, A*02:07 and A*02:11 are also common HLA-A02 subtypes. The ability of anti-histone H3/HLA-A02 antibodies to recognize not only target histone H3 peptide (such as mutant histone K27M-H3.3 26-35 or mutant histone K27M-H3.1 26-35) in the context of HLA-A*02:01, but also other subtypes of HLA-A02, will greatly broaden the patient population that might be able to benefit from anti-histone H3 peptide/HLA-A02 antibody drug treatment. To determine cross-reactivity, histone H3 peptide/MHC class I complexes (such as mutant histone K27M-H3.3/MHCI or mutant histone K27M-H3.1/MHCI complexes) with other subtypes of the HLA-A02 allele are generated and the binding affinity of the target histone H3 peptide/HLA-A*02:01-specific (such as mutant histone K27M-H3.3/HLA-A*02:01-specific or mutant histone K27M-H3.1/HLA-A*02:01-specific) antibodies for these other complexes is tested. Binding affinity is determined, for example, using a ForteBio Octet QK. Briefly, 5 µg/mL biotinylated target histone H3 peptide/HLA-A02 MHCI complex (such as mutant histone K27M-H3.3 26-35 peptide/HLA-A02 MHCI complex or mutant histone K27M-H3.1 26-35 peptide/HLA-A02 MHCI complex) having varying HLA subtypes is loaded onto a streptavidin biosensor. After washing off excess antigen, BsAbs are tested at, for example, 10 µg/mL for association and dissociation kinetics. Binding parameters are calculated using a 1:1 binding site, partial fit model.

Example 6. Generation of Histone H3 Peptide/HLA-A*02:01-Specific Chimeric Antigen Receptor-Presenting T Cells (CAR T Cells)

Chimeric antigen receptor therapy (CAR-T therapy) is a relatively new form of targeted immunotherapy. It merges the exquisite targeting specificity of monoclonal antibodies with the potent cytotoxicity and long-term persistence provided by cytotoxic T cells. This technology enables T cells to acquire long-term novel antigenic specificity independent of the endogenous TCR. Clinical trials have shown clinically significant antitumor activity of CAR-T therapy in neuroblastoma (Louis C. U. et al., *Blood* 118(23):6050-6056), B-ALL (Maude S. L. et al., *N. Engl. J. Med.* 371(16):1507-1517, 2014), CLL (Brentjens R. J. et al., *Blood* 118(18): 4817-4828, 2011), and B cell lymphoma (Kochenderfer J. N. et al., *Blood.* 116(20):4099-4102, 2010). In one study, a 90% complete remission rate in 30 patients with B-ALL treated with CD19-CAR T therapy was reported (Maude S. L. et al., supra).

To further explore the potency of the histone H3 peptide/ HLA-A*02:01-specific (such as mutant histone K27M-H3.3/HLA-A*02:01-specific or mutant histone K27M-H3.1/HLA-A*02:01-specific) antibodies, anti-HMC scFv-containing CARs are constructed and transduced into T cells. For example, mutant histone K27M-H3.3/HLA-A*02: 01 specific CARs are constructed using a lentiviral CAR expression vector. Anti-mutant histone K27M-H3.3/HLA-A*02:01 scFvs are grafted onto a second generation CAR (Mackall C. L. et al., *Nat. Rev. Clin. Oncol.* 11(12):693-703, 2014) with a co-stimulatory signaling domain (such as from CD28 or 4-1BB) and a signaling domain from CD3ζ engineered in cis to provide intracellular T cell stimulation signals and to activate T cells. For example, the anti-mutant histone K27M-H3.3/HLA-A*02:01 scFvs are grafted onto a CAR polypeptide having the amino acid sequence of SEQ ID NO: 49 or 50.

Example 7. Generation of Histone H3 Peptide/HLA-A*02:01-Specific Chimeric Antibody/TCR Receptor-Presenting T Cells (abTCR T Cells)

Chimeric antibody/T cell receptors (abTCRs) are regulated by the naturally occurring machinery that controls TCR activation, and can thus avoid being constitutively activated and negative outcomes associated with such activation. abTCR T cells are expected to signal and respond to endogenous T-cell regulatory mechanisms and to demonstrate increased persistence in vivo.

To further explore the potency of the histone H3 peptide/ HLA-A*02:01-specific (such as mutant histone K27M-H3.3/HLA-A*02:01-specific or mutant histone K27M-H3.1/HLA-A*02:01-specific) antibodies, anti-HMC abTCRs are constructed and transduced into T cells. For example, mutant histone K27M-H3.3/HLA-A*02:01 specific abTCRs are constructed using one or more lentiviral abTCR expression vectors. Anti-mutant histone K27M-H3.3/HLA-A*02:01 Fab-like antigen-binding modules are grafted onto a T cell receptor transmembrane module comprising T cell receptor subunit transmembrane domains to provide intracellular T cell stimulation signals through association with endogenous TCR-associated signaling molecules (such as CD3δε, CD3γε, and ζζ) and to activate T cells. For example, the anti-mutant histone K27M-H3.3/ HLA-A*02:01 Fab-like antigen-binding modules are grafted onto abTCR polypeptides comprising the amino acid sequences of SEQ ID NOs: 69 and 70 (γδ abTCR) or SEQ ID NOs: 71 and 72 (αβ abTCR).

Example 8A. Characterization of Anti-HMC Chimeric Receptor T Cells

In Vitro Cytotoxicity Study of Anti-HMC Chimeric Receptor T Cells

Lentiviruses encoding histone H3 peptide/HLA-A*02:01-specific (such as mutant histone K27M-H3.3/HLA-A*02: 01-specific or mutant histone K27M-H3.1/HLA-A*02:01-specific) chimeric antigen receptors (CARs) or chimeric antibody/TCRs (abTCRs) are produced, for example, by transfection of 293T cells with anti-HMC CAR vectors or anti-HMC abTCR vectors, respectively. Human T-cells are used for transduction after 2-day stimulation with CD3/ CD28 beads (Dynabeads®, Invitrogen) in the presence of interleukin-2 at 100 U/ml. Concentrated lentiviruses are applied to T-cells in Retronectin (Takara) coated 6-well plates for 72 hours. Transduction efficiency is assessed by FACS using biotinylated target histone H3 peptide tetramer (such as mutant histone K27M-H3.3 26-35 tetramer or mutant histone K27M-H3.1 26-35 tetramer) and PE-conjugated streptavidin. Repeat FACS analyses are done, for example, at 72 hours and every 3-4 days thereafter.

Functional assessment of the transduced T cells (anti-HMC CAR T cells or anti-HMC abTCR T cells) is performed using LDH Cytotoxicity Assay. Effector-to-target ratios used include, for example, 5:1 and 10:1. The target cell lines may include, for example, SK-HEP-1, MCF-7, HeLa, and primary T cells, such as CD4$^+$ T cells. SK-HEP-1, MCF-7, HeLa, and/or primary T cells are transduced with a mutant histone K27M-H3.3-expressing minigene cassette encoding mutant histone K27M-H3.3 (SEQ ID NO: 3), mutant histone K27M-H3.1 (SEQ ID NO: 4), WT H3.3 (SEQ ID NO: 1), or WT H3.1 (SEQ ID NO: 2), which results in a high level of cell surface expression of histone H3 26-35/HLA-A*02:01 complex. The specificity and efficiency of the anti-HMC CAR-expressing T cells or anti-HMC abTCR-expressing T cells to kill the target-positive cells is determined as described above using LDH assay.

Proliferation of Anti-HMC Chimeric Receptor-Transduced CD3$^+$ T Cells in Response to K27M-H3-Expressing Cells The purpose of this experiment is to measure the proliferative capacity of CD3$^+$ T cells (such as CD4$^+$ or CD8$^+$ T cells) transduced with either an anti-HMC CAR or an anti-HMC abTCR in response to exposure to K27M-H3-expressing cells (such as K27M-H3.3-expressing or K27M-H3.1-expressing cells).

K27M-H3-expressing target cells are derived from a K27M-H3.3$^+$ cell line (such as SF7761 or SF8628) or produced by transfection of parental cells (such as SK-HEP-1, MCF-7, or HeLa cells) with a minigene cassette encoding mutant histone K27M-H3.3 (SEQ ID NO: 3), mutant histone K27M-H3.1 (SEQ ID NO: 4), WT H3.3 (SEQ ID NO: 1), or WT H3.1 (SEQ ID NO: 2). Target cells are irradiated, for example, with high-dose gamma-radiation (e.g., 10,000 rad). Anti-HMC chimeric receptor T cells (anti-HMC CAR T cells or anti-HMC abTCR T cells) are labeled, for example, with Cell Tracer CFSE (ThermoFisher) according to the manufacturer's instructions. Target cells and anti-HMC chimeric receptor T cells are mixed, for example, at 1:1 ratio. The media is changed after 3 days and Cell Tracer CFSE fluorescence is measured after 5 days. For examples of proliferation studies see Ali, A. et al. (2016) *Journal of virology* JVI-00805.

Cytokine Release by Activated Anti-HMC Chimeric Receptor-Transduced CD3$^+$ T Cells The purpose of this assay is to measure cytokine release by activated CD3$^+$ (such as CD4$^+$ or CD8$^+$) anti-HMC chimeric receptor T cells (anti-HMC CAR T cells or anti-HMC abTCR T cells) in response to target histone H3-expressing cells (such as K27M-H3.3-expressing or K27M-H3.1-expressing cells). For examples of analysis of cytokine production by transduced CD3$^+$ T cells see Varela-Rohena, A. et al. (2008) *Nature medicine* 14(12): 1390-1395.

Histone H3-expressing target cells (such as K27M-H3.3-expressing or K27M-H3.1-expressing cells) are produced as described above. Target cells and anti-HMC chimeric receptor T cells are mixed, for example, at 1:1 or 1:8 exemplary E:T ratios. Cytokines released by CD3$^+$ chimeric receptor T cells are analyzed, for example, using ELISA Kits for Granzyme B (Neobioscience), IL-2 (MultiSciences, Lianke Biotech), and IFN-γ. See for example Liu, B. et al. (2016) *Journal of Virology* JVI-00852.

Example 8B. Characterization of Anti-HMC CAR T Cells

In Vitro Cytotoxicity Study of Anti-HMC CAR T Cells

Lentiviruses encoding histone H3 peptide/HLA-A*02:01-specific (such as mutant histone K27M-H3.3/HLA-A*02:01-specific or mutant histone K27M-H3.1/HLA-A*02:01-specific) chimeric antigen receptors (CARs) are produced, for example, by transfection of 293T cells with anti-HMC CAR vectors. Human T-cells are used for transduction after 1-day stimulation with CD3/CD28 beads (Dynabeads®, Invitrogen) in the presence of interleukin-2 at 100 U/ml. Concentrated lentiviruses are applied to T-cells in Retronectin (Takara) coated 6-well plates for 72 hours. Transduction efficiency may be assessed by FACS using biotinylated target histone H3 peptide tetramer (such as mutant histone K27M-H3.3 26-35 tetramer or mutant histone K27M-H3.1 26-35 tetramer) and PE-conjugated streptavidin. Repeat FACS analyses may be done, for example, at 72 hours, and optionally every 3-4 days thereafter. Functional assessment of the transduced anti-HMC CAR T cells is performed using LDH Cytotoxicity Assay. Effector-to-target cell ratios can include, for example, 5:1 and 10:1.

Cancer cell lines positive for K27M H3.3/HLA*A02:01, such as K27M-H3.3 brainstem glioma cell lines SF7761 and SF8628, or negative for K27M H3.3, such as WT-H3.3 glioma cell lines SF9012, SF9402, SF9427, and GBM43 (See Hashizume et al, 2012), are tested for killing by anti-HMC CAR T cells, for example at an effector-to-target ratio of 5:1. Primary T cells that are mock-transduced or transduced with anti-HMC CAR are tested for their ability to specifically kill K27M H3.3/HLA*A02:01-positive cancer cells as compared to K27M H3.3-negative cancer cells.

Parental cell lines negative for K27M H3.3 and K27M H3.1, such as SK-Hep1, MCF-7 and HeLa cells, and SK-Hep1, MCF-7 and HeLa cells transfected with a minigene to stably express (a) mutant histone K27M-H3.3 (SEQ ID NO: 3) (SK-Hep1 K27M-H3.3, MCF-7 K27M-H3.3 and HeLa K27M-H3.3, respectively), (b) mutant histone K27M-H3.1 (SEQ ID NO: 4) (SK-Hep1 K27M-H3.1, MCF-7 K27M-H3.1 and HeLa K27M-H3.1, respectively), (c) WT H3.3 (SEQ ID NO: 1) (SK-Hep1 WT-H3.3, MCF-7 WT-H3.3 and HeLa WT-H3.3, respectively), or (d) WT H3.1 (SEQ ID NO: 2) (SK-Hep1 WT-H3.1, MCF-7 WT-H3.1 and HeLa WT-H3.1, respectively), are tested for killing by anti-HMC CAR T cells, for example at an effector-to-target ratio of 5:1. Primary T cells that are mock-transduced or transduced with anti-HMC CAR are tested for their ability to specifically kill K27M H3.3/HLA*A02:01-positive or K27M H3.1/HLA*A02:01-positive cells as compared to K27M H3.3-negative or K27M H3.1-negative cells.

Example 8C. Characterization of Anti-HMC abTCR T Cells

In Vitro Cytotoxicity Study of Anti-HMC abTCR T Cells

Primary T cells are mock-transduced or transduced with lentiviral vectors encoding an anti-HMC abTCR containing anti-histone H3 peptide/HLA-A*02:01 (such as anti-K27M-H3.3 26-35/HLA-A*02:01 or anti-K27M-H3.1 26-35/HLA-A*02:01) variable domains. The transduction efficiency may be determined, for example, by staining with PE-labeled histone H3 peptide/HLA-A*02:01 tetramers. T cell populations with similar transduction rates are used to test their abilities to kill target cell lines. Effector-to-target cell ratios can include, for example, 2.5:1, 5:1, and 10:1.

Cancer cell lines positive for K27M H3.3/HLA*A02:01, such as K27M-H3.3 brainstem glioma cell lines SF7761 and SF8628, or negative for K27M H3.3, such as WT-H3.3 glioma cell lines SF9012, SF9402, SF9427, and GBM43 (See Hashizume et al, 2012), are tested for killing by anti-HMC abTCR T cells, for example at an effector-to-target ratio of 2.5:1. Primary T cells that are mock-transduced or transduced with anti-HMC abTCR are tested for their ability to specifically kill K27M H3.3/HLA*A02:01-positive cancer cells as compared to K27M H3.3-negative cancer cells, for example by measuring specific lysis after 16 hr incubation, such as by using the Cytox 96 Non-radioactive Cytotoxicity Assay (Promega).

Parental cell lines negative for K27M H3.3 and K27M H3.1, such as SK-Hep1, MCF-7 and HeLa cells, and SK-Hep1, MCF-7 and HeLa cells transfected with a minigene to stably express (a) mutant histone K27M-H3.3 (SEQ ID NO: 3) (SK-Hep1 K27M-H3.3, MCF-7 K27M-H3.3 and HeLa K27M-H3.3, respectively), (b) mutant histone K27M-H3.1 (SEQ ID NO: 4) (SK-Hep1 K27M-H3.1, MCF-7 K27M-H3.1 and HeLa K27M-H3.1, respectively), (c) WT H3.3 (SEQ ID NO: 1) (SK-Hep1 WT-H3.3, MCF-7 WT-H3.3 and HeLa WT-H3.3, respectively), or (d) WT H3.1 (SEQ ID NO: 2) (SK-Hep1 WT-H3.1, MCF-7 WT-H3.1 and HeLa WT-H3.1, respectively), are tested for killing by anti-HMC abTCR T cells, for example at an effector-to-target ratio of 2.5:1. Primary T cells that are mock-transduced or transduced with anti-HMC abTCR are tested for their ability to specifically kill K27M H3.3/HLA*A02:01-positive or K27M H3.1/HLA*A02:01-positive cells as compared to K27M H3.3-negative or K27M H3.1-negative cells, for example by measuring specific lysis after 16 hr incubation, such as by using the Cytox 96 Non-radioactive Cytotoxicity Assay (Promega).

The cell killing activity of anti-HMC abTCR T cells can be compared to the corresponding cell killing activity of anti-HMC CAR T cells containing the same anti-histone H3/HLA-A*02:01 variable domains.

Example 9. Generation and Characterization of Full-Length IgG1 Anti-Histone H3 Peptide/HLA-A02 Antibodies Full-length human IgG1 of selected phage clones are produced, for example, in HEK293 and Chinese hamster ovary (CHO) cell lines, as described (Tomimatsu K. et al., Biosci. Biotechnol. Biochem. 73(7):1465-1469, 2009). In brief, antibody variable regions are subcloned into mammalian expression vectors, with matching human lambda or kappa light chain constant region and human IgG1 constant region sequences. Applying the same cloning strategy, chimeric anti-histone H3 peptide/MHC (such as anti-K27M-H3.3 26-35/MHC or anti-K27M-H3.1 26-35/MHC) full-length antibodies with mouse IgG1 heavy chain and light chain constant regions are generated. Molecular weight of the purified full length IgG antibodies is measured under both reducing and non-reducing conditions by electrophoresis. SDS-PAGE of purified anti-histone H3 peptide/MHC mouse chimeric IgG1 antibodies is performed to determine protein purity. In brief, 2 g of the protein is mixed with 2.5 µL of NuPAGE LDS Sample Buffer (Life Technologies, NP0008) and brought up to 10 µL with deionized water. The sample is heated at 70° C. for 10 minutes, and then loaded onto the gel. Gel electrophoresis is performed at 180V for 1 hour.

Anti-histone H3 peptide/MHC chimeric IgG1 antibodies are tested for binding towards mutant target histone H3-presenting (such as K27M-H3.3-presenting or K27M-H3.1-presenting) cells (such as SK-Hep1, MCF-7, HeLa, and/or primary CD4$^+$ cells transduced with a minigene cassette as described above) by flow cytometry. For example, a mutant histone K27M-H3.3 minigene cassette is transfected into cells to generate mutant histone K27M-H3.3-presenting target cells. 10 µg/mL of antibody is added to cells on ice for 1 hour. After washing, R-PE conjugated anti-mouse IgG(H+L) (Vector Labs #EI-2007) is added to detect antibody binding. Binding affinity of the mouse chimeric IgG1 anti-histone H3 peptide/MHC antibodies is determined by ForteBio Octet QK. 5 µg/mL biotinylated target histone H3 peptide/HLA-A*02:01 complex (such as K27M-H3.3/HLA-A*02:01 complex or K27M-H3. 1/HLA-A*02:01) is loaded onto a streptavidin biosensor. After washing off excess antigen, mouse chimeric full-length antibodies are tested at 10 µg/mL for association and dissociation kinetics. Binding parameters are calculated using a 1:1 binding site, partial fit model.

Histone H3 peptide/MHC-specific and negative control mouse chimeric IgG1 are tested for binding towards target histone H3 peptide/HLA-A*02:01 (such as mutant histone K27M-H3.3/HLA-A*02:01 or mutant histone K27M-H3. 1/HLA-A*02:01), target histone H3 recombinant protein (such as mutant histone K27M-H3.3 or mutant histone K27M-H3.1), and free target histone H3 peptide (such as mutant histone K27M-H3.3 26-35 peptide or mutant histone K27M-H3.1 26-35 peptide) in an ELISA assay. Antibodies are tested, for example, at 3× serial dilution, starting from 100 ng/mL for a total of 8 concentrations. Biotinlyated histone H3 peptide/A*02:01 MHC (such as mutant histone K27M-H3.3/A*02:01 or mutant histone K27M-H3.1/A*02:01) is coated onto streptavidin plates at 2 µg/mL, histone H3 protein (such as mutant histone K27M-H3.3 protein or mutant histone K27M-H3.1 protein) is coated at 2 µg/mL, and histone H3 peptide (such as mutant histone K27M-H3.3 26-35 peptide or mutant histone K27M-H3.1 26-35 peptide) is coated at 40 ng/mL. The ability of full-length anti-histone H3 peptide/HLA-A*02:01 antibodies to recognize the target histone H3 peptide only in the context of HLA-A02, and not bind target histone H3 protein or free target histone H3 peptide is determined.

Example 10. In Vivo Efficacy Studies

Anti-HMC Chimeric Receptor T Cell Treatment in Mice

Anti-HMC chimeric receptor T cells (such as anti-HMC CAR T cells or anti-HMC abTCR cells) are evaluated in a mouse model of histone H3-related (such as K27M-H3.3-positive or K27M-H3.1-positive) cancer (such as a mouse model of K27M-H3.3-positive or K27M-H3.1-positive glioma or glioblastoma; see for example Martens, T., et al. (2008). Clinical Cancer Research, 14(17), 5447-5458; Ahmed, A. U., et al. (2011). Molecular Therapy, 19(9), 1715). For example, HLA-A02$^+$/K27M-H3.3$^+$ and/or HLA-A02$^+$/K27M-H3.1$^+$ glioma or glioblastoma cell line intracranial xenograft models are generated in immunodeficient mice (such as nude mice, SCID-beige (no functional T-, B-, NK-cells) mice, or NSG (NOD SCID gamma) mice). HLA-A02$^+$/WT-H3.3 and/or HLA-A02$^+$/WT-H3.1 glioma or glioblastoma cell line intracranial xenograft mice may also be generated for use as controls to demonstrate specificity of the anti-HMC constructs for cells presenting the mutant histone H3 peptide. Animals are randomized, for example, when tumors reach sufficient volume. Mice are divided into at least 3 groups that receive one of the following: (i) no treatment; (ii) mock treatment; or (iii) treatment with anti-HMC chimeric receptor T cells (anti-HMC CAR T cells or anti-HMC abTCR T cells). The animals in each group are monitored for tumor volume, adverse response, human cytokine profile, histopathology of tumor for human CD3$^+$ cells in tumor and organs for chimeric receptor T cell infiltration, body weight and general health condition (eating, walking, daily activities).

Example 11. Affinity Maturation of Anti-Histone H3 Peptide/MHC Antibody Agents This example describes the affinity maturation of anti-histone H3 peptide/MHC (such as anti-mutant histone K27M-H3.3/MHC or anti-mutant histone K27M-H3.1/MHC) antibody agents. In particular, this example specifically describes the generation of a series of antibody variants by incorporation of random mutations into a representative anti-histone H3 peptide/MHC antibody followed by screening and characterization of the antibody variants.

Generation of Variant Phage Libraries

For example, DNA encoding an anti-histone H3 peptide/MHC scFv (such as mutant histone K27M-H3.3 26-35/MHC scFv or mutant histone K27M-H3.1 26-35/MHC scFv) is subjected to random mutagenesis using GeneMorph II Random Mutagenesis kit (Agilent Technologies) according to the manufacturer's specifications. After mutagenesis, DNA sequences are cloned into an scFv-expressing phagemid vector to build a variant human antibody phage library which contains, for example, about 5×10 unique phage clones. On average, variant clones have two nucleotide mutations compared with the parental anti-histone H3 peptide/MHC clone, ranging from 1 to 4 nucleotide mutations, per scFv sequence.

Cell Panning

The human phage scFv library with mutants is used to pan against target histone H3 peptide/HLA-A*02:01 complex (such as mutant histone K27M-H3.3 26-35 peptide/HLA-A*02:01 complex or mutant histone K27M-H3.1 26-35 peptide/HLA-A*02:01 complex) as described in Example 2. In particular, cell panning is used. For example, human scFv phage library is first mixed with T2 cells loaded with 50 ug/ml of a pool of 20 different endogenous peptides (P20, SEQ ID NOs: 25-44) as negative control panning. The negative control-depleted human scFv phage library is then mixed with T2 cells loaded with target histone H3 peptide (1.5 ug/ml first round, 0.8 ug/ml second round, 0.4 ug/ml third round) for positive selection. To load peptide, T2 cells are pulsed with peptides in serum-free RPMI1640 medium in the presence of 20 µg/ml 32M overnight. After extended washing with PBS, peptide-loaded T2 cells with bound scFv antibody phage are spun down. The bound clones are then eluted and used to infect E. coli XL1-Blue cells. The phage clones expressed in bacteria are then purified. The panning is performed for 3 rounds to enrich for scFv phage clones that bind target histone H3 peptide/HLA-A*02:01 specifically.

Streptavidin ELISA plates are coated with biotinylated target histone H3 peptide/HLA-A*02:01 complex monomer (such as mutant histone K27M-H3.3 26-35 peptide/HLA-A*02:01 complex monomer or mutant histone K27M-H3.1 26-35 peptide/HLA-A*02:01 complex monomer) or biotinylated P20 control peptides/HLA-A*02:01 monomer. Individual phage clones from enriched phage display panning pools against target histone H3 peptide/HLA-A*02:01 complex are incubated in the coated plates. Binding of the phage clones is detected by HRP-conjugated anti-M13 antibodies and developed using HRP substrate. The absorbance is read at 450 nm. Positive clones are identified through ELISA screening of phage clones enriched from phage panning. Unique clones are identified by DNA sequencing of the ELISA-positive phage clones. Specific and unique clones are further tested for their binding to HLA-A*02:01/peptide complexes on the live cell surface by flow cytometry (FACS analysis) using target histone H3 peptide-loaded live T2 cells. Controls include T2 cells without peptide loading (cells only) and R-PE conjugated horse anti-mouse IgG control (secondary antibody only). Briefly, T2 cells loaded with target histone H3 peptide or P20 peptide pool are first stained with purified scFv phage clones, followed by a second staining with mouse anti-M13 mAb, and a third staining with R-PE conjugated horse anti-mouse IgG (such as from Vector Labs). Each staining step is performed, for example, for 30-60 minutes on ice and the cells are washed twice between staining steps. Specific binding to target histone H3 peptide-loaded T2 cells and not T2 cells loaded with P20 peptide pool in the context of HLA-A*02:01, or T2 cells without peptide loaded is determined.

Example 12. Characterization of Bi-Specific Antibody Molecules Based on Anti-Histone H3 Peptide/MHC Affinity Maturation Variants Generation of Bispecific Antibodies Bispecific antibodies (BsAbs) are generated using scFv sequences of the affinity matured histone H3 peptide/HLA-A*02:01-specific phage clones isolated in Example 11 using the method described in Example 4. The resulting single-chain bispecific antibodies comprise the scFv sequence of a histone H3 peptide/HLA-A*02:01-specific phage clone (such as a mutant histone K27M-H3.3 26-35/HLA-A*02:01-specific or a mutant histone K27M-H3.1 26-35/HLA-A*02:01-specific phage clone) at the N-terminal end and an anti-human CD3ε mouse monoclonal scFv at the C-terminal end.

Determination of Binding Affinities of Bispecific Antibodies to Mutant Histone K27M-H3.3/HLA-A*02:01

The binding affinity of anti-histone H3 peptide/MHC (such as anti-mutant histone K27M-H3.3 26-35/HLA-A*02:01 or anti-mutant histone K27M-H3.1 26-35/HLA-A*02:01) BsAb antibodies (derived from affinity matured clones) to recombinant target histone H3 peptide/HLA-A*02:01 complex is measured by Surface Plasmon Resonance (BiaCore). The binding parameters between the anti-histone H3 peptide/MHC BsAbs and target histone H3 peptide/HLA-A*02:01 complex are measured using a Biotin CAPture Kit (GE Healthcare, Cat #28920233) on a Biacore X100 (GE Healthcare) according to the manufacturer's protocol for multi-cycle kinetics measurement. All of the proteins used in the assay are diluted using HBS-EP running buffer. 5 µg/mL of biotinylated target histone H3 peptide/HLA-A*02:01/2M complex is immobilized onto a Sensor Chip CAP pre-functionalized with streptavidin (~3,800 RU of streptavidin captured) by flowing the solution through the flow cell at 5 µL/min for 75 seconds (~120 RU of MHC complex was captured per cycle). Binding towards the anti-histone H3 peptide/MHC BsAbs is analyzed, for example, at 150 nM, 75 nM, 37.5 nM, 18.8 nM, and 9.4 nM, each run consisting of a 2 minute association and 10 minute dissociation at 30 µL/min. At the end of cycle, the surface is regenerated, for example using the regeneration buffer from the Biotin CAPture kit. The data is analyzed using 1:1 binding site model with the BiaCore X-100 evaluation software. The binding parameters (association on rate constant $k_a$, dissociation constant $k_d$, and equilibrium dissociation constant $K_d$) are then calculated.

Cross-Reactivity and Binding Affinities of Anti-Histone H3 Peptide/HLA-A02 Bispecific Antibodies Against Multiple HLA-A02 Alleles As described above in Example 5, the different subtypes of the HLA-A02 group are quite conserved, and cross-reactivity against multiple HLA-A02 subtypes is highly desired. Therefore, experiments are performed to determine whether the bi-specific antibodies (BsAb) generated from the parental clone and the affinity maturation variants cross-react with non-HLA-A*02:01 subtypes of the HLA-A02 group. Specifically, target histone H3 peptide/MHC class I complexes (such as mutant histone K27M-H3.3 26-35/MHCI or mutant histone K27M-H3.1 26-35/MHCI complexes) with various subtypes of the HLA-A02 allele are generated, and their binding affinities to the histone H3 peptide/HLA-A*02:01-specific antibodies are determined, for example, using the Octet® QKe System by Pall ForteBio LLC (Menlo Park, Calif.), which utilizes the Biolayer Interferometry (BLI) technology. The BsAbs tested include the parental clone and affinity maturation variant clones. Five µg/mL biotinylated target histone H3 peptide/HLA-A02 complex having varying subtypes of HLA-A02 is loaded onto a streptavidin biosensor. After washing off excess antigen (the histone H3 peptide/HLA-A02 complex), BsAbs are tested at 10 µg/mL for association and dissociation kinetics. Binding parameters are calculated using a 1:1 binding site, partial fit model.

Peptide Binding Specificity Assay

In order to confirm the specificity of the peptide recognized by the affinity maturation variant antibodies, a FACS analysis is performed with T2 cells loaded with target histone H3 peptide (such as mutant histone K27M-H3.3 26-35 or mutant histone K27M-H3.1 26-35), the P20 peptide pool, or no peptide.

Epitope Mapping by Alanine Walking

To investigate with precision the sensitive residues of the target histone H3 peptide (such as mutant histone K27M-H3.3 26-35 or mutant histone K27M-H3.1 26-35) for recognition by BsAb affinity maturation variants, alanine walking experiments as described above are performed.

Sequence Listing

| SEQ ID NO | Sequence | Description |
|---|---|---|
| 1 | ARTKQTARKSTGGKAPRKQLATKAARKSAPSTGGVKKPHRYRPGTVALREIRRYQKSTELLIRKLPFQRLVREIAQDFKTDLRFQSAAIGALQEASEAYLVGLFEDTNLCAIHAKRVTIMPKDIQLARRIRGERA | Histone H3.3, amino acid |
| 2 | ARTKQTARKSTGGKAPRKQLATKAARKSAPATGGVKKPHRYRPGTVALREIRRYQKSTELLIRKLPFQRLVREIAQDFKTDLRFQSSAVMALQEACEAYLVGLFEDTNLCAIHAKRVTIMPKDIQLARRIRGERA | Histone H3.1, amino acid |
| 3 | ARTKQTARKSTGGKAPRKQLATKAARMSAPSTGGVKKPHRYRPGTVALREIRRYQKSTELLIRKLPFQRLVREIAQDFKTDLRFQSAAIGALQEASEAYLVGLFEDTNLCAIHAKRVTIMPKDIQLARRIRGERA | Histone K27M-H3.3, amino acid |
| 4 | ARTKQTARKSTGGKAPRKQLATKAARMSAPATGGVKKPHRYRPGTVALREIRRYQKSTELLIRKLPFQRLVREIAQDFKTDLRFQSSAVMALQEACEAYLVGLFEDTNLCAIHAKRVTIMPKDIQLARRIRGERA | Histone K27M-H3.1, amino acid |
| 5 | RKSAPSTGGV | Histone H3.3 26-35 |
| 6 | RKSAPATGGV | Histone H3.1 26-35 |
| 7 | RMSAPSTGGV | Histone H3.3 26-35 K27M |
| 8 | RMSAPATGGV | Histone H3.1 26-35 K27M |
| 9 | AMSAPSTGGV | K27M-H3.3 A1 |
| 10 | RASAPSTGGV | K27M-H3.3 A2 |
| 11 | RMAAPSTGGV | K27M-H3.3 A3 |
| 12 | RMSAASTGGV | K27M-H3.3 A5 |
| 13 | RMSAPSAGGV | K27M-H3.3 A7 |
| 14 | RMSAPSTAGV | K27M-H3.3 A8 |
| 15 | RMSAPSTGAV | K27M-H3.3 A9 |
| 16 | RMSAPSTGGA | K27M-H3.3 A10 |
| 17 | AMSAPATGGV | K27M-H3.1 A1 |
| 18 | RASAPATGGV | K27M-H3.1 A2 |
| 19 | RMAAPATGGV | K27M-H3.1 A3 |
| 20 | RMSAAATGGV | K27M-H3.1 A5 |
| 21 | RMSAPAAGGV | K27M-H3.1 A7 |
| 22 | RMSAPATAGV | K27M-H3.1 A8 |
| 23 | RMSAPATGAV | K27M-H3.1 A9 |
| 24 | RMSAPATGGA | K27M-H3.1 A10 |

Sequence Listing

| SEQ ID NO | Sequence | Description |
|---|---|---|
| 25 | YLLPAIVHI | C3 control peptide (A2E-7) |
| 26 | LLDVPTAAV | A2E-1 |
| 27 | TLWVDPYEV | A2E-2 |
| 28 | FLLDHLKRV | A2E-3 |
| 29 | LLLDVPTAAV | A2E-4 |
| 30 | VLFRGGPRGLLAV | A2E-5 |
| 31 | SLLPAIVEL | A2E-6 |
| 32 | FLLPTGAEA | A2E-8 |
| 33 | LLDPKLCYLL | A2E-9 |
| 34 | MLLSVPLLLG | A2E-11 |
| 35 | MVDGTLLLL | A2E-17 |
| 36 | SLPHFHHPET | DMTN control |
| 37 | LLYDMVCGDIP | PIM1 control |
| 38 | LLLDVPTAAVQ | IFI30 control |
| 39 | LLLDVPTAAVQA | IFI30 control |
| 40 | VLFRGGPRGLLAVA | SSR1 control |
| 41 | YMAPEILMRS | RPS6KB1 control |
| 42 | FIYNADLMNC | CSF2RA control |
| 43 | KQYESVLMVSI | IL7 control |
| 44 | KVNVDEVGGE | Beta globin control |
| 45 | DVVMTQSPLSLPVTLGQPASISCRSSQSLVYSNGNTYLNWFHQRPGQSPRRLIYEVSNRDSGVPDRFSGSGSGTDFTLKISRVEAEDVGVYYCMQGTHWPPTFGGGTKLEIKRSRGGGGSGGGGSGGGGSLEMAEVQLVQSGAEVKKPGESLKISCKGSGYSFTSYWIGWVRQMPGKGLEWMGIIYPGDSDTRYSPSFQGQVTISADKSISTAYLQWSSLKASDTAMYYCARGYDGWGQGTLVTVSS | anti-HMC scFv 5 |
| 46 | SRGGGGSGGGGSGGGGSLEMA | scFv linker |
| 47 | DVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDDHYCLDYWGQGTTVTVSSGEGTSTGSGGSGGSGGADDIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIK | anti-CD3 scFv |
| 48 | TSGGGGS | BiTE linker |
| 49 | AAAIEVMYPPPYLDNEKSNGTIIHVKGKHLCPSPLFPGPSKPFWVLVVVGGVLACYSLLVTVAFIIFWVRSKRSRLLHSDYMNMTPRRPGPTRKHYQPYAPPRDFAAYRSRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | CD28/CD3ζ |
| 50 | TGTTTPAPRPPTPAPTIASQPLSLRPEACRPAAGGAVHTRGLDFACDIYIWAPLAGTCGVLLLSLVITLYCKRGRKKLLYIFKQPFMRPVQTTQEEDGCSCRFPEEEEGGCELRVKFSRSADAPAYQQGQNQLYNELNLGRREEYDVLDKRRGRDPEMGGKPRRKNPQEGLYNELQKDKMAEAYSEIGMKGERRRGKGHDGLYQGLSTATKDTYDALHMQALPPR | 4-1BB/CD3ζ |
| 51 | PNIQNPDPAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS | TCRα constant domain |

-continued

Sequence Listing

| SEQ ID NO | Sequence | Description |
|---|---|---|
| 52 | EDLNKVFPPEVAVFEPSEAEISHTQKATLVCLATGFFPDHVELSWWVNGKEVHSG VSTDPQPLKEQPALNDSRYCLSSRLRVSATFWQNPRNHFRCQVQFYGLSENDEW TQDRAKPVTQIVSAEAWGRADCGFTSVSYQQGVLSATILYEILLGKATLYAVLVSAL VLMAMVKRKDF | TCRβ constant domain |
| 53 | SQPHTKPSVFVMKNGTNVACLVKEFYPKDIRINLVSSKKITEFDPAIVISPSGKYNAV KLGKYEDSNSVTCSVQHDNKTVHSTDFEVKTDSTDHVKPKETENTKQPSKSCHKPK AIVHTEKVNMMSLTVLGLRMLFAKTVAVNFLLTAKLFFL | TCRδ constant domain |
| 54 | DKQLDADVSPKPTIFLPSIAETKLQKAGTYLCLLEKFFPDVIKIHWQEKKSNTILGSQE GNTMKTNDTYMKFSWLTVPEKSLDKEHRCIVRHENNKNGVDQEIIFPPIKTDVIT MDPKDNCSKDANDTLLLQLTNTSAYYMYLLLLLKSVVYFAIITCCLLRRTAFCCNGEKS | TCRγ constant domain |
| 55 | ILLLKVAGFNLLMTLRLWSS | TCRα transmembrane domain |
| 56 | TILYEILLGKATLYAVLVSALVL | TCRβ transmembrane domain |
| 57 | MLFAKTVAVNFLLTAKLFFL | TCRδ transmembrane domain |
| 58 | YYMYLLLLLKSVVYFAIITCCLL | TCRγ transmembrane domain |
| 59 | ESSCDVKLVEKSFETDTNLNFQNLSVIGFR | TCRα connecting peptide |
| 60 | ADCGFTSVSYQQGVLSA | TCRβ connecting peptide |
| 61 | DHVKPKETENTKQPSKSCHKPKAIVHTEKVNMMSLTVLGLR | TCRδ connecting peptide |
| 62 | MDPKDNCSKDANDTLLLQLTNTSA | TCRγ connecting peptide |
| 63 | IPEDTFFPSPESSCDVKLVEKSFETDTNLNFQNLSVIGFR | TCRα connecting peptide MD |
| 64 | GRADCGFTSVSYQQGVLSA | TCRβ connecting peptide MD |
| 65 | EVKTDSTDHVKPKETENTKQPSKSCHKPKAIVHTEKVNMMSLTVLGLR | TCRδ connecting peptide MD |
| 66 | PIKTDVITMDPKDNCSKDANDTLLLQLTNTSA | TCRγ connecting peptide MD |
| 67 | MAMVKRKDF | TCRβ intracellular domain |
| 68 | RRTAFCCNGEKS | TCRγ intracellular domain |
| 69 | EVKTDSTDHVKPKETENTKQPSKSCHKPKAIVHTEKVNMMSLTVLGLRMLFAKTV AVNFLLTAKLFFL | T cell receptor domain delta |
| 70 | PIKTDVITMDPKDNCSKDANDTLLLQLTNTSAYYMYLLLLLKSVVYFAIITCCLLRRTA FCCNGEKS | T cell receptor domain gamma |
| 71 | IPEDTFFPSPESSCDVKLVEKSFETDTNLNFQNLSVIGFRILLLKVAGFNLLMTLRLWSS | T cell receptor domain alpha |
| 72 | GRADCGFTSVSYQQGVLSATILYEILLGKATLYAVLVSALVLMAMVKRKDF | T cell receptor domain beta |
| 73 | METDTLLLWVLLLWVPGSTG | Signal peptide |

| SEQ ID NO | Sequence | Description |
|---|---|---|
| 74 | IEVMYPPPYLDNEKSNGTIIHVKGKHLCPSPLFPGPSKPFWVLVVVGGVLACYSLLV TVAFIIFWVRSKRSRLLHSDYMNMTPRRPGPTRKHYQPYAPPRDFAAYRS | fragment of CD28 |
| 75 | EVQLVQSGAEVKKPGESLKISCKGSGYSFTSYWIGWVRQMPGKGLEWMGIIYPGD SDTRYSPSFQGQVTISADKSISTAYLQWSSLKASDTAMYYCARGYDGWGQGTLVT VSS | HCVR 5 |
| 76 | EVQLVQSGAEVKKPGESLKISCKGSGYSFTSYWIGWVRQMPGKGLEWMGIIYPGD SDTRYSPSFQGQVTISADKSISTAYLQWSSLKASDTAMYYCARGFDNWGQGTLVT VSS | HCVR 10 |
| 77 | EVQLVQSGAEVKKPGESLKISCKGSGYSFTSYWIGWVRQMPGKGLEWMGIIYPGD SDTRYSPSFQGQVTISADKSISTAYLQWSSLKASDTAMYYCARGYDVWGQGTLVT VSS | HCVR 13 |
| 78 | EVQLVQSGAEVKKPGESLKISCKGSGYSFTSYWIGWVRQMPGKGLEWMGIIYPGD SDTRYSPSFQGQVTISADKSISTAYLQWSSLKASDTAMYYCARGYDSWGQGTLVT VSS | HCVR 16 |
| 79 | EVQLVESGGGLVQPGGSLRLSCAASGLTFDRYAMSWVRQAAGKGLERFSAITGDG YYTYYADSVKGRFTISRDNSKNTLYLQMNSLGAEDTAVYYCARLSGIGRSSYDGWG QGTLVTVSS | HCVR 31 |
| 80 | QVQLVESGAEVKKPGASVKVSCKASGYTFTSYTITWVRQAPGQGLEWMGWISPY NGNTNYAQNLQGRVTMTTDTSTTTAYMELRSLTSDDTAVYYCARSWEHGFPYDE WGQGTLVTVSS | HCVR 32 |
| 81 | EVQLVQSGAEVRKPGSSVKVSCKASAGTFNRYSLSWVRQAPGQGLEWVGRIIPIIG VADYAQKFQGRVTITADKSATTAYMELHSLRSEDTAVYYCARQEYSYAMDYWGQ GTLVTVSS | HCVR 33 |
| 82 | QVQLVQSGAEVKKPGSSVKVSCKASGGTFSSYAISWVRQAPGQGLEWMGGIIPIF GTANYAQKFQGRVTITADESTSTAYMELSSLRSEDTAVYYCARSYWTFEYSIDSWG QGTLVTVSS | HCVR 34 |
| 83 | EVQLVQSGAEVKKPGASVKVSCKASGYTFTSYGISWVRQAPGQGLEWMGWISAY NGNTNYAQKLQGRVTMTTDTSTSTAYMELRSLRSDDTAVYYCARYYESGYPFDW WGQGTLVTVSS | HCVR 35 |
| 84 | EVQLVQSGAEVKKPGASVKVSCKASGYTFTGYYMHWVRQAPGKGLEWMGGFD PEDGETIYAQKFQGRVTMTEDTSTDTAYMELSSLRSEDTAVYYCARSSWWSPVTY YDIWGQGTLVTVSS | HCVR 36 |
| 85 | QMQLVQSGAEVKKPGASMKVSCKASGYTVTSYGLSWVRQAPGQGLEWVGWIS AYNGDTIYAQKLQGRVTMTTDTSTSTAYMELRSLSDDTAMYYCARSSLPFGVVP NAFDIWGQGTMVTVSS | HCVR 37 |
| 86 | QMQLVQSGAEVKTTGASVRVSCKASGYTFTDYYLHWVRQAPGQGLEWMGWIN PHSGGTNYAQKFQGRVTMTRDTSISTAYMELSSLRSDDTAVYYCAREDYSGSGSS DAWGQGTLVTVSS | HCVR 38 |
| 87 | DVVMTQSPLSLPVTLGQPASISCRSSQSLVYSNGNTYLNWFHQRPGQSPRRLIYEV SNRDSGVPDRFSGSGSGTDFTLKISRVEAEDVGVYYCMQGTHWPPTFGGGTKLEI KR | LCVR 5 |
| 88 | EIVLTQSPLSLPVTLGQPASISCRSSQSLVYSNGNTYLSWFHQRPGQSPRRLIYKVSK RDSGVPDRFSGSGSGTDFTLKISRVEAEDVGVFYCMQGTYWPYTFGQGTKLEIKR | LCVR 10 |
| 89 | DVVMTQSPLSLPVTLGQPASISCRSSQSLIYSNGNTYLTWFHQRPGQPPRRLIHKVS NRDSGVPDRFSGSGSGSDFTLKISRVEAEDVGIYYCMQGTHWPPTFGGGTKLEIKR | LCVR 13 |
| 90 | DVVMTQSPLSLPVTLGQPASISCRSSQSLIYSNGNTYLTWFHQRPGQPPRRLIHKVS NRDSGVPDRFSGSGSGSDFTLKISRVEAEDVGIYYCMQGTHWPPTFGGGTKLEIKR | LCVR 16 |
| 91 | QAVLTQPSSLSASPGASASLTCTLRSGINVGTYRIYWYQQKPGSPPQYLLRYKSDSD KQQGSGVPSRFSGSKDASANAGILLISGLQSEDEADYYCMIWHSSAWVFGGGTKL TVLG | LCVR 31 |
| 92 | QSVLTQPPSVSGAPGQRVTISCTGSSSNLGAGYDVHWYQQLPGTAPKVLVYFNN NRPSGVPDRFSGSKSGTSASLAITGLQAEDEADYYCQSYDSSLSASVFGTGTKVTVL G | LCVR 32 |
| 93 | QSVLTQPPSVSGAPGQRVTIFCTGSSSNIGAGYDVHWYQQLPGTAPKLLIYGNNN RPSGVPDRFSGSKSGTSASLAITGLQAEDEADYYCQSYDTSLTPVFGGGTKLTVLG | LCVR 33 |

-continued

Sequence Listing

| SEQ ID NO | Sequence | Description |
|---|---|---|
| 94 | QSVLTQPPSVSGAPGQRVTISCTGSSLNLGAGYDVHWYQQFPGTAPKLLIFANTN RPSGVPDRFSASKSGTSASLAITGLQAEDEADYFCQSYDNSLSGYVFGTGTKVTVLG | LCVR 34 |
| 95 | SYVLTQPPSASGTPGQRVTISCSGSTFNIGSNTVNWYQQLPATAPKLLIYSNNQRPS GVPDRFSGSKSGTSASLAISGLQSEDAAAYYCAAWDDSLSGHVVFGGGTKLTVLG | LCVR 35 |
| 96 | SSELTQDPAVSVALGQTVRITCQGDSLRSYYANWYQQKPGQAPVLVIYAKSNRPS GIADRFSGSSSGNTASLTITGAQAEDEADYYCNSRDSSGNRWVFGGGTKVTVLG | LCVR 36 |
| 97 | SYVLTQPPSASGTPGQRVTISCSGSSSNIGSNTVNWYQQLPGTAPKLLIYSNNQRPS GVPDRFSGSKSGTSASLAISGLQSEDEADYYCAAWDDSLNGYVFGTGTKVTVLG | LCVR 37 |
| 98 | SYELTQPPSVSAPGKTARITCGGNNIGSKSVNWYQQKPGQAPVLVIYYDNDRPS GIPERFSGSNSGNTATLTISRVEAGDEADYYCQVWNSSSDHYVFGTGTKVTVLG | LCVR 38 |
| 99 | GYSFTSYW | HC-CDR1 1 5 |
| 100 | GLTFDRYA | HC-CDR1 1 31 |
| 101 | GYTFTSYT | HC-CDR1 1 32 |
| 102 | AGTFNRYS | HC-CDR1 1 33 |
| 103 | GGTFSSYA | HC-CDR1 1 34 |
| 104 | GYTFTSYG | HC-CDR1 1 35 |
| 105 | GYTFTGYY | HC-CDR1 1 36 |
| 106 | GYTVTSYG | HC-CDR11 3 7 |
| 107 | GYTFTDYY | HC-CDR11 3 8 |
| 108 | IYPGDSDT | HC-CDR2 1 5 |
| 109 | ITGDGYYT | HC-CDR2 1 31 |
| 110 | ISPYNGNT | HC-CDR2 1 32 |
| 111 | IIPIIGVA | HC-CDR2 1 33 |
| 112 | IIPIFGTA | HC-CDR2 1 34 |
| 113 | ISAYNGNT | HC-CDR2 1 35 |
| 114 | FDPEDGET | HC-CDR2 1 36 |
| 115 | ISAYNGDT | HC-CDR2 1 37 |
| 116 | INPHSGGT | HC-CDR2 1 38 |
| 117 | ARGYDG | HC-CDR3 1 5 |
| 118 | ARGFDN | HC-CDR3 1 10 |
| 119 | ARGYDV | HC-CDR3 1 13 |
| 120 | ARGYDS | HC-CDR3 1 16 |
| 121 | ARLSGIGRSSYDG | HC-CDR3 1 31 |
| 122 | ARSWEHGFPYDE | HC-CDR3 1 32 |
| 123 | ARQEYSYAMDY | HC-CDR3 1 33 |
| 124 | ARSYWTFEYSIDS | HC-CDR3 1 34 |
| 125 | ARYYESGYPFDW | HC-CDR3 1 35 |
| 126 | ARSSWWSPVTYYDI | HC-CDR3 1 36 |
| 127 | ARSSLPFGVVPNAFDI | HC-CDR3 1 37 |

-continued

Sequence Listing

| SEQ ID NO | Sequence | Description |
|---|---|---|
| 128 | AREDYSGSGSSDA | HC-CDR3 1 38 |
| 129 | QSLVYSNGNTY | LC-CDR1 1 5 |
| 130 | QSLIYSNGNTY | LC-CDR1 1 13 |
| 131 | SGINVGTYR | LC-CDR1 1 31 |
| 132 | SSNLGAGYD | LC-CDR1 1 32 |
| 133 | SSNIGAGYD | LC-CDR1 1 33 |
| 134 | SLNLGAGYD | LC-CDR1 1 34 |
| 135 | TFNIGSNT | LC-CDR1 1 35 |
| 136 | SLRSYY | LC-CDR1 1 36 |
| 137 | SSNIGSNT | LC-CDR1 1 37 |
| 138 | NIGSKS | LC-CDR1 1 38 |
| 139 | EVS | LC-CDR2 1 5 |
| 140 | KVS | LC-CDR2 1 10 |
| 141 | YKSDSDK | LC-CDR2 1 31 |
| 142 | FNN | LC-CDR2 1 32 |
| 143 | GNN | LC-CDR2 1 33 |
| 144 | ANT | LC-CDR2 1 34 |
| 145 | SNN | LC-CDR2 1 35 |
| 146 | AKS | LC-CDR2 1 36 |
| 147 | YDN | LC-CDR2 1 38 |
| 148 | MQGTHWPPT | LC-CDR3 1 5 |
| 149 | MQGTYWPYT | LC-CDR3 1 10 |
| 150 | MIWHSSA | LC-CDR3 1 31 |
| 151 | QSYDSSLSASV | LC-CDR3 1 32 |
| 152 | QSYDTSLTPV | LC-CDR3 1 33 |
| 153 | QSYDNSLSGYV | LC-CDR3 1 34 |
| 154 | AAWDDSLSGHVV | LC-CDR3 1 35 |
| 155 | NSRDSSGNR | LC-CDR3 1 36 |
| 156 | AAWDDSLNGYV | LC-CDR3 1 37 |
| 157 | QVWNSSSDHYV | LC-CDR3 1 38 |
| 158 | $X_1X_2X_3FX_4X_5Y$, wherein $X_1$ = A or G, $X_2$ = G or Y, $X_3$ = S or T, $X_4$ = S or T, and $X_5$ = any AA | HC-CDR1 consensus |
| 159 | $IX_1X_2X_3X_4GX_5X_6$, wherein $X_1$ = any AA, $X_2$ = A or P, $X_3$ = any AA, $X_4$ = any AA, $X_5$ = any AA, and $X_6$ = A or T | HC-CDR2 consensus |
| 160 | $ARGX_1D$, wherein $X_1$ = F or Y | HC-CDR3 consensus 1 |
| 161 | $ARX_1X_2EX_3GX_4PX_5D$, wherein $X_1$ = any AA, $X_2$ = W or Y, $X_3$ = any AA, $X_4$ = F or Y, and $X_5$ = F or Y | HC-CDR3 consensus 2 |
| 162 | $X_1X_2NX_3GX_4$, wherein $X_1$ = S or T, $X_2$ = any AA, $X_3$ = I, L, or N, and $X_4$ = A, S, or T | LC-CDR1 consensus |

| SEQ ID NO | Sequence | Description |
|---|---|---|
| 163 | $X_1X_2X_3DX_4SL$, wherein $X_1$ = A or Q, $X_2$ = A or S, $X_3$ = W or Y, and $X_4$ = any AA | LC-CDR3 consensus |
| 164 | QSVLTQPPSVSGAPGQRVTISCTGSSSNLGAGYDVHWYQQLPGTAPKVLVYFNNNRPSGVPDRFSGSKSGTSASLAITGLQAEDEADYYCQSYDSSLSASVFGTGTKVTVLGSRGGGGSGGGGSGGGGSLEMAQVQLVESGAEVKKPGASVKVSCKASGYTFTSYTITWVRQAPGQGLEWMGWISPYNGNTNYAQNLQGRVTMTTDTSTTTAYMELRSLTSDDTAVYYCARSWEHGFPYDEWGQGTLVTVSSTSGGGGSDVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDDHYCLDYWGQGTTVTVSSGEGTSTGSGGSGGSGGADDIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIK | BsAb #32 |
| 165 | QSVLTQPPSVSGAPGQRVTISCTGSSLNLGAGYDVHWYQQFPGTAPKLLIFANTNRPSGVPDRFSASKSGTSASLAITGLQAEDEADYFCQSYDNSLSGYVFGTGTKVTVLGSRGGGGSGGGGSGGGGSLEMAQVQLVQSGAEVKKPGSSVKVSCKASGGTFSSYAISWVRQAPGQGLEWMGGIIPIFGTANYAQKFQGRVTITADESTSTAYMELSSLRSEDTAVYYCARSYWTFEYSIDSWGQGTLVTVSSTSGGGGSDVQLVQSGAEVKKPGASVKVSCKASGYTFTRYTMHWVRQAPGQGLEWIGYINPSRGYTNYADSVKGRFTITTDKSTSTAYMELSSLRSEDTATYYCARYYDDHYCLDYWGQGTTVTVSSGEGTSTGSGGSGGSGGADDIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIK | BsAb #34 |
| 166 | SYVLTQPPSASGTPGQRVTISCSGSTFNIGSNTVNWYQQLPATAPKLLIYSNNQRPSGVPDRFSGSKSGTSASLAISGLQSEDAAAYYCAAWDDSLSGHVVFGGGTKLTVLGSRGGGGSGGGGSGGGGSLEMAEVQLVQSGAEVKKPGASVKVSCKASGYTFTSYGISWVRQAPGQGLEWMGWISAYNGNTNYAQKLQGRVTMTTDTSTSTAYMELRSLRSDDTAVYYCARYYESGYPFDWWGQGTLVTVSSTSGGGGSDVQLVQSGAEVKKPGASVKVSCKASGYTFTRYTMHWVRQAPGQGLEWGYINPSRGYTNYADSVKGRFTITTDKSTSTAYMELSSLRSEDTATYYCARYYDDHYCLDYWGQGTTVTVSSGEGTSTGSGGSGGSGGADDIVLTQSPATLSLSPGERATLSCRASQSVSYMNWYQQKPGKAPKRWIYDTSKVASGVPARFSGSGSGTDYSLTINSLEAEDAATYYCQQWSSNPLTFGGGTKVEIK | BsAb #35 |
| 167 | YQYMDDLYV | Control HIV peptide |

What is claimed is:

1. An isolated anti-HMC construct comprising an antibody moiety that specifically binds to a complex comprising a histone H3 peptide and a major histocompatibility (MHC) class I protein ("HMC"); wherein:

the histone H3 peptide is the peptide set forth in SEQ ID NO: 7;

the MEW is HLA-A02; and the antibody moiety comprises:

i) a heavy chain variable domain (VH) comprising a heavy chain complementarity determining region (HC-CDR) 1 comprising the amino acid sequence of SEQ ID NO: 99, an HC-CDR2 comprising the amino acid sequence of SEQ ID NO: 108, and an HC-CDR3 comprising the amino acid sequence of SEQ ID NO: 117; and a light chain variable domain (VL) comprising a light chain complementarity determining region (LC-CDR) 1 comprising the amino acid sequence of SEQ ID NO: 129, an LC-CDR2 comprising the amino acid sequence of SEQ ID NO: 139, and an LC-CDR3 comprising the amino acid sequence of SEQ ID NO: 148; or ii) a VH comprising an HC-CDR1 comprising the amino acid sequence of SEQ ID NO: 99, an HC-CDR2 comprising the amino acid sequence of SEQ ID NO: 108, and an HC-CDR3 comprising the amino acid sequence of SEQ ID NO: 118; and a VL comprising an LC-CDR1 comprising the amino acid sequence of SEQ ID NO: 129, an LC-CDR2 comprising the amino acid sequence of SEQ ID NO: 140, and an LC-CDR3 comprising the amino acid sequence of SEQ ID NO: 149; or iii) a VH comprising an HC-CDR1 comprising the amino acid sequence of SEQ ID NO: 99, an HC-CDR2 comprising the amino acid sequence of SEQ ID NO: 108, and an HC-CDR3 comprising the amino acid sequence of SEQ ID NO: 119; and a VL comprising an LC-CDR1 comprising the amino acid sequence of SEQ ID NO: 130, an LC-CDR2 comprising the amino acid sequence of SEQ ID NO: 140, and an LC-CDR3 comprising the amino acid sequence of SEQ ID NO: 148; or iv) a VH comprising an HC-CDR1 comprising the amino acid sequence of SEQ ID NO: 99, an HC-CDR2 comprising the amino acid sequence of SEQ ID NO: 108, and an HC-CDR3 comprising the amino acid sequence of SEQ ID NO: 120; and a VL comprising an LC-CDR1 comprising the amino acid sequence of SEQ ID NO: 130, an LC-CDR2 comprising the amino acid sequence of SEQ ID NO: 140, and an LC-CDR3 comprising the amino acid sequence of SEQ ID NO: 148; or v) a VH comprising an HC-CDR1 comprising the amino acid sequence of SEQ ID NO: 100, an HC-CDR2 comprising the amino acid sequence of SEQ ID NO: 109, and an HC-CDR3 comprising the amino acid sequence of SEQ ID NO: 121; and a VL comprising an LC-CDR1 comprising the amino acid sequence of SEQ ID NO: 131, an LC-CDR2 comprising the amino acid sequence of SEQ ID NO: 141, and an LC-CDR3 comprising the amino acid sequence of SEQ ID NO: 150; or vi) a VH comprising an HC-CDR1 comprising the amino acid sequence of SEQ ID NO: 101, an HC-CDR2 comprising the amino acid sequence of SEQ ID NO: 110, and an HC-CDR3 comprising the amino acid sequence of SEQ ID NO: 122; and a VL comprising an LC-CDR1 comprising the amino acid sequence of SEQ ID NO: 132, an LC-CDR2 comprising the amino acid sequence of SEQ ID NO: 142, and an LC-CDR3 comprising the amino acid sequence of SEQ ID NO: 151; or vii) a VH comprising an HC-CDR1 comprising the amino acid sequence of SEQ ID NO: 102, an HC-CDR2 comprising the amino acid sequence of SEQ ID NO: 111, and an HC-CDR3 comprising the amino acid sequence of SEQ ID NO: 123; and a VL comprising an LC-CDR1 comprising the amino acid sequence of SEQ ID NO: 133, an LC-CDR2 comprising the amino acid sequence of SEQ ID NO: 143, and an LC-CDR3 comprising the amino acid sequence of SEQ ID NO: 152; or viii) a VH comprising an HC-CDR1 comprising the amino acid sequence of SEQ ID NO: 103, an HC-CDR2 comprising the amino acid sequence of SEQ ID NO: 112, and an HC-CDR3 comprising the amino acid sequence of SEQ ID NO: 124; and a VL comprising an LC-CDR1 comprising the amino acid sequence of SEQ ID NO: 134, an LC-CDR2 comprising the amino acid sequence of SEQ ID NO: 144, and an LC-CDR3 comprising the amino acid sequence of SEQ ID NO: 153; or ix) a VH comprising an HC-CDR1 comprising the amino acid sequence of SEQ ID NO: 104, an HC-CDR2 comprising the amino acid sequence of SEQ ID NO: 113, and an HC-CDR3 comprising the amino acid sequence of SEQ ID NO: 125; and a VL comprising an LC-CDR1 comprising the amino acid sequence of SEQ ID NO: 135, an LC-CDR2 comprising the amino acid sequence of SEQ ID NO: 145, and an LC-CDR3 comprising the amino acid sequence of SEQ ID NO: 154; or x) a VH comprising an HC-CDR1 comprising the amino acid sequence of SEQ ID NO: 105, an HC-CDR2 comprising the amino acid sequence of SEQ ID NO: 114, and an HC-CDR3 comprising the amino acid sequence of SEQ ID NO: 126; and a VL comprising an LC-CDR1 comprising the amino acid sequence of SEQ ID NO: 136, an LC-CDR2 comprising the amino acid sequence of SEQ ID NO: 146, and an LC-CDR3 comprising the amino acid sequence of SEQ ID NO: 155; or xi) a VH comprising an HC-CDR1 comprising the amino acid sequence of SEQ ID NO: 106, an HC-CDR2 comprising the amino acid sequence of SEQ ID NO: 115, and an HC-CDR3 comprising the amino acid sequence of SEQ ID NO: 127; and a VL comprising an LC-CDR1 comprising the amino acid sequence of SEQ ID NO: 137, an LC-CDR2 comprising the amino acid sequence of SEQ ID NO: 145, and an LC-CDR3 comprising the amino acid sequence of SEQ ID NO: 156; or xii) a VH comprising an HC-CDR1 comprising the amino acid sequence of SEQ ID NO: 107, an HC-CDR2 comprising the amino acid sequence of SEQ ID NO: 116, and an HC-CDR3 comprising the amino acid sequence of SEQ ID NO: 128; and a VL comprising an LC-CDR1 comprising the amino acid sequence of SEQ ID NO: 138, an LC-CDR2 comprising the amino acid sequence of SEQ ID NO: 147, and an LC-CDR3 comprising the amino acid sequence of SEQ ID NO: 157.

2. The isolated anti-HMC construct of claim 1 wherein the antibody moiety comprises:

a) a heavy chain variable domain comprising the amino acid sequence of SEQ ID NO: 75 or a variant thereof having at least 95% sequence identity to SEQ ID NO: 75, and a light chain variable domain comprising the amino acid sequence of SEQ ID NO: 87 or a variant thereof having at least 95% sequence identity to SEQ ID NO: 87; or b) a heavy chain variable domain comprising the amino acid sequence of SEQ ID NO: 76 or a variant thereof having at least 95% sequence identity to SEQ ID NO: 76, and a light chain variable domain comprising the amino acid sequence of SEQ ID NO: 88 or a variant thereof having at least 95% sequence identity to SEQ ID NO: 88; or c) a heavy chain variable domain comprising the amino acid sequence of SEQ ID NO: 77 or a variant thereof having at least 95% sequence identity to SEQ ID NO: 77, and a light chain variable domain comprising the amino acid sequence of SEQ ID NO: 89 or a variant thereof having at least 95% sequence identity to SEQ ID NO: 89; or d) a heavy chain variable domain comprising the amino acid sequence of SEQ ID NO: 78 or a variant thereof having at least 95% sequence identity to SEQ ID NO: 78, and a light chain variable domain comprising the amino acid sequence of SEQ ID NO: 90 or a variant thereof having at least 95% sequence identity to SEQ ID NO: 90; or e) a heavy chain variable domain comprising the amino acid sequence of SEQ ID NO: 79 or a variant thereof having at least 95% sequence identity to SEQ ID NO: 79, and a light chain variable domain comprising the amino acid sequence of SEQ ID NO: 91 or a variant thereof having at least 95% sequence identity to SEQ ID NO: 91; or f) a heavy chain variable domain comprising the amino acid sequence of SEQ ID NO: 80 or a variant thereof having at least 95% sequence identity to SEQ ID NO: 80, and a light chain variable domain comprising the amino acid sequence of SEQ ID NO: 92 or a variant thereof having at least 95% sequence identity to SEQ ID NO: 92; or g) a heavy chain variable domain comprising the amino acid sequence of SEQ ID NO: 81 or a variant thereof having at least 95% sequence identity to SEQ ID NO: 81, and a light chain variable domain comprising the amino acid sequence of SEQ ID NO: 93 or a variant thereof having at least 95% sequence identity to SEQ ID NO: 93; or h) a heavy chain variable domain comprising the amino acid sequence of SEQ ID NO: 82 or a variant thereof having at least 95% sequence identity to SEQ ID NO: 82, and a light chain variable domain comprising the amino acid sequence of SEQ ID NO: 94 or a variant thereof having at least 95% sequence identity to SEQ ID NO: 94; or i) a heavy chain variable domain comprising the amino acid sequence of SEQ ID NO: 83 or a variant thereof having at least 95% sequence identity to SEQ ID NO: 83, and a light chain variable domain comprising the amino acid sequence of SEQ ID NO: 95 or a variant thereof having at least 95% sequence identity to SEQ ID NO: 95; or j) a heavy chain variable domain comprising the amino acid sequence of SEQ ID NO: 84 or a variant thereof having at least 95% sequence identity to SEQ ID NO: 84, and a light chain variable domain comprising the amino acid sequence of SEQ ID NO: 96 or a variant thereof having at least 95% sequence identity to SEQ ID NO: 96; or k) a heavy chain variable domain comprising the amino acid sequence of SEQ ID NO: 85 or a variant thereof having at least 95% sequence identity to SEQ ID NO: 85, and a light chain variable domain comprising the amino acid sequence of SEQ ID NO: 97 or a variant thereof having at least 95% sequence identity to SEQ ID NO: 97; or l) a heavy chain variable domain comprising the amino acid sequence of SEQ ID NO: 86 or a variant thereof having at least 95% sequence identity to SEQ ID NO: 86, and a light chain variable domain comprising the amino acid sequence of SEQ ID NO: 98 or a variant thereof having at least 95% sequence identity to SEQ ID NO: 98.

3. The isolated anti-HMC construct of claim 1, wherein the isolated anti-HMC construct is multispecific.

4. The isolated anti-HMC construct of claim 3, wherein the isolated anti-HMC construct is a tandem scFv comprising two scFvs linked by a peptide linker.

5. The isolated anti-HMC construct of claim 3, wherein the isolated anti-HMC construct further comprises a second antibody moiety that specifically binds to a second antigen, wherein the second antigen is selected from the group consisting of CD3γ, CD3δ, CD3ε, CD3ζ, CD28, OX40, GITR, CD137, CD27, CD40L, and HVEM.

6. The isolated anti-HMC construct of claim 5, wherein the second antigen is CD3ε, and wherein the isolated anti-HMC construct is a tandem scFv comprising a first scFv specific for the histone H3/MHC class I complex and a second scFv specific for CD3ε.

7. The isolated anti-HMC construct of claim 1, wherein the isolated anti-HMC construct is a chimeric antigen receptor (CAR) comprising an extracellular domain comprising the antibody moiety, a transmembrane domain, and an intracellular signaling domain.

8. The isolated anti-HMC construct of claim 7, wherein:
(i) the intracellular signaling domain comprises a CD3ζ intracellular signaling sequence and a CD28 intracellular signaling sequence; or
(ii) the intracellular signaling domain comprises a CD3ζ intracellular signaling sequence and a 4-1BB intracellular signaling sequence; or (iii) the intracellular signaling domain comprises a CD3ζ intracellular signaling sequence, a CD28 intracellular signaling sequence and a 4-1BB intracellular signaling sequence.

9. An effector cell expressing the anti-HMC construct of claim 7.

10. The effector cell of claim 9, wherein the effector cell is a T cell.

11. A pharmaceutical composition comprising the effector cell of claim 10 and a pharmaceutically acceptable carrier.

12. The isolated anti-HMC construct of claim 1, wherein the isolated anti-HMC construct is a chimeric antibody/T cell receptor (abTCR) comprising an extracellular domain comprising the antibody moiety and a T cell receptor (TCR) module (TCRM) comprising TCR transmembrane domains.

13. The isolated anti-HMC construct of claim 12, wherein the antibody moiety comprises:
 a) a first polypeptide chain comprising a first antigen-binding domain comprising $V_H$ and $C_H1$ antibody domains; and
 b) a second polypeptide chain comprising a second antigen-binding domain comprising $V_L$ and $C_L$ antibody domains,
 wherein the $V_H$ and $C_H1$ domains of the first antigen-binding domain and the $V_L$ and $C_L$ domains of the second antigen-binding domain form a Fab-like antigen-binding module that specifically binds to the HMC.

14. An effector cell expressing the anti-HMC construct of claim 12.

15. The effector cell of claim 14, wherein the effector cell is a T cell.

16. A pharmaceutical composition comprising the effector cell of claim 15 and a pharmaceutically acceptable carrier.

17. The isolated anti-HMC construct of claim 1, wherein the isolated anti-HMC construct is an immunoconjugate comprising the antibody moiety and an effector molecule, wherein the effector molecule is a therapeutic agent selected from the group consisting of a drug, a toxin, a radioisotope, a protein, a peptide, and a nucleic acid.

18. A pharmaceutical composition comprising the immunoconjugate of claim 17 and a pharmaceutically acceptable carrier.

19. The isolated anti-HMC construct of claim 1, wherein the isolated anti-HMC construct is an immunoconjugate comprising the antibody moiety and a label.

20. The isolated anti-HMC construct of claim 1, wherein the antibody moiety comprises a VH comprising an HC-CDR1 comprising the amino acid sequence of SEQ ID NO: 103, an HC-CDR2 comprising the amino acid sequence of SEQ ID NO: 112, and an HC-CDR3 comprising the amino acid sequence of SEQ ID NO: 124; and a VL comprising an LC-CDR1 comprising the amino acid sequence of SEQ ID NO: 134, an LC-CDR2 comprising the amino acid sequence of SEQ ID NO: 144, and an LC-CDR3 comprising the amino acid sequence of SEQ ID NO: 153.

21. The isolated anti-HMC construct of claim 1, wherein the antibody moiety comprises a VH comprising an HC-CDR1 comprising the amino acid sequence of SEQ ID NO: 106, an HC-CDR2 comprising the amino acid sequence of SEQ ID NO: 115, and an HC-CDR3 comprising the amino acid sequence of SEQ ID NO: 127; and a VL comprising an LC-CDR1 comprising the amino acid sequence of SEQ ID NO: 137, an LC-CDR2 comprising the amino acid sequence of SEQ ID NO: 145, and an LC-CDR3 comprising the amino acid sequence of SEQ ID NO: 156.

22. A pharmaceutical composition comprising the anti-HMC construct of claim 1 and a pharmaceutically acceptable carrier.

23. A host cell expressing the anti-HMC construct of claim 1.

24. A nucleic acid encoding the anti-HMC construct of claim 1.

25. An isolated antibody construct comprising an antibody moiety that specifically binds to a complex comprising the histone H3 peptide set forth in SEQ ID NO: 7 and HLA-A02; wherein the antibody moiety comprises
 a) a heavy chain variable domain comprising the amino acid sequence of SEQ ID NO: 75 and a light chain variable domain comprising the amino acid sequence of SEQ ID NO: 87; or
 b) a heavy chain variable domain comprising the amino acid sequence of SEQ ID NO: 76 and a light chain variable domain comprising the amino acid sequence of SEQ ID NO: 88; or
 c) a heavy chain variable domain comprising the amino acid sequence of SEQ ID NO: 77 and a light chain variable domain comprising the amino acid sequence of SEQ ID NO: 89; or
 d) a heavy chain variable domain comprising the amino acid sequence of SEQ ID NO: 78 and a light chain variable domain comprising the amino acid sequence of SEQ ID NO: 90; or
 e) a heavy chain variable domain comprising the amino acid sequence of SEQ ID NO: 79 and a light chain variable domain comprising the amino acid sequence of SEQ ID NO: 91; or
 f) a heavy chain variable domain comprising the amino acid sequence of SEQ ID NO: 80 and a light chain variable domain comprising the amino acid sequence of SEQ ID NO: 92; or
 g) a heavy chain variable domain comprising the amino acid sequence of SEQ ID NO: 81 and a light chain variable domain comprising the amino acid sequence of SEQ ID NO: 93; or
 h) a heavy chain variable domain comprising the amino acid sequence of SEQ ID NO: 82 and a light chain variable domain comprising the amino acid sequence of SEQ ID NO: 94; or
 i) a heavy chain variable domain comprising the amino acid sequence of SEQ ID NO: 83 and a light chain variable domain comprising the amino acid sequence of SEQ ID NO: 95; or
 j) a heavy chain variable domain comprising the amino acid sequence of SEQ ID NO: 84 and a light chain variable domain comprising the amino acid sequence of SEQ ID NO: 96; or
 k) a heavy chain variable domain comprising the amino acid sequence of SEQ ID NO: 85 and a light chain variable domain comprising the amino acid sequence of SEQ ID NO: 97; or
 l) a heavy chain variable domain comprising the amino acid sequence of SEQ ID NO: 86 and a light chain variable domain comprising the amino acid sequence of SEQ ID NO: 98.

26. The isolated anti-HMC construct of claim 25, wherein the antibody moiety comprises a heavy chain variable domain comprising the amino acid sequence of SEQ ID NO: 82 and a light chain variable domain comprising the amino acid sequence of SEQ ID NO: 94.

27. The isolated anti-HMC construct of claim 25, wherein the antibody moiety comprises a heavy chain variable domain comprising the amino acid sequence of SEQ ID NO:

85 and a light chain variable domain comprising the amino acid sequence of SEQ ID NO: 97.

28. A nucleic acid encoding the antibody moiety of claim 25.

* * * * *

UNITED STATES PATENT AND TRADEMARK OFFICE
CERTIFICATE OF CORRECTION

| | |
|---|---|
| PATENT NO. | : 11,274,157 B2 |
| APPLICATION NO. | : 16/477509 |
| DATED | : March 15, 2022 |
| INVENTOR(S) | : Vivien Wai-Fan Chan |

It is certified that error appears in the above-identified patent and that said Letters Patent is hereby corrected as shown below:

In the Claims

Column 265, Claim 1, Line 19, delete "MEW" and insert --MHC--.

Signed and Sealed this
Sixteenth Day of August, 2022

Katherine Kelly Vidal
*Director of the United States Patent and Trademark Office*